US012760061B2

(12) United States Patent
Bender et al.

(10) Patent No.: US 12,760,061 B2
(45) Date of Patent: Oct. 13, 2026

(54) SYNTHETIC TRITERPENOIDS WITH NITROGEN-BASED SUBSTITUENTS AT C-17 AND METHODS OF USE THEREOF

(71) Applicant: REATA PHARMACEUTICALS, INC., Irving, TX (US)

(72) Inventors: Christopher F. Bender, Garland, TX (US); Ha Do, Irving, TX (US); Xin Jiang, Coppell, TX (US); Haizhou Sun, Irving, TX (US); Melean Visnick, Irving, TX (US); Ingo Janser, Ann Arbor, MI (US); Lloyd J. Simons, Kalamazoo, MI (US); Heinrich J. Schostarez, Kalamazoo, MI (US)

(73) Assignee: REATA PHARMACEUTICALS, INC, Irving, TX (US)

( * ) Notice: Subject to any disclaimer, the term of this patent is extended or adjusted under 35 U.S.C. 154(b) by 1150 days.

(21) Appl. No.: 17/757,701

(22) PCT Filed: Dec. 18, 2020

(86) PCT No.: PCT/US2020/066073
§ 371 (c)(1),
(2) Date: Jun. 17, 2022

(87) PCT Pub. No.: WO2021/127480
PCT Pub. Date: Jun. 24, 2021

(65) Prior Publication Data

US 2023/0111914 A1 Apr. 13, 2023

Related U.S. Application Data

(60) Provisional application No. 63/198,310, filed on Oct. 9, 2020, provisional application No. 62/950,919, filed
(Continued)

(51) Int. Cl.
*A61P 39/06* (2006.01)
*C07J 63/00* (2006.01)

(52) U.S. Cl.
CPC ............. *C07J 63/008* (2013.01); *A61P 39/06* (2018.01)

(58) Field of Classification Search
CPC . C07J 63/008; A61P 39/06; A61P 9/10; A61P 17/06; A61P 19/02; A61P 25/00;
(Continued)

(56) References Cited

U.S. PATENT DOCUMENTS 4,395,423 A 7/1983 Neumann
5,064,823 A 11/1991 Lee et al.
(Continued)

FOREIGN PATENT DOCUMENTS

KR 2011-0010611 2/2011
MX 2021/003643 8/2021
(Continued)

OTHER PUBLICATIONS

AACR Cancer Progress Report 2022, CancerProgressReport.org, Philadelphia, AACR 2022, ISBN: 979-8-9857852-5-8 (Year: 2022).*
(Continued)

*Primary Examiner* — James H Alstrum-Acevedo
*Assistant Examiner* — Allen Chao
(74) *Attorney, Agent, or Firm* — pH IP Law

(57) ABSTRACT

In some aspects, the present disclosure provides compounds of the formula: (I) and (II), wherein the variables are defined herein. Also provided are pharmaceutical compositions thereof. In some aspects, the compounds and compositions provided herein may be used as antioxidant inflammation modulators. In some aspects, the present disclosure provides methods wherein the compounds and composition described herein are used for the treatment of diseases and disorders associated with inflammation and cancer.

(I)

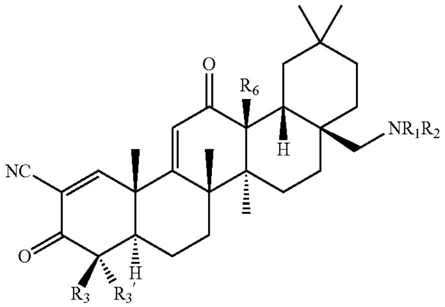

(II)

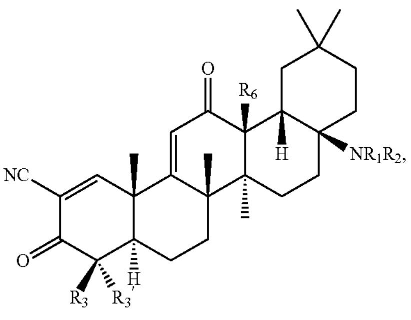

63 Claims, No Drawings

Related U.S. Application Data on Dec. 19, 2019, provisional application No. 62/950,927, filed on Dec. 19, 2019.

(58) Field of Classification Search
CPC .......... A61P 25/02; A61P 25/04; A61P 25/08; A61P 25/24; A61P 25/28; A61P 27/02; A61P 27/06; A61P 27/14; A61P 29/00; A61P 35/00; A61P 37/06; A61K 31/56; A61K 31/58
See application file for complete search history.

(56) References Cited

U.S. PATENT DOCUMENTS

| | | | |
|---|---|---|---|
| 6,326,507 | B1 | 12/2001 | Gribble et al. |
| 6,369,101 | B1 | 4/2002 | Carlson et al. |
| 6,503,913 | B1 | 1/2003 | Goldmann et al. |
| 6,552,075 | B2 | 4/2003 | Gribble et al. |
| 6,642,217 | B2 | 11/2003 | Krasutsky et al. |
| 6,649,654 | B1 | 11/2003 | Karin et al. |
| 6,951,847 | B2 | 10/2005 | Gibson et al. |
| 6,974,801 | B2 | 12/2005 | Honda et al. |
| 7,053,119 | B2 | 5/2006 | Karin et al. |
| 7,144,875 | B2 | 12/2006 | Gibson et al. |
| 7,176,237 | B2 | 2/2007 | Honda et al. |
| 7,288,568 | B2 | 10/2007 | Gribble et al. |
| 7,399,606 | B2 | 7/2008 | Karin et al. |
| 7,410,958 | B2 | 8/2008 | Krasutsky et al. |
| 7,435,755 | B2 | 10/2008 | Konopleva et al. |
| 7,678,830 | B2 | 3/2010 | Honda et al. |
| 7,714,012 | B2 | 5/2010 | Honda et al. |
| 7,795,305 | B2 | 9/2010 | Konopleva et al. |
| 7,863,327 | B2 | 1/2011 | Gribble et al. |
| 7,915,402 | B2 | 3/2011 | Anderson et al. |
| 7,943,778 | B2 | 5/2011 | Jiang et al. |
| 8,034,955 | B2 | 10/2011 | Gribble et al. |
| 8,067,394 | B2 | 11/2011 | Honda et al. |
| 8,067,465 | B2 | 11/2011 | Honda et al. |
| 8,071,632 | B2 | 12/2011 | Jiang et al. |
| 8,088,824 | B2 | 1/2012 | Walling et al. |
| 8,124,656 | B2 | 2/2012 | Anderson et al. |
| 8,124,799 | B2 | 2/2012 | Anderson et al. |
| 8,129,429 | B2 | 3/2012 | Sporn et al. |
| 8,258,329 | B2 | 9/2012 | Anderson et al. |
| 8,299,046 | B2 | 10/2012 | Sporn et al. |
| 8,338,618 | B2 | 12/2012 | Jiang et al. |
| 8,394,967 | B2 | 3/2013 | Jiang et al. |
| 8,440,820 | B2 | 5/2013 | Anderson et al. |
| 8,440,854 | B2 | 5/2013 | Anderson et al. |
| 8,455,544 | B2 | 6/2013 | Sporn et al. |
| 8,513,436 | B2 | 8/2013 | Anderson et al. |
| 8,586,775 | B2 | 11/2013 | Gribble et al. |
| RE45,288 | E | 12/2014 | Anderson et al. |
| 8,921,419 | B2 | 12/2014 | Gribble et al. |
| RE45,325 | E | 1/2015 | Anderson et al. |
| 8,993,640 | B2 | 3/2015 | Anderson et al. |
| 9,090,574 | B2 | 7/2015 | Anderson et al. |
| 9,102,681 | B2 | 8/2015 | Anderson et al. |
| 9,174,941 | B2 | 11/2015 | Anderson et al. |
| 9,233,998 | B2 | 1/2016 | Anderson et al. |
| 9,249,089 | B2 | 2/2016 | Jiang et al. |
| 9,278,912 | B2 | 3/2016 | Jiang et al. |
| 9,278,913 | B2 | 3/2016 | Gribble et al. |
| 9,290,536 | B2 | 3/2016 | Anderson et al. |
| 9,512,094 | B2 | 12/2016 | Jiang et al. |
| 9,556,222 | B2 | 1/2017 | Anderson et al. |
| 9,593,074 | B2 | 3/2017 | Bender et al. |
| 9,670,147 | B2 | 6/2017 | Anderson et al. |
| 9,701,709 | B2 | 7/2017 | Anderson et al. |
| 9,757,359 | B2 | 9/2017 | Sporn et al. |
| 9,796,668 | B2 | 10/2017 | Anderson et al. |
| 9,856,286 | B2 | 1/2018 | Sheikh et al. |
| 9,884,809 | B2 | 2/2018 | Anderson et al. |
| 9,889,143 | B2 | 2/2018 | Jiang et al. |
| 10,093,614 | B2 | 10/2018 | Anderson et al. |
| 10,105,372 | B2 | 10/2018 | Meyer et al. |
| 10,398,711 | B2 | 9/2019 | Jiang et al. |
| 10,501,489 | B2 | 12/2019 | Bender et al. |
| 10,556,858 | B2 | 2/2020 | Anderson et al. |
| 10,898,499 | B2 | 1/2021 | Jiang et al. |
| 10,953,020 | B2 | 3/2021 | Meyer et al. |
| 11,078,230 | B2 | 8/2021 | Anderson et al. |
| 11,091,430 | B2 | 8/2021 | Anderson et al. |
| 11,117,927 | B2 | 9/2021 | Sheikh et al. |
| 11,192,852 | B2 | 12/2021 | Anderson et al. |
| 11,292,781 | B2 | 4/2022 | Jiang et al. |
| 2002/0042535 | A1 | 4/2002 | Gribble et al. |
| 2003/0119732 | A1 | 6/2003 | Konopleva et al. |
| 2003/0232786 | A1 | 12/2003 | Honda et al. |
| 2003/0236303 | A1 | 12/2003 | Gribble et al. |
| 2004/0002463 | A1 | 1/2004 | Honda et al. |
| 2004/0097436 | A1 | 5/2004 | Krasutsky et al. |
| 2005/0208151 | A1 | 9/2005 | Hurez et al. |
| 2005/0288363 | A1 | 12/2005 | Gribble et al. |
| 2006/0258752 | A1 | 11/2006 | Vander Jagt et al. |
| 2007/0155742 | A1 | 7/2007 | Honda et al. |
| 2007/0232577 | A1 | 10/2007 | Xu et al. |
| 2007/0244081 | A1 | 10/2007 | Krasutsky et al. |
| 2007/0249561 | A1 | 10/2007 | Taylor |
| 2007/0259839 | A1 | 11/2007 | Krasutsky et al. |
| 2007/0259842 | A1 | 11/2007 | Krasutsky et al. |
| 2008/0220057 | A1 | 9/2008 | Gribble et al. |
| 2008/0233195 | A1 | 9/2008 | Sporn et al. |
| 2008/0261985 | A1 | 10/2008 | Honda et al. |
| 2009/0048204 | A1 | 2/2009 | Walling et al. |
| 2009/0048205 | A1 | 2/2009 | Meyer et al. |
| 2009/0060873 | A1 | 3/2009 | Sporn et al. |
| 2009/0093447 | A1 | 4/2009 | Konopleva et al. |
| 2009/0326063 | A1 | 12/2009 | Sporn et al. |
| 2010/0041904 | A1 | 2/2010 | Jiang et al. |
| 2010/0048887 | A1 | 2/2010 | Anderson et al. |
| 2010/0048892 | A1 | 2/2010 | Anderson et al. |
| 2010/0048911 | A1 | 2/2010 | Jiang et al. |
| 2010/0056777 | A1 | 3/2010 | Anderson et al. |
| 2010/0261930 | A1 | 10/2010 | Honda et al. |
| 2011/0009363 | A1 | 1/2011 | Honda et al. |
| 2011/0196007 | A1 | 8/2011 | Honda et al. |
| 2011/0245206 | A1 | 10/2011 | Jiang et al. |
| 2011/0245233 | A1 | 10/2011 | Anderson et al. |
| 2011/0281955 | A1 | 11/2011 | Meyer et al. |
| 2012/0022156 | A1 | 1/2012 | Zhang et al. |
| 2012/0071684 | A1 | 3/2012 | Walling et al. |
| 2012/0196880 | A1 | 8/2012 | Anderson et al. |
| 2012/0214814 | A1 | 8/2012 | Anderson et al. |
| 2012/0220652 | A1 | 8/2012 | Sporn et al. |
| 2012/0238767 | A1 | 9/2012 | Jiang et al. |
| 2012/0245374 | A1 | 9/2012 | Anderson et al. |
| 2012/0252776 | A1 | 10/2012 | Anderson et al. |
| 2012/0283450 | A1 | 11/2012 | Anderson et al. |
| 2012/0330050 | A1 | 12/2012 | Walling et al. |
| 2013/0237721 | A1 | 9/2013 | Gribble et al. |
| 2013/0303607 | A1 | 11/2013 | Gribble et al. |
| 2013/0317007 | A1 | 11/2013 | Anderson et al. |
| 2013/0324599 | A1 | 12/2013 | Anderson et al. |
| 2013/0345276 | A1 | 12/2013 | Sporn et al. |
| 2014/0051739 | A1 | 2/2014 | Anderson et al. |
| 2014/0066408 | A1 | 3/2014 | Jiang et al. |
| 2014/0073700 | A1 | 3/2014 | Wagner et al. |
| 2014/0088163 | A1 | 3/2014 | Jiang et al. |
| 2014/0088188 | A1 | 3/2014 | Jiang et al. |
| 2014/0100227 | A1 | 4/2014 | Bender et al. |
| 2014/0179928 | A1 | 6/2014 | Anderson et al. |
| 2014/0275618 | A1 | 9/2014 | Gribble et al. |
| 2014/0323579 | A1 | 10/2014 | Sheikh et al. |
| 2015/0080465 | A1 | 3/2015 | Chin et al. |
| 2015/0148384 | A1 | 5/2015 | Anderson et al. |
| 2015/0152071 | A1 | 6/2015 | Jiang et al. |
| 2015/0259377 | A1 | 9/2015 | Anderson et al. |
| 2015/0376121 | A1 | 12/2015 | Anderson et al. |
| 2016/0130220 | A1 | 5/2016 | Anderson et al. |
| 2016/0145200 | A1 | 5/2016 | Anderson et al. |
| 2017/0165278 | A1 | 6/2017 | Jiang et al. |
| 2017/0260227 | A1 | 9/2017 | Bender et al. |
| 2018/0002277 | A1 | 1/2018 | Anderson et al. |

(56) References Cited

U.S. PATENT DOCUMENTS

| | | | |
|---|---|---|---|
| 2018/0009839 | A1 | 1/2018 | Anderson et al. |
| 2018/0161311 | A1 | 6/2018 | Sporn et al. |
| 2018/0235981 | A1 | 8/2018 | Jiang et al. |
| 2018/0237383 | A1 | 8/2018 | Anderson et al. |
| 2018/0265455 | A1 | 9/2018 | Anderson et al. |
| 2019/0076443 | A1 | 3/2019 | Meyer et al. |
| 2019/0091194 | A1 | 3/2019 | Chin et al. |
| 2019/0119202 | A1 | 4/2019 | Anderson et al. |
| 2019/0153022 | A1 | 5/2019 | Visnick et al. |
| 2019/0350941 | A1 | 11/2019 | Meyer |
| 2020/0062800 | A1 | 2/2020 | Sheikh et al. |
| 2020/0129530 | A1 | 4/2020 | Jiang et al. |
| 2020/0131148 | A1 | 4/2020 | Jiang et al. |
| 2020/0207706 | A1 | 7/2020 | Anderson et al. |
| 2020/0239410 | A1 | 7/2020 | Anderson et al. |
| 2021/0040142 | A1 | 2/2021 | Jiang et al. |
| 2021/0137947 | A1 | 5/2021 | Jiang et al. |
| 2021/0161914 | A1 | 6/2021 | Meyer |
| 2021/0355156 | A1 | 11/2021 | Anderson et al. |
| 2022/0073559 | A1 | 3/2022 | Sheikh et al. |
| 2022/0135534 | A1 | 5/2022 | Jiang et al. |

FOREIGN PATENT DOCUMENTS

| | | |
|---|---|---|
| WO | WO 1999/065478 | 12/1999 |
| WO | WO 2000/073253 | 12/2000 |
| WO | WO 2002/003996 | 1/2002 |
| WO | WO 2002/026761 | 4/2002 |
| WO | WO 2002/026762 | 4/2002 |
| WO | WO 2002/047611 | 6/2002 |
| WO | WO 2003/059339 | 7/2003 |
| WO | WO 2003/062260 | 7/2003 |
| WO | WO 2004/064723 | 8/2004 |
| WO | WO 2005/042002 | 5/2005 |
| WO | WO 2005/046732 | 5/2005 |
| WO | WO 2006/029221 | 3/2006 |
| WO | WO 2007/005879 | 1/2007 |
| WO | WO 2007/112043 | 10/2007 |
| WO | WO 2007/127791 | 11/2007 |
| WO | WO 2008/000068 | 1/2008 |
| WO | WO 2008/000070 | 1/2008 |
| WO | WO 2008/016095 | 2/2008 |
| WO | WO 2008/064132 | 5/2008 |
| WO | WO 2008/064133 | 5/2008 |
| WO | WO 2008/097596 | 8/2008 |
| WO | WO 2008/111497 | 9/2008 |
| WO | WO 2008/136838 | 11/2008 |
| WO | WO 2009/023232 | 2/2009 |
| WO | WO 2009/023845 | 2/2009 |
| WO | WO 2009/058849 | 5/2009 |
| WO | WO 2009/089545 | 7/2009 |
| WO | WO 2009/129546 | 10/2009 |
| WO | WO 2009/129548 | 10/2009 |
| WO | WO 2009/129545 | 11/2009 |
| WO | WO 2009/146216 | 12/2009 |
| WO | WO 2009/146218 | 12/2009 |
| WO | WO 2010/011782 | 1/2010 |
| WO | WO 2010/053817 | 5/2010 |
| WO | WO 2010/093944 | 8/2010 |
| WO | WO 2011/130302 | 10/2011 |
| WO | WO 2012/083306 | 6/2012 |
| WO | WO 2012/096718 | 7/2012 |
| WO | WO 2012/106190 | 8/2012 |
| WO | WO 2012/125488 | 9/2012 |
| WO | WO 2013/163344 | 10/2013 |
| WO | WO 2013/169740 | 11/2013 |
| WO | WO 2013/188818 | 12/2013 |
| WO | WO 2014/040052 | 3/2014 |
| WO | WO 2014/040056 | 3/2014 |
| WO | WO 2014/040060 | 3/2014 |
| WO | WO 2014/040073 | 3/2014 |
| WO | WO 2014/176415 | 10/2014 |
| WO | WO 2015/027206 | 2/2015 |
| WO | WO 2016/033132 | 3/2016 |
| WO | WO 2017/053868 | 3/2017 |
| WO | WO 2018/089539 | 5/2018 |
| WO | WO 2018/111315 | 6/2018 |
| WO | WO 2020/068689 | 4/2020 |
| WO | WO 2021/016191 | 1/2021 |
| WO | WO 2021/104391 | 6/2021 |
| WO | WO 2021/127480 | 6/2021 |
| WO | WO 2021/231208 | 11/2021 |

OTHER PUBLICATIONS

D. Hanahan, R. A. Weinberg, The Hallmarks of Cancer, Cell, 2000, 100, 57-70 (Year: 2000).*

K. R. McGovern-Gooch, Synthetic triterpenoid inhibition of human ghrelin o-acyltransferase: the involvement of a functionally required cysteine provides mechanistic insight into ghrelin acylation, Biochemistry 2017, 56, 919-931 (Year: 2017).*

L. S. Rallidis et al. Causes, Angiographic characteristics, and Management of Premature Myocardial Infarction, 2022, 79, 24, 2431-2449. (Year: 2022).*

R. C. Rowe et al. Handbook of Pharmaceutical Excipients Sixth Edition, Pharmaceutical Press and American Pharmacists Association, 2009 (Year: 2009).*

Ambeed—Omaveloxolone product page. (Year: 2026).*

Ahmad et al., "Combining the FLT3 inhibitor PKC412 and the triterpenoid CDDO-Me synergistically induces apoptosis in acute myeloid leukemia with the internal tandem duplication mutation," *Mol. Cancer Res.* 8(7):986-993, 2010.

Ahmad et al., "Triterpenoid CDDO-Me blocks the NF-κB pathway by direct inhibition of IKKbeta on Cys-179," *J. Biol. Chem.*, 281:35764-35769, 2006.

Ahmad et al., "Triterpenoid CDDO-methyl ester inhibits the Janus-activated kinase-1 (JAK1) signal transducer and activator of transcription-3 (STAT3) pathway by direct inhibition of JAK1 and STAT3," *Cancer Res.*, 68 (8): 2920-2926, 2008.

Albini and Sporn, "Opinion: the tumour microenvironment as a target for chemoprevention," Nature Reviews Cancer, 7: 13-147, 2007.

Ames et al., "The Triterpenoid CDDO-Me Promotes Hematopoietic Progenitor Expansion and Myelopoiesis in Mice," Biol. Blood Marrow Transplant, 18(3):396-405, 2012.

Aminzadeh et al., "The synthetic triterpenoid RTA dh404 (CDDO-dhTFEA) restores endothelial function impaired by reduced Nrf2 activity in chronic kidney disease." Redox. Biol., 1:527-31, 2013.

Aminzadeh et al., "The synthetic triterpenoid RTA dh404 (CDDO-dhTFEA) restores Nrf2 activity and attenuates oxidative stress, inflammation, and fibrosis in rats with chronic kidney disease," Xenobiotica, 44(6):570-578, 2014.

Atilano-Roque et al., "Bardoxolone methyl modulates efflux transporter and detoxifying enzyme expression in cisplatin-induced kidney cell injury," Toxicology Lett., 259:52-59, 2016.

Auletta et al., "The synthetic triterpenoid, CDDO-Me, modulates the proinflammatory response to in vivo lipopolysaccharide challenge," J. Interferon Cytokine Res., 30(7):497-508, 2010.

Ball et al., "CDDO-Me redirects activation of breast tumor associated macrophages," PLoS One, 11(2):e0149600/1-e0149600/18, 2016.

Ball, "CDDO-Me Redirects Activation of Tumor Associated Macrophages and Attenuates Immunosuppression in the Breast Tumor Microenvironment," Ph.D. Thesis, Dartmouth College, 2017.

Bensasson et al., "Potency ranking of triterpenoids as inducers of a cytoprotective enzyme and as inhibitors of a cellular inflammatory response via their electron affinity and their electrophilicity index," Chem. Biol. Interact., 186(2):118-126, 2010.

Bore et al., "The anti-inflammatory triterpenoid methyl 2-cyano-3, 12-dioxoolean 1,9(11)-dien-28-oate methanol solvate hydrate," *Acta Crystallorg C.*, 58(Pt 3):o199-o200, 2002.

Borella et al., "Synthesis and anticancer activity of CDDO and CDDO-Me, two derivatives of natural triterpenoids", Molecules, 24(22):4097, 2019.

Brookes et al., "The triterpenoid 2-cyano-3,12-dioxooleana-1,9-dien-28-oic acid and its derivatives elicit human lymphoid cell

(56) References Cited

OTHER PUBLICATIONS apoptosis through a novel pathway involving the unregulated mitochondrial permeability transition pore," *Cancer Res.*, 67:1793-1802, 2007.
Bubb et al., "The NRF2 activator DH404 attenuates Adverse Ventricular Remodeling Post-Myocardial Infarction by Moducation of Redox Signaling, " Free Radical Biology & Medicine, 108:585-594, 2017.
Bynum et al., "Time Course Expression Analysis of 1[2-cyano-3,12-dioxooleana-1,9(11)-dien-28-oyl]imidazole Induction of Cytoprotection in Human Endothelial Cells," Gene Reg. Sys. Biol., 11:1-10, 2017.
Camer et al., "Bardoxolone methyl prevents insulin resistance and the development of hepatic steatosis in mice fed a highfat diet," Mol. Cell. Endrocrinol., 412:36-43, 2015.
Camer et al., "Bardoxolone methyl prevents obesity and hypothalamic dysfunction," Chem. Biol. Interact., 256:178-187, 2016.
Camer et al., "Bardoxolone methyl prevents the development and progression of cardiac and renal pathophysiologies in mice fed a high-fat diet." Chem. Biol. Interact., 243:10-18, 2016.
Cao et al., "Novel synthetic pyridyl analogues of CDDO-Imidazolide are useful new tools in cancer prevention, " Pharm. Research, 100:135-147, 2015.
Chadalapaka et al., "Structure-dependent inhibition of bladder and pancreatic cancer cell growth by 2-substituted glycyrrhetinic and ursolic acid derivatives," Bioorganic & Medicinal Chemistry Letters, 18:2633-2639, 2008.
Chaudhari and Ravanan, "Bardoxolone methyl induces neuritogenesis in Neuro2a cells," Pharmacol. Rep., 70:730-736, 2018.
Chauhan et al., "The bortezomib/proteasome inhibitor PS-341 and triterpenoid CDDO-Im induce synergistic anti-multiple myeloma (MM) activity and overcome bortezomib resistance," *Blood*, 103:3158-3166, 2004.
Chen et al., "The protective effect of CDDO-Me on lipopolysaccharide-induced acute lung injury in mice," Int. Immunopharmacol., 25(1):55-64, 2015.
Chertow et al., "Effects of bardoxolone methyl on body weight, waist circumference and glycemic control in obese patients with type 2 diabetes mellitus and stage 4 chronic kidney disease", J. Diabetes Complications, 32:1113-1117, 2018.
Chin et al., "Bardoxolone Methyl Improves Kidney function in Patients with Chronic Kidney Disease Stage 4 and Type 2 Diabetes: Post-Hoc Analyses from Bardoxolone Methyl Evaluation in Patients with Chronic Kidney Disease and Type 2 Diabetes Study," Am. J. Nephrol., 47:40-47, 2018.
Chin et al., "Effects of Bardoxolone Methyl on QT Interval in Healthy Volunteers", CardioRenal Med., 9(5):326-333, 2019.
Chintharlapalli et al., "2-Cyano-3,12-dioxoolean-1,9-dien-28-oic acid and related compounds inhibit growth of colon cancer cells through peroxisome proliferator-activated receptor γ-dependent and -independent pathways," *Mol. Pharmacol.*, 68:119-128, 2005.
Couch et al., "2-cyano-3,12-dioxooleana-1,9(11)-diene-28-oic acid disrupts microtubule polymerization: a possible mechanism contributing to apoptosis," *Molecular Pharmacology*, 69 (4): 1158-1165, 2006.
Couch et al., "Studies on the reactivity of CDDO, a promising new chemopreventive and chemotherapeutic agent: implications for a molecular mechanism of action," *Bioorganic and Medicinal Chemistry Letters*, 15 (9): 2215-2219, 2005.
Creelan et al., "Safety, pharmacokinetics, and pharmacodynamics of oral omaveloxolone (RTA 408), a synthetic triterpenoid, in a first-in-human trial of patients with advanced solid tumors", OncoTargets Ther., 10:4239-4250, 2017.
Crowley et al., "Synthetic oleanane triterpenoids enhance blood brain barrier integrity and improve survival in experimental cerebral malaria", Malar. J., 16:463, 2017.
De Zeeuw et al., "Bardoxolone methyl in type 2 diabetes and stage 4 chronic kidney disease," N. Engl. J. Med., 369(26):2492-2503, 2013.
Deeb et al., "CDDO-Me: a novel synthetic triterpenoid for the treatment of pancreatic cancer," Cancers, 2:1779-1793, 2010.
Deeb et al., "CDDO-Me inhibits proliferation, induces apoptosis, down-regulates Akt, mTOR, NF-κB and NF-κB-regulated antiapoptotic and proangiogenic proteins in TRAMP prostate cancer cells," J. Experimental Therapeutics and Oncology, 7:31-39, 2007.
Deeb et al., "Inhibition of cell proliferation and induction of apoptosis by CDDO-Me in pancreatic cancer cells is ROS-dependent," J. Exp. Ther. Oncol., 10(1):51-64, 2012.
Deeb et al., "Inhibition of cell proliferation and induction of apoptosis by oleanane triterpenoid (CDDO-Me) in pancreatic cancer cells is associated with the suppression of hTERT gene expression and its telomerase activity," Biochem. Biophys. Res. Comm., 422(4):561-567, 2012.
Deeb et al., "Oleanane triterpenoid CDDO-Me inhibits growth and induces apoptosis in prostate cancer cells by independently targeting pro-survival Akt and mTOR," Prostate, 69(8), 2009.
Deeb et al., "Oleanane triterpenoid CDDO-Me inhibits growth and induces apoptosis in prostate cancer cells through a ROS-dependent mechanism," Biochem. Pharmacol. 79(3):350-360, 2010.
Dezube et al., "Interim results of a phase I trial with a novel orally administered synthetic triterpenoid RTA 402 (CDDO-Me) in patients with solid tumors and lymphoid malignancies," *J. Clin. Oncol.*, 2007 ASCO Annual Meeting Proceedings, 25(18S):14101, 2007.
Ding et al., "The synthetic triterpenoid, RTA 405, increases the glomerular filtration rate and reduces angiotensin II-induced contraction of glomerular mesangial cells," Kidney Int., 83:845-854, 2013.
Dinkova-Kostova et al., "Direct evidence that sulfhydryl groups of Keap1 are the sensors regulating induction of phase 2 enzymes that protect against carcinogens and oxidants," *Proc. Natl. Acad. Sci.*, 99(18): 11908-11913, 2002.
Dinkova-Kostova et al., "Extremely potent triterpenoid inducers of the phase 2 response: correlations of protection against oxidant and inflammatory stress," *Proc. Natl. Acad. Sci.*, 102(12): 4584-4589, 2005.
Duan et al., "CDDO-Me, a synthetic triterpenoid, inhibits expression of IL-6 and Stat3 phosphorylation in multi-drug resistant ovarian cancer cells," Cancer Chemother. Pharmacol., 63(4):681-689, 2009.
Dulubova et al., "RTA 1701 is an orally-bioavailable, potent, and selective RORγt inhibitor that suppresses Th17 differentiation in vitro and is efficacious in mouse models of autoimmune disease," *J. Immunol.*, 200 (1 Suppl.):121.14, 2018. (Abstract only).
Elliot et al., "The triterpenoid CDDO inhibits expression of matrix metalloproteinase-1, matrix metalloproteinase-13 and Bcl-3 in primary human chondrocytes," *Arthritis Res. Ther.*, 5:R285-R291, 2003.
Elsawa et al., "CDDO-imidazole mediated inhibition of malignant cell growth in Waldenstroem macroglobulinemia, " Leukemia Res., 32(12):1985-1902, 2008.
Elsawa et al., "Preferential Inhibition of Malignant Cell Growth by CDDO in Waldenstrom Macroglobulinemia," *Blood*, 108(11):2528, 2006.
Eskiocak et al., "CDDO-Me protects against space radiation-induced transformation of human colon epithelial cells," Radiat. Res., 174(1): 27-36, 2010.
Favaloro et al., "Design and synthesis of tricyclic compounds with enone functionalities in rings A and C: a novel class of highly active inhibitors of nitric oxide production in mouse macrophages," J. Med. Chem., 45:4801-4805, 2002.
Fu et al., "Design, Synthesis, and Biological Activity of Second-Generation Synthetic Oleanane Triterpenoids," Org. & Biomol. Chem., 15:6001-6005, 2017.
Gao et al., "CDDO-Me inhibits tumor growth and prevents recurrence of pancreatic ductal adenocarcinoma," Int. J. Oncol. 47(6):2100-2106, 2015.
Gao et al., "Immunomodulatory activity of synthetic triterpenoids: inhibition of lymphocyte proliferation, cell-mediated cytotoxity, and cytokine gene expression through suppression of NF-κB," *Immunopharacol. Immunotoxicol.*, 30(3):581-600, 2008.
Gao et al., "Synthetic triterpenoids inhibit growth and induce apoptosis in human glioblastoma and neuroblastoma cells through

(56) References Cited

OTHER PUBLICATIONS inhibition of prosurvival Akt, NF-κB and Notch1 signaling," *J. of Neuro-oncology*, 84 (2):147-157, 2007.
Gao et al., "SZC017, a novel oleanolic acid derivative, induces apoptosis and autophagy in human breast cancer cells," Apoptosis, 20(12):1636-1650, 2015.
Getachew et al., "The Synthetic Triterpenoid RTA 405 (CDDO-EA) Halts Progression of Liver Fibrosis and Reduces Hepatocellular Carcinoma Size Resulting in Increased Survival in an Experimental Model of Chronic Liver Injury," Toxicological Studies, 149(1):111-20, 2016.
Goldman et al., "The Triterpenoid RTA 408 is a Robust Mitigator of Hematopoietic Acute Radiation Syndrome in Mice", Radiat. Res., 183(3):338-344, 2015.
Graber et al., "Synthetic Triterpenoid CDDO Derivatives Modulate Cytoprotective or Immunological Properties in Astrocytes, Neurons, and Microglia", J. Neuroimmune Pharmacol., 6(1):107-120, 2011.
Hail et al., "Evidence supporting a role for calcium in apoptosis induction by the synthetic triterpenoid 2-cyano-3,12-dioxooleana-1,9-dien-28-oic acid (CDDO)," *J. Biol. Chem.*, 279:11179-11187, 2004.
Han et al., "CDDO-Imidazolide inhibits growth and survival of c-Myc-induced mouse B cell and plasma cell neoplasms," *Molecular Cancer*, 5:22, 2006.
Han et al., "RTA-408 Protects Kidney from Ischemia-Reperfusion Injury in Mice via Activating Nrf2 and Downstream GSH Biosynthesis Gene", Oxidat. Med. Cell. Longevity, 2017(7612182):1-15, 2017.
Hisamichi et al., "Role of bardoxolone methyl, a nuclear factor erythroid 2-related factor 2 activator, in aldosterone- and salt-induced renal injury," Hypertens. Res., 41(1):8-17, 2018.
Honda et al. "2-Cyano-3,10-diooleana-1,9(11)-dien-28-oic acid anhydride. A novel and potent anti-inflammatory and cytoprotective agent," Bioorg. Med. Chem. Lett., 20(7):2275-2278, 2010.
Honda et al., "A novel dicyanotriterpenoid, 2-cyano-3,12-dioxooleana-1,9(11)-dien-28-onitrile, active at picomolar concentrations for inhibition of nitric oxide production," *Bioorg. Med. Chem. Lett.*, 12:1027-1030, 2002.
Honda et al., "An efficient synthesis of tricyclic compounds (+)—(4aβ, 8aβ, 10aα)—1,2,3,4,4a,6,7,8,8a,9,1-,10a-Dodecahydro-1,1,4a-Trimethyl-2-Oxophenanthrene-8a-Carboxolic acid, its methyl ester, and (+)-(4aβ,8aβ,10aα)-3,4,4a,6,7,8,8a,9,10,10a-Decahydro-8a, hydroxymethyl-1,1,4a-trimethylphenanthren-2(1H)-one," *Org. Prep. Proced. Int.*, 37(6): 546-550, 2005.
Honda et al., "Design and synthesis of 23, 24-dinoroleanolic acid derivatives, novel triterpenoid-steroid hybrid molecules," *J. Org. Chem.*, 63:4846-4849, 1998.
Honda et al., "Design and synthesis of 2-cyano-3,12-dioxoolean-1,9-dien-28-oic acid, a novel and highly active inhibitor of nitric oxide production in mouse macrophages," *Bioorg Med Chem Lett.*, 8(19):2711-2714, 1998.
Honda et al., "Design, synthesis, and biological evaluation of biotin conjugates of 2-cyano-3,12-dioxooleana-1,9(11)-dien-28-oic acid for the isolation of the protein targets," *J. Med. Chem.*, 47 (20): 4923-4932, 2004.
Honda, et al., "Design, Synthesis, and anti-inflammatory activity both in vitro and in vivo of new betulinic acid analogues having an enone functionality in ring A", Bioorg. Med. Chem. Lett., 16(24):6306-6309. 2006.
Honda et al., "Efficient synthesis of (−)- and (+)-tricyclic compounds with enone functionalities in rings A and C. A novel class of orally active anti-inflammatory and cancer chemopreventive agents," *Org Biomol Chem.*, 1:4384-4391, 2003.
Honda et al., "New enone derivatives of oleanolic acid and ursolic acid as inhibitors of nitric oxide production in mouse macrophages," *Bioorg. Med. Chem. Lett.*, 7:1623-1628, 1997.
Honda et al., "New synthetic oleanane and ursane triterpenoids as inhibitors of nitric oxide production in mouse macrophages," The Fifth Chemical Congress of North America, Cancun, Mexico, Abstract 552 and slides for oral presentation, Nov. 1997.
Honda et al., "Novel synthetic oleanane and ursane triterpenoids with various enone functionalities in ring A as inhibitors of nitric oxide production in mouse macrophages," *J. Med. Chem.*, 43:1866-1877, 2000.
Honda et al., "Novel synthetic oleanane triterpenoids: a series of highly active inhibitors of nitric oxide production in mouse macrophages," *Bioorg Med Chem Lett*, 9(24):3429-3434, 1999.
Honda et al., "Novel tricyclic compounds having acetylene groups at C-8a and cyano enones in rings A and C: highly potent anti-inflammatory and cytoprotective agents," *J. Med. Chem.*, 50:1731-1734, 2007.
Honda et al., "Revision and confirmation of the regiochemistry of isoxazoles derived from methyl oleanonate and lanost-8-en-3-one. Synthesis of a new lanostane triterpenoid with a cyano-enone functionality in ring A," *J. Org. Chem.*, 68:4991-4993, 2003.
Honda et al., "Synthesis of (±)-3,3-ethylenedioxy-14a-hydroxy-5-picrasene-11,16-dione, a 14aH-picrasane derivative," *Chem. Lett.*, 299-302, 1981.
Honda et al., "Synthesis of a novel dicyano abietane analogue: a potential 17nflammatory17tory agent," *J. Org. Chem.*, 71:3314-3316, 2006.
Honda et al., "Synthetic oleanane and ursane triterpenoids with modified rings A and C: A series of highly active inhibitors of nitric oxide production in mouse macrophages," *J. Med. Chem.*, 43:4233-4246, 2000.
Honda et al., "Tricyclic Compounds Containing Nonenolizable Cyano Enones. A Novel Class of Highly Potent Anti-Inflammatory and Cytoprotective Agents," J. Med. Chem., 54(6):1762-1778, 2011.
Hong et al., "A Phase I First-in-Human Trial of Bardoxolone Methyl in Patients with Advanced Solid Tumors and Lymphomas," Clinical Cancer Research 18:3396-3406, 2012.
Huang et al., "Novel Derivative of Bardoxolone Methyl Improves Safety for the Treatment of Diabetic Nephropathy", J. Med. Chem., 60(21):8847-8857, 2017.
Hughes et al., "The Synthetic Triterpenoid CDDO-Im Inhibits Fatty Acid Synthase Expression and Has Antiproliferative and Proapoptotic Effects in Human Liposarcoma Cells," Cancer Investigation, 26:118-127, 2008.
Hybertson et al., "Oxidative Stress in health and disease: The therapeutic potential of Nrf2 activation," Molecular Aspects of Medicine, 32:234-246, 2011.
Hyer et al., "Apoptotic activity and mechanism of 2-cyano-3,12-dioxoolean-1,9-dien-28-oic acid and related synthetic triterpenoids in prostate cancer," Cancer Res., 68:2927-2933, 2008.
Hyer et al., "Synthetic triterpenoids cooperate with tumor necrosis factor-related apoptosis-inducing ligand to induce apoptosis of breast cancer cells," *Cancer Res.*, 65:4799-4808, 2005.
Ichikawa et al., "Dihydro-CDDO-Trifluoroethyl Amide (dh404), a Novel Nrf2 Activator, Suppresses Oxidative Stress in Cardiomyocytes", PloS One, 4(12):e8391, 2009.
Ikeda et al., "Induction of redox imbalance and apoptosis in multiple myeloma cells by the novel triterpenoid 2-cyano-3,12-dioxoolean-1,9-dien-28-oic acid," *Mol. Cancer Ther.*, 3:39-45, 2004.
Ikeda et al., "The novel triterpenoid CDDO and its derivatives induce apoptosis by disruption of intracellular redox balance," *Cancer Res.*, 63:5551-5558, 2003.
Ikeda et al., "Triterpenoid CDDO-Im downregulates PML/RAR αexpression in acute promyelocytic leukemia cell," *Cell Death and Differentiation*, 12 (5): 523-531, 2005.
Inoue et al., "CDDO induces apoptosis via the intrinsic pathway in lymphoid cells," *Leukemia*, 18 (5): 948-952, 2004.
International Preliminary Report on Patentability issued in corresponding PCT Application No. PCT/US2020/066073, mailed on Jun. 30, 2022.
International Search Report and Written Opinion issued in corresponding PCT Application No. PCT/US2020/066073, mailed on Mar. 25, 2021.
Ito and Nangaku, "Increased albuminuria in bardoxolone methyl-treated type 2 diabetes patients: mere reflection of eGFR improvement? ", Kidney Int., 96(4):823-825, 2019.

(56) References Cited

OTHER PUBLICATIONS

Ito et al., "Involvement of caspase-8 in the induction of osteosarcoma cell apoptosis by the novel triterpenoid CDDO," 47th Annual Meeting, Orthopaedic Research Society, Feb. 25-28, 2001, San Francisco, California, p. 0863, Poster Session, 2001.

Ito et al., "The novel triterpenoid 2-cyano-3, 12-dioxoolean-1,9-dien-28-oic acid induces apoptosis of human myeloid leukemia cells by a caspase-8-dependent mechanism," *Cell Growth & Differentiation*, 11(5):261-267, 2000.

Ito et al., "The novel triterpenoid CDDO induces apoptosis and differentiation of human osteosarcoma cells by a caspase-8 dependent mechanism," *Mol. Pharmacol.*, 59:1094-1099, 2001.

Ji et al., "The synthetic triterpenoid CDDO-imidazolide induces monocytic differentiation by activating the Smad and ERK signaling pathways in HL60 leukemia cells," *Molecular Cancer Therapeutics*, 5 (6): 1452-1458, 2006.

Jin et al., "Bardoxolone Methyl and a Related Triterpenoid Downregulates cMyc Expression in Leukemia Cells," Molecular Pharmacology, 91(5):438-450, 2017.

Johansen et al., "Pharmacology and preclinical pharmacokinetics of the triterpenoid CDDO methyl ester," *Proc. Amer. Assoc. Cancer Res.*, 44:1728, 2003.

Jutooru et al., "Methyl 2-cyano-3,12-dioxooleana-1,9-dien-28-oate decreases specificity protein transcription factors and inhibits pancreatic tumor growth: role of microRNA-27a," Mol. Pharmacol., 78(2):226-236, 2010.

Kamel et al., "In Vitro Biotransformation of the Nrf2 Activator Bardoxolone: Formation of an Epoxide Metabolite That Undergoes Two Novel Glutathione-Mediated Metabolic Pathways: Epoxide Reduction and Oxidative Elimination of Nitrile Moiety", Chem. Res. Toxicol., 2019, Ahead of Print.

Kang et al., "Design and synthesis of new hybrids from 2-cyano-3,12-dioxooleana- 9-dien-28-oic acid and O2-(2,4-dinitrophenyl) diazeniumdiolate for intervention of drug-resistant lung cancer," Eur. J. Med. Chem., 149:269-280, 2018.

Kim et al., "CDDO-Me attenuates vasogenic edema and astroglial death by regulating NF-κB p65 phosphorylations and Nrf2 expression following status epilepticus", Int. J. Mol. Sci., 20(19):4862, 2019.

Kim et al., "CDDO-Me selectively attenuates CA1 neuronal death induced by status epilepticus via facilitating mitochondrial fission independent of LONP1", Cells, 8(8):833, 2019.

Kim et al., "CDDO-methyl ester delays breast cancer development in Brca1-mutated mice," Cancer Prev. Res., 5(1):89-97, 2012.

Kim et al., "Identification of a novel synthetic triterpenoid, methyl-2-cyano-3,12-dioxooleana-1,9-dien-28-oate, that potently induces caspase-mediated apoptosis in human lung cancer cells," *Molecular Cancer Therapeutics*, 1:177-184, 2002.

Kocak et al., "Effects of captopril, telmisartan and bardoxolone methyl (CDDO-Me) in ischemia-reperfusion-induced acute kidney injury in rats: an experimental comparative study," Clin. Exp. Pharmacol. Physiol., 43(2):230-241, 2016.

Kong et al., "Synthetic triterpenoids have cytotoxicity in pediatric acute lmphoblastic leukemia cell lines but cytotoxicity is independent of induced ceramide increase in MOLT-4 cells," Leukemia, 22(6): 1258-1262, 2008.

Konopleva et al., "Activation of nuclear transcription factor PPARγ by the novel triterpenoid CDDO as targeted therapy in breast cancer," 2002 Keystone Symposium, Abstract No. 539, 2002.

Konopleva et al., "Mechanisms and Activity of PPARγ-Active Triterpenoids CDDO and CDDO-Me in Leukemias," *Blood*, 106:2460, 2005.

Konopleva et al., "Novel synthetic triterpenoid CDDO-Me: potent antiproliferative, proapoptotic and differentiating agent in AML," *Blood*, 96(11), Part 1: 121A, abstract # 522, 2000.

Konopleva et al., "Novel synthetic triterpenoid, CDDO, and its methyl ester: Potent antiproliferative, proapoptotic and differentiating agents in AML," *Blood*, 94(Suppl 1):479a, Abstract #2140, 1999.

Konopleva et al., "Novel triterpenoid CDDO-Me is a potent inducer of apoptosis and differentiation in acute myelogenous leukemia," *Blood*, 99(1):326-335, 2002.

Konopleva et al., "Peroxisome proliferator-activated receptor vand retinoid X receptor ligands are potent inducers of differentiation and apoptosis in leukemias," *Mol. Cancer Ther.*, 3:1249-1262, 2004.

Konopleva et al., "PPARγ Ligand CDDO Induces Apoptosis in Leukemias Via Multiple Apoptosis Pathways," Abstracts of the 44th Annual Meeting of the American Society of Hematology, Abstract No. 2209, 2002.

Konopleva et al., "PPARγ Ligands Are Potent Inducers of Apoptosis in Leukemias and Lymphomas," American Society of Hematology 43rd Annual Meeting and Exposition, Abstract No. 501, 2001.

Konopleva et al., "PPARγ Nuclear Receptor as a Novel Molecular Target in Leukemia Therapy," *Proc. Amer. Assoc. Cancer Res.*, 43:4730, 2002.

Konopleva et al., "PPARγ nuclear receptor as a novel therapeutic target in AML," Blood, 96(11):460a, Abstract #1982, 2000.

Konopleva et al., "PPARγ nuclear receptor as a novel therapeutic target in AML," Proc. Of the AACR, 42, Abstract #4458, 2001.

Konopleva et al., "Suppression of ERK Activation is Required for Triterpenoid Methyl-CDDO-Induced Apoptosis in AML," *Blood*, 102(11):1404, 2003.

Konopleva et al., "Synthetic triterpenoid 2-cyano-3,12-dioxooleana-1,9-dien-28-oic acid induces growth arrest in HER2-overexpressing breast cancer cells," *Mol. Cancer Ther.*, 5:317-328, 2006.

Konopleva et al., "Synthetic triterpenoid CDDO as a novel therapy for resistant breast cancer," *Proc. Amer. Assoc. Cancer Res.*, 44:2726, 2003.

Konopleva et al., "The novel triterpenoid CDDO-Me suppresses MAPK pathways and promotes p38 activation in acute myeloid leukemia cells," *Leukemia*, 19:1350-1354, 2005.

Konopleva et al., "The synthetic triterpenoid 2-cyano-3,12-dioxooleana-1,9-dien-28-oic acid induces caspase-dependent and -independent apoptosis in acute myelogenous leukemia," *Cancer Res.*, 64:7927-7935, 2004.

Konopleva et al., "Triterpenoid methyl-CDDO s a potent inducer of apoptosis in CD34+ AML progenitor cells via activation of SAPK pathways and inhibition of MAPK cascades," Blood, 104:2533, 2004.

Koschmieder et al. "CDDO induces granulocytic differentiation of myeloid leukemic blasts through translational up-regulation of p42 CCAAT enhancer-binding protein alpha," *Blood*, 110 (10): 3695-3705, 2007.

Kress et al., "Triterpenoids display single agent activity in a mouse model of CLL/SBL," Blood, 108(11):2530, 2006.

Kress et al., "Triterpenoids display single agent anti-tumor activity in a transgenic mouse model of chronic lymphocytic leukemia and small B cell lymphoma," PLOS ONE, 6(e559):1-11, 2007.

Kurinna et al., "The novel triterpenoid CDDO-Me promotes apoptosis in Gleevec-resistant chronic myeloid leukemia cells by caspase-independent mechanisms," *Proc. Amer. Assoc. Cancer Res.*, 46:2240, 2005.

Lapillonne et al., "Activation of peroxisome proliferator-activated receptor γ by a novel synthetic triterpenoid 2-cyano-3,12-dioxooleana-1,9-dien-28-oic acid induces growth arrest and apoptosis in breast cancer cells," *Cancer Res.*, 63:5926-5939, 2003.

Leal et al., "The triterpenoid CDDO-imidazolide reduces immune cell infiltration and cytokine secretion in the KrasG12D;Pdx1-Cre (KC) mouse model of pancreatic cancer," Carcinogenesis, 37(12):1170-1179, 2016.

Li et al., "The triterpenoid CDDO-Me delays murine acute graft-versus-host disease with the preservation of graft-versus-tumor effects after allogeneic bone marrow transplantation," Bio. Blood Marrow Transplant, 16(6):739-750, 2010.

Liby and Sporn, "Synthetic Oleanane Triterpenoids: Multifunctional drugs with a broad range of applications for prevention and treatment of chronic disease," Pharmacol. Rev., 64(4):972-1003, 2012.

Liby et al., "A novel acetylenic tricyclic bis-(cyano enone) potently induces phase 2 cytoprotective pathways and blocks liver carcinogenesis induced by aflatoxin," *Cancer Res.*, 68:6727-6733, 2008.

(56) References Cited

OTHER PUBLICATIONS

Liby et al., "Novel semisynthetic analogues of betulinic acid with diverse cytoprotective, antiproliferative, and proapoptotic activities," *Mol. Cancer. Ther.*, 6(7): 2113-2119, 2007.
Liby et al., "Prevention and treatment of experimental estrogen receptor-negative mammary carcinogenesis by the synthetic triterpenoid CDDO-methyl ester and the Rexinoid LG100268," Clin. Cancer Res. 14(14):4556-4563, 2008.
Liby et al., "Synthetic triterpenoids prolong survival in a transgenic mouse model of pancreatic cancer," Cancer Prev. Res., 3(11):1427-1434, 2010.
Liby et al., "The rexinoid LG100268 and the synthetic triterpenoid CDDO-methyl amide are more potent than erlotinib for prevention of mouse lung carcinogenesis," *Mol. Cancer Ther.*, 7:1251-1257, 2008.
Liby et al., "The synthetic triterpenoid CDDO-Imidazolide suppresses STAT phosphorylation and induces apoptosis in myeloma and lung cancer cells," *Clinical Cancer Research*, 12 (14 Part 1): 4288-4293, 2006.
Liby et al., "The synthetic triterpenoids CDDO-Methyl ester and CDDO-ethyl amide prevent lung cancer induced by vinyl carbamate in A/J mice," *Cancer Research*, 67 (6): 1-7, 2007.
Liby et al., "The synthetic triterpenoids, CDDO and CDDO-imidazolide, are potent inducers of heme oxygenase-1 and Nrf2/ARE signaling," *Cancer Res.*, 65:4789-4798, 2005.
Liby et al., "Triterpenoids and rexinoids as multifunctional agents for the prevention and treatment of cancer," *Nat. Rev. Cancer*, 7 (5): 357-369, 2007.
Liby et al. "Triterpenoids CDDO-methyl ester or CDDO-ethyl amide and rexinoids LG100268 or NRX194204 for prevention and treatment of lung cancer in mice," Cancer Prev. Res., 2(12):1050-1058, 2009.
Ling et al., "The novel triterpenoid C-28 methyl ester of 2-cyano-3, 12-dioxoolen-1, 9-dien-28-oic acid inhibits metastatic murine breast tumor growth through inactivation of STAT3 signaling," *Cancer Res.*, 67:4210-4218, 2007.
Ling et al., "The novel triterpenoid CDDO-Me inhibits metastatic murine breast tumor through inhibition of Stat3 signaling," 2007 AACR Annual Meeting, Abstract No. 301, 2007.
Ling et al., Correction to "The novel triterpenoid C-28 methyl ester of 2-cyano-3,12-dioxoolen-1,9-dien-28-oic acid inhibits metastatic murine breast tumor growth inactivation of STAT3 signaling," Cancer Res., 68(12): 4958, 2008.
Liu et al., "New lupane-type triterpenoid saponins from leaves of *Oplopanax horridus* (Devil's Club)," Nat Prod Comm., 5(7): 1019-1022, 2010.
Liu et al., "Oleanane triterpenoid CDDO-Me inhibits Akt activity without affecting PDK1 kinase or PP2A phosphatase activity in cancer cells," Biochem. Biophys. Res. Comm., 417(1):570-575, 2012.
Liu et al., "Oleanolic acid reprograms the liver to protect against hepatotoxicants, but is hepatotoxic at high doses", Liver Int., 39:427-439, 2019.
Liu et al., "The novel triterpenoid RTA 408 protects human retinal pigment epithelial cells against $H_2O_2$-induced cell injury via NF-E2-related factor 2 (Nrf2) activation," Redox Biol., 8:98-109, 2016.
Liu et al., "The nrf2 triterpenoid activator, CDDO-imidazolide, protects kidneys from ischemia-reperfusion injury in mice," Kidney International, 85(1):134-141, 2014.
Liu et al., "Telomerase reverse transcriptase (TERT) is a therapeutic target of oleanane triterpenoid CDDO-Me in prostate cancer," Molecules, 17:14795-14809, 2012.
Markov et al., "Soloxolone Methyl Inhibits Influenza Virus Replication and Reduces Virus-Induced Lung Inflamation," ScRep., 7(1):1-15, 2017.
Martinez et al., "Regulation and Function of Proinflammatory TH17 Cells," *Ann. N.Y. Acad. Sci.*, 1143:188-211, 2008.
Marty et al., "RTA 402 (CDDO-Me) increases survival of mice administered high doses of cytotoxic chemotherapy," presented by Reata Pharmaceuticals, Nov. 2005.
Masullo et al., "Oleanane Derivatives for Pharmaceutical Use: A Patent Review (2000-2016)," Expert Opinion on Therapeutic Patents, 2016.
Mathis and Cui, "CDDO and Its Role in Chronic Diseases," Drug Discov. Mother Nat. Adv. Exp. Med. Biol., 929:291-314, 2016.
McCullough et al., "Cardiac and renal function in patients with type 2 diabetes who have chronic kidney disease: potential effects of bardoxolone methyl," Drug Des. Dev. Ther., 6:141-149, 2012.
McGovern-Gooch et al., "Synthetic Triterpenoid Inhibition of Human Ghrelin 0-Acyltransferase: The Involvement of a Functionally Required Cysteine Provides Mechanistic Insight into Ghrelin Acylation," Biochemistry, 56(7):919-931, 2017.
Melichar et al., "Growth-inhibitory effect of a novel synthetic triterpenoid, 2-cyano-3,12-dioxoolean-1,9-dien-28-oic acid, on ovarian carcinoma cell lines not dependent on peroxisome proliferator-activated receptor-γ expression," *Gynecologic Oncology*, 93:149-154, 2004.
Mencherini et al., "Triterpenoid constituents from the roots of the *Paeonia rockii* ssp. Rockii," J Nat Prod., 74(10): 2116-2121, 2011.
Meyer et al., "A Phase 2/3 Study of the Efficacy and Safety of Bardoxolone Methyl in Patients with Alport Syndrome," Neph. Dial. Transplant., 32(suppl. 3):iii480-iii480, 2017.
Minns et al., "A novel triterpenoid induces transforming growth factor beta production by intraepithelial lymphocytes to prevent ileitis," Gastroenterology, 127:119-126, 2004.
Mix et al., "A synthetic triterpenoid selectively inhibits the induction of matrix metalloproteinases 1 and 13 by inflammatory cytokines," Arthritis Rheum., 44:1096-1104, 2001.
Mix et al., "Peroxisome proliferator-activated receptor-γ-independent repression of collagenase gene expression by 2-cyano-3,12-dioxooleana-1,9-dien-28-oic acid and prostaglandin 15-deoxy-delta(12,14) J2: a role for Smad signaling," *Mol. Pharmacol.*, 65(2): 309-318, 2004.
Murphy et al., "Immunomodulatory Effects of the Triterpenoid CDDO after Allogeneic Bone Marrow Transplantation in Mice: Reduction of Acute Graft-Versus-Host Disease Lethality," *Blood*, 106:1316, 2005.
Nagasu et al., "Bardoxolone methyl analog attenuates proteinuria-induced tubular damage by modulating mitochondrial function", FASEB J., 33(11):12253-12263, 2019.
Neymotin et al., "Neuroprotective effect of Nrf2/ARE activators, CDDO ethylamide and CDDO trifluoroethylamide, in a mouse model of amyotropic lateral sclerosis," Free Radical Biol. Med., 51(1):88-96, 2011.
Niikura et al., "The effects of synthetic triterpenoids on superficial zone protein synthesis in articular chondrocytes," Abstract, *Orthopedic Research Society*, San Diego, 2007.
Niikura et al., "The effects of synthetic triterpenoids on szp synthesis in articular chondrocytes," Abstract P197, *Osteoarthritis and Cartilage*, 14(Suppl B):S112-S113, 2006.
Nio et al., "Bardoxolone methyl as a novel potent antiviral agent against hepatitis B and C viruses in human hepatocyte cell culture systems," Antiviral Res., 169:104537, 2019.
Oudiz et al., "Results of Interim Analysis of the Efficacy and Safety of Bardoxolone Methyl in Patients with Pulmonary Arterial Hypertension Associated with Connective Tissue Disease", Am. J. Resp. Crit. Care Med., 195:A6896, 2017.
Pannitteri et al., "Triterpenoids in cardiovascular medicine: Basic biology and clinical applications," Curr. Topics Pharmacol., 19:39-50, 2015.
Pareek et al., "Triterpenoid modulation of IL-17 and Nrf-2 expression ameliorates neuroinflammation and promotes remyelination in autoimmune encephalomyelitis", Sci. Rep., 1:201, 2011.
Pedersen et al., "The triterpenoid CDDO induces apoptosis in refractory CLL B cells," *Blood*, 100:2965-2972, 2002.
Pergola et al., "Bardoxolone Methyl and Kidney Function in CKD with Type 2 Diabetes" N. Engl. J. Med., 365:327-336, 2011.
Pergola et al., "Effect of bardoxolone methyl on kidney function in patients with T2D and stage 3b-4 CKD," Am. J. Nephrol., 33(5):469-476, 2011.
Pergola et al., Supplement to "Bardoxolone methyl and kidney function in CKD with type 2 diabetes," Supplementary Appendix appended, N. Engl. J. Med., 365(4):327-336, 2011.

(56) References Cited

OTHER PUBLICATIONS

Petronelli, et al., "CDDO-Im is a stimulator of megakaryocytic differentiation," Leukemia Research, 35(4):534-544, 2011.
Petronelli et al., "High sensitivity of ovarian cancer cells to the synthetic triterpenoid CDDO-Imidazolide," Cancer Lett., 282(2):214-228, 2009.
Place, "Pre-Clinical Evaluation of the Novel Synthetic Triterpenoid CDDO-Imidazolide," Dissertation, Dartmouth College, May 4, 2005.
Place et al., "The novel synthetic triterpenoid, CDDO-imidazolide, inhibits inflammatory response and tumor growth in vivo," *Clin. Cancer Res.*, 9:2798-2806, 2003.
Probst et al., "RTA 408, a novel synthetic triterpenoid with broad anti-cancer and anti-inflammatory activity, " PLoS One, 10(4):e0122942, 2015.
Qin et al. , "Identification of unique sensitizing targets for anti-inflammatory CDDO-Me in metastatic melanoma by a large-scale synthetic lethal RNAi screening," Pigment Cell Melanoma Res., 26(1):97-112, 2013.
Rabbani et al., "Targeted Nrf2 activation therapy with RTA 408 enhances regenerative capacity of diabetic wounds," Diabetes Res. Clin. Prac., 139:11-23, 2018.
Ray et al., "The novel triterpenoid 2-cyano-3,12-dioxooleana-1,9-dien-28-oic acid (CDDO) induces apoptosis of human diffuse large B-cell lymphoma cells through a peroxisome proliferator-activated receptor γ-independent pathway," *Exp. Hematology*, 34:1201-1210, 2006.
Reddy et al., "The Triterpenoid CDDO-Imidazolide Confers Potent Protection Against Hyperoxic Acute Lung Injury in Mice," American Journal of Respiratory and Critical Care Medicine, 180(9):867-874, 2009.
Refaat et al., "Bardoxolone-methyl inhibits migration and metabolism in MCF7 cells," Free Radic. Res., 51(2):211-221, 2017.
Reisman et al., "Bardoxolone methyl decreases megalin and activates Nrf2 in the kidney," J. Am. Soc. Nephrol., 23(10):1663-1673, 2012.
Reisman, et al., "CDDO-9,11-dihydro-trifluoroethyl amide (CDDO-dhTFEA) induces hepatic cytoprotective genes and increases bile flow in rats," Xenobiotica, 43(7):571-578, 2013.
Reisman et al., "RTA 1701 is an oral RORγt inhibitor that suppresses the IL-17A response in non-human primates," *J. Immunol.*, 200(1 Suppl.):175.22, 2018. (Abstract only).
Reisman et al., "Topical application of RTA 408 lotion activates Nrf2 in human skin and is well-tolerated by healthy human volunteers," BMC Dermatology, 15(10):1-11, 2015.
Reisman et al., "Topical application of the synthetic triterpenoid RTA 408 activates Nrf2 and induces cytoprotective genes in rat skin," Archives of Dermatological Research, 306(5):447-454, 2014.
Reisman et al., "Topical Application of the Synthetic Triterpenoid RTA408 Protects Mice from Radiation-Induced Dermatitis," *Radiat. Res. Soc.*, 2014.
Reisman et al., "Pharmacokinetics and pharmacodynamics of the novel Nrf2 activator omaveloxolone in primates", Drug Des. Dev. Ther., 13:1259-1270, 2019.
Ren and Kinghorn, "Natural Product Triterpenoids and Their Semi-Synthetic Derivatives with Potential Anticancer Activity", Planta Med., 2019.
Riccioni et al., "Resistance of acute myeloid leukemic cells to the triterpenoid CDDO-Imidazolide is associated with low caspase-8 and FADD levels," Leukemia Research, 32:1244-1258, 2008.
Rizk et al., "Effects of Bardoxolone Methyl on Magnesium in Patients with Type 2 Diabetes Mellitus and Chronic Kidney Disease", CardioRenal Med., 9(5):316-325, 2019.
Rojas-Rivera et al., "Antioxidants in kidney diseases: the impact of bardoxolone methyl," Int. J. Nephrol., 321714:11pp, 2012.
Rossing et al., "Effect of bardoxolone methyl on the urine albumin-to-creatinine ratio in patients with type 2 diabetes and stage 4 chronic kidney disease", Kidney Int., 96(4):1030-1036, 2019.
Ruvolo et al., "The novel triterpenoid methyl-CDDO inhibits Bc12 phosphorylation and potently kills U937 cells," *Blood*, 94(10), Suppl. 1, Part 1: 280A, abstract #1251, 1999.
Ryu et al. "Oleanane triterpenoid CDDO-Me induces apoptosis in multidrug resistant osteosarcoma cells through inhibition of Stat3 pathway," BMC Cancer, 10:187, 2010.
Saha et al., "The triterpenoid 2-cyano-3,12-dioxo-oleana-19-dien-28-oic acid methyl ester has potent anti-diabetic effects in diet-induced diabetic mice and Lepr(db/db) mice," J. Biol. Chem, 285(52):40581-40592, 2010.
Samudio et al., "2, cyano-3,12 dioxoolean-1,9 diene-28-imidazolide induces apoptosis in pancreatic cancer via redox-dependent cytoplasmic stress," *Proc. Amer. Assoc. Cancer Res.*, 46: Abstract No. 5899, 2005.
Samudio et al., "2-Cyano-3,12-dioxooleana-1,9-dien-28-imidazolide (CDDO-Im) directly targets mitochondrial glutathione to induce apoptosis in pancreatic cancer," *J. Biol. Chem.*, 280:36273-36282, 2005.
Samudio et al., "A novel mechanism of action of methyl-2-cyano-3,12 dioxoolean-1,9 diene-28-oate (CDDO-Me): Direct permeabilization of the inner mitochondrial membrane to inhibit electron transport and induce apoptosis," *Proc. Am. Assoc. Cancer Res.*, 47, Abstract 4693, 2006.
Samudio et al., "A novel mechanism of action of methyl-2-cyano-3,12 dioxoolean-1,9 diene-28-oate: direct permeabilization of the inner mitochondrial membrane to inhibit electron transport and induce apoptosis," *Mol. Pharmacol.*, 69:1182-1193, 2006.
Samudio et al., "Inhibition of mitochondrial metabolism by methyl-2-cyano-3,12-dioxoolean-1,9-diene-28-oate induces apoptotic or autophagic cell death in chronic myelogenous leukemia cells," Mol. Cancer Ther., 7(5):1130-1139, 2008.
Samudio et al., "The novel triterpenoid CDDO-me potently synergizes with inhibition of bcl-2 function to induce apoptosis in AML via disruption of intracellular redox homeostasis," *Proc. Amer. Assoc. Cancer Res.*, 46: Abstract No. 4955, 2005.
Scholz et al., "Sensitive and specific methods for the determination of CDDO methyl ester in mouse, rat, dog, monkey, and human plasma by LC-tandem mass spectrometry," *Proc. Amer. Assoc. Cancer Res.*, 4: Abstract No. 6321, 2003.
Shanmugam et al., "Oleanolic acid and its synthetic derivatives for the prevention and therapy of cancer: Preclinical and clinical evidence," Cancer Lett., 346(2):206-216, 2014.
Shin et al., "Inhibitory roles of NRF2 and an oleanolic triterpenoid on adipocyte differentiation and obesity," dissertation submitted to John Hopkins University in conformity with the requirements for the degree of Doctor of Philosophy, Mar. 2009.
Shin et al., "Role of Nrf2 in prevention of high-fat diet-induced obesity by synthetic triterpenoid CDDO-imidazolide" *Eur. J. Pharmacol.*, 620(1-3):138-144, 2009.
Shishodia et al., "A synthetic triterpenoid, CDDO-Me, inhibits IκBα kinase and enhances apoptosis induced by TNF and chemotherapeutic agents through down-regulation of expression of nuclear factor κB-regulated gene products in human leukemic cells," *Clin Cancer Research*, 12(6):1828-1838, 2006.
Sogno et al. "Anti-angiogenic activity of a novel class of chemopreventive compounds: oleanic acid terpenoids, " Recent Results Cancer Res., 181:209-212, 2009.
Song et al., "Bardoxolone ameliorates TGF-β1-associated renal fibrosis through Nrf2/Smad7 elevation", Free Rad. Biol. Med., 138:33-42, 2019.
Sporn and Liby, "NRF2 and cancer: the good, the bad and the importance of context", *Nat. Rev. Cancer*, 12(8):564-71, 2012.
Sporn and Roberts, "Peptide growth factors and inflammation, tissue repair, and cancer," *J. Clin. Invest.*, 78:329-332, 1986.
Sporn et al., "New synthetic triterpenoids: potent agents for prevention and treatment of tissue injury caused by inflammatory and oxidative stress," J. Nat. Prod., 74(3):537-545, 2011.
Sporn et al., "Prospects for prevention and treatment of cancer with selective PPARγ modulators (SPARMs)," *Trends in Molecular Medicine*, 7(9):395-400, 2001.
Stack et al., "Triterpenoids CDDO-ethyl amide and CDDO-trifluoroethyl amide improve the behavioral phenotype and brain pathology in a transgenic mouse model of Huntington's disease", Free Radic. Biol. Med., 49:147-158, 2010.

(56) References Cited

OTHER PUBLICATIONS

Stadheim et al., "The novel triterpenoid 2-cyano-3,12-dioxooleana-1,9-dien-28-oic acid (CDDO) potently enhances apoptosis induced by tumor necrosis factor in human leukemia cells," *J. Biol. Chem.*, 277:16448-16455, 2002.
Subba Rao et al., "Chemical modifications of natural triterpenes—glycyrrhetinic and boswellic acids: evaluation of their biological activity," Tetrahedron, 64(51):11541-11548, 2008.
Suh et al., "A novel synthetic oleanane triterpenoid, 2-cyano-3,12-dioxoolean-1,9-dien-28-oic acid (CDDO), induces cell differentiation in human myeloid leukemias," Proceedings of the American Association for Cancer Research Annual Meeting, 40:300, abstract 1988.
Suh et al., "A novel synthetic oleanane triterpenoid, 2-cyano-3,12-dioxoolean-1,9-dien-28-oic acid, with potent differentiating, antiproliferative, and anti-inflammatory activity," *Cancer Res.*, 59(2):336-341, 1999.
Suh et al., "New triterpenoids as cancer preventive and anti-inflammatory agents," Proceedings of the American Association for Cancer Research, Abstract No. 1457, 38:216, 1997.
Suh et al., "Novel triterpenoids suppress inducible nitric oxide synthase (iNOS) and inducible cyclooxygenase (COX-2) in mouse macrophages," *Cancer Res.*, 58:717-723, 1998.
Suh et al., "Novel triterpenoids suppress inducible nitric oxide synthase (iNOS) and inducible cyclooxygenase (COX-2)," Proceedings of the American Association for Cancer Research Annual Meeting, 39: Abstract No. 1821, 1998.
Suh et al., "Synthetic triterpenoids activate a pathway for apoptosis in AML cells involving downregulation of FLIP and sensitization to TRAIL," *Leukemia*, 17:2122-2129, 2003.
Suh et al., "Synthetic triterpenoids enhance transforming growth factor β/Smad signaling," *Cancer Res.*, 63:1371-1376, 2003.
Suh et al., "Triterpenoids CDDO and CDDO-Me Down-Regulate FLIP Expression and Sensitize AML Cells to Trail-Induced Apoptosis," American Society of Hematology 43rd Annual Meeting and Exposition, Abstract No. 498, 2001.
Sultana, "Triterpenes and Triterpenoids Clinically Useful with Multiple Targets in Cancer, Malaria and More Treatment: Focus on Potential Therapeutic Value," Int. J. Biochem. Res., 16(2):1-35, 2017.
Sun et al., "Structure-activity relationships of oleanan- and ursane-type triterpenoids," *Botanical Studies*, 47:339-368, 2006.
Sun et al., "The Synthetic Triterpenoid, CDDO, Suppresses Alloreactive T Cell Responses and Reduces Murine Early Acute Graft-versus-Host Disease Mortality," *Biology of Blood and Marrow Transplantation*, 13 (5): 521-529, 2007.
Sun, "Therapeutic potential of synthetic triterpenoids in neuroblastoma," Cancer Biology & Therapy, 7(5):720-7, 2008.
Sussan et al., "Targeting Nrf2 with the triterpenoid CDDO-Imidazolide atttenuate cigarette smoke-induced emphysema and cardiac dysfunction in mice," Proc. Natl. Acad. Sci. USA, 106:250-255, 2009.
Tabe et al., "Chromatin-Mediated Transcriptional Activation with Novel Peroxisome Proliferator—Activated Receptor gamma(PPARγ) Ligand 2-cyano-1,9-dien-28-oic Acid (CDDO) in Acute Promyelocytic Leukemia Cells," Abstracts of the 44th Annual Meeting of the American Society of Hematology, Abstract 2191, 2002.
Takeuchi et al., "CDODA-Me Decreases Specificity Protein Transcription Factors and Induces Apoptosis in Bladder Cancer Cells Through Induction of Reactive Oxygen Species," Urologic Oncology: Seminars and Original Investigations, 34(8):337.e11-337.e18, 2016.
Tan et al., "A derivative of Bardoxolone methyl, dh404, in an inverse dose-dependent manner, lessens diabetes-associated atherosclerosis and improves diabetic kidney disease," Diabetes, 63:3091-3103, 2014.
Thimmulappa et al., "Nrf2-dependent protection from LPS induced inflammatory response and mortality by CDDO-imidazolide," *Biochem. Biophys. Res. Commun.*, 351:883-889, 2006.
Thimmulappa et al., "Preclinical evaluation of targeting the Nrf2 pathway by triterpenoids (CDDO-Im and CDDO-Me) for protection from LPS-induced inflammatory response and reactive oxygen species in human peripheral blood mononuclear cells and neutrophils," *Antioxidants and Redox Signalling*, 9:1-8, 2007.
Tian et al., "Therapeutic effects of Nrf2 activation by bardoxolone methyl in chronic heart failure", J. Pharmacol. Exper. Ther., 371(3):642-656, 2019.
To et al., "Dimethyl fumarate and the oleanane triterpenoids, CDDO-imidazolide and CDDO-methyl ester, both activate the Nrf2 pathway but have opposite effects in the A/J model of lung carcinogenesis, " Carcinogenesis, 36(7):769-781, 2015.
To et al., "Synthetic triterpenoids target the Arp2/3 complex and inhibit branched actin polymerization," J. Biol. Chem., 285(36):27944-27957, 2010.
To et al., "The Synthetic Triterpenoid 2-cyano-3,12-dioxooleana-1,9-dien-28-oic acid-imidazolide alters transforming growth factor B-dependent signaling and cell migration by affecting the cytoskeleton and the polarity complex," J. Biol. Chem., 283:11700-11713, 2008.
Toto, "Bardoxolone—the Phoenix?" J. Am. Nephrol., 29:360-361, 2018.
Tran et al., "The synthetic triterpenoid CDDO-methyl ester delays estrogen receptor- negative mammary carcinogenesis in polyoma middle T mice," Cancer Prev. Res., 5(5):726-734, 2012.
Tran et al., "The synthetic triterpenoid CDDO-methyl ester modulates microglial activities, inhibits TNF production, and provides dopaminergic neuroprotection," *Journal of Neuroinflammation*, 5:1-14, 2008.
Tsao et al., "DRIP205 co-activator overexpression enhances PPARγ-mediated differentiation of leukemia cells by CDDO," *Proc. Amer. Assoc. Cancer Res.*, 46: Abstract No. 1855, 2005.
Vannini et al., "The synthetic oleanane triterpenoid, CDDO-methyl ester, is a potent antiangiogenic agent," *Molecular Cancer Therapeutics*, 6 (12 Part 1), 3139-3146, 2007.
Vene et al., "Glycogen Synthase Kinase 3B Regulates Cell Death Induced by Synthetic Triterpenoids," Cancer Res., 68(17):6987-6996, 2008.
Vincenti et al., "The synthetic triterpenoid TP-222 inhibits RANKL induction of differentiation and MMP-9 gene expression in osteoclasts," Abstract 1385, American College of Rheumatology Annual Scientific Meeting, 2006.
Wada and Tanaka, "Synthetic lanostane-type triterpenoids as inhibitors of DNA topoisomerase II ," Bioorganic and Medicinal Chemistry Letters, 15 (12): 2966-2969, 2005.
Wang et al., "A novel synthetic triterpenoid, 2-cyano-3,12-dioxoolean-1,9-dien-28-oic acid (CDDO) induces adipocyte differentiation in 3T3-L1 cells, " *Proceedings of the American Association for Cancer Research Annual Meeting*, 40:300, abstract # 1989, 1999.
Wang et al., "A synthetic triterpenoid, 2-cyano-3,12-dioxooleana-1,9-dien-28-oic acid (CDDO), is a ligand for the peroxisome proliferator-activated receptor γ," *Mol. Endocrin.*, 14(10):1550-1556, 2000.
Wang et al., "Bardoxolone methyl (CDDO-Me) as a therapeutic agent: an update on its pharmacokinetic and pharmacodynamic properties", Drug Des. Devel. Ther., 8:2075-2088, 2014.
Wang et al., "Bardoxolone methyl (CDDO-Me or RTA402) induces cell cycle arrest, apoptosis and autophagy via PI3K/Akt/mTOR and p38 MAPK/Erk1/2 signaling pathways in K562 cells", Am. J. Transl. Res., 9(10):4652-4672, 2017.
Wang et al., "Bardoxolone methyl induces apoptosis and autophagy and inhibits epithelial-to-mesenchymal transition and stemness in esophageal squamous cancer cells," Drug Des. Develop. Ther., 9:993-1026, 2015.
Wang, et al., "Cytoprotection of human endothelial cells against oxidative stress by 1-[2-cyano-3,12-dioxooleana-1,9(11)-dien-28-oyl]imidazole (CDDO-Im): Application of systems biology to understand the mechanism of action," European J. of Pharmacology, 734:122-131, 2014.
Wang, "Differentiating and anti-inflammatory activities of the triterpenoid, CDDO," Thesis, Dartmouth College, May 4, 2001.

(56) References Cited

OTHER PUBLICATIONS

Wang et al., "Synthetic triterpenoid CDDO and its derivatives increase ceramides and are cytotoxic to pediatric acute lymphoblastic leukemia cell lines," *Proc. Am. Assoc. Cancer Res.*, 47: 4643, 2006.
Wang et al., "The therapeutic response of CDDO-Me in the esophageal squamous cell carcinoma (ESCC) cells is mediated by CaMKIIγ," Am. J. Transl. Res., 8(4):1695-1707, 2016.
Wang et al., "Therapeutic effects of C-28 methyl ester of 2-cyano-3,12-dioxoolean-1,9-dien-28-oic acid (CDDO-Me; bardoxolone methyl) on radiation-induced lung inflammation and fibrosis in mice," Drug Des. Develop. Ther., 9:3163-3178, 2015.
Wei et al., "A unique tolerizing dendritic cell phenotype induced by the synthetic triterpenoid CDDO-DFPA (RTA-408) is protective against EAE," Sci. Rep., 7(9886):1-13, 2017.
Wong et al., "Design and synthesis of irreversible analogues of bardoxolone methyl for the identification of pharmacologically-relevant targets and interaction sites," J. Med. Chem., 59(6):2396-2409, 2016.
Wu et al., "Bardoxolone methyl (BARD) ameliorates ischemic AKI and increases expression of protective genes Nrf2, PPARγ, and HO-1," Am. J. Physiol. 300(5, Pt. 2):F1180-F1192, 2011.
Wu et al., "Targeting multiple signaling axes and oxidative stress using a synthetic triterpenoid prevents murine lupus nephritis," Arthritis. Rheum., 66(11):3129-3139, 2014.
Xing et al., "Triterpenoid dihydro-CDDO-trifluoroethyl amide protects against maladaptive cardiac remodeling and dysfunction in mice: a critical role of Nrf2," PLoS One, 7(9):e44899, 2012.
Xu et al., "The triterpenoid CDDO-imidazolide ameliorates mouse liver ischemia-reperfusion injury through activating the Nrf2/HO-1 pathway enhanced autophagy", Cell Death Dis., 8(8):e2983, 2017.
Xue et al., "CDDO-Me, Sulforaphane and tBHQ attenuate the RANKL-induced osteoclast differentiation via activating the NRF2-mediated antioxidant response", Biochem. Biophys. Res. Comm., 511(3):637-643, 2019.
Yang et al., "Neuroprotective effects of the triterpenoid, CDDO methyl amide, a potent inducer of Nrf2-mediated transcription", PLoS One, 4:e5757, 2009.
Yang et al., "RTA 408 inhibits interleukin-1β-induced MMP-9 expression via suppressing protein kinase-dependent NF-κB and AP-1 activation in rat brain astrocytes", Int. J. Mol. Sci., 20(11):2826, 2019.
Yates et al., "Pharmacodynamic characterization of chemopreventive triterpenoids as exceptionally potent inducers of Nrf2-regulated genes," *Mol. Cancer Ther.*, 6:154-162, 2007.
Yates et al., "Potent protection against aflatoxin-induced tumorigenesis through induction of Nrf2-regulated pathways by the triterpenoid 1-[2-cyano-3-,12-dioxooleana-1,9(11)-dien-28-oyl]imidazole," *Cancer Res.*, 66 (4): 2488-2494, 2007.
Yore et al., "The synthetic triterpenoid 1-[2-cyano-3,12-dioxooleana-1,9(11)-dien-28-oyl]imidazole blocks nuclear factor-κB activation through direct inhibition of IkappaB kinase β," *Mol. Cancer Ther.*, 5 (12): 3232-3239, 2006.
Yue et al., "Depletion of intracellular glutathione contributes to JNK-mediated death receptor 5 upregulation and apoptosis induction by the novel synthetic triterpenoid methyl-2-cyano-3, 12-dioxooleana-1, 9-dien-28-oate (CDDO-Me)," *Cancer & Biology Ther.*, 5(5):492-497, 2006.
Zagorski et al., "Differential effects of the Nrf2 activators tBHQ and CDDO-Im on the early events of T cell activation," Biochem. Pharm., 147:67-76, 2018.
Zagorski et al., "Nrf2-Dependent and -Independent Effects of tert-Butylhydroquinone, CDDO-Im, and H2O2 in Human Jurkat T Cells as Determined by CRISPR/Cas9 Gene Editing," J. Pharmacol. Exp. Ther., 361(2):259-267, 2017.
Zapata et al., "CDDO and CDDO-Im Reduce Tumor Burden in a Transgenic Mouse Model of CLL," *Blood*, 104:3477, 2004.
Zapata et al., "Triterpenoids show activity against leukemic cells in a transgenic mouse model of CLL," *Proc. Amer. Assoc. Cancer Res.*, 46: Abstract No. 5179, 2005.
Zhang et al., "Synthetic triterpenoid CDDO as effective therapy for HER2-expressing resistant breast cancer," *Proc. Amer. Assoc. Cancer Res.*, Abstract No. 3799, 2004.
Zhang et al., "The novel synthetic oleanane triterpenoid CDDO (2-cyano-3, 12-dioxoolean-1, 9-dien-28-oic acid) induces apoptosis in Mycosis fungoides/Sézary syndrome cells," *J. Invest. Dermatol.*, 123:380-387, 2004.
Zhang et al., "Nrf2 Activator RTA-408 Protects Against Ozone-Induced Acute Asthma Exacerbation by Suppressing ROS and γσT17 Cells", Inflammation, 42(5): 1843-1856, 2019.
Zoja, et al., "Analogs of Bardoxolone Methyl Worsen Diabetic Nephropathy in Rats with Additional Adverse Events," Am. J. Physiology, 304(3, Part 2):F808-F819, 2013.
Zou et al., "c-FLIP downregulation contributes to apoptosis induction by the novel synthetic triterpenoid methyl-2-cyano-3,12-dioxooleana-1,9-dien-28-oate (CDDO-Me) in Human Lung Cancer Cells," Cancer Biology & Therapy, 6(10):1614-1620, 2007.
Zou et al., "c-Jun NH2-terminal kinase-mediated up-regulation of death receptor 5 contributes to induction of apoptosis by the novel synthetic triterpenoid methyl-2-cyano-3,12-dioxooleana-1, 9-dien-28-oate in human lung cancer cells," *Cancer Res.*, 64:7570-7578, 2004.
Zou et al., "Coupling of Endoplasmic Reticulum Stress to CDDO-Me-Induced Up-Regulation of Death Receptor 5 via a CHOP-Dependent Mechanism Involving JNK Activation," Cancer Research, 68(18):7484-7492, 2008.
Office Action issued in Korean Application No. 10-2022-7023129, dated May 19, 2025, and English translation thereof.
Office Action issued in Mexican Application No. MX/a/2022/007595, dated May 22, 2025, and English translation thereof.

* cited by examiner

SYNTHETIC TRITERPENOIDS WITH NITROGEN-BASED SUBSTITUENTS AT C-17 AND METHODS OF USE THEREOF

REFERENCE TO RELATED APPLICATIONS

This application is a national phase application under 35 U.S.C. § 371 of International Application No. PCT/US2020/066073, filed Dec. 19, 2020, which claims the benefit of priority to U.S. Provisional Application No. 63/198,310, filed on Oct. 9, 2020, 62/950,927, filed on Dec. 19, 2019, and 62/950,919, filed on Dec. 19, 2019, the entire contents of all of which are hereby incorporated by reference.

BACKGROUND OF THE INVENTION

I. Field of the Invention

The present invention relates generally to the fields of biology, chemistry, and medicine. More particularly, it concerns compounds, compositions and methods for the treatment and prevention of diseases and disorders such as those associated with oxidative stress and inflammation.

II. Description of Related Art

The anti-inflammatory and anti-proliferative activity of the naturally occurring triterpenoid, oleanolic acid, has been improved by chemical modifications. For example, 2-cyano-3,12-diooxooleana-1,9(11)-dien-28-oic acid (CDDO) and related compounds have been developed (Honda et al., 1997; Honda et al., 1998; Honda et al., 1999; Honda et al., 2000a; Honda et al., 2000b; Honda, et al., 2002; Suh et al. 1998; Suh et al., 1999; Place et al., 2003; Liby et al., 2005; and U.S. Pat. Nos. 7,915,402; 7,943,778; 8,071,632; 8,124,799; 8,129,429; 8,338,618, 8,993,640, 9,701,709, 9,512,094, and 9,889,143). The methyl ester, bardoxolone methyl (CDDO-Me), has been evaluated clinically for the treatment of cancer and chronic kidney disease (Pergola et al., 2011; Hong et al., 2012).

Synthetic triterpenoid analogs of oleanolic acid have also been shown to be inhibitors of cellular inflammatory processes, such as the induction by IFN-γ of inducible nitric oxide synthase (iNOS) and of COX-2 in mouse macrophages. See Honda et al. (2000a); Honda et al. (2000b), and Honda et al. (2002). Synthetic derivatives of another triterpenoid, betulinic acid, have also been shown to inhibit cellular inflammatory processes, although these compounds have been less extensively characterized (Honda et al., 2006). The pharmacology of these synthetic triterpenoid molecules is complex. Compounds derived from oleanolic acid have been shown to affect the function of multiple protein targets and thereby modulate the activity of several important cellular signaling pathways related to oxidative stress, cell cycle control, and inflammation (e.g., Dinkova-Kostova et al., 2005; Ahmad et al., 2006; Ahmad et al., 2008; Liby et al., 2007a). Derivatives of betulinic acid, though they have shown comparable anti-inflammatory properties, also appear to have significant differences in their pharmacology compared to OA-derived compounds (Liby et al., 2007b). Given that the biological activity profiles of known triterpenoid derivatives vary, and in view of the wide variety of diseases that may be treated or prevented with compounds having potent antioxidant and anti-inflammatory effects, and the high degree of unmet medical need represented within this variety of diseases, it is desirable to synthesize new compounds with diverse structures that may have improved biological activity profiles for the treatment of one or more indications.

SUMMARY OF THE INVENTION

The present disclosure provides novel synthetic triterpenoid derivatives with anti-inflammatory and/or antioxidant properties, pharmaceutical compositions thereof, methods for their manufacture, and methods for their use. In some embodiments, the synthetic triterpenoid derivatives have either a nitrogen atom directly attached to the C17 position or through a methylene group. In some embodiments, the nitrogen atom is part of a heterocycloalkyl or a heteroaryl group. In some embodiments, the nitrogen atom is part of an acyclic group, such as an amide group.

In some aspects, the present disclosure provides compounds of the formula:

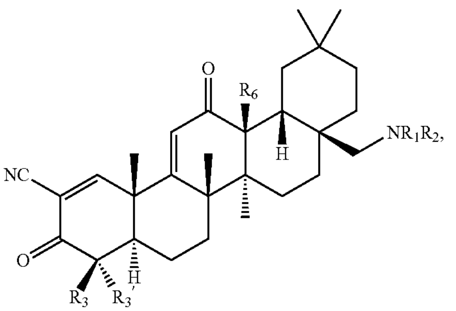

(I)

wherein:

$R_1$ is hydrogen; or
  alkyl$_{(C\leq8)}$, substituted alkyl$_{(C\leq8)}$, a monovalent amino protecting group, or —C(O)$R_4$, wherein:
    $R_4$ is hydrogen; or
      alkyl$_{(C\leq8)}$, alkenyl$_{(C\leq8)}$, alkynyl$_{(C\leq8)}$, alkoxy$_{(C\leq8)}$, alkylamino$_{(C\leq8)}$, dialkylamino$_{(C\leq8)}$, cycloalkyl$_{(C\leq8)}$, cycloalkoxy$_{(C\leq8)}$, cycloalkylamino$_{(C\leq8)}$, heterocycloalkyl$_{(C\leq8)}$, or a substituted version of any one of these groups; or
  $R_1$ and $R_2$ are taken together as defined below;

$R_2$ is alkyl$_{(C\leq8)}$ or substituted alkyl$_{(C\leq8)}$; or
  —N$R_c$$R_d$, wherein:
    $R_c$ and $R_d$ are each independently hydrogen, alkyl$_{(C\leq8)}$, substituted alkyl$_{(C\leq8)}$, acyl$_{(C\leq8)}$, substituted acyl$_{(C\leq8)}$, or a monovalent amino protecting group; or
  —C(O)$R_5$, wherein:
    $R_5$ is hydrogen; or
      alkyl$_{(C\leq8)}$, alkenyl$_{(C\leq8)}$, alkynyl$_{(C\leq8)}$, alkylamino$_{(C\leq8)}$, dialkylamino$_{(C\leq8)}$, cycloalkyl$_{(C\leq8)}$, cycloalkoxy$_{(C\leq8)}$, cycloalkylamino$_{(C\leq8)}$, heterocycloalkyl$_{(C\leq8)}$, or a substituted version of any one of these groups; or
  $R_2$ and $R_1$ are taken together as defined below;

$R_1$ and $R_2$, when taken together with the nitrogen atom of the —N$R_1$$R_2$ group, is N-heteroaryl$_{(C\leq8)}$, substituted N-heteroaryl$_{(C\leq8)}$, N-heterocycloalkyl$_{(C\leq8)}$, substituted N-heterocycloalkyl$_{(C\leq8)}$, or 3-oxo-1-(t-butoxycarbonyl)pyrazolidin-2-yl;

$R_3$ and $R_3$' are each independently hydrogen, alkyl$_{(C\leq8)}$, or substituted alkyl$_{(C\leq8)}$; and $R_6$ is hydrogen, hydroxy, or amino; or acyloxy$_{(C\le 8)}$, alkoxy$_{(C\le 8)}$, alkylamino$_{(C\le 8)}$, dialkylamino$_{(C\le 8)}$, amido$_{(C\le 8)}$, or a substituted version of any of these groups; or a compound of the formula:

(II)

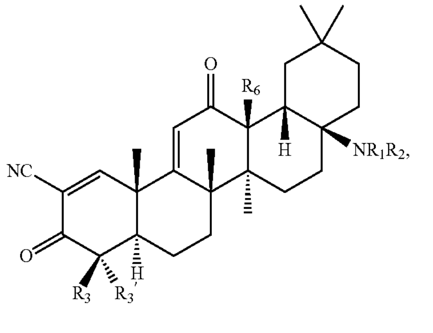

wherein:

$R_1$ is hydrogen; or alkyl$_{(C\le 8)}$ or substituted alkyl$_{(C\le 8)}$, or a monovalent amino protecting group; or $R_1$ and $R_2$ are taken together as defined below;

$R_2$ is —$NR_cR_d$, wherein:

$R_c$ and $R_d$ are each independently hydrogen, alkyl$_{(C\le 8)}$, substituted alkyl$_{(C\le 8)}$, acyl$_{(C\le 8)}$, substituted acyl$_{(C\le 8)}$, or a monovalent amino protecting group; or $R_1$ and $R_2$ are taken together as defined below;

$R_1$ and $R_2$, when taken together with the nitrogen atom of the —$NR_1R_2$ group, is N-heteroaryl$_{(C\le 8)}$, substituted N-heteroaryl$_{(C\le 8)}$, N-heterocycloalkyl$_{(C\le 8)}$, substituted N-heterocycloalkyl$_{(C\le 8)}$, or 3-oxo-1-(t-butoxycarbonyl)pyrazolidin-2-yl;

$R_3$ and $R_3'$ are each independently hydrogen, alkyl$_{(C\le 8)}$, or substituted alkyl$_{(C\le 8)}$; and $R_6$ is hydrogen, hydroxy, or amino; or acyloxy$_{(C\le 8)}$, alkoxy$_{(C\le 8)}$, alkylamino$_{(C\le 8)}$, dialkylamino$_{(C\le 8)}$, amido$_{(C\le 8)}$, or a substituted version of any of these groups;

or a pharmaceutically acceptable salt of either of these formulae.

In some embodiments, the compound is further defined as:

(I)

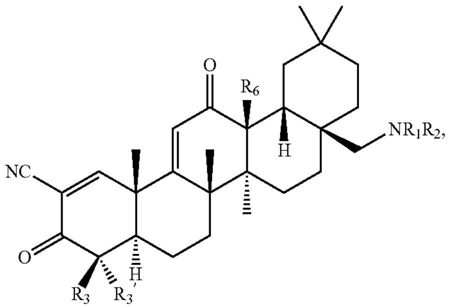

wherein:

$R_1$ is hydrogen; or alkyl$_{(C\le 8)}$, substituted alkyl$_{(C\le 8)}$, a monovalent amino protecting group, or —$C(O)R_4$, wherein:

$R_4$ is hydrogen; or alkyl$_{(C\le 8)}$, alkenyl$_{(C\le 8)}$, alkynyl$_{(C\le 8)}$, alkoxy$_{(C\le 8)}$, alkylamino$_{(C\le 8)}$, dialkylamino$_{(C\le 8)}$, cycloalkyl$_{(C\le 8)}$, cycloalkoxy$_{(C\le 8)}$, cycloalkylamino$_{(C\le 8)}$, heterocycloalkyl$_{(C\le 8)}$, or a substituted version of any one of these groups; or $R_1$ and $R_2$ are taken together as defined below;

$R_2$ is alkyl$_{(C\le 8)}$ or substituted alkyl$_{(C\le 8)}$; or

—$NR_cR_d$, wherein:

$R_c$ and $R_d$ are each independently hydrogen, alkyl$_{(C\le 8)}$, substituted alkyl$_{(C\le 8)}$, acyl$_{(C\le 8)}$, substituted acyl$_{(C\le 8)}$, or a monovalent amino protecting group; or —$C(O)R_5$, wherein:

$R_5$ is hydrogen; or alkyl$_{(C\le 8)}$, alkenyl$_{(C\le 8)}$, alkynyl$_{(C\le 8)}$, alkylamino$_{(C\le 8)}$, dialkylamino$_{(C\le 8)}$, cycloalkyl$_{(C\le 8)}$, cycloalkoxy$_{(C\le 8)}$, cycloalkylamino$_{(C\le 8)}$, heterocycloalkyl$_{(C\le 8)}$, or a substituted version of any one of these groups; or $R_2$ and $R_1$ are taken together as defined below;

$R_1$ and $R_2$, when taken together with the nitrogen atom of the —$NR_1R_2$ group, is N-heteroaryl$_{(C\le 8)}$, substituted N-heteroaryl$_{(C\le 8)}$, N-heterocycloalkyl$_{(C\le 8)}$, substituted N-heterocycloalkyl$_{(C\le 8)}$, or 3-oxo-1-(t-butoxycarbonyl)pyrazolidin-2-yl;

$R_3$ and $R_3'$ are each independently hydrogen, alkyl$_{(C\le 8)}$, or substituted alkyl$_{(C\le 8)}$; and $R_6$ is hydrogen, hydroxy, or amino; or acyloxy$_{(C\le 8)}$, alkoxy$_{(C\le 8)}$, alkylamino$_{(C\le 8)}$, dialkylamino$_{(C\le 8)}$, amido$_{(C\le 8)}$, or a substituted version of any of these groups;

or a pharmaceutically acceptable salt thereof.

In some embodiments, the compound is further defined as:

(I-A)

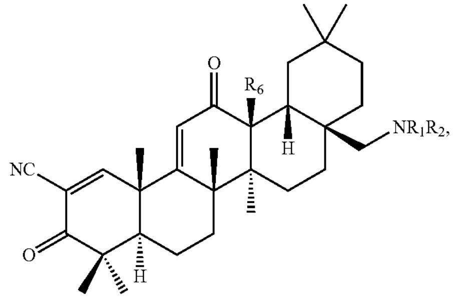

wherein:

$R_1$ is hydrogen; or alkyl$_{(C\le 8)}$, substituted alkyl$_{(C\le 8)}$, a monovalent amino protecting group, or —$C(O)R_4$, wherein:

$R_4$ is hydrogen; or alkyl$_{(C\le 8)}$, alkenyl$_{(C\le 8)}$, alkynyl$_{(C\le 8)}$, alkoxy$_{(C\le 8)}$, alkylamino$_{(C\le 8)}$, dialkylamino$_{(C\le 8)}$, cycloalkyl$_{(C\le 8)}$, cycloalkoxy$_{(C\le 8)}$, cycloalkylamino$_{(C\le 8)}$, heterocycloalkyl$_{(C\le 8)}$, or a substituted version of any one of these groups; or $R_1$ and $R_2$ are taken together as defined below;

$R_2$ is alkyl$_{(C\le 8)}$ or substituted alkyl$_{(C\le 8)}$; or

—$NR_cR_d$, wherein:

$R_c$ and $R_d$ are each independently hydrogen, alkyl$_{(C\le 8)}$, substituted alkyl$_{(C\le 8)}$, acyl$_{(C\le 8)}$, substituted acyl$_{(C\le 8)}$, or a monovalent amino protecting group; or —C(O)$R_5$, wherein:

$R_5$ is hydrogen; or alkyl$_{(C\leq8)}$, alkenyl$_{(C\leq8)}$, alkynyl$_{(C\leq8)}$, alkylamino$_{(C\leq8)}$, dialkylamino$_{(C\leq8)}$, cycloalkyl$_{(C\leq8)}$, cycloalkoxy$_{(C\leq8)}$, cycloalkylamino$_{(C\leq8)}$, heterocycloalkyl$_{(C\leq8)}$, or a substituted version of any one of these groups; or $R_2$ and $R_1$ are taken together as defined below;

$R_1$ and $R_2$, when taken together with the nitrogen atom of the —$NR_1R_2$ group, is N-heteroaryl$_{(C\leq8)}$, substituted N-heteroaryl$_{(C\leq8)}$, N-heterocycloalkyl$_{(C\leq8)}$, substituted N-heterocycloalkyl$_{(C\leq8)}$, or 3-oxo-1-(t-butoxycarbonyl)pyrazolidin-2-yl; and $R_6$ is hydrogen, hydroxy, or amino; or acyloxy$_{(C\leq8)}$, alkoxy$_{(C\leq8)}$, alkylamino$_{(C\leq8)}$, dialkylamino$_{(C\leq8)}$, amido$_{(C\leq8)}$, or a substituted version of any of these groups;

or a pharmaceutically acceptable salt thereof.

In some embodiments, the compound is further defined as:

(I-B)

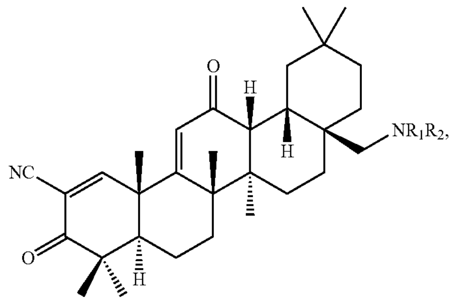

wherein:

$R_1$ is hydrogen; or alkyl$_{(C\leq8)}$, substituted alkyl$_{(C\leq8)}$, a monovalent amino protecting group, or C(O)$R_4$, wherein:

$R_4$ is hydrogen; or alkyl$_{(C\leq8)}$, alkenyl$_{(C\leq8)}$, alkynyl$_{(C\leq8)}$, alkoxy$_{(C\leq8)}$, alkylamino$_{(C\leq8)}$, dialkylamino$_{(C\leq8)}$, cycloalkyl$_{(C\leq8)}$, cycloalkoxy$_{(C\leq8)}$, cycloalkylamino$_{(C\leq8)}$, heterocycloalkyl$_{(C\leq8)}$, or a substituted version of any one of these groups; or $R_1$ and $R_2$ are taken together as defined below;

$R_2$ is alkyl$_{(C\leq8)}$ or substituted alkyl$_{(C\leq8)}$; or $NR_cR_d$, wherein:

$R_c$ and $R_d$ are each independently hydrogen, alkyl$_{(C\leq8)}$, substituted alkyl$_{(C\leq8)}$, acyl$_{(C\leq8)}$, substituted acyl$_{(C\leq8)}$, or a monovalent amino protecting group; or —C(O)$R_5$, wherein:

$R_5$ is hydrogen; or alkyl$_{(C\leq8)}$, alkenyl$_{(C\leq8)}$, alkynyl$_{(C\leq8)}$, alkylamino$_{(C\leq8)}$, dialkylamino$_{(C\leq8)}$, cycloalkyl$_{(C\leq8)}$, cycloalkoxy$_{(C\leq8)}$, cycloalkylamino$_{(C\leq8)}$, heterocycloalkyl$_{(C\leq8)}$, or a substituted version of any one of these groups; or $R_2$ and $R_1$ are taken together as defined below; and $R_1$ and $R_2$, when taken together with the nitrogen atom of the —$NR_1R_2$ group, is N-heteroaryl$_{(C\leq8)}$, substituted N-heteroaryl$_{(C\leq8)}$, N-heterocycloalkyl$_{(C\leq8)}$, substituted N-heterocycloalkyl$_{(C\leq8)}$, or 3-oxo-1-(t-butoxycarbonyl)pyrazolidin-2-yl;

or a pharmaceutically acceptable salt thereof.

In some embodiments, the compound is further defined as:

(II)

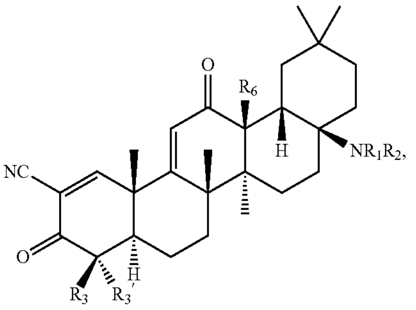

wherein:

$R_1$ is hydrogen; or alkyl$_{(C\leq8)}$, substituted alkyl$_{(C\leq8)}$, or a monovalent amino protecting group; or $R_1$ and $R_2$ are taken together as defined below;

$R_2$ is —$NR_cR_d$, wherein:

$R_c$ and $R_d$ are each independently hydrogen, alkyl$_{(C\leq8)}$, substituted alkyl$_{(C\leq8)}$, acyl$_{(C\leq8)}$, substituted acyl$_{(C\leq8)}$, or a monovalent amino protecting group; or $R_1$ and $R_2$ are taken together as defined below;

$R_1$ and $R_2$, when taken together with the nitrogen atom of the —$NR_1R_2$ group, is N-heteroaryl$_{(C\leq8)}$, substituted N-heteroaryl$_{(C\leq8)}$, N-heterocycloalkyl$_{(C\leq8)}$, substituted N-heterocycloalkyl$_{(C\leq8)}$, or 3-oxo-1-(t-butoxycarbonyl)pyrazolidin-2-yl;

$R_3$ and $R_3'$ are each independently hydrogen, alkyl$_{(C\leq8)}$, or substituted alkyl$_{(C\leq8)}$; and $R_6$ is hydrogen, hydroxy, or amino; or acyloxy$_{(C\leq8)}$, alkoxy$_{(C\leq8)}$, alkylamino$_{(C\leq8)}$, dialkylamino$_{(C\leq8)}$, amido$_{(C\leq8)}$, or a substituted version of any of these groups;

or a pharmaceutically acceptable salt of either of these formulae.

In some embodiments, the compound is further defined as:

(II)

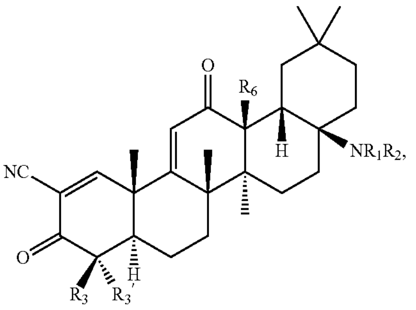

wherein:

$R_1$ is hydrogen; or alkyl$_{(C\leq8)}$, substituted alkyl$_{(C\leq8)}$, or a monovalent amino protecting group; or $R_1$ and $R_2$ are taken together as defined below;

$R_2$ is —$NR_cR_d$, wherein:

$R_c$ and $R_d$ are each independently hydrogen, alkyl$_{(C\leq8)}$, substituted alkyl$_{(C\leq8)}$, acyl$_{(C\leq8)}$, substituted acyl$_{(C\leq8)}$, or a monovalent amino protecting group; or $R_1$ and $R_2$ are taken together as defined below;

$R_1$ and $R_2$, when taken together with the nitrogen atom of the —$NR_1R_2$ group, is N-heteroaryl$_{(C\leq8)}$, substituted N-heteroaryl$_{(C\leq8)}$, N-heterocycloalkyl$_{(C\leq8)}$, or 3-oxo-1-(t-butoxycarbonyl)pyrazolidin-2-yl; or substituted N-heterocycloalkyl$_{(C\leq8)}$, further wherein the —$NR_1R_2$ group is of the formula:

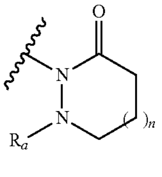 or 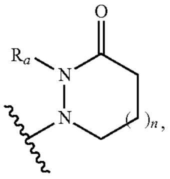

wherein:

n is 0, 1, 2, or 3;

$R_a$ is hydrogen, alkyl$_{(C\leq8)}$, or substituted alkyl$_{(C\leq8)}$; or substituted N-heterocycloalkyl$_{(C\leq8)}$, further wherein the —$NR_1R_2$ group is of the formula:

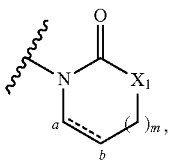

wherein:

the bond between atoms a and b is a single bond or a double bond;

m is 0, 1, 2, or 3; and $X_1$ is —$CH_2$—, —O—, or —N($R_b$)—, wherein:

$R_b$ is hydrogen, alkyl$_{(C\leq8)}$, or substituted alkyl$_{(C\leq8)}$; or substituted N-heterocycloalkyl$_{(C\leq8)}$, further wherein the —$NR_1R_2$ group is of the formula:

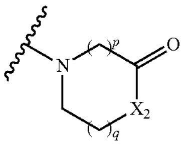 or 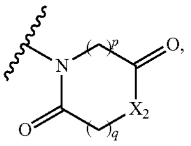

wherein:

p is 0 or 1;

q is 0 or 1; and $X_2$ is —$CH_2$—, —O—, or —N($R_e$)—, wherein:

$R_c$ is hydrogen, alkyl$_{(C\leq8)}$, substituted alkyl$_{(C\leq8)}$, or a monovalent amino protecting group;

$R_3$ and $R_3$' are each independently hydrogen, alkyl$_{(C\leq8)}$, or substituted alkyl$_{(C\leq8)}$; and $R_6$ is hydrogen, hydroxy, or amino; or acyloxy$_{(C\leq8)}$, alkoxy$_{(C\leq8)}$, alkylamino$_{(C\leq8)}$, dialkylamino$_{(C\leq8)}$, amido$_{(C\leq8)}$, or a substituted version of any of these groups;

or a pharmaceutically acceptable salt of either of these formulae.

In some embodiments, the compound is further defined as:

(II-A)

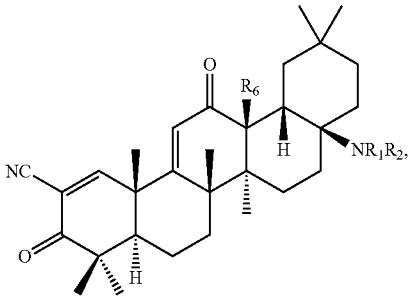

wherein:

$R_1$ is hydrogen; or alkyl$_{(C\leq8)}$, substituted alkyl$_{(C\leq8)}$, or a monovalent amino protecting group; or $R_1$ and $R_2$ are taken together as defined below;

$R_2$ is —$NR_cR_d$, wherein:

$R_c$ and $R_d$ are each independently hydrogen, alkyl$_{(C\leq8)}$, substituted alkyl$_{(C\leq8)}$, acyl$_{(C\leq8)}$, substituted acyl$_{(C\leq8)}$, or a monovalent amino protecting group; or $R_1$ and $R_2$ are taken together as defined below;

$R_1$ and $R_2$, when taken together with the nitrogen atom of the —$NR_1R_2$ group, is N-heteroaryl$_{(C\leq8)}$, substituted N-heteroaryl$_{(C\leq8)}$, N-heterocycloalkyl$_{(C\leq8)}$, or 3-oxo-1-(t-butoxycarbonyl)pyrazolidin-2-yl; or substituted N-heterocycloalkyl$_{(C\leq8)}$, further wherein the —$NR_1R_2$ group is of the formula:

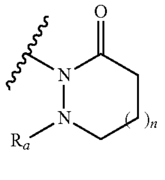 or 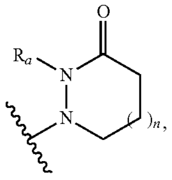

wherein:

n is 0, 1, 2, or 3;

$R_a$ is hydrogen, alkyl$_{(C\leq8)}$, or substituted alkyl$_{(C\leq8)}$; or substituted N-heterocycloalkyl$_{(C\leq8)}$, further wherein the —$NR_1R_2$ group is of the formula:

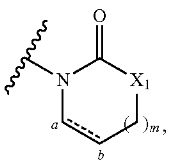

wherein:

the bond between atoms a and b is a single bond or a double bond;

m is 0, 1, 2, or 3; and $X_1$ is —$CH_2$—, —O—, or —N($R_b$)—, wherein:

$R_b$ is hydrogen, alkyl$_{(C\leq8)}$, or substituted alkyl$_{(C\leq8)}$; or substituted N-heterocycloalkyl$_{(C\leq8)}$, further wherein the —$NR_1R_2$ group is of the formula:

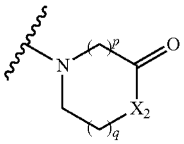 or 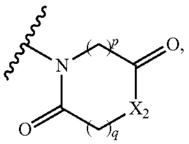

wherein:

p is 0 or 1;

q is 0 or 1; and $X_2$ is —$CH_2$—, —O—, or —N($R_e$)—, wherein:

$R_c$ is hydrogen, alkyl$_{(C\leq8)}$, substituted alkyl$_{(C\leq8)}$, or a monovalent amino protecting group; and $R_6$ is hydrogen, hydroxy, or amino; or acyloxy$_{(C\leq8)}$, alkoxy$_{(C\leq8)}$, alkylamino$_{(C\leq8)}$, dialkylamino$_{(C\leq8)}$, amido$_{(C\leq8)}$, or a substituted version of any of these groups;

or a pharmaceutically acceptable salt of either of these formulae.

In some embodiments, the compound is further defined as:

(II-B)

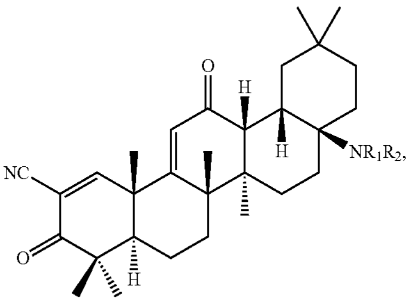

wherein:

$R_1$ is hydrogen; or alkyl$_{(C\leq8)}$, substituted alkyl$_{(C\leq8)}$, or a monovalent amino protecting group; or $R_1$ and $R_2$ are taken together as defined below;

$R_2$ is —$NR_cR_d$, wherein:

$R_c$ and $R_d$ are each independently hydrogen, alkyl$_{(C\leq8)}$, substituted alkyl$_{(C\leq8)}$, acyl$_{(C\leq8)}$, substituted acyl$_{(C\leq8)}$, or a monovalent amino protecting group; or $R_1$ and $R_2$ are taken together as defined below; or $R_1$ and $R_2$, when taken together with the nitrogen atom of the —$NR_1R_2$ group, is N-heteroaryl$_{(C\leq8)}$, substituted N-heteroaryl$_{(C\leq8)}$, N-heterocycloalkyl$_{(C\leq8)}$, or 3-oxo-1-(t-butoxycarbonyl)pyrazolidin-2-yl; or substituted N-heterocycloalkyl$_{(C\leq8)}$, further wherein the —$NR_1R_2$ group is of the formula:

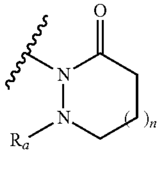 or 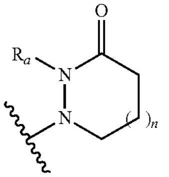

wherein:

n is 0, 1, 2, or 3;

$R_a$ is hydrogen, alkyl$_{(C\leq8)}$, or substituted alkyl$_{(C\leq8)}$; or substituted N-heterocycloalkyl$_{(C\leq8)}$, further wherein the —$NR_1R_2$ group is of the formula:

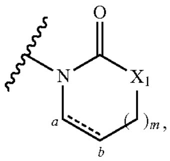

wherein:

the bond between atoms a and b is a single bond or a double bond;

m is 0, 1, 2, or 3; and $X_1$ is —$CH_2$—, —O—, or —N($R_b$)—, wherein:

$R_b$ is hydrogen, alkyl$_{(C\leq8)}$, or substituted alkyl$_{(C\leq8)}$; or substituted N-heterocycloalkyl$_{(C\leq8)}$, further wherein the —$NR_1R_2$ group is of the formula:

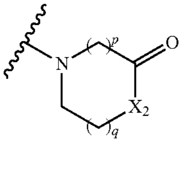 or 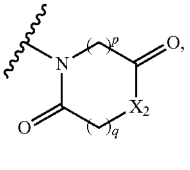

wherein:

p is 0 or 1;

q is 0 or 1; and $X_2$ is —$CH_2$—, —O—, or —N($R_e$)—, wherein:

$R_e$ is hydrogen, alkyl$_{(C\leq8)}$, substituted alkyl$_{(C\leq8)}$, or a monovalent amino protecting group; and or a pharmaceutically acceptable salt of either of these formulae.

In some embodiments, $R_3$ is hydrogen. In other embodiments, $R_3$ is alkyl$_{(C\leq8)}$ or substituted alkyl$_{(C\leq8)}$. In further embodiments, $R_3$ is alkyl$_{(C\leq8)}$, such as methyl. In some embodiments, $R_3$' is alkyl$_{(C\leq8)}$ or substituted alkyl$_{(C\leq8)}$. In further embodiments, $R_3$' is alkyl$_{(C\leq8)}$, such as methyl. In some embodiments, $R_6$ is hydroxy. In other embodiments, $R_6$ is hydrogen.

In some embodiments, $R_1$ is hydrogen; or alkyl$_{(C\leq8)}$, substituted alkyl$_{(C\leq8)}$, a monovalent amino protecting group, or —C(O)$R_4$, wherein:

$R_4$ is hydrogen; or alkyl$_{(C\leq8)}$, alkenyl$_{(C\leq8)}$, alkynyl$_{(C\leq8)}$, alkoxy$_{(C\leq8)}$, alkylamino$_{(C\leq8)}$, dialkylamino$_{(C\leq8)}$, cycloalkyl$_{(C\leq8)}$, cycloalkoxy$_{(C\leq8)}$, cycloalkylamino$_{(C\leq8)}$, heterocycloalkyl$_{(C\leq8)}$, or a substituted version of any one of these groups.

In some embodiments, $R_1$ is alkyl$_{(C\leq8)}$, substituted alkyl$_{(C\leq8)}$, a monovalent amino protecting group, or —C(O)$R_4$, wherein:

$R_4$ is hydrogen; or alkyl$_{(C\leq8)}$, alkenyl$_{(C\leq8)}$, alkynyl$_{(C\leq8)}$, alkoxy$_{(C\leq8)}$, alkylamino$_{(C\leq8)}$, dialkylamino$_{(C\leq8)}$, cycloalkyl$_{(C\leq8)}$, cycloalkoxy$_{(C\leq8)}$, cycloalkylamino$_{(C\leq8)}$, heterocycloalkyl$_{(C\leq8)}$, or a substituted version of any one of these groups.

In some embodiments, $R_1$ is hydrogen, alkyl$_{(C\leq8)}$, substituted alkyl$_{(C\leq8)}$, or —C(O)$R_4$, wherein:

$R_4$ is hydrogen; or alkyl$_{(C≤8)}$, alkenyl$_{(C≤8)}$, alkynyl$_{(C≤8)}$, alkylamino$_{(C≤8)}$, dialkylamino$_{(C≤8)}$, cycloalkyl$_{(C≤8)}$, cycloalkoxy$_{(C≤8)}$, cycloalkylamino$_{(C≤8)}$, heterocycloalkyl$_{(C≤8)}$, or a substituted version of any one of these groups.

In some embodiments, $R_1$ is hydrogen, substituted alkyl$_{(C≤8)}$, or —C(O)$R_4$, wherein:

$R_4$ is hydrogen; or alkyl$_{(C≤8)}$, alkenyl$_{(C≤8)}$, alkynyl$_{(C≤8)}$, alkoxy$_{(C≤8)}$, alkylamino$_{(C≤8)}$, dialkylamino$_{(C≤8)}$, cycloalkyl$_{(C≤8)}$, cycloalkoxy$_{(C≤8)}$, cycloalkylamino$_{(C≤8)}$, heterocycloalkyl$_{(C≤8)}$, or a substituted version of any one of these groups.

In some embodiments, $R_1$ is hydrogen, alkyl$_{(C≤8)}$, substituted alkyl$_{(C≤8)}$, or —C(O)$R_4$, wherein:

$R_4$ is hydrogen; or alkenyl$_{(C≤8)}$, alkynyl$_{(C≤8)}$, alkoxy$_{(C≤8)}$, alkylamino$_{(C≤8)}$, dialkylamino$_{(C≤8)}$, cycloalkyl$_{(C≤8)}$, cycloalkoxy$_{(C≤8)}$, cycloalkylamino$_{(C≤8)}$, heterocycloalkyl$_{(C≤8)}$, or a substituted version of any one of these groups.

In some embodiments, $R_1$ is hydrogen, alkyl$_{(C≤8)}$, substituted alkyl$_{(C≤8)}$, or —C(O)$R_4$, wherein:

$R_4$ is hydrogen; or alkyl$_{(C≤8)}$, alkenyl$_{(C≤8)}$, alkynyl$_{(C≤8)}$, alkoxy$_{(C≤8)}$, dialkylamino$_{(C≤8)}$, cycloalkyl$_{(C≤8)}$, cycloalkoxy$_{(C≤8)}$, cycloalkylamino$_{(C≤8)}$, heterocycloalkyl$_{(C≤8)}$, or a substituted version of any one of these groups.

In some embodiments, $R_1$ is hydrogen, substituted alkyl$_{(C≤8)}$, or —C(O)$R_4$, wherein:

$R_4$ is hydrogen; or alkenyl$_{(C≤8)}$, alkynyl$_{(C≤8)}$, alkoxy$_{(C≤8)}$, dialkylamino$_{(C≤8)}$, cycloalkyl$_{(C≤8)}$, cycloalkoxy$_{(C≤8)}$, cycloalkylamino$_{(C≤8)}$, heterocycloalkyl$_{(C≤8)}$, or a substituted version of any one of these groups.

In some embodiments, $R_1$ is hydrogen, alkyl$_{(C≤8)}$, or substituted alkyl$_{(C≤8)}$. In further embodiments, $R_1$ is hydrogen. In other embodiments, $R_1$ is alkyl$_{(C≤8)}$ or substituted alkyl$_{(C≤8)}$. In further embodiments, $R_1$ is alkyl$_{(C≤8)}$, such as methyl. In other embodiments, $R_1$ is a monovalent amino protecting group, such as tert-butyloxycarbonyl.

In some embodiments, $R_2$ is substituted alkyl$_{(C≤8)}$ or —C(O)$R_5$, wherein:

$R_5$ is hydrogen; or alkyl$_{(C≤8)}$, alkenyl$_{(C≤8)}$, alkynyl$_{(C≤8)}$, alkylamino$_{(C≤8)}$, dialkylamino$_{(C≤8)}$, cycloalkyl$_{(C≤8)}$, cycloalkoxy$_{(C≤8)}$, cycloalkylamino$_{(C≤8)}$, heterocycloalkyl$_{(C≤8)}$, or a substituted version of any one of these groups.

In some embodiments, $R_2$ is alkyl$_{(C≤8)}$, substituted alkyl$_{(C≤8)}$, or —C(O)$R_5$, wherein:

$R_5$ is hydrogen; or alkenyl$_{(C≤8)}$, alkynyl$_{(C≤8)}$, alkylamino$_{(C≤8)}$, dialkylamino$_{(C≤8)}$, cycloalkyl$_{(C≤8)}$, cycloalkoxy$_{(C≤8)}$, cycloalkylamino$_{(C≤8)}$, heterocycloalkyl$_{(C≤8)}$, or a substituted version of any one of these groups.

In some embodiments, $R_2$ is alkyl$_{(C≤8)}$, substituted alkyl$_{(C≤8)}$, or —C(O)$R_5$, wherein:

$R_5$ is hydrogen; or alkyl$_{(C≤8)}$, alkenyl$_{(C≤8)}$, alkynyl$_{(C≤8)}$, dialkylamino$_{(C≤8)}$, cycloalkyl$_{(C≤8)}$, cycloalkoxy$_{(C≤8)}$, cycloalkylamino$_{(C≤8)}$, heterocycloalkyl$_{(C≤8)}$, or a substituted version of any one of these groups.

In some embodiments, $R_2$ is substituted alkyl$_{(C≤8)}$, or —C(O)$R_5$, wherein:

$R_5$ is hydrogen; or alkenyl$_{(C≤8)}$, alkynyl$_{(C≤8)}$, dialkylamino$_{(C≤8)}$, cycloalkyl$_{(C≤8)}$, cycloalkoxy$_{(C≤8)}$, cycloalkylamino$_{(C≤8)}$, heterocycloalkyl$_{(C≤8)}$, or a substituted version of any one of these groups.

In some embodiments, $R_2$ is alkyl$_{(C≤8)}$ or substituted alkyl$_{(C≤8)}$. In further embodiments, $R_2$ is alkyl$_{(C≤8)}$, such as methyl. In other embodiments, $R_2$ is substituted alkyl$_{(C≤8)}$, such as 1-hydroxyeth-2-yl. In some embodiments, $R_c$ is hydrogen. In other embodiments, $R_c$ is a monovalent amino protecting group, such as tert-butyloxycarbonyl. In still other embodiments, $R_c$ is acyl$_{(C≤8)}$ or substituted acyl$_{(C≤8)}$. In further embodiments, $R_c$ is substituted acyl$_{(C≤8)}$, such as trifluoroacetyl. In some embodiments, $R_d$ is hydrogen. In some embodiments, $R_4$ is alkyl$_{(C≤8)}$ or substituted alkyl$_{(C≤8)}$. In further embodiments, $R_4$ is alkyl$_{(C≤8)}$, such as methyl or ethyl. In further embodiments, the $R_4$ is methyl, further wherein the methyl is substantially trideuteriomethyl. In still further embodiments, the isotopic enrichment of deuterium at each of the three positions is greater than 90%. In other embodiments, $R_4$ is substituted alkyl$_{(C≤8)}$, such as 1,1-difluoroeth-1-yl, difluoromethyl, or fluoromethyl. In still other embodiments, $R_4$ is cycloalkyl$_{(C≤8)}$ or substituted cycloalkyl$_{(C≤8)}$. In further embodiments, $R_4$ is cycloalkyl$_{(C≤8)}$, such as cyclopropyl. In yet other embodiments, $R_4$ is alkoxy$_{(C≤8)}$ or substituted alkoxy$_{(C≤8)}$. In further embodiments, $R_4$ is alkoxy$_{(C≤8)}$, such as t-butoxy. In other embodiments, $R_4$ is alkylamino$_{(C≤8)}$ or substituted alkylamino$_{(C≤8)}$. In further embodiments, $R_4$ is alkylamino$_{(C≤8)}$, such as methylamino. In still other embodiments, $R_4$ is alkenyl$_{(C≤8)}$ or substituted alkenyl$_{(C≤8)}$. In further embodiments, $R_4$ is alkenyl$_{(C≤8)}$, such as ethenyl.

In some embodiments, $R_5$ is alkyl$_{(C≤8)}$ or substituted alkyl$_{(C≤8)}$. In further embodiments, $R_5$ is alkyl$_{(C≤8)}$, such as methyl or ethyl. In still further embodiments, $R_5$ is methyl, further wherein the methyl is substantially trideuteriomethyl. In yet further embodiments, the isotopic enrichment of deuterium at each of the three positions is greater than 90%. In other embodiments, $R_5$ is substituted alkyl$_{(C≤8)}$, such as 1,1-difluoroeth-1-yl, difluoromethyl, or fluoromethyl. In still other embodiments, $R_5$ is cycloalkyl$_{(C≤8)}$ or substituted cycloalkyl$_{(C≤8)}$. In further embodiments, $R_5$ is cycloalkyl$_{(C≤8)}$, such as cyclopropyl. In yet other embodiments, $R_5$ is alkylamino$_{(C≤8)}$ or substituted alkylamino$_{(C≤8)}$. In further embodiments, $R_5$ is alkylamino$_{(C≤8)}$, such as methylamino. In other embodiments, $R_5$ is alkenyl$_{(C≤8)}$ or substituted alkenyl$_{(C≤8)}$. In further embodiments, $R_5$ is alkenyl$_{(C≤8)}$, such as ethenyl.

In some embodiments, $R_1$ and $R_2$ are taken together with the nitrogen atom of the —$NR_1R_2$ group and is N-heteroaryl$_{(C≤8)}$, substituted N-heteroaryl$_{(C≤8)}$, N-heterocycloalkyl$_{(C≤8)}$, or substituted N-heterocycloalkyl$_{(C≤8)}$. In further embodiments, $R_1$ and $R_2$ are taken together with the nitrogen atom of the —$NR_1R_2$ group and is N-heteroaryl$_{(C≤8)}$ or substituted N-heteroaryl$_{(C≤8)}$. In still further embodiments, $R_1$ and $R_2$ are taken together with the nitrogen atom of the —$NR_1R_2$ group and is N-heteroaryl$_{(C≤8)}$, such as 3,5-dimethylpyrazol-1-yl, triazol-1-yl, 4-methyltriazol-1-yl, 1,2,4-triazol-1-yl, 1H-1,2,4-triazol-1-yl, 4H-1,2,4-triazol-4-yl, pyrazol-1-yl, tetrazol-1-yl, or imidazol-1-yl. In other embodiments, $R_1$ and $R_2$ are taken together with the nitrogen atom of the —$NR_1R_2$ group and is substituted N-heteroaryl$_{(C≤8)}$, such as 4-methylcarbamoyl-triazol-1-yl, 4-(hydroxymethyl)triazol-1-yl, 4-(fluoromethyl)triazol-1-yl, 4-(difluoromethyl)triazol-1-yl, 5-(trifluoromethyl)-1H-pyrazol-1-yl, or 3-(trifluoromethyl)-1H-pyrazol-1-yl.

In still other embodiments, $R_1$ and $R_2$ are taken together with the nitrogen atom of the —$NR_1R_2$ group and is N-heterocycloalkyl$_{(C\leq 8)}$ or substituted N-heterocycloalkyl$_{(C\leq 8)}$. In further embodiments, $R_1$ and $R_2$ are taken together with the nitrogen atom of the —$NR_1R_2$ group and is N-heterocycloalkyl$_{(C\leq 8)}$, such as oxazolidin-3-yl, azetidin-1-yl, or

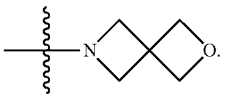 [SMILES: *N1CC2(COC2)C1]

In yet other embodiments, $R_1$ and $R_2$ are taken together with the nitrogen atom of the —$NR_1R_2$ group and is substituted N-heterocycloalkyl$_{(C\leq 8)}$, such as imidazolidin-2-one-1-yl, 3-methylimidazolidin-2-one-1-yl, oxazolidin-2-one-3-yl, azetidin-2-one-1-yl, pyrrolidin-2-one-1-yl, 3-oxoazetidin-1-yl, 3-oxopyrazolidin-1-yl, 5-oxopyrazolidin-1-yl, 3-hydroxyazetidin-1-yl, 3-fluoroazetidin-1-yl, 2-oxooxazolidin-3-yl, 2-oxoxazol-3 (2H)-yl, 2-oxo-2,3-dihydro-TH-imidazol-1-yl, 3-methyl-2-oxo-2,3-dihydro-1H-imidazol-1-yl, 3,3-difluoroazetidin-1-yl, 4-methyl-2,5-dioxopiperazin-1-yl, or 4-methyl-3-oxopiperazin-1-yl. In some embodiments, $R_1$ and $R_2$ are taken together with the nitrogen atom of the —$NR_1R_2$ group, wherein the —$NR_1R_2$ group is 3-oxo-1-(tert-butoxycarbonyl)pyrazolidin-2-yl.

In some embodiments, $R_1$ and $R_2$ are taken together with the nitrogen atom of the —$NR_1R_2$ group, wherein the —$NR_1R_2$ group is a group of the formula:

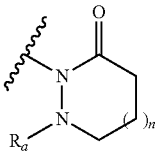 or 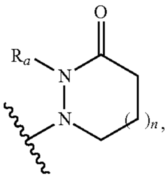, wherein:

n is 0, 1, 2, or 3;

$R_a$ is hydrogen, alkyl$_{(C\leq 8)}$, or substituted alkyl$_{(C\leq 8)}$.

In some embodiments, n is 0 or 1. In further embodiments, n is 0. In some embodiments, $R_a$ is hydrogen. In some embodiments, the —$NR_1R_2$ group is 3-oxopyrazolidin-1-yl or 5-oxopyrazolidin-1-yl. In other embodiments, $R_1$ and $R_2$ are taken together with the nitrogen atom of the —$NR_1R_2$ group and is substituted N-heterocycloalkyl$_{(C\leq 8)}$, such as a group of the formula:

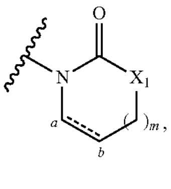, wherein:

the bond between atoms a and b is a single bond or a double bond;

m is 0, 1, 2, or 3; and $X_1$ is —$CH_2$—, —O— or —N($R_b$)—, wherein:

$R_b$ is hydrogen, alkyl$_{(C\leq 8)}$, or substituted alkyl$_{(C\leq 8)}$.

In still other embodiments, $R_1$ and $R_2$ are taken together with the nitrogen atom of the —$NR_1R_2$ group and is substituted N-heterocycloalkyl$_{(C\leq 8)}$, such as a group of the formula:

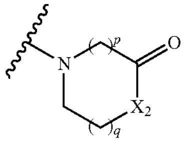 or 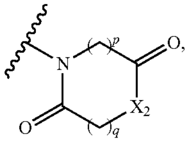, wherein:

p is 0 or 1;

q is 0 or 1; and $X_2$ is —$CH_2$—, —O—, or —N($R_e$)—, wherein:

$R_e$ is hydrogen, alkyl$_{(C\leq 8)}$, or substituted alkyl$_{(C\leq 8)}$.

In some embodiments, the bond between atoms a and b is a single bond. In other embodiments, the bond between atoms a and b is a double bond. In some embodiments, the m is 0 or 1. In further embodiments, the m is 0. In some embodiments, $X_1$ is —O—. In other embodiments, $X_1$ is —N($R_b$)—. In some embodiments, $R_b$ is hydrogen. In other embodiments, $R_b$ is alkyl$_{(C\leq 8)}$ or substituted alkyl$_{(C\leq 8)}$. In further embodiments, $R_b$ is alkyl$_{(C\leq 8)}$, such as methyl. In some embodiments, $R_1$ and $R_2$ are taken together with the nitrogen atom of the —$NR_1R_2$ group, wherein the —$NR_1R_2$ group is 3-oxo-1-(tert-butoxycarbonyl)pyrazolidin-2-yl.

In some embodiments, the compound is further defined as:

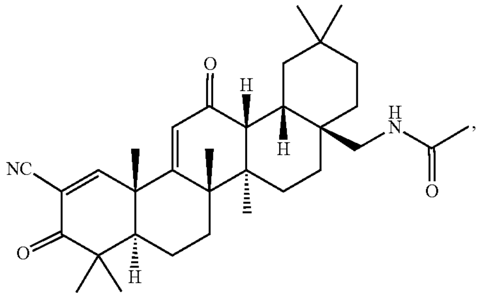,

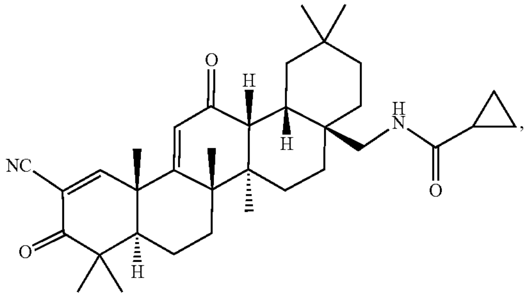,

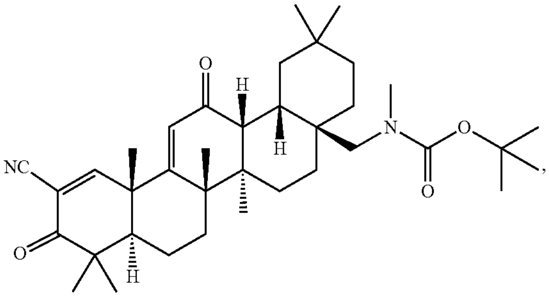,

-continued
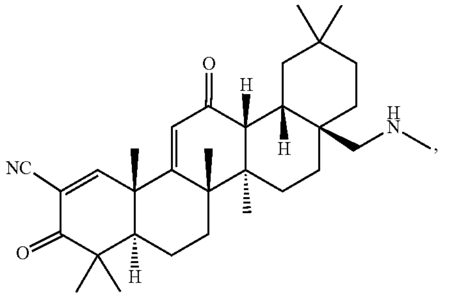
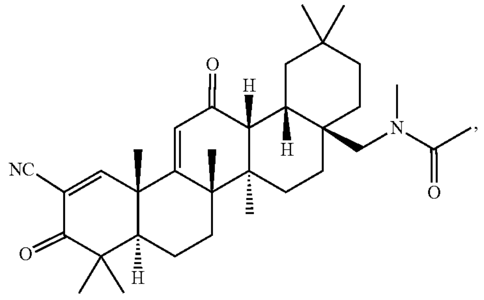
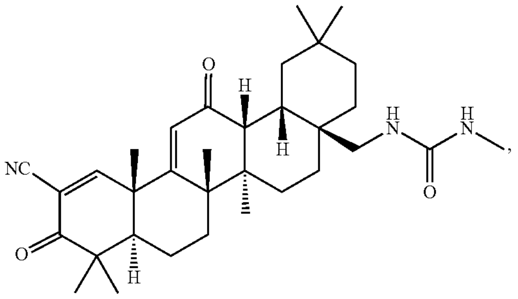
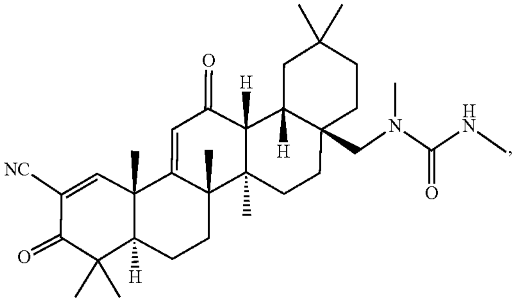
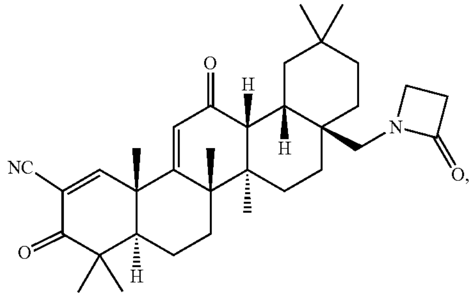
-continued
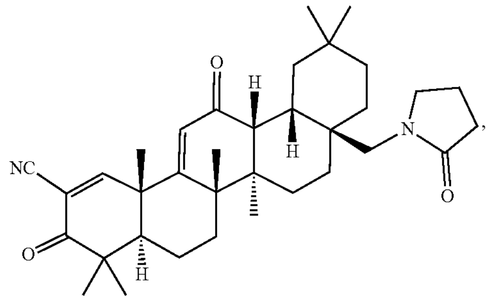
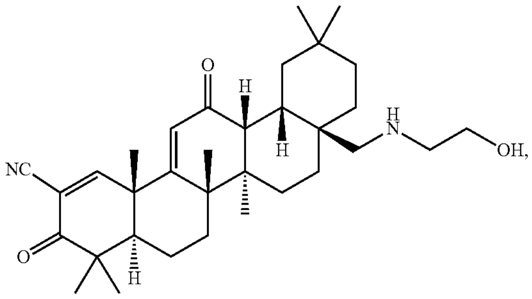
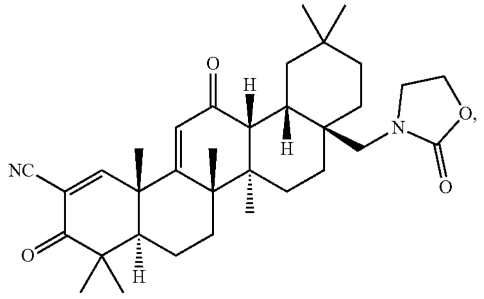
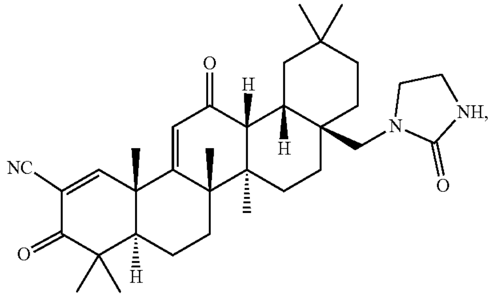
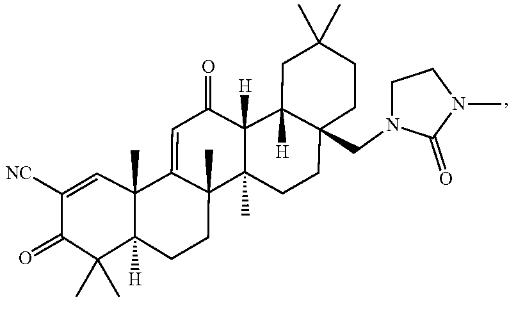

-continued
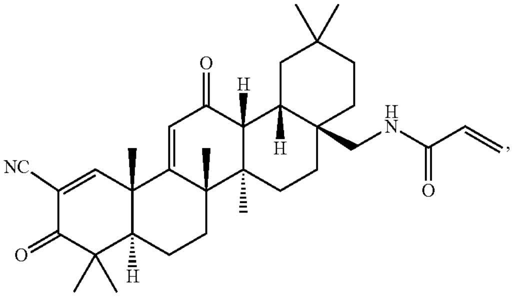
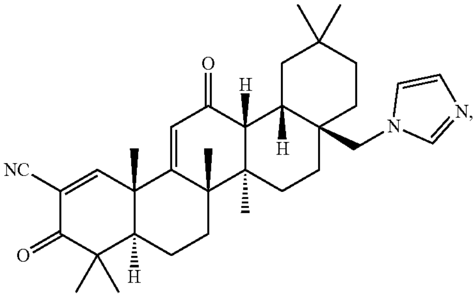
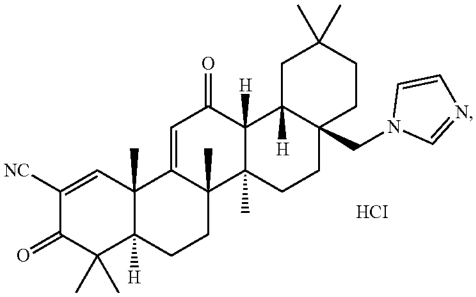
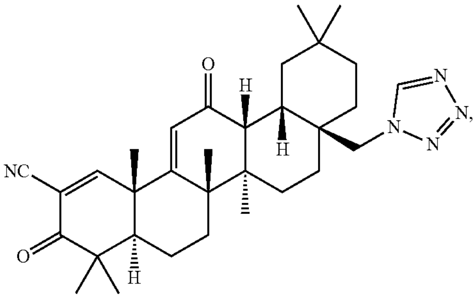
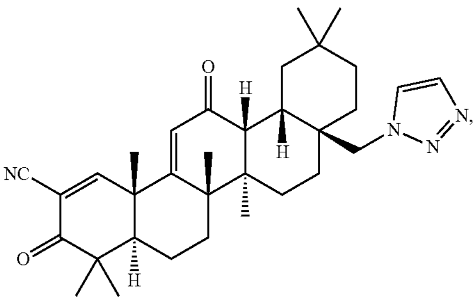
-continued
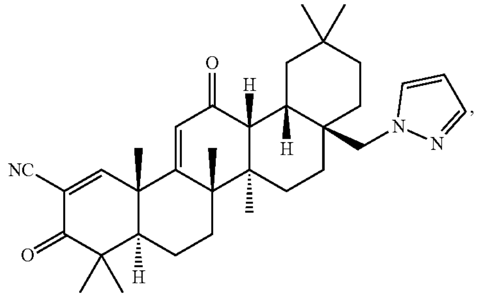
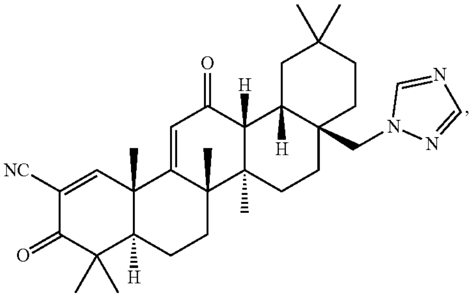
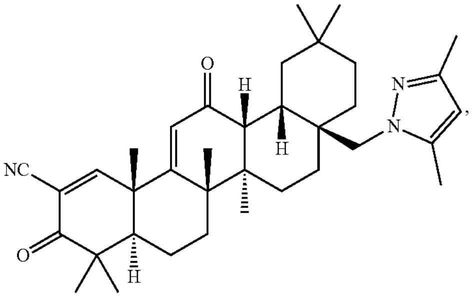
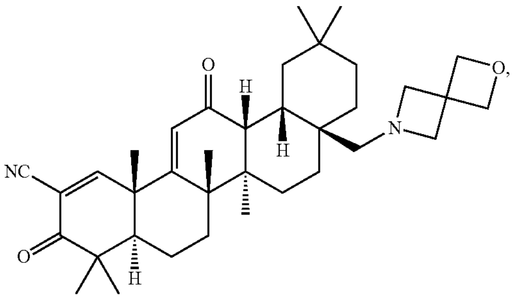
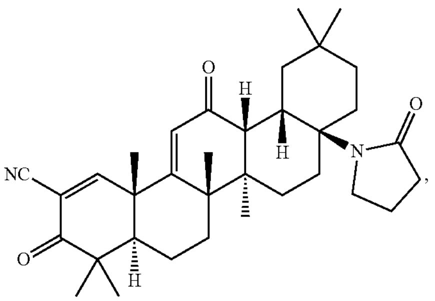

-continued
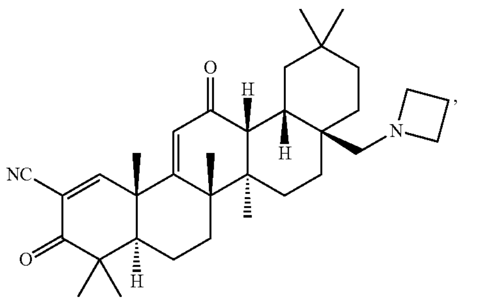
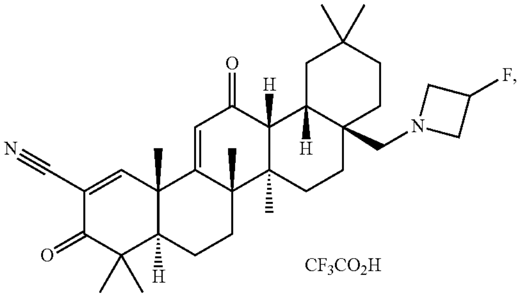
$CF_3CO_2H$
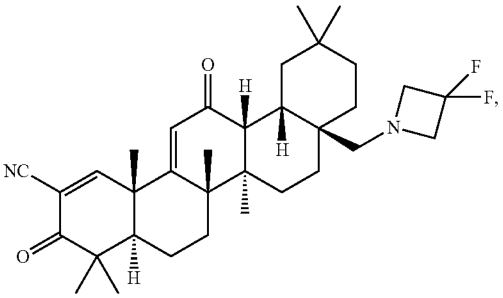
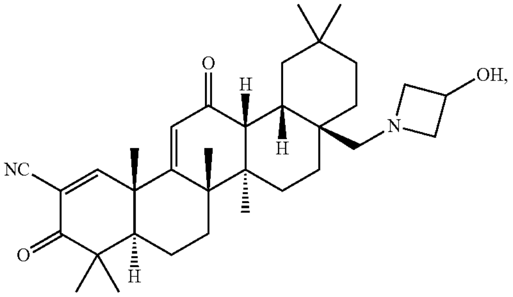
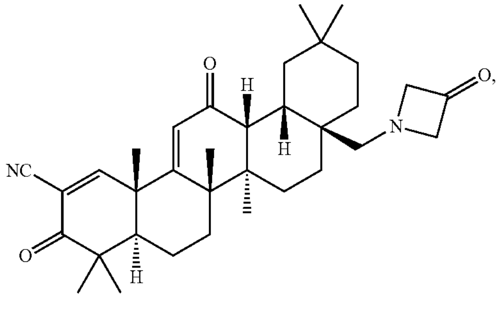
-continued
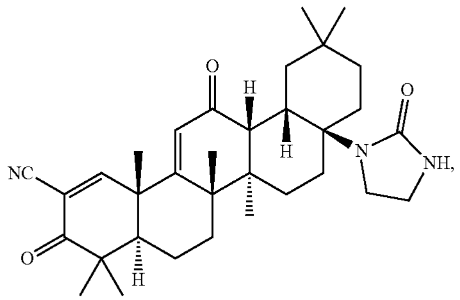
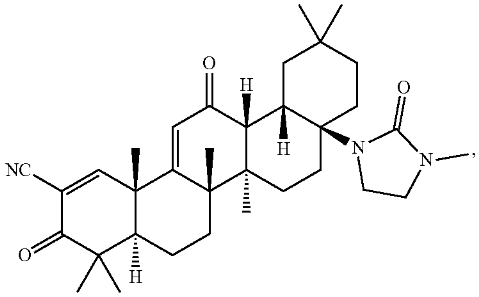
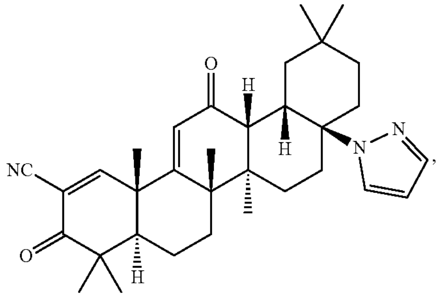
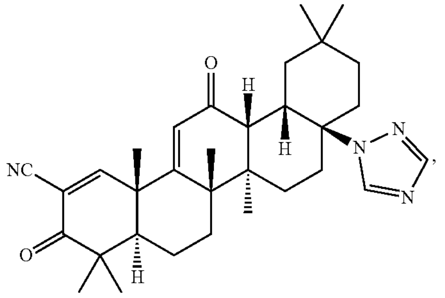
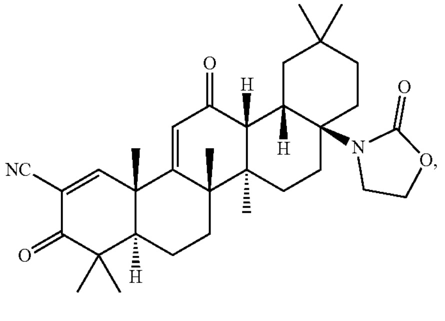

-continued
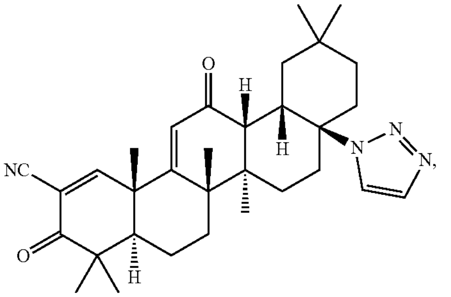
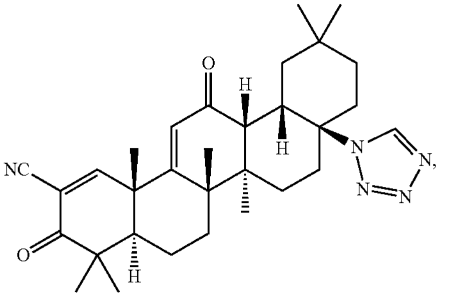
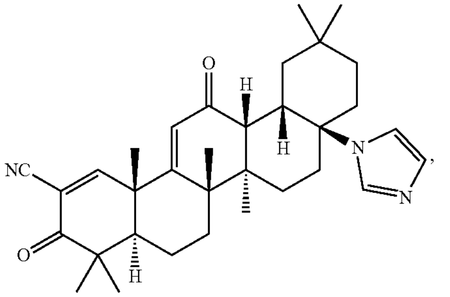
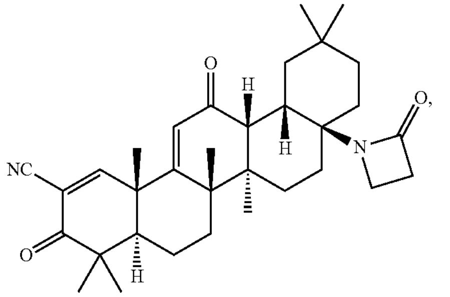
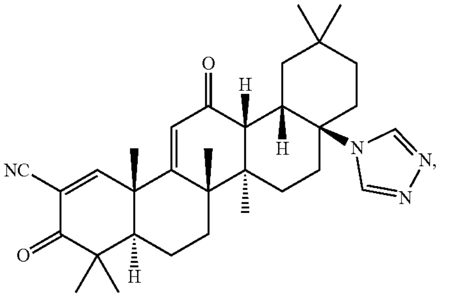
-continued
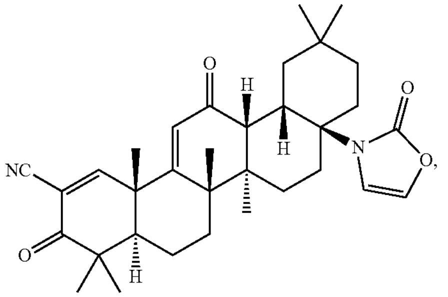
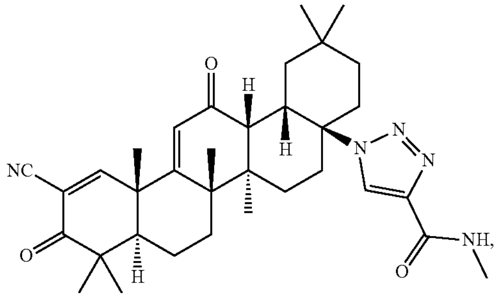
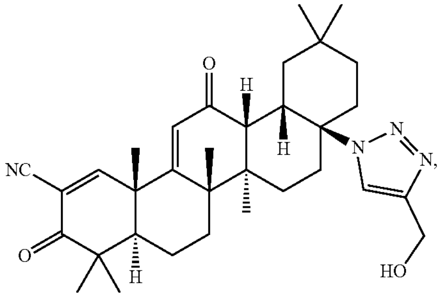
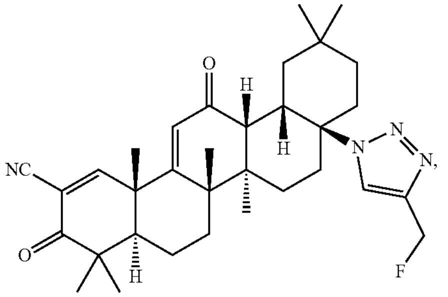
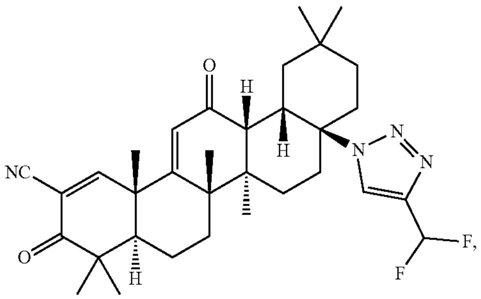

-continued
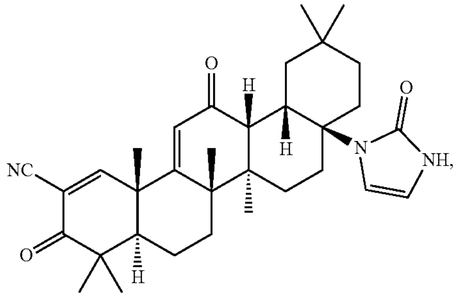
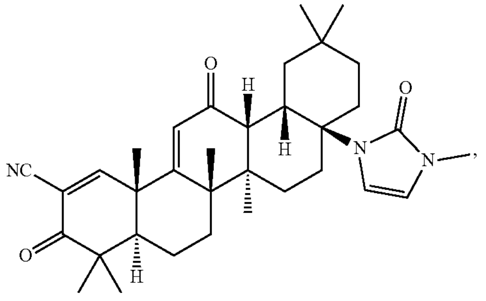
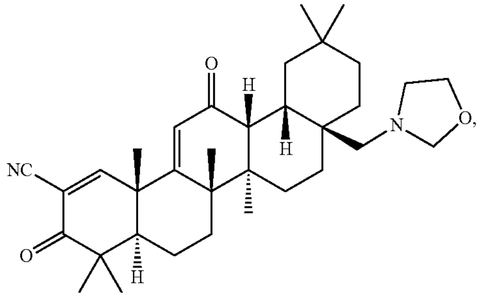
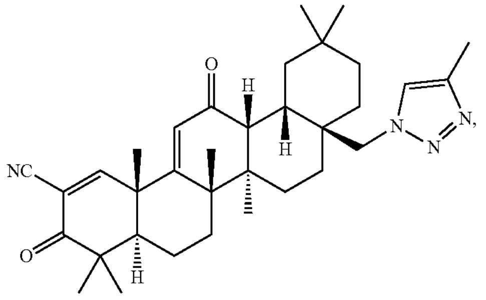
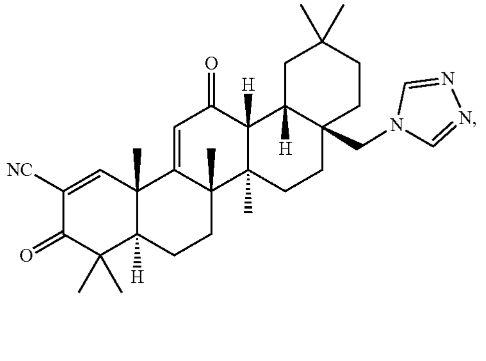
-continued
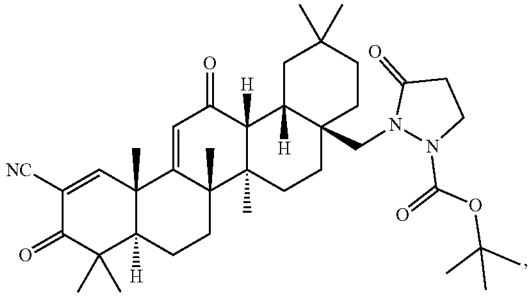
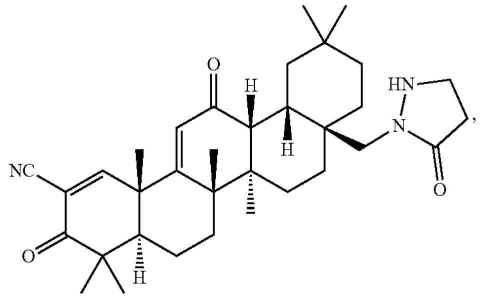
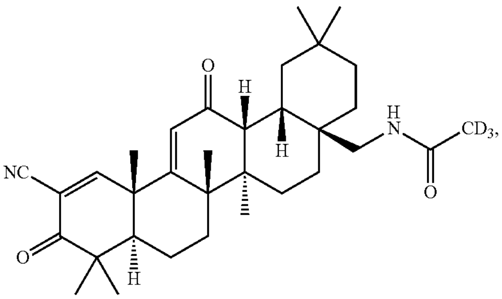
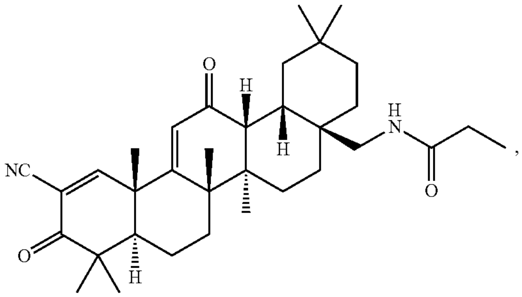
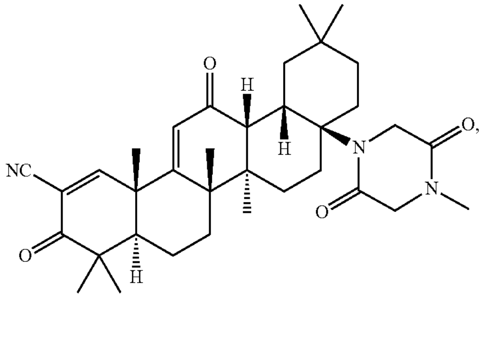

-continued
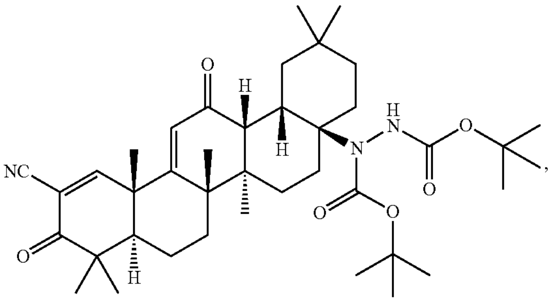
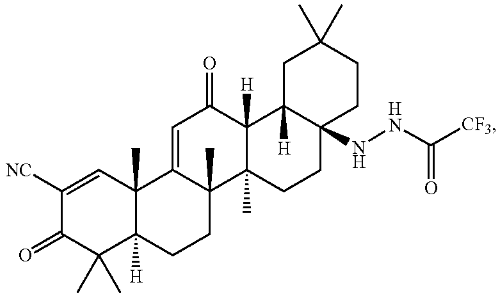
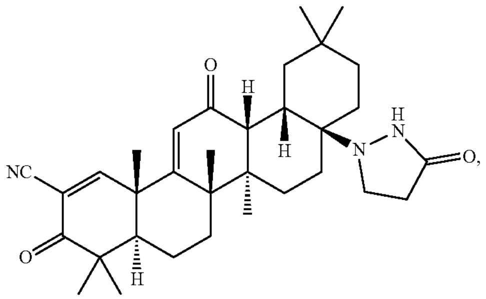
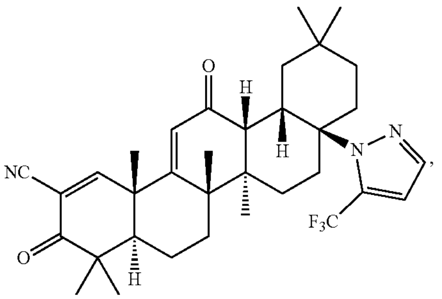
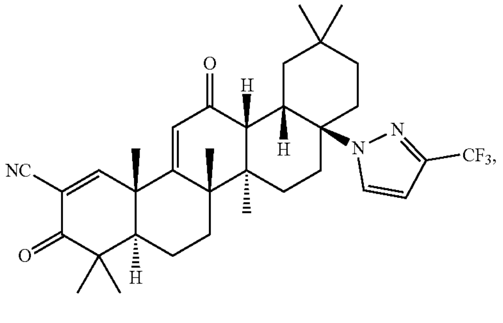
-continued
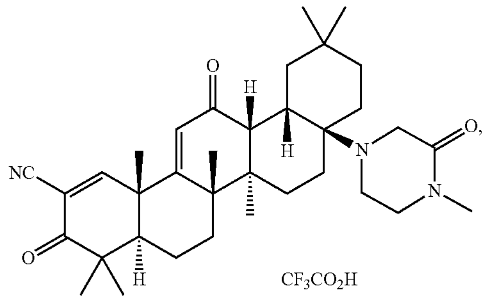
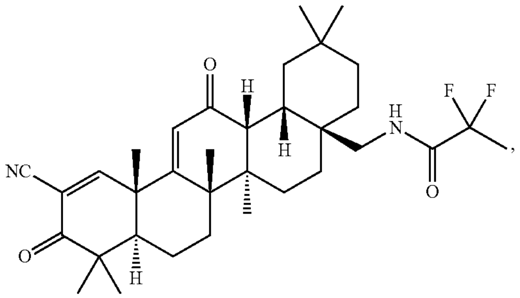
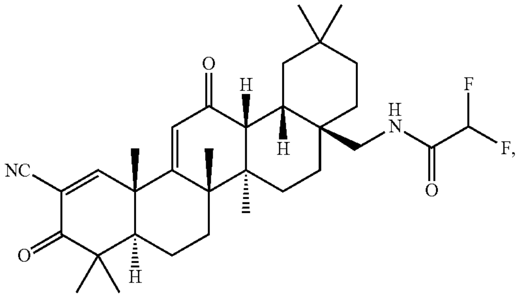
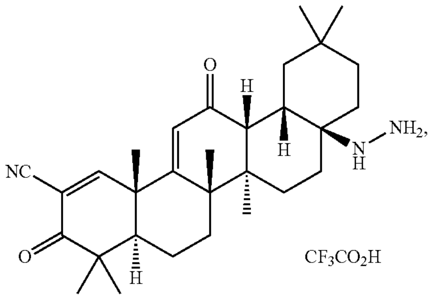
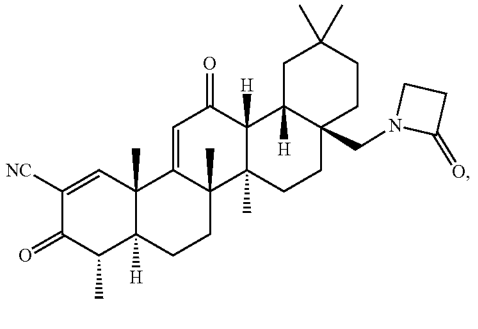

-continued

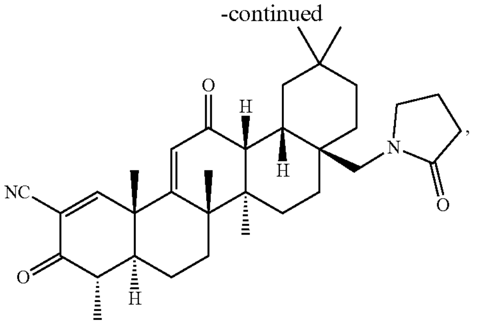

or

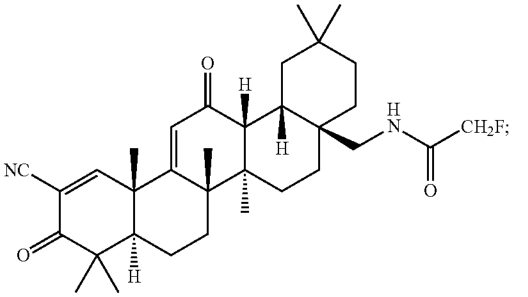

or a pharmaceutically acceptable salt of any of these formulas.

In some embodiments, the compound is further defined as:

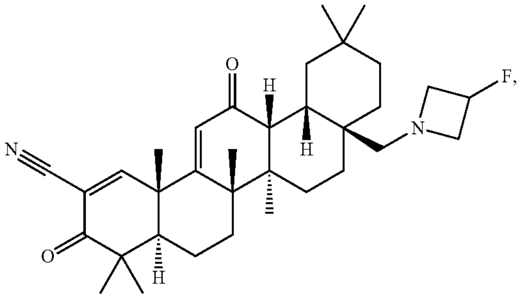

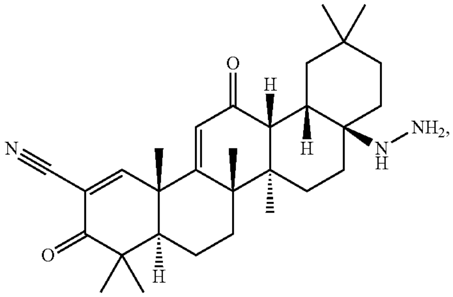

or

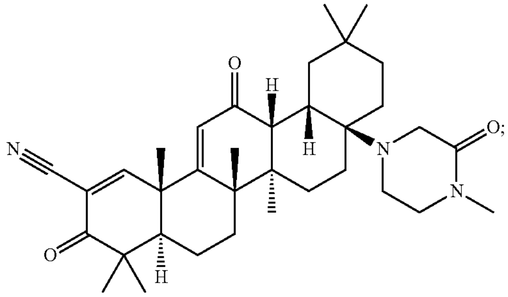

or a pharmaceutically acceptable salt of any of these formulas.

In some embodiments, the compound is further defined as:

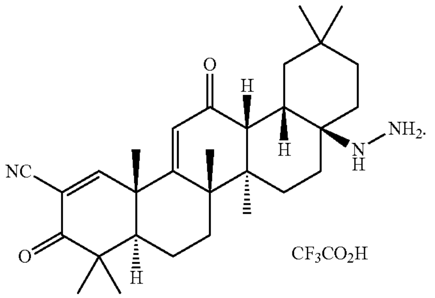

In some embodiments, the compound is further defined as:

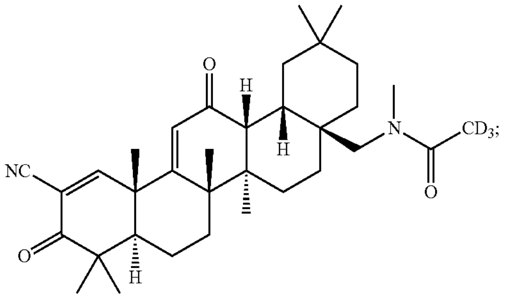

or a pharmaceutically acceptable salt of any of these formulas.

In other aspects, the present disclosure provides compounds of the formula:

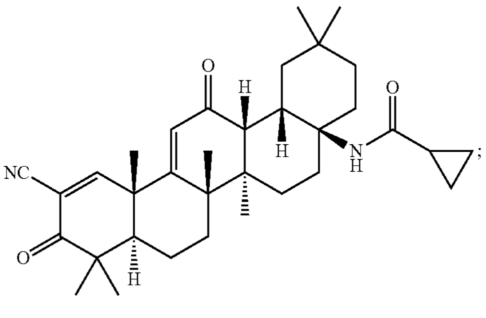

or a pharmaceutically acceptable salt of any of these formulas.

In still other aspects, the present disclosure provides pharmaceutical compositions comprising:

(A) a compound of the present disclosure; and (B) an excipient.

In some embodiments, the pharmaceutical composition is formulated for administration orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctival, subcutaneously, sublingually, topically, transbuccally, transdermally, vaginally, in crémes, in lipid compositions, via a catheter, via a lavage, via continuous infusion, via infusion, via inhalation, via injection, via local delivery, or via localized perfusion. In further embodiments, the pharmaceutical composition is formulated for oral administration. In other embodiments, the pharmaceutical composition is formulated for administration via injection. In still other embodiments, the pharmaceutical composition is formulated for intraarterial administration, intramuscular administration, intraperitoneal administration, or intravenous administration. In yet other embodiments, the pharmaceutical composition is formulated for administration topically. In further embodiments, the pharmaceutical composition is formulated for topical administration to the skin or to the eye. In some embodiments, the pharmaceutical composition is formulated as a unit dose.

In yet other aspects, the present disclosure provides methods of treating or preventing a disease or disorder in a patient in need thereof comprising administering to the patient a pharmaceutically effective amount of a compound or composition of the present disclosure. In some embodiments, the patient is a mammal, such as a human. In some embodiments, the disease or disorder is a condition associated with inflammation and/or oxidative stress. In some embodiments, the disease or disorder is cancer. In some embodiments, the disease or disorder is a cardiovascular disease, such as atherosclerosis. In some embodiments, the disease or disorder is an autoimmune disease, such as Crohn's disease, rheumatoid arthritis, lupus, or psoriasis. In some embodiments, the disease or disorder is a neurodegenerative disease, such as Alzheimer's disease, Parkinson's disease, amyotrophic lateral sclerosis, or Huntington's disease. In some embodiments, the disease or disorder is chronic kidney disease, diabetes, mucositis, inflammatory bowel disease, dermatitis, sepsis, ischemia-reperfusion injury, influenza, osteoarthritis, osteoporosis, pancreatitis, asthma, chronic obstructive pulmonary disease, cystic fibrosis, idiopathic pulmonary fibrosis, multiple sclerosis, muscular dystrophy, cachexia, or graft-versus-host disease. In some embodiments, the disease or disorder is an eye disease, such as uveitis, glaucoma, macular degeneration, or retinopathy. In some embodiments, the disease or disorder is neurological or neuropsychiatric, such as schizophrenia, depression, bipolar disorder, epilepsy, post-traumatic stress disorder, attention deficit disorder, autism, or anorexia nervosa. In some embodiments, the disease or disorder is associated with mitochondrial dysfunction, such as Friedreich's ataxia. In some embodiments, the disease or disorder is chronic pain, such as neuropathic pain.

In other aspects, the present disclosure provides methods of inhibiting nitric oxide production comprising administering to a patient in need thereof an amount of a compound or composition of the present disclosure sufficient to cause inhibition of IFN-γ-induced nitric oxide production in one or more cells of the patient.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula doesn't mean that it cannot also belong to another generic formula.

DESCRIPTION OF ILLUSTRATIVE EMBODIMENTS

Disclosed herein are new compounds and compositions with antioxidant and/or anti-inflammatory properties, methods for their manufacture, and methods for their use, including for the treatment and/or prevention of disease.

I. COMPOUNDS OF THE PRESENT INVENTION

The compounds of the present invention (also referred to as "synthetic triterpenoid derivatives," "compounds of the present disclosure" or "compounds disclosed herein") are shown, for example, above, in the summary of the invention section, the Examples below, Table 1, and in the claims below. They may be made using the synthetic methods outlined in the Examples section. These methods can be further modified and optimized using the principles and techniques of organic chemistry as applied by a person skilled in the art. Such principles and techniques are taught, for example, in Smith, *March's Advanced Organic Chemistry: Reactions, Mechanisms, and Structure*, (2013), which is incorporated by reference herein. In addition, the synthetic methods may be further modified and optimized for preparative, pilot- or large-scale production, either batch or continuous, using the principles and techniques of process chemistry as applied by a person skilled in the art. Such principles and techniques are taught, for example, in Anderson, *Practical Process Research & Development—A Guide for Organic Chemists* (2012), which is incorporated by reference herein.

TABLE 1
Examples of Synthetic Triterpenoid Derivatives Provided Herein and Selected Comparison Compounds
| Compound ID | Structural Formula |
| --- | --- |
| RTA 402 | 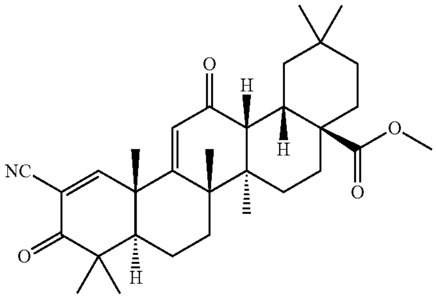 |
| CC1 | 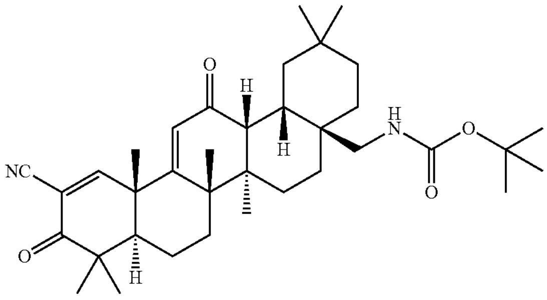 |
| CC2 | 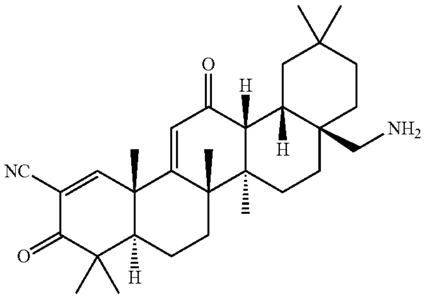 |
| CC4 | 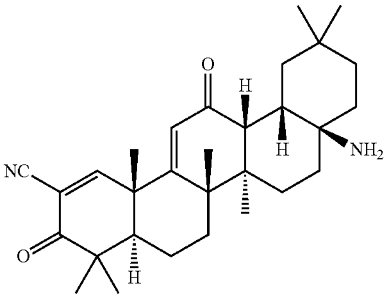 |
| T3 | 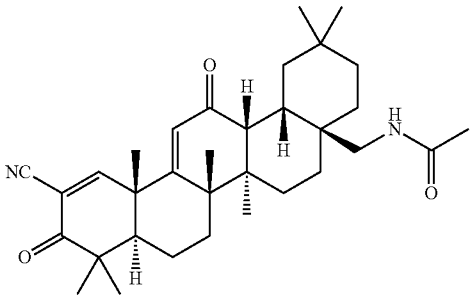 |

TABLE 1-continued
Examples of Synthetic Triterpenoid Derivatives Provided Herein and Selected Comparison Compounds
| Compound ID | Structural Formula |
| --- | --- |
| T4 | 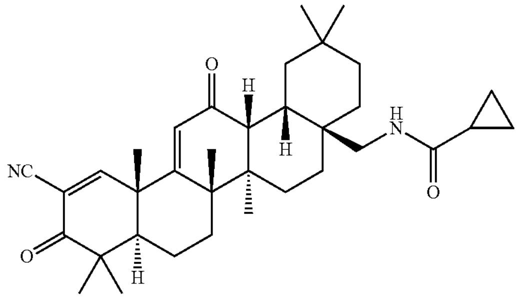 |
| T5 | 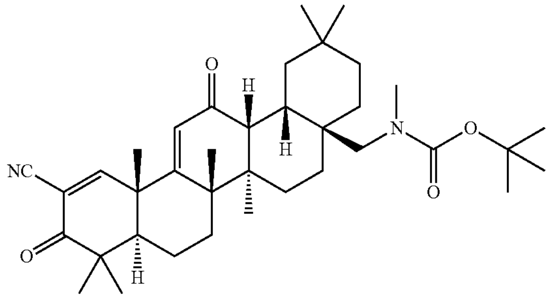 |
| T6 | 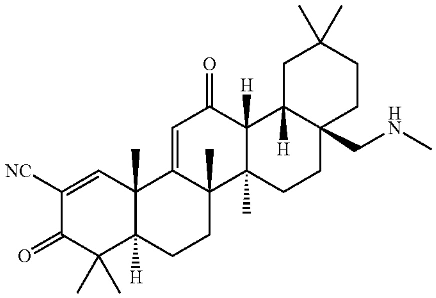 |
| T7 | 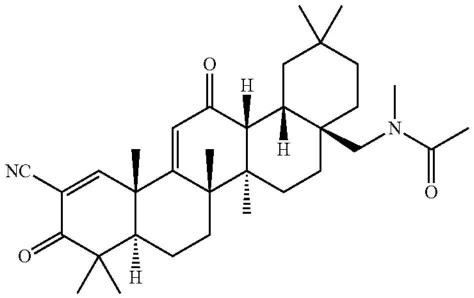 |
| T8 | 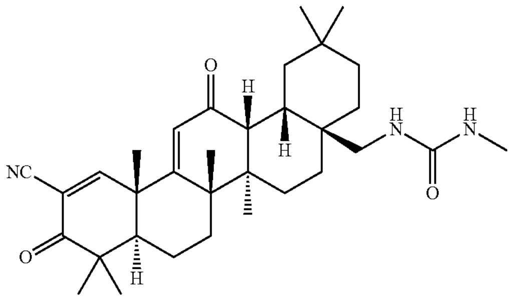

TABLE 1-continued
Examples of Synthetic Triterpenoid Derivatives Provided Herein and Selected Comparison Compounds
| Compound ID | Structural Formula |
| --- | --- |
| T9 | 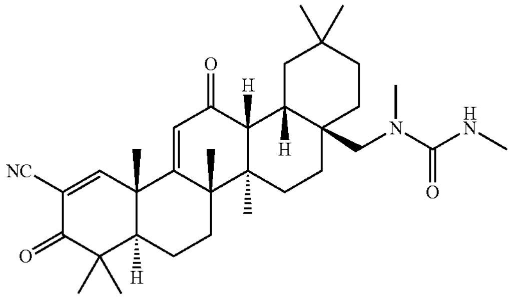 |
| T10 | 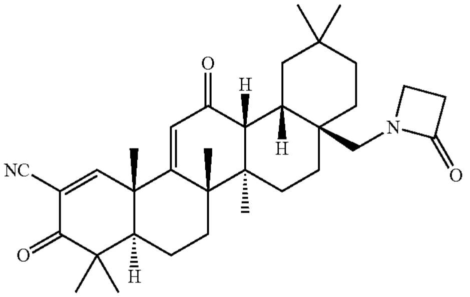 |
| T11 | 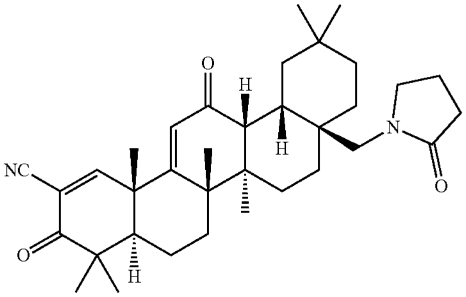 |
| T12 | 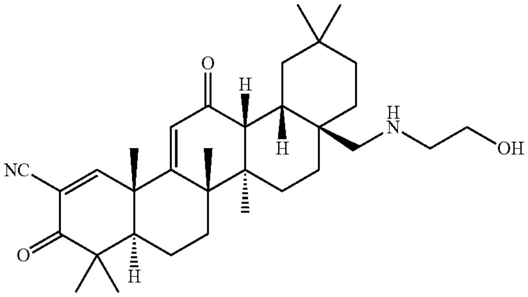 |
| T13 | 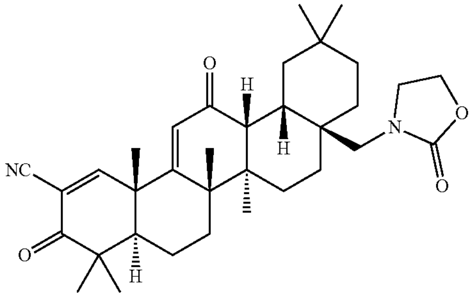 |

TABLE 1-continued
Examples of Synthetic Triterpenoid Derivatives Provided Herein and Selected Comparison Compounds
| Compound ID | Structural Formula |
| --- | --- |
| T14 | 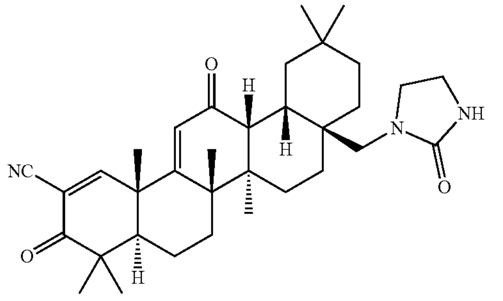 |
| T15 | 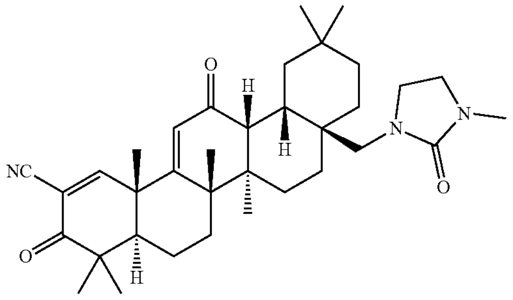 |
| T16 | 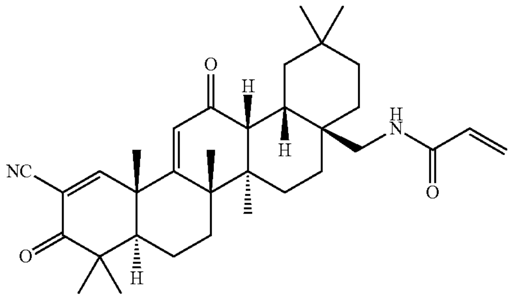 |
| T17 | 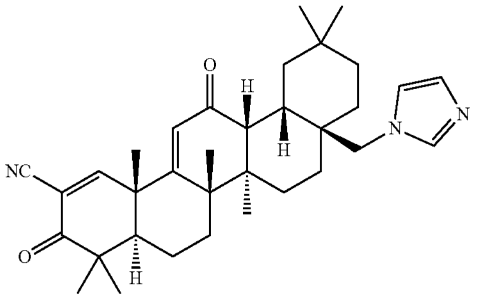 |
| T18 | 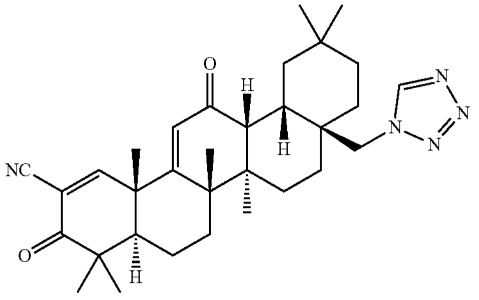 |

TABLE 1-continued
| Examples of Synthetic Triterpenoid Derivatives Provided Herein and Selected Comparison Compounds | |
|---|---|
| Compound ID | Structural Formula |
| T19 | 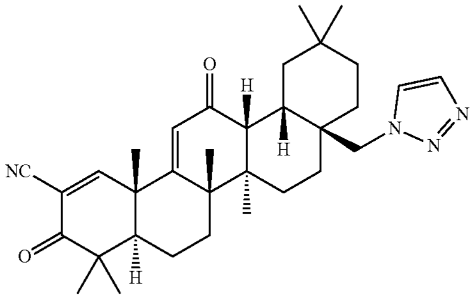 |
| T20 | 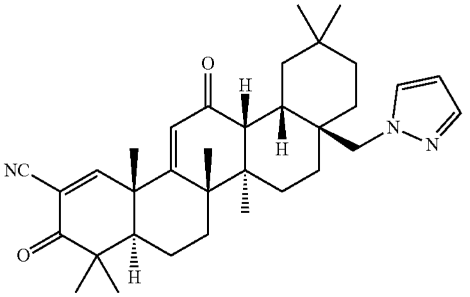 |
| T21 | 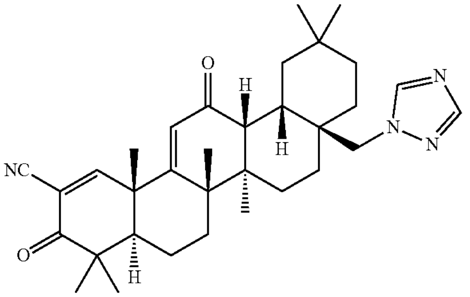 |
| T22 | 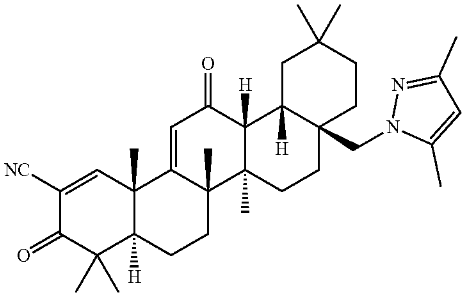 |
| T23 | 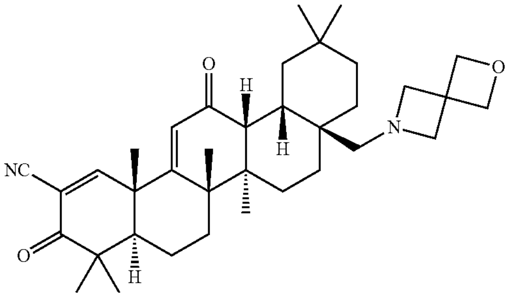 |

TABLE 1-continued
| Examples of Synthetic Triterpenoid Derivatives Provided Herein and Selected Comparison Compounds | |
|---|---|
| Compound ID | Structural Formula |
| T24 | 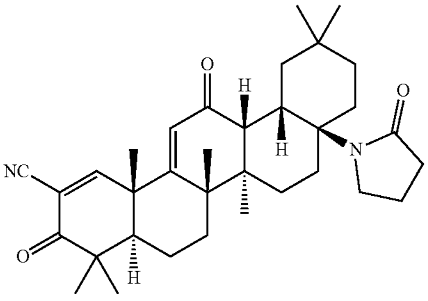 |
| T25 | 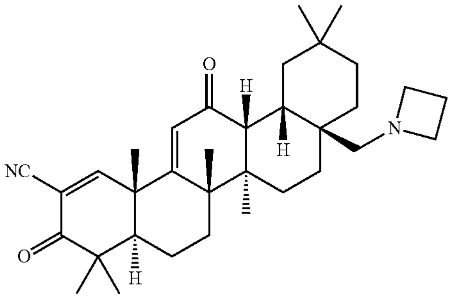 |
| T26 | 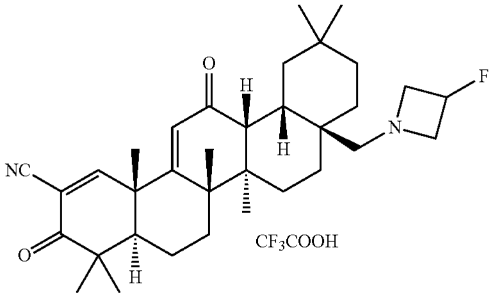 $CF_3COOH$ |
| T27 | 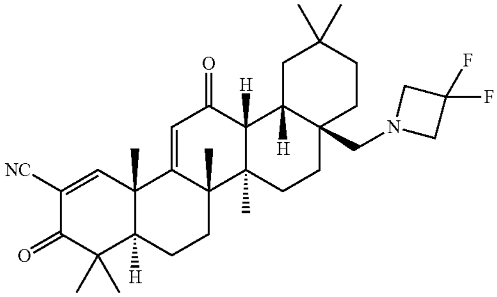 |
| T28 | 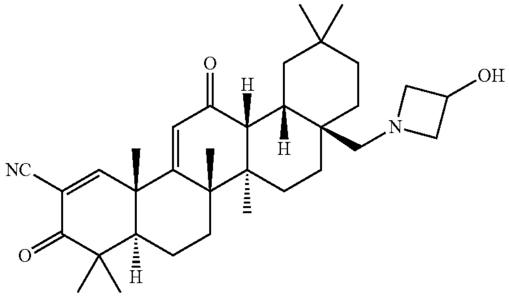 |

TABLE 1-continued
| Examples of Synthetic Triterpenoid Derivatives Provided Herein and Selected Comparison Compounds | |
|---|---|
| Compound ID | Structural Formula |
| T29 | 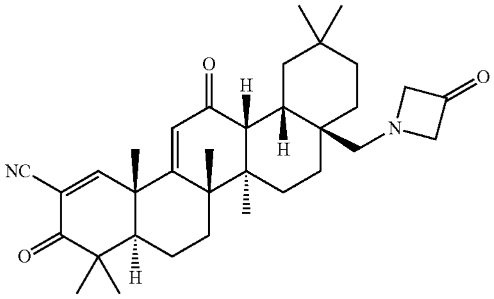 |
| T30 | 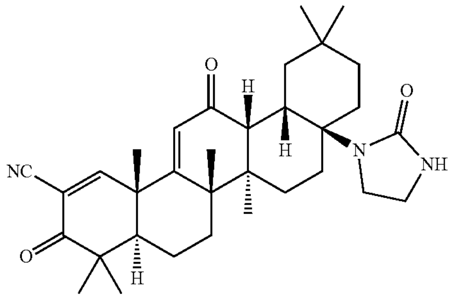 |
| T31 | 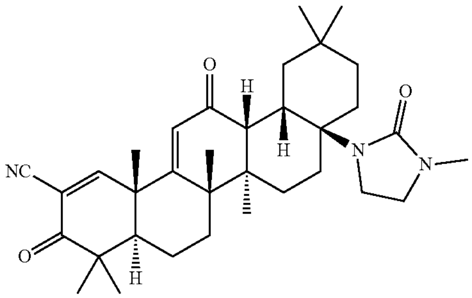 |
| T32 | 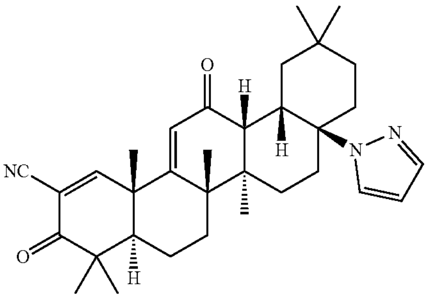 |
| T33 | 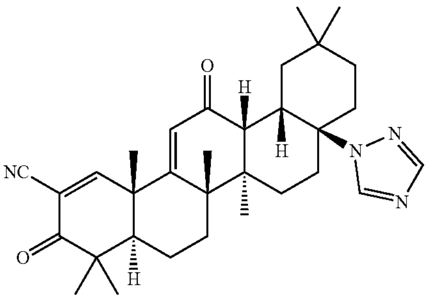 |

TABLE 1-continued
| Examples of Synthetic Triterpenoid Derivatives Provided Herein and Selected Comparison Compounds | |
|---|---|
| Compound ID | Structural Formula |
| T34 | 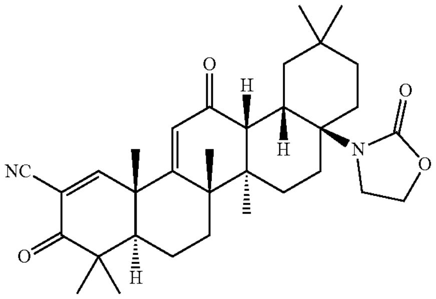 |
| T35 | 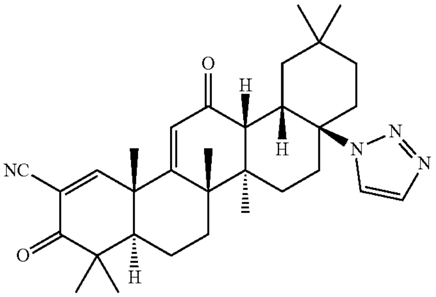 |
| T36 | 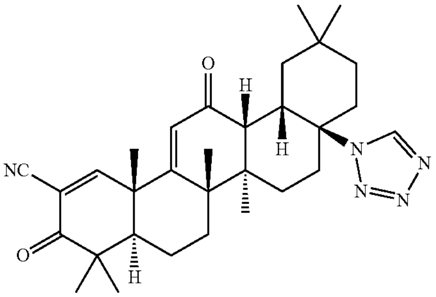 |
| T37 | 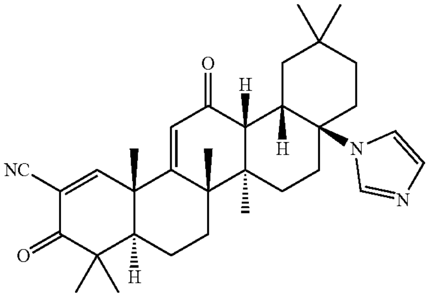 |
| T38 | 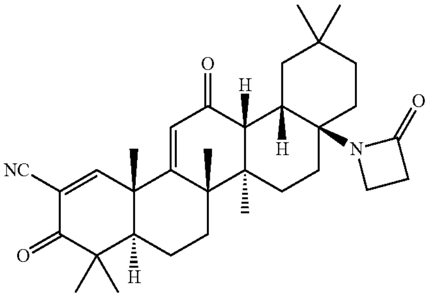 |

TABLE 1-continued
Examples of Synthetic Triterpenoid Derivatives Provided Herein and Selected Comparison Compounds
| Compound ID | Structural Formula |
|---|---|
| T39 | 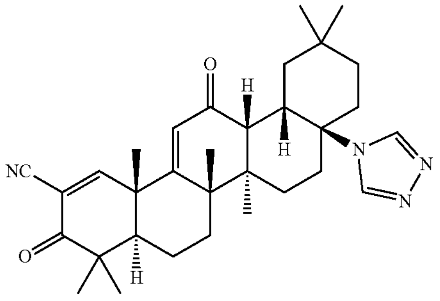 |
| T40 | 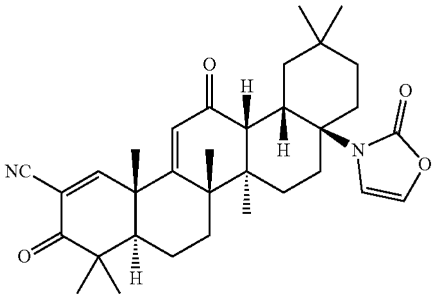 |
| T41 | 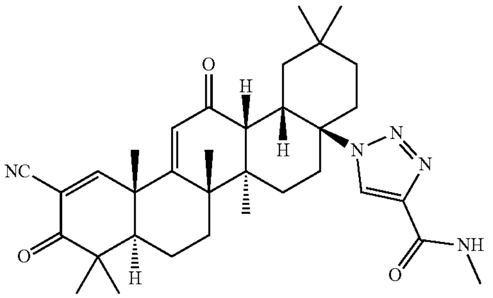 |
| T42 | 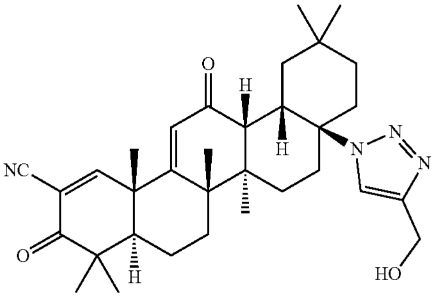 |
| T43 | 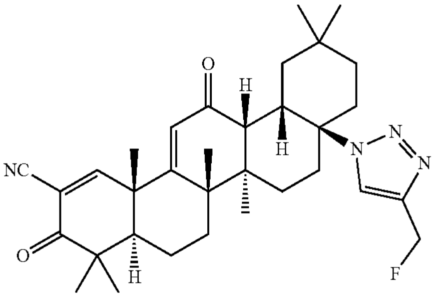 |

TABLE 1-continued
| Examples of Synthetic Triterpenoid Derivatives Provided Herein and Selected Comparison Compounds | |
|---|---|
| Compound ID | Structural Formula |
| T44 | 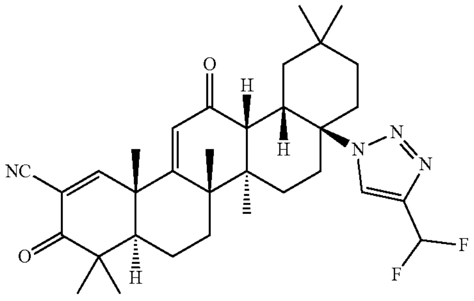 |
| T45 | 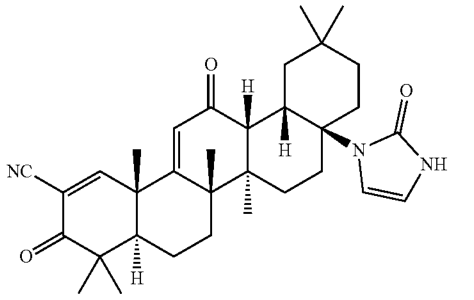 |
| T46 | 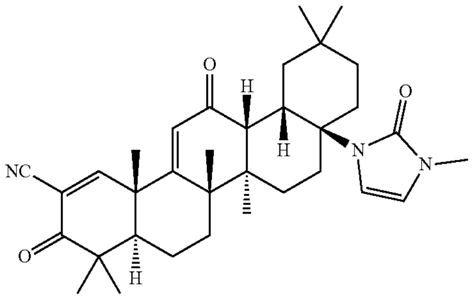 |
| T47 | 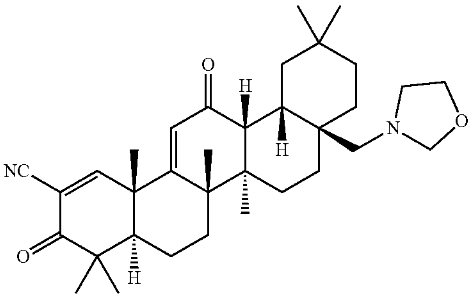 |
| T48 | 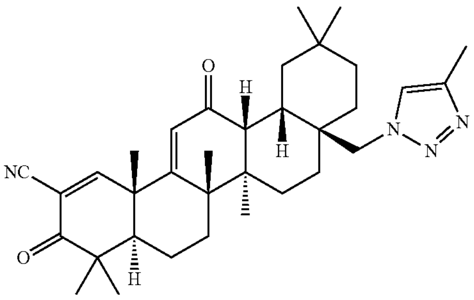 |

TABLE 1-continued
| Examples of Synthetic Triterpenoid Derivatives Provided Herein and Selected Comparison Compounds | |
|---|---|
| Compound ID | Structural Formula |
| T49 | 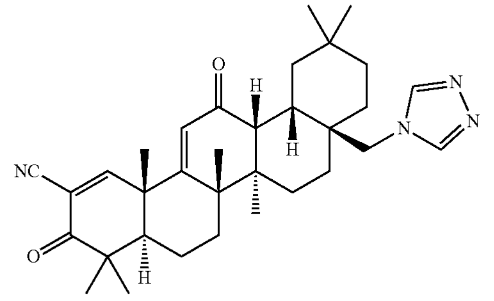 |
| T50 | 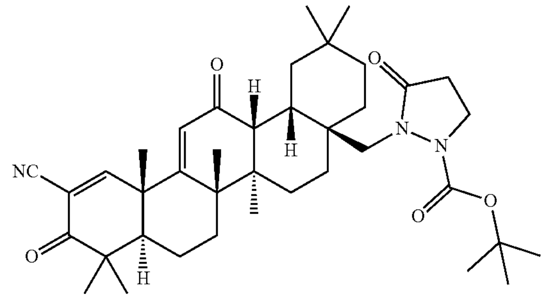 |
| T51 | 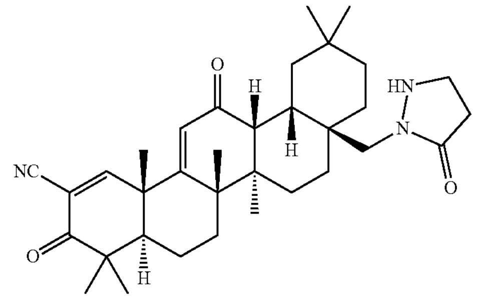 |
| T52 | 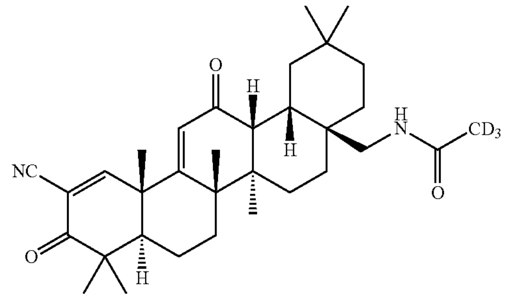 |
| T53 | 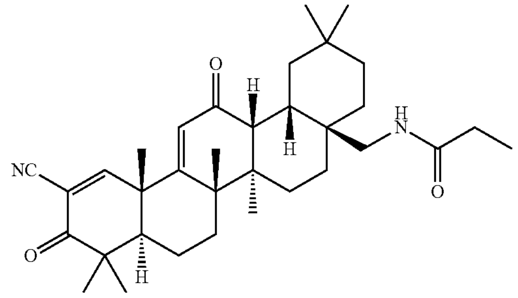 |

TABLE 1-continued
| Examples of Synthetic Triterpenoid Derivatives Provided Herein and Selected Comparison Compounds | |
|---|---|
| Compound ID | Structural Formula |
| T54 | 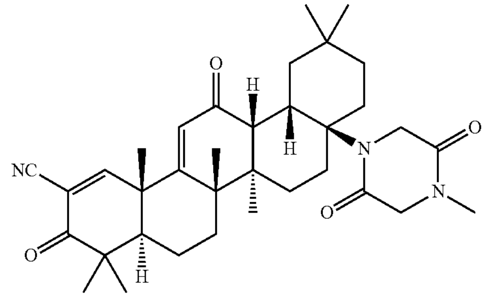 |
| T55 | 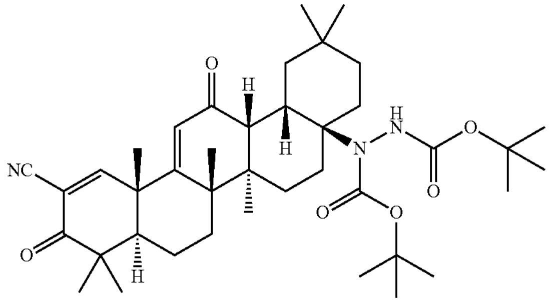 |
| T56 | 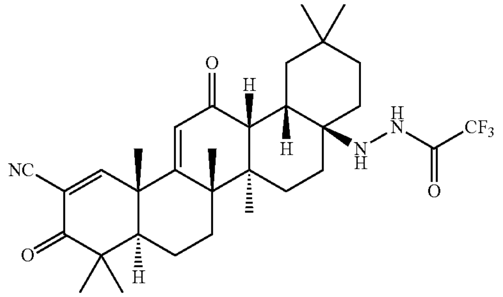 |
| T57 | 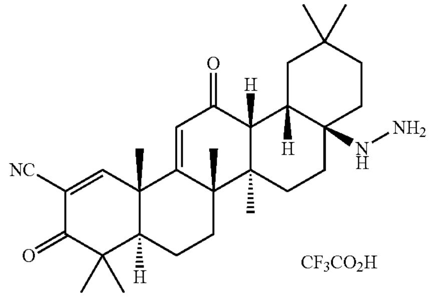 |
| T58 | 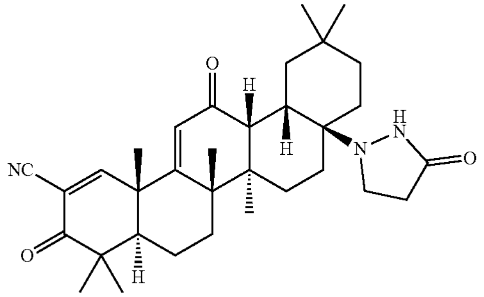 |

TABLE 1-continued
Examples of Synthetic Triterpenoid Derivatives Provided Herein and Selected Comparison Compounds
| Compound ID | Structural Formula |
|---|---|
| T59 | 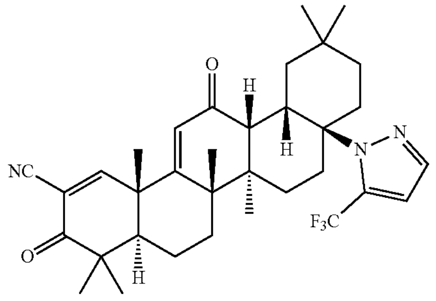 |
| T60 | 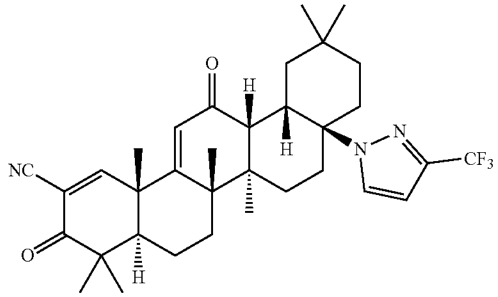 |
| T61 | 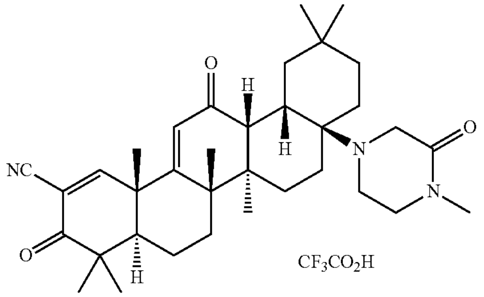 $CF_3CO_2H$ |
| T62 | 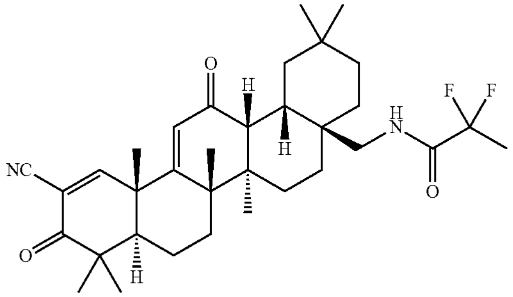 |
| T63 | 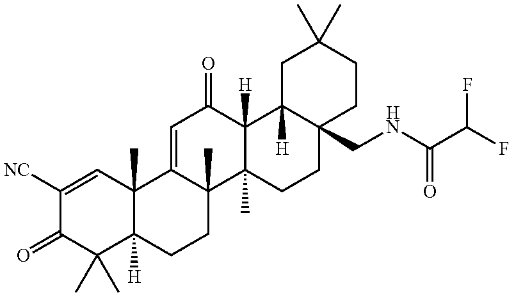 |

TABLE 1-continued
| Examples of Synthetic Triterpenoid Derivatives Provided Herein and Selected Comparison Compounds | |
|---|---|
| Compound ID | Structural Formula |
| T64 | 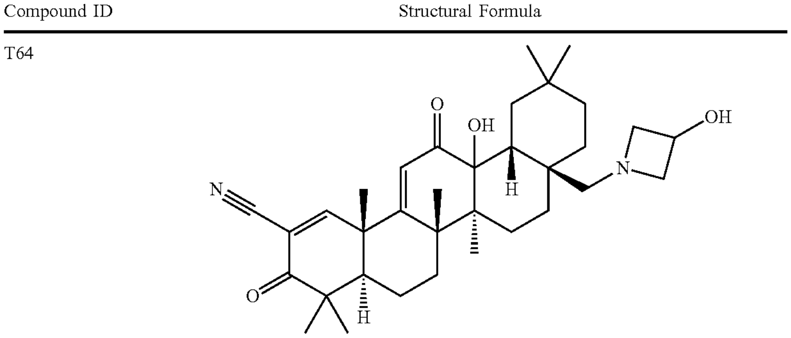 |
| T65 | 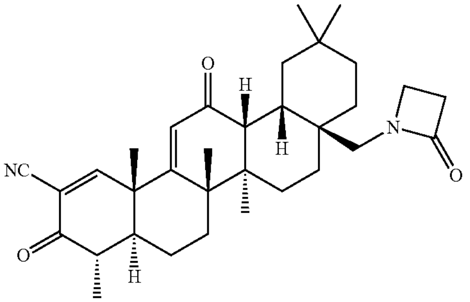 |
| T66 | 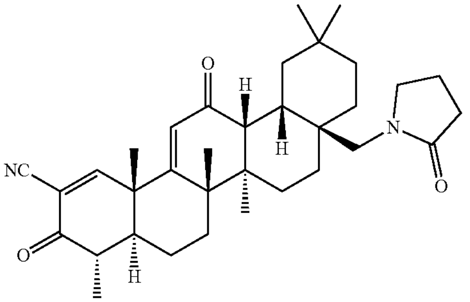 |
| T67 | 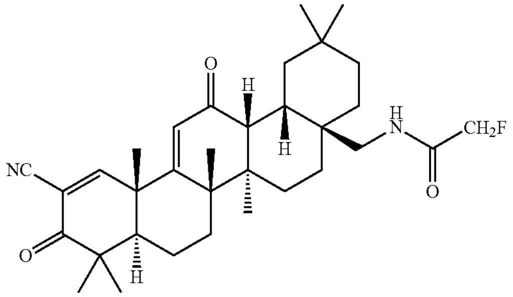 |
| T68 | 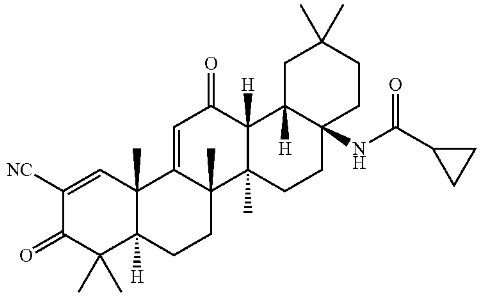 |

TABLE 1-continued

| Examples of Synthetic Triterpenoid Derivatives Provided Herein and Selected Comparison Compounds | |
|---|---|
| Compound ID | Structural Formula |
| P3 | 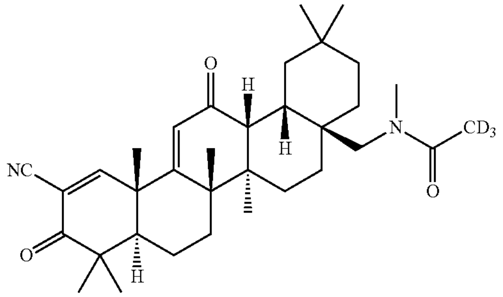 |

All the compounds of the present invention may in some embodiments be used for the prevention and treatment of one or more diseases or disorders discussed herein or otherwise. In some embodiments, one or more of the compounds characterized or exemplified herein as an intermediate, a metabolite, and/or prodrug, may nevertheless also be useful for the prevention and treatment of one or more diseases or disorders. As such unless explicitly stated to the contrary, all the compounds of the present invention are deemed "active compounds" and "therapeutic compounds" that are contemplated for use as active pharmaceutical ingredients (APIs). Actual suitability for human or veterinary use is typically determined using a combination of clinical trial protocols and regulatory procedures, such as those administered by the Food and Drug Administration (FDA). In the United States, the FDA is responsible for protecting the public health by assuring the safety, effectiveness, quality, and security of human and veterinary drugs, vaccines and other biological products, and medical devices.

In some embodiments, the compounds of the present invention have the advantage that they may be more efficacious than, be less toxic than, be longer acting than, be more potent than, produce fewer side effects than, be more easily absorbed than, more metabolically stable, more lipophilic than, more hydrophilic than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

Chemical formulas used to represent compounds of the present invention will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

In some embodiments, compounds of the present invention exist in prodrug form. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a patient, cleaves to form a hydroxy, amino, or carboxylic acid, respectively.

In some embodiments, compounds of the present invention exist in salt or non-salt form. With regard to the salt form(s), in some embodiments the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

It will be appreciated that many organic compounds can form complexes with solvents in which they are reacted or from which they are precipitated or crystallized. These complexes are known as "solvates." Where the solvent is water, the complex is known as a "hydrate." It will also be appreciated that many organic compounds can exist in more than one solid form, including crystalline and amorphous forms. All solid forms of the compounds provided herein, including any solvates thereof are within the scope of the present invention.

The present invention particularly relates to the following items:

1. A compound of the formula:

(I)

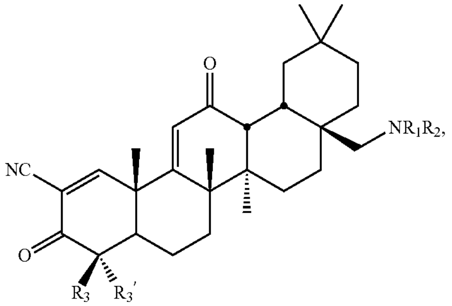

wherein:

$R_1$ and $R_2$ are each independently hydrogen, alkyl$_{(C\leq 8)}$, substituted alkyl$_{(C\leq 8)}$, or —C(O)$R_4$, wherein:

$R_4$ is hydrogen; or alkyl$_{(C\leq 8)}$, alkenyl$_{(C\leq 8)}$, alkynyl$_{(C\leq 8)}$, alkoxy$_{(C\leq 8)}$, alkylamino$_{(C\leq 8)}$, dialkylamino$_{(C\leq 8)}$, cycloalkyl$_{(C\leq 8)}$, cycloalkoxy$_{(C\leq 8)}$, cycloalkylamino$_{(C\leq 8)}$, heterocycloalkyl$_{(C\leq 8)}$, or a substituted version of any one of these groups; or $R_1$ and $R_2$ are taken together with the nitrogen atom of the —$NR_1R_2$ group, wherein the —$NR_1R_2$ group is N-heteroaryl$_{(C\leq 8)}$, substituted N-heteroaryl$_{(C\leq 8)}$, N-heterocycloalkyl$_{(C\leq 8)}$, or substituted N-heterocycloalkyl$_{(C\leq 8)}$; and $R_3$ and $R_3$' are each independently hydrogen, alkyl$_{(C\leq 8)}$, or substituted alkyl$_{(C\leq 8)}$;

or a pharmaceutically acceptable salt thereof.

2. The compound of item 1 further defined as:

(IA)

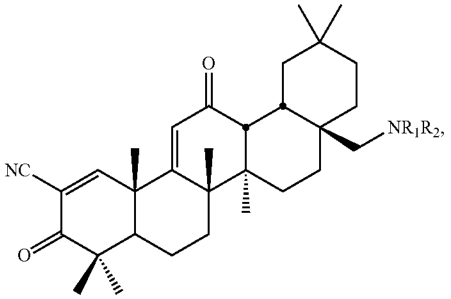

wherein:

$R_1$ and $R_2$ are each independently hydrogen, alkyl$_{(C\leq 8)}$, substituted alkyl$_{(C\leq 8)}$, or —C(O)$R_4$, wherein:

$R_4$ is hydrogen; or alkyl$_{(C\leq 8)}$, alkenyl$_{(C\leq 8)}$, alkynyl$_{(C\leq 8)}$, alkoxy$_{(C\leq 8)}$, alkylamino$_{(C\leq 8)}$, dialkylamino$_{(C\leq 8)}$, cycloalkyl$_{(C\leq 8)}$, cycloalkoxy$_{(C\leq 8)}$, cycloalkylamino$_{(C\leq 8)}$, heterocycloalkyl$_{(C\leq 8)}$, or a substituted version of any one of these groups; or $R_1$ and $R_2$ are taken together with the nitrogen atom of the —$NR_1R_2$ group, wherein the —$NR_1R_2$ group is N-heteroaryl$_{(C\leq 8)}$, substituted N-heteroaryl$_{(C\leq 8)}$, N-heterocycloalkyl$_{(C\leq 8)}$, or substituted N-heterocycloalkyl$_{(C\leq 8)}$;

or a pharmaceutically acceptable salt thereof.

3. The compound of item 1, wherein $R_3$ is alkyl$_{(C\leq 8)}$ or substituted alkyl$_{(C\leq 8)}$.
4. The compound of either item 1 or item 3, wherein $R_3$ is alkyl$_{(C\leq 8)}$.
5. The compound according to any one of items 1, 3, and 4, wherein $R_3$ is methyl.
6. The compound according to any one of items 1 and 3-5, wherein $R_3$' is alkyl$_{(C\leq 8)}$ or substituted alkyl$_{(C\leq 8)}$.
7. The compound according to any one of items 1 and 3-6, wherein $R_3$' is alkyl$_{(C\leq 8)}$.
8. The compound according to any one of item 1 and 3-7, wherein $R_3$' is methyl.
9. The compound according to any one of items 1-8, wherein $R_1$ is hydrogen, alkyl$_{(C\leq 8)}$, or substituted alkyl$_{(C\leq 8)}$.
10. The compound according to any one of items 1-9, wherein $R_1$ is hydrogen.
11. The compound according to any one of items 1-9, wherein $R_1$ is alkyl$_{(C\leq 8)}$ or substituted alkyl$_{(C\leq 8)}$.
12. The compound according to any one of items 1-9 and 11, wherein $R_1$ is alkyl$_{(C\leq 8)}$.
13. The compound according to any one of items 1-9, 11, and 12, wherein $R_1$ is methyl.
14. The compound according to any one of items 1-13, wherein $R_2$ is hydrogen, alkyl$_{(C\leq 8)}$, or substituted alkyl$_{(C\leq 8)}$.
15. The compound according to any one of items 1-14, wherein $R_2$ is hydrogen.
16. The compound according to any one of items 1-14, wherein $R_2$ is alkyl$_{(C\leq 8)}$ or substituted alkyl$_{(C\leq 8)}$.
17. The compound according to any one of items 1-14 and 16, wherein $R_2$ is alkyl$_{(C\leq 8)}$.
18. The compound according to any one of items 1-14, 16, and 17, wherein $R_2$ is methyl.
19. The compound according to any one of items 1-14 and 16, wherein $R_2$ is substituted alkyl$_{(C\leq 8)}$.
20. The compound according to any one of items 1-14, 16, and 19, wherein $R_2$ is 1-hydroxyeth-2-yl.
21. The compound according to any one of items 1-13, wherein $R_4$ is alkyl$_{(C\leq 8)}$ or substituted alkyl$_{(C\leq 8)}$.
22. The compound according to any one of items 1-13 and 21, wherein $R_4$ is alkyl$_{(C\leq 8)}$.
23. The compound according to any one of items 1-13, 21, and 22, wherein $R_4$ is methyl.
24. The compound of item 23, wherein the methyl is substantially trideuteriomethyl.
25. The compound of item 24, wherein the isotopic enrichment of deuterium at each of the three positions is greater than 90%.
26. The compound according to any one of items 1-13, wherein $R_4$ is cycloalkyl$_{(C\leq 8)}$ or substituted cycloalkyl$_{(C\leq 8)}$.
27. The compound according to any one of items 1-13 and 26, wherein $R_4$ is cycloalkyl$_{(C\leq 8)}$.
28. The compound according to any one of items 1-13, 26, and 27, wherein $R_4$ is cyclopropyl.
29. The compound according to any one of items 1-13, wherein $R_4$ is alkoxy$_{(C\leq 8)}$ or substituted alkoxy$_{(C\leq 8)}$.
30. The compound according to any one of items 1-13 and 29, wherein $R_4$ is alkoxy$_{(C\leq 8)}$.
31. The compound according to any one of items 1-13, 29, and 30, wherein $R_4$ is t-butoxy.

32. The compound according to any one of items 1-13, wherein $R_4$ is alkylamino$_{(C\leq8)}$ or substituted alkylamino$_{(C\leq8)}$.

33. The compound according to any one of items 1-13 and 32, wherein $R_4$ is alkylamino$_{(C\leq8)}$.

34. The compound according to any one of items 1-13, 32, and 33, wherein $R_4$ is methylamino.

35. The compound according to any one of items 1-13, wherein $R_4$ is alkenyl$_{(C\leq8)}$ or substituted alkenyl$_{(C\leq8)}$.

36. The compound according to any one of items 1-13 and 35, wherein $R_4$ is alkenyl$_{(C\leq8)}$.

37. The compound according to any one of items 1-13, 35, and 36, wherein $R_4$ is ethenyl.

38. The compound according to any one of items 1-8, wherein $R_1$ and $R_2$ are taken together with the nitrogen atom of the —$NR_1R_2$ group, wherein the —$NR_1R_2$ group is N-heteroaryl$_{(C\leq8)}$, substituted N-heteroaryl$_{(C\leq8)}$, N-heterocycloalkyl$_{(C\leq8)}$, or substituted N-heterocycloalkyl$_{(C\leq8)}$.

39. The compound according to any one of items 1-8 and 38, wherein $R_1$ and $R_2$ are taken together with the nitrogen atom of the —$NR_1R_2$ group, wherein the —$NR_1R_2$ group is N-heteroaryl$_{(C\leq8)}$ or substituted N-heteroaryl$_{(C\leq8)}$.

40. The compound according to any one of items 1-8, 38, and 39, wherein $R_1$ and $R_2$ are taken together with the nitrogen atom of the —$NR_1R_2$ group, wherein the —$NR_1R_2$ group is N-heteroaryl$_{(C\leq8)}$.

41. The compound according to any one of items 1-8 and 38-40, wherein $R_1$ and $R_2$ are taken together with the nitrogen atom of the —$NR_1R_2$ group, wherein the —$NR_1R_2$ group is 3,5-dimethylpyrazol-1-yl, triazoly-1-yl, 1,2,4-triazoly-1-yl, pyrazol-1-yl, tetrazoly-1-yl, or imidazol-1-yl.

42. The compound according to any one of items 1-8 and 38, wherein $R_1$ and $R_2$ are taken together with the nitrogen atom of the —$NR_1R_2$ group, wherein the —$NR_1R_2$ group is N-heterocycloalkyl$_{(C\leq8)}$ or substituted N-heterocycloalkyl$_{(C\leq8)}$.

43. The compound according to any one of items 1-8, 38, and 42, wherein $R_1$ and $R_2$ are taken together with the nitrogen atom of the —$NR_1R_2$ group, wherein the —$NR_1R_2$ group is N-heterocycloalkyl$_{(C\leq8)}$.

44. The compound according to any one of items 1-8, 38, 42, and 43, wherein $R_1$ and $R_2$ are taken together with the nitrogen atom of the —$NR_1R_2$ group, wherein the —$NR_1R_2$ group is oxazolidin-3-yl or

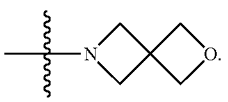 [SMILES: *N1CC2(COC2)C1]

45. The compound according to any one of items 1-8, 38, and 42, wherein $R_1$ and $R_2$ are taken together with the nitrogen atom of the —$NR_1R_2$ group, wherein the —$NR_1R_2$ group is substituted N-heterocycloalkyl$_{(C\leq8)}$.

46. The compound according to any one of items 1-8, 38, 42, and 45, wherein $R_1$ and $R_2$ are taken together with the nitrogen atom of the —$NR_1R_2$ group, wherein the —$NR_1R_2$ group is imidazolidin-2-one-1-yl, 3-methylimidazolidin-2-one-1-yl, oxazolidin-2-one-3-yl, azetidin-2-one-1-yl, pyrrolidin-2-one-1-yl, or 3,3-difluoroazetidin-1-yl.

47. The compound according to any one of items 1-46, wherein the compound is further defined as:

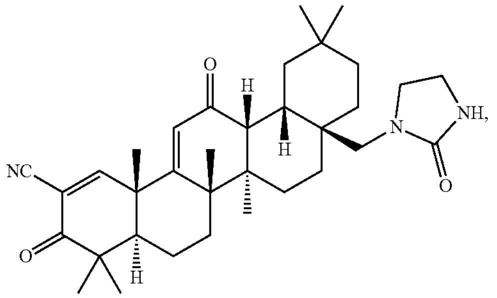

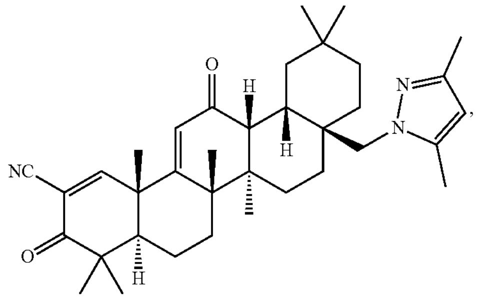

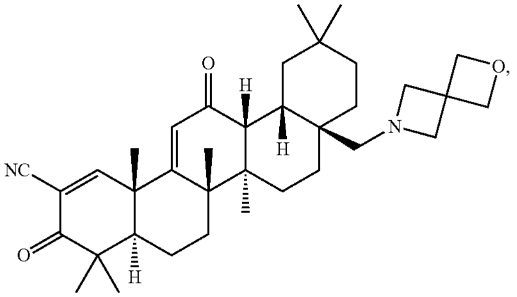

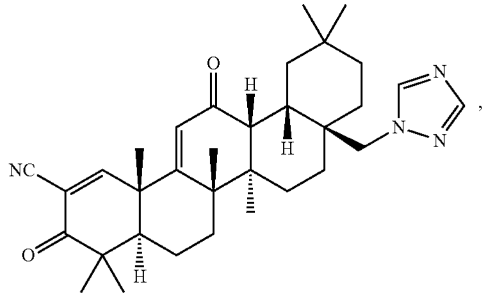

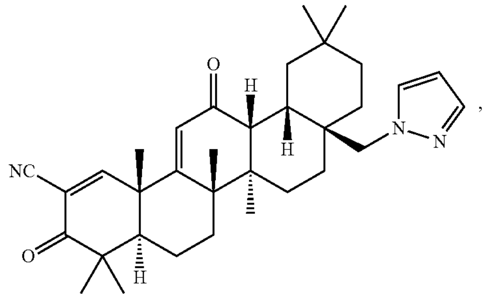

-continued
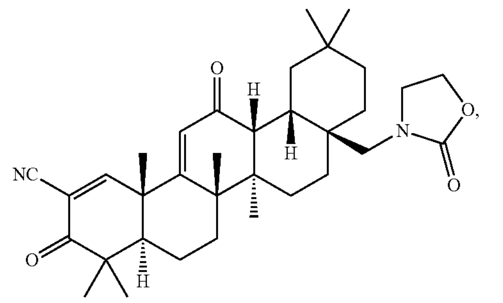
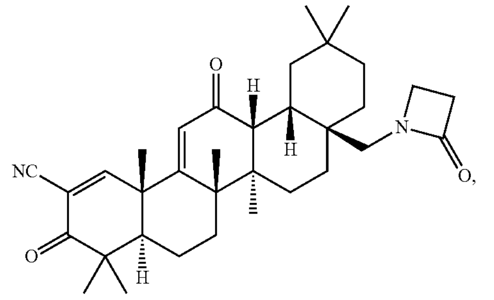
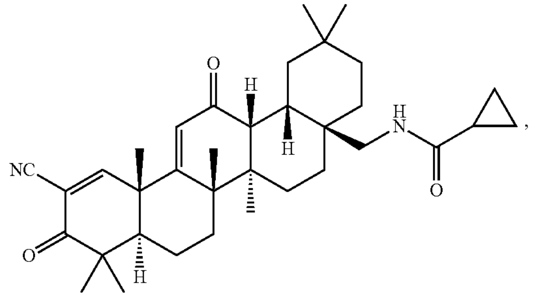
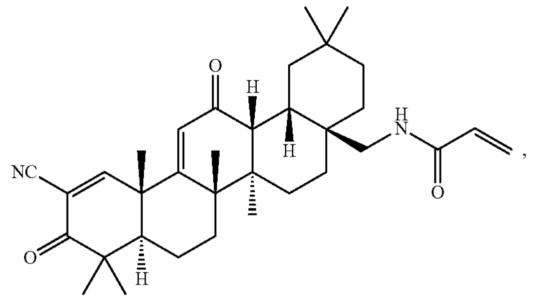
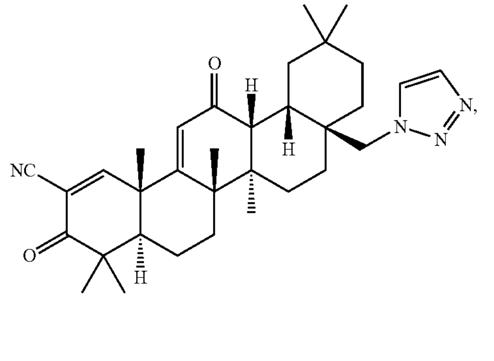
-continued
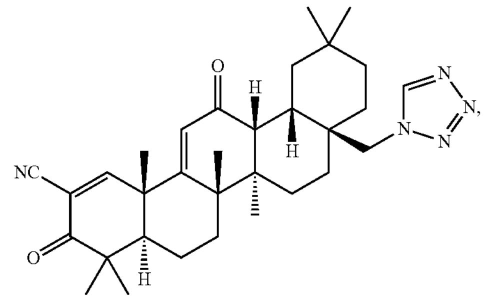
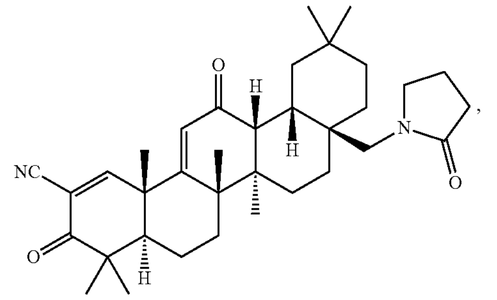
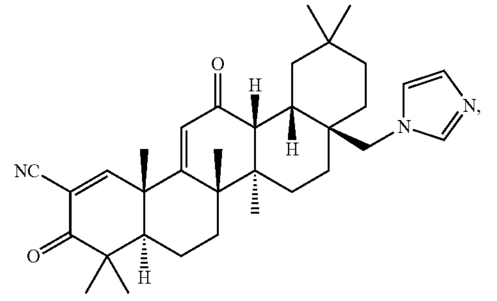
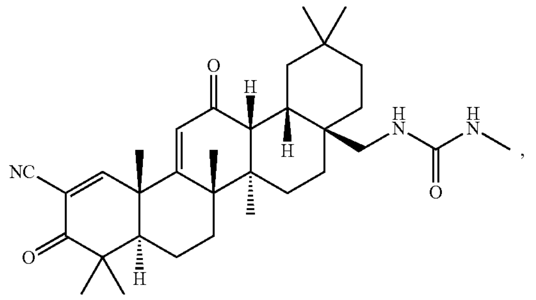
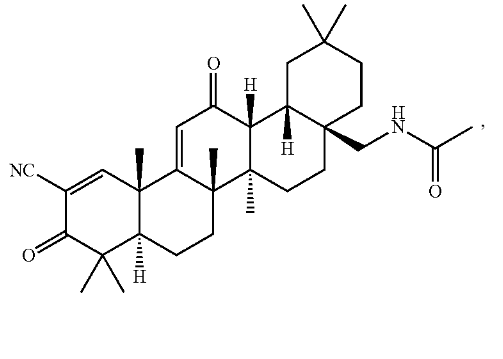

-continued
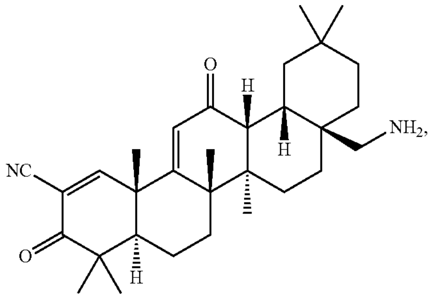
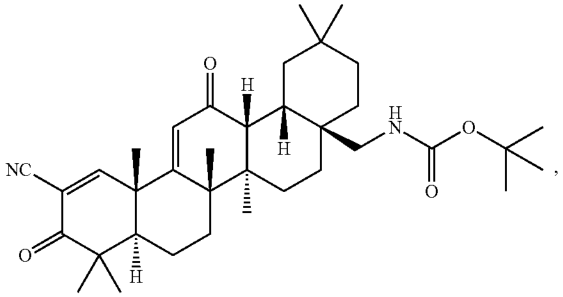
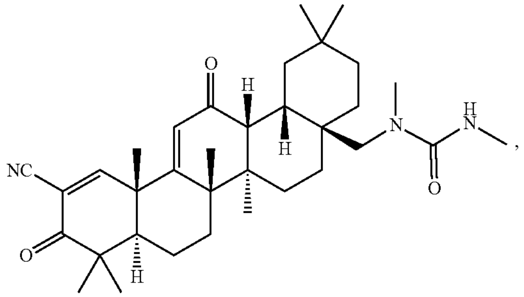
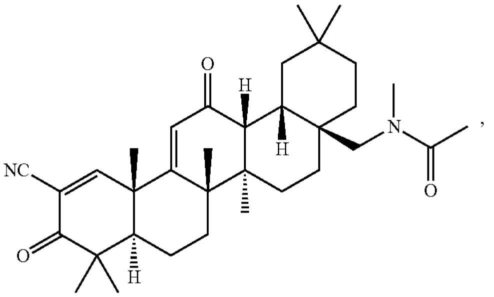
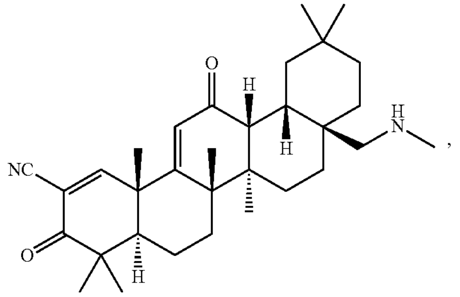
-continued
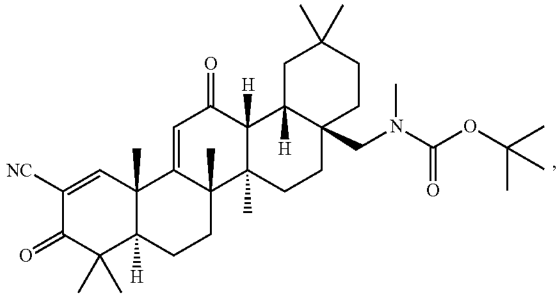
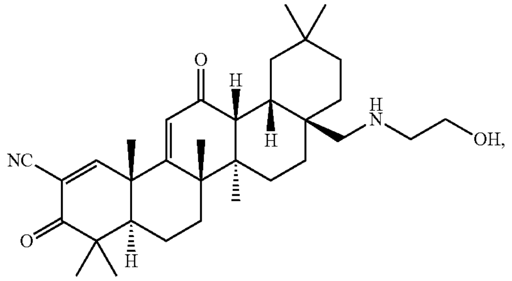
or
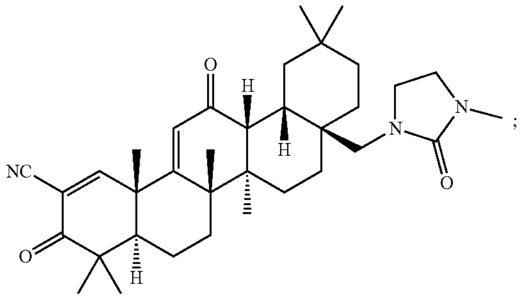
or a pharmaceutically acceptable salt of any of these formulas.
48. The compound according to any one of items 1-46, wherein the compound is further defined as:
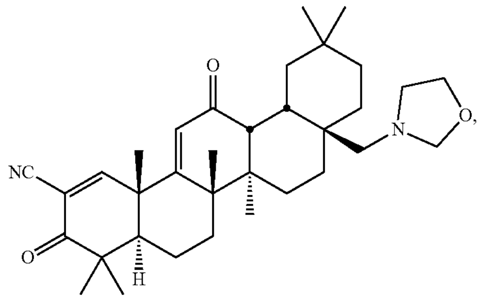
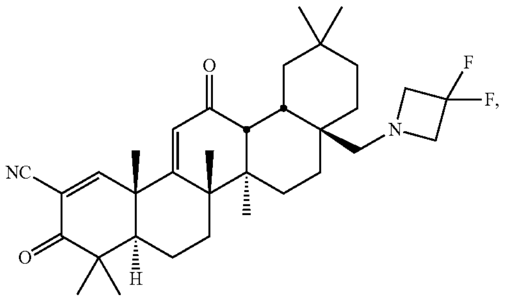

-continued

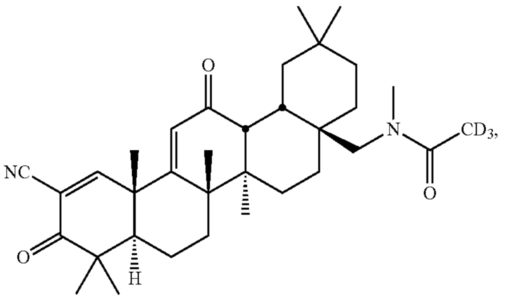

or

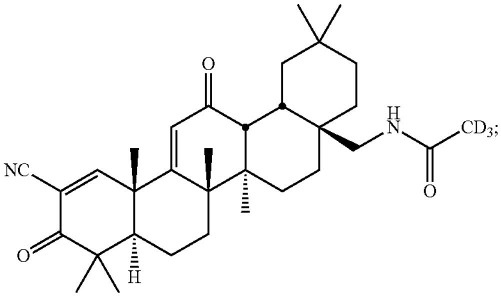

;

or a pharmaceutically acceptable salt of any of these formulas.

49. A compound of the formula:

(II)

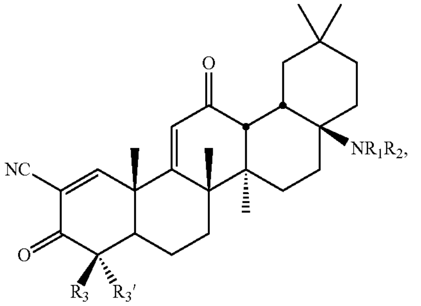

wherein:

$R_1$ and $R_2$ are taken together with the nitrogen atom of the —$NR_1R_2$ group, wherein the $NR_1R_2$ group is N-heteroaryl$_{(C\leq8)}$, substituted N-heteroaryl$_{(C\leq8)}$, N-heterocycloalkyl$_{(C\leq8)}$, or substituted N-heterocycloalkyl$_{(C\leq8)}$; and $R_3$ and $R_3$' are each independently hydrogen, alkyl (cg), or substituted alkyl$_{(C\leq8)}$;

or a pharmaceutically acceptable salt thereof.

50. The compound of item 49 further defined as:

(IIA)

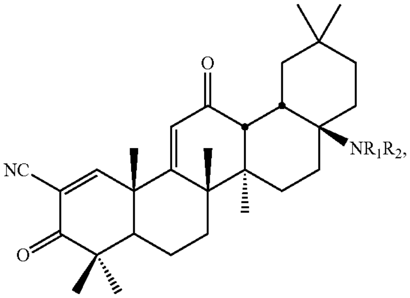

wherein:

$R_1$ and $R_2$ are taken together with the nitrogen atom of the —$NR_1R_2$ group, wherein the —$NR_1R_2$ group is N-heteroaryl$_{(C\leq8)}$, substituted N-heteroaryl$_{(C\leq8)}$, N-heterocycloalkyl$_{(C\leq8)}$, or substituted N-heterocycloalkyl$_{(C\leq8)}$;

or a pharmaceutically acceptable salt thereof.

51. The compound of item 49, wherein $R_3$ is alkyl$_{(C\leq8)}$ or substituted alkyl$_{(C\leq8)}$.

52. The compound of either item 49 or item 51, wherein $R_3$ is alkyl$_{(C\leq8)}$ 53. The compound according to any one of items 49, 51, and 52, wherein $R_3$ is methyl.

54. The compound according to any one of items 49 and 51-53, wherein $R_3$' is alkyl$_{(C\leq8)}$ or substituted alkyl$_{(C\leq8)}$.

55. The compound according to any one of items 49 and 51-54, wherein $R_3$' is alkyl$_{(C\leq8)}$.

56. The compound according to any one of item 49 and 51-55, wherein $R_3$' is methyl.

57. The compound according to any one of items 49-56, wherein $R_1$ and $R_2$ are taken together with the nitrogen atom of the —$NR_1R_2$ group, wherein the —$NR_1R_2$ group is N-heterocycloalkyl$_{(C\leq8)}$ or substituted N-heterocycloalkyl$_{(C\leq8)}$.

58. The compound according to any one of items 49-57, wherein $R_1$ and $R_2$ are taken together with the nitrogen atom of the $NR_1R_2$ group, wherein the —$NR_1R_2$ group is substituted N-heterocycloalkyl$_{(C\leq8)}$.

59. The compound according to any one of items 49-58, wherein $R_1$ and $R_2$ are taken together with the nitrogen atom of the —$NR_1R_2$ group, wherein the —$NR_1R_2$ group is pyrrolidine-2-one-1-yl.

60. The compound according to any one of items 49-59, wherein the compound is further defined as:

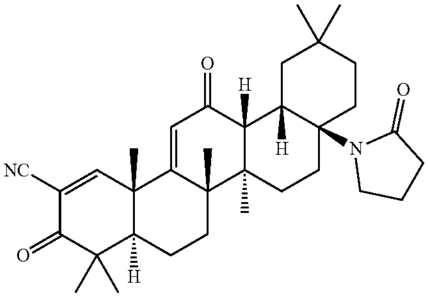

;

or a pharmaceutically acceptable salt of any of these formulas.

61. A pharmaceutical composition comprising:

(A) a compound according to any one of items 1-60; and (B) an excipient.

62. The pharmaceutical composition of item 61, wherein the pharmaceutical composition is formulated for administration orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctival, subcutaneously, sublingually, topically, transbuccally, transdermally, vaginally, in crémes, in lipid compositions, via a catheter, via a lavage, via continuous infusion, via infusion, via inhalation, via injection, via local delivery, or via localized perfusion.

63. The pharmaceutical composition of item 62, wherein the pharmaceutical composition is formulated for oral administration.

64. The pharmaceutical composition of item 62, wherein the pharmaceutical composition is formulated for administration via injection.

65. The pharmaceutical composition of item 64, wherein the pharmaceutical composition is formulated for intraarterial administration, intramuscular administration, intraperitoneal administration, or intravenous administration.

66. The pharmaceutical composition of item 62, wherein the pharmaceutical composition is formulated for administration topically.

67. The pharmaceutical composition of item 66, wherein the pharmaceutical composition is formulated for topical administration to the skin or to the eye.

68. The pharmaceutical composition according to any one of items 61-67, wherein the pharmaceutical composition is formulated as a unit dose.

69. A method of treating or preventing a disease or disorder in a patient in need thereof comprising administering to the patient a pharmaceutically effective amount of a compound or composition according to any one of items 1-68.

70. The method of item 69, wherein the patient is a mammal.

71. The method of item 70, wherein the patient is a human.

72. The method of item 69, wherein the disease or disorder is a condition associated with inflammation and/or oxidative stress.

73. The method of item 69, wherein the disease or disorder is cancer.

74. The method of item 69, wherein the disease or disorder is a cardiovascular disease.

75. The method of item 74, wherein the cardiovascular disease is atherosclerosis.

76. The method of item 69, wherein the disease or disorder is an autoimmune disease.

77. The method of item 76, wherein the autoimmune disease is Crohn's disease, rheumatoid arthritis, lupus, or psoriasis.

78. The method of item 69, wherein the disease or disorder is a neurodegenerative disease.

79. The method of item 78, wherein the neurodegenerative disease is Alzheimer's disease, Parkinson's disease, amyotrophic lateral sclerosis, or Huntington's disease.

80. The method of item 69, wherein the disease or disorder is chronic kidney disease, diabetes, mucositis, inflammatory bowel disease, dermatitis, sepsis, ischemia-reperfusion injury, influenza osteoarthritis, osteoporosis, pancreatitis, asthma, chronic obstructive pulmonary disease, cystic fibrosis, idiopathic pulmonary fibrosis, multiple sclerosis, muscular dystrophy, cachexia, or graft-versus-host disease.

81. The method of item 69, wherein the disease or disorder is an eye disease.

82. The method of item 81, wherein the eye disease is uveitis, glaucoma, macular degeneration, or retinopathy.

83. The method of item 69, wherein the disease or disorder is neuropsychiatric.

84. The method of item 83, wherein the neuropsychiatric disease or disorder is schizophrenia, depression, bipolar disorder, epilepsy, post-traumatic stress disorder, attention deficit disorder, autism, or anorexia nervosa.

85. A method of inhibiting nitric oxide production comprising administering to a patient in need thereof an amount of a compound or composition of items 1-68 sufficient to cause inhibition of IFN-γ-induced nitric oxide production in one or more cells of the patient.

II. BIOLOGICAL ACTIVITY

Assay results for the suppression of IFNγ-induced NO production are shown for several of the compounds of the present disclosure in Table 10 in Example 3. Details regarding this assay are provided in the Examples section below.

In some embodiments, the compounds of the present disclosure exhibit improved nitric oxide inhibition over other triterpenoid compounds, such as those disclosed in U.S. Pat. Nos. 7,943,778, 7,915,402, and 8,124,799, all of which are incorporated by reference herein. For example, T3 exhibits a NO $IC_{50}$ of 0.44 nM, which is more than 29 times more active than 63170 relative to RTA 402 (8.45 nM; see U.S. Pat. No. 8,124,799 and Table 2 below).

TABLE 2
| Structures and NO activity of T3 and 63170. | | | |
|---|---|---|---|
| Compound ID | Structure | NO $IC_{50}$ (nM) | NO $IC_{50}$ Rel. to RTA 402 (fold) |
| 63170 | 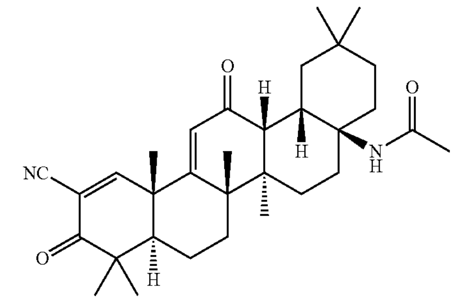 | 8.45 | 4.95 |
| T3 | 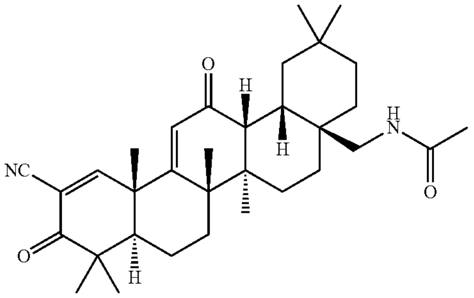 | 0.44 | 0.17 |
Additionally, T53 exhibits a NO $IC_{50}$ of 0.38 nM, which more than 19 times more active than 63189 relative to RTA 402 (7.20 nM; see U.S. Pat. No. 8,124,799 and Table 3 below).
TABLE 3
| Structures and NO activity of T53 and 63189. | | | |
|---|---|---|---|
| Compound ID | Structure | NO $IC_{50}$ (nM) | NO $IC_{50}$ Rel. to RTA 402 (fold) |
| 63189 | 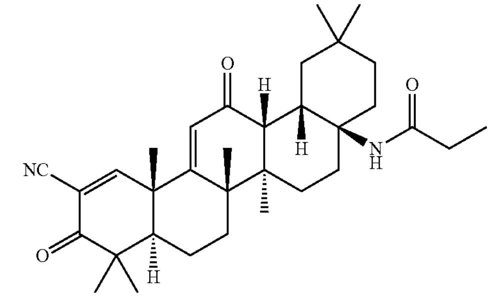 | 7.20 | 4.06 |
| T53 | 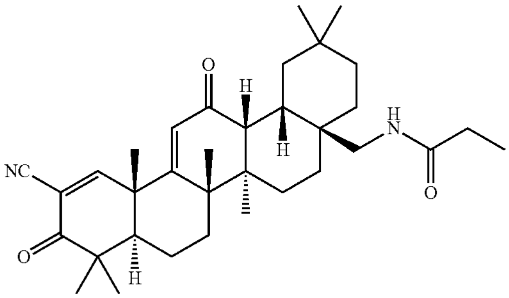 | 0.38 | 0.21 |

Furthermore, T16 exhibits a NO $IC_{50}$ of 0.37 nM, which is more than 6 times more active than 63183 relative to RTA 402 (4 nM; see U.S. Pat. No. 8,124,799 and Table 4 below)

TABLE 4

Structures and NO activity of T16 and 63183.

| Compound ID | Structure | NO $IC_{50}$ (nM) | NO $IC_{50}$ Rel. to RTA 402 (fold) |
|---|---|---|---|
| 63183 | 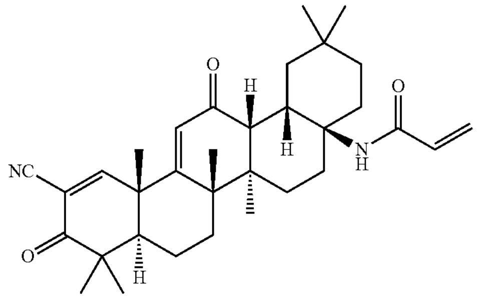 | 2.39 | 1.35 |
| T16 | 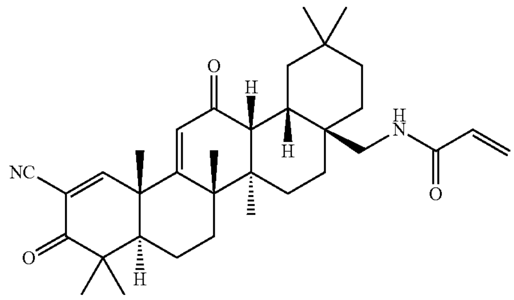 | 0.37 | 0.21 |

Yet further, T8 exhibits a NO $IC_{50}$ of 0.46 nM, which is roughly 37 times more active than 63172 relative to RTA 402 (21.57 nM; see U.S. Pat. No. 8,124,799 and Table 5 below).

TABLE 5

Structures and NO activity of T8 and 63172.

| Compound ID | Structure | NO $IC_{50}$ (nM) | NO $IC_{50}$ Rel. to RTA 402 (fold) |
|---|---|---|---|
| 63172 | 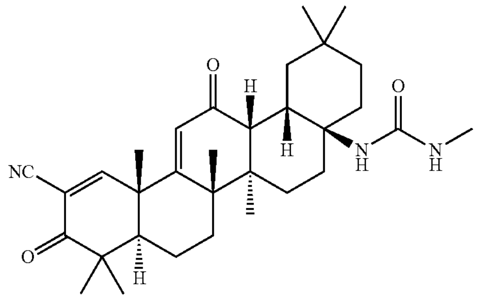 | 21.57 | 7.73 |

TABLE 5-continued

Structures and NO activity of T8 and 63172.

| Compound ID | Structure | NO $IC_{50}$ (nM) | NO $IC_{50}$ Rel. to RTA 402 (fold) |
|---|---|---|---|
| T8 | 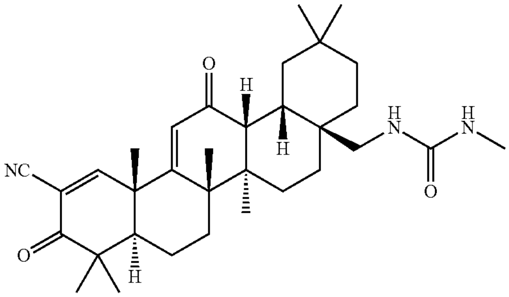 | 0.46 | 0.21 |

Further, T4 exhibits a NO $IC_{50}$ of 0.51 nM, which is more than 220 times more active than 63236 relative to RTA 402 (143.1 nM; see U.S. Pat. No. 8,124,799 and Table 6 below) and is roughly 4.5 times more active than 63866 relative to RTA 402 (1.43 nM; see U.S. Pat. No. 9,290,536 and Table 6 below).

TABLE 6

Structures and NO activity of T4, 63236, 63866.

| Compound ID | Structure | NO $IC_{50}$ (nM) | NO $IC_{50}$ Rel. to RTA 402 (fold) |
|---|---|---|---|
| 63236 | 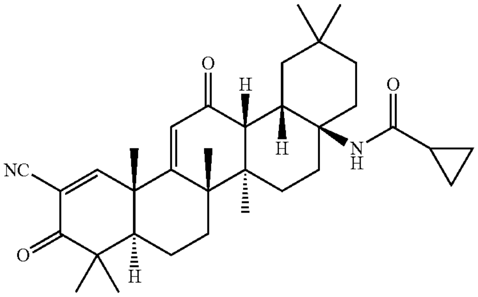 | 143.10 | 57.25 |
| 63866 | 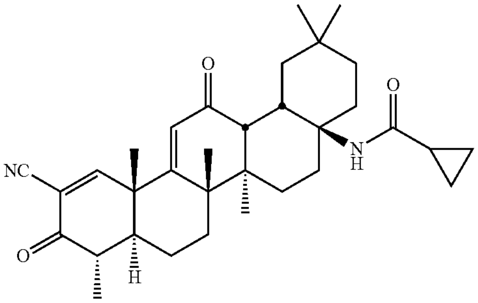 | 1.43 | 1.16 |
| T4 | 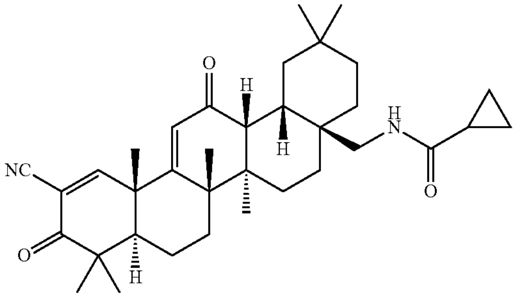 | 0.51 | 0.26 |

Still further, T36 exhibits a NO $IC_{50}$ of 1.96 nM, which is greater than 98.5 times more active than 63229 relative to RTA 402 (>200 nM; see U.S. Pat. No. 7,915,402 and Table 7 below).

TABLE 7

Structures and NO activity of T36 and 63229.

| Compound ID | Structure | NO $IC_{50}$ (nM) | NO $IC_{50}$ Rel. to RTA 402 (fold) |
|---|---|---|---|
| 63229 | 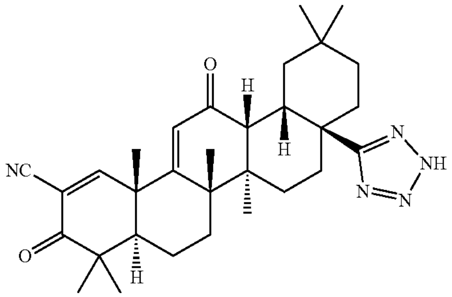 | >200 | >75.85 |
| T36 | 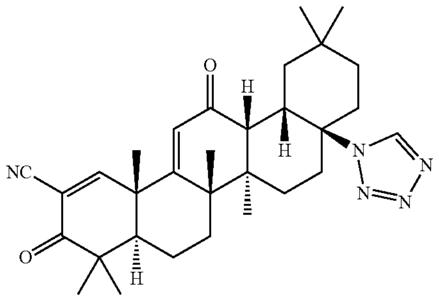 | 1.96 | 0.77 |

Yet further, 135 exhibits a NO $IC_{50}$ of 1.30 nM, which is almost 4 times more active than CC4 relative to RTA 402 (3.75 nM; see compound 63169 of U.S. Pat. No. 8,124,799 and Table 8 below). T36 exhibits a NO $IC_{50}$ of 1.96 nM, which is roughly 3.1 times as active as CC4 relative to RTA 402. T43 exhibits a NO $IC_{50}$ of 2.68 nM, which is roughly 3.7 times more active than CC4 relative to RTA 402.

TABLE 8

Structures and NO activity of T35, T36, T43, and CC4.

| Compound ID | Structure | NO $IC_{50}$ (nM) | NO $IC_{50}$ Rel. to RTA 402 (fold) |
|---|---|---|---|
| CC4 | 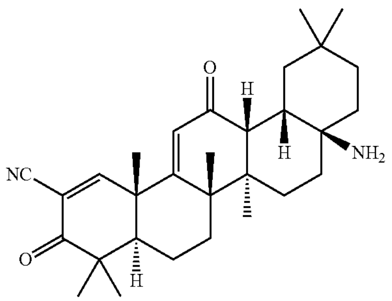 | 3.75 | 2.41 |

TABLE 8-continued

Structures and NO activity of T35, T36, T43, and CC4.

| Compound ID | Structure | NO $IC_{50}$ (nM) | NO $IC_{50}$ Rel. to RTA 402 (fold) |
|---|---|---|---|
| T35 | 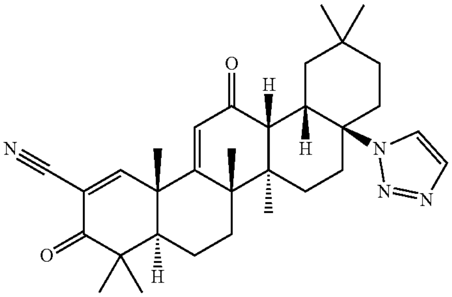 | 1.30 | 0.64 |
| T36 | 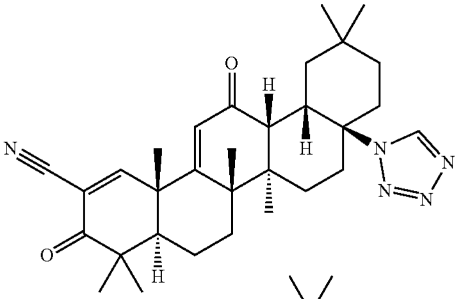 | 1.96 | 0.77 |
| T43 | 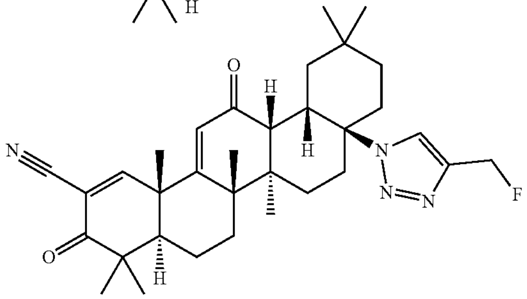 | 2.68 | 0.66 |

Yet further, T18 exhibits a NO $IC_{50}$ of 0.92 nM, which is more than twice as active than CC2 relative to RTA 402 (3.15 nM; see Table 9 below). T19 exhibits a NO $IC_{50}$ of 1.11 M, which is roughly 1.6 times more active than CC2 relative to RTA 402. T48 exhibits a NO $IC_{50}$ of 2.50 nM, which is roughly 1.3 times more active than CC2 relative to RTA 402.

TABLE 9

Structures and NO activity of T18, T19, T48, and CC2.

| Compound ID | Structure | NO $IC_{50}$ (nM) | NO $IC_{50}$ Rel. to RTA 402 (fold) |
|---|---|---|---|
| CC2 | 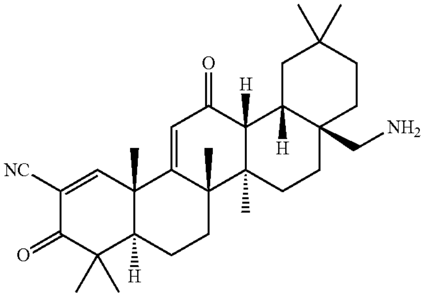 | 3.15 | 1.55 |

TABLE 9-continued

Structures and NO activity of T18, T19, T48, and CC2.

| Compound ID | Structure | NO $IC_{50}$ (nM) | NO $IC_{50}$ Rel. to RTA 402 (fold) |
|---|---|---|---|
| T18 | 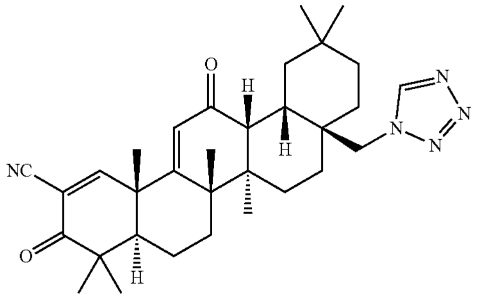 | 0.92 | 0.76 |
| T19 | 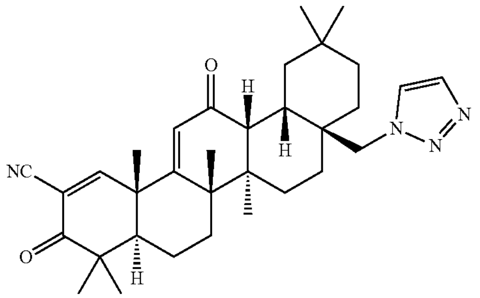 | 1.11 | 0.93 |
| T48 | 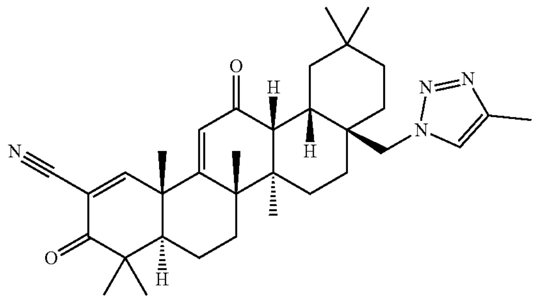 | 2.50 | 1.19 |

In some embodiments, the compounds of the present disclosure exhibit reduced inhibition of cytochrome P450 3A4 (CYP3A4) relative to known compounds. CYP3A4 is an important enzyme in the body, which oxidizes small foreign organic molecules (xenobiotics), such as toxins or drugs, so that they can be removed from the body. Modulation of CYP3A4 may amplify or weaken the action of drugs that are modified by CYP3A4. Inhibition of CYP3A4 may have negative side effects (e.g. reduced drug clearance, amplification of the action of the drug, and/or increase the probability of drug-drug interactions) and may complicate dosing. Therefore, drugs that do not inhibit CYP3A4 are often more desirable. However, in some applications, inhibition of CYP3A4 may be desirable, such as to potentiate the effect of the drug or of another co-administered drug. Assay results for the inhibition of CYP3A4 are shown for several of the compounds of the present disclosure in Table 11 in Example 4.

III. DISEASES ASSOCIATED WITH INFLAMMATION AND/OR OXIDATIVE STRESS

Inflammation is a biological process that provides resistance to infectious or parasitic organisms and the repair of damaged tissue. Inflammation is commonly characterized by localized vasodilation, redness, swelling, and pain, the recruitment of leukocytes to the site of infection or injury, production of inflammatory cytokines such as TNF-α and IL-1, and production of reactive oxygen or nitrogen species such as hydrogen peroxide, superoxide and peroxynitrite. In later stages of inflammation, tissue remodeling, angiogenesis, and scar formation (fibrosis) may occur as part of the wound healing process. Under normal circumstances, the inflammatory response is regulated and temporary and is resolved in an orchestrated fashion once the infection or injury has been dealt with adequately. However, acute inflammation can become excessive and life-threatening if regulatory mechanisms fail. Alternatively, inflammation can become chronic and cause cumulative tissue damage or systemic complications. Based at least on the evidence presented above, the compounds of this invention may be used in the treatment or prevention of inflammation or diseases associated with inflammation.

Many serious and intractable human diseases involve dysregulation of inflammatory processes, including diseases such as cancer, atherosclerosis, and diabetes, which were not traditionally viewed as inflammatory conditions. In the case of cancer, the inflammatory processes are associated with tumor formation, progression, metastasis, and resistance to therapy. Atherosclerosis, long viewed as a disorder of lipid metabolism, is now understood to be primarily an inflammatory condition, with activated macrophages playing an important role in the formation and eventual rupture of atherosclerotic plaques. Activation of inflammatory signaling pathways has also been shown to play a role in the development of insulin resistance, as well as in the peripheral tissue damage associated with diabetic hyperglycemia. Excessive production of reactive oxygen species and reactive nitrogen species such as superoxide, hydrogen peroxide, nitric oxide, and peroxynitrite is a hallmark of inflammatory conditions. Evidence of dysregulated peroxynitrite production has been reported in a wide variety of diseases (Szabo et al., 2007; Schulz et al., 2008; Forstermann, 2006; Pall, 2007).

Autoimmune diseases such as rheumatoid arthritis, lupus, psoriasis, and multiple sclerosis involve inappropriate and chronic activation of inflammatory processes in affected tissues, arising from dysfunction of self vs. non-self recognition and response mechanisms in the immune system. In neurodegenerative diseases such as Alzheimer's and Parkinson's diseases, neural damage is correlated with activation of microglia and elevated levels of pro-inflammatory proteins such as inducible nitric oxide synthase (iNOS). Chronic organ failure such as renal failure, heart failure, liver failure, and chronic obstructive pulmonary disease is closely associated with the presence of chronic oxidative stress and inflammation, leading to the development of fibrosis and eventual loss of organ function. Oxidative stress in vascular endothelial cells, which line major and minor blood vessels, can lead to endothelial dysfunction and is believed to be an important contributing factor in the development of systemic cardiovascular disease, complications of diabetes, chronic kidney disease and other forms of organ failure, and a number of other aging-related diseases including degenerative diseases of the central nervous system and the retina.

Many other disorders involve oxidative stress and inflammation in affected tissues, including inflammatory bowel disease; inflammatory skin diseases; mucositis related to radiation therapy and chemotherapy; eye diseases such as uveitis, glaucoma, macular degeneration, and various forms of retinopathy; transplant failure and rejection; ischemia-reperfusion injury; chronic pain; degenerative conditions of the bones and joints including osteoarthritis and osteoporosis; asthma and cystic fibrosis; seizure disorders; and neuropsychiatric conditions including schizophrenia, depression, bipolar disorder, post-traumatic stress disorder, attention deficit disorders, autism-spectrum disorders, and eating disorders such as anorexia nervosa. Dysregulation of inflammatory signaling pathways is believed to be a major factor in the pathology of muscle wasting diseases including muscular dystrophy and various forms of cachexia.

A variety of life-threatening acute disorders also involve dysregulated inflammatory signaling, including acute organ failure involving the pancreas, kidneys, liver, or lungs, myocardial infarction or acute coronary syndrome, stroke, septic shock, trauma, severe burns, and anaphylaxis.

Many complications of infectious diseases also involve dysregulation of inflammatory responses. Although an inflammatory response can kill invading pathogens, an excessive inflammatory response can also be quite destructive and in some cases can be a primary source of damage in infected tissues. Furthermore, an excessive inflammatory response can also lead to systemic complications due to overproduction of inflammatory cytokines such as TNF-α and IL-1. This is believed to be a factor in mortality arising from severe influenza, severe acute respiratory syndrome, and sepsis.

The aberrant or excessive expression of either iNOS or cyclooxygenase-2 (COX-2) has been implicated in the pathogenesis of many disease processes. For example, it is clear that NO is a potent mutagen (Tamir and Tannebaum, 1996), and that nitric oxide can also activate COX-2 (Salvemini et al., 1994). Furthermore, there is a marked increase in iNOS in rat colon tumors induced by the carcinogen, azoxymethane (Takahashi et al., 1997). A series of synthetic triterpenoid analogs of oleanolic acid have been shown to be powerful inhibitors of cellular inflammatory processes, such as the induction by IFN-γ of inducible nitric oxide synthase (iNOS) and of COX-2 in mouse macrophages. See Honda et al. (2000a); Honda et al. (2000b), and Honda et al. (2002), which are all incorporated herein by reference.

In one aspect, compounds disclosed herein are characterized by their ability to inhibit the production of nitric oxide in macrophage-derived RAW 264.7 cells induced by exposure to γ-interferon. They are further characterized by their ability to induce the expression of antioxidant proteins such as NQO1 and reduce the expression of pro-inflammatory proteins such as COX-2 and inducible nitric oxide synthase (iNOS). These properties are relevant to the treatment of a wide array of diseases and disorders involving oxidative stress and dysregulation of inflammatory processes including cancer, complications from localized or total-body exposure to ionizing radiation, mucositis resulting from radiation therapy or chemotherapy, autoimmune diseases, cardiovascular diseases including atherosclerosis, ischemia-reperfusion injury, acute and chronic organ failure including renal failure and heart failure, respiratory diseases, diabetes and complications of diabetes, severe allergies, transplant rejection, graft-versus-host disease, neurodegenerative diseases, diseases of the eye and retina, acute and chronic pain including neuropathic pain, degenerative bone diseases including osteoarthritis and osteoporosis, inflammatory bowel diseases, dermatitis and other skin diseases, sepsis, burns, seizure disorders, and neuropsychiatric disorders.

Without being bound by theory, the activation of the antioxidant/anti-inflammatory Keap1/Nrf2/ARE pathway is believed to be implicated in both the anti-inflammatory and anti-carcinogenic properties of the compounds disclosed herein.

In another aspect, compounds disclosed herein may be used for treating a subject having a condition caused by elevated levels of oxidative stress in one or more tissues. Oxidative stress results from abnormally high or prolonged levels of reactive oxygen species such as superoxide, hydrogen peroxide, nitric oxide, and peroxynitrite (formed by the reaction of nitric oxide and superoxide). The oxidative stress may be accompanied by either acute or chronic inflammation. The oxidative stress may be caused by mitochondrial dysfunction, by activation of immune cells such as macrophages and neutrophils, by acute exposure to an external agent such as ionizing radiation or a cytotoxic chemotherapy agent (e.g., doxorubicin), by trauma or other acute tissue injury, by ischemia/reperfusion, by poor circulation or anemia, by localized or systemic hypoxia or hyperoxia, by elevated levels of inflammatory cytokines and other inflammation-related proteins, and/or by other abnormal physiological states such as hyperglycemia or hypoglycemia.

In animal models of many such conditions, stimulating expression of inducible heme oxygenase (HO-1), a target gene of the Nrf2 pathway, has been shown to have a significant therapeutic effect including models of myocardial infarction, renal failure, transplant failure and rejection, stroke, cardiovascular disease, and autoimmune disease (e.g., Sacerdoti et al., 2005; Abraham & Kappas, 2005; Bach, 2006; Araujo et al., 2003; Liu et al., 2006; Ishikawa et al., 2001; Kruger et al., 2006; Satoh et al., 2006; Zhou et al., 2005; Morse and Choi, 2005; Morse and Choi, 2002). This enzyme breaks free heme down into iron, carbon monoxide (CO), and biliverdin (which is subsequently converted to the potent antioxidant molecule, bilirubin).

In another aspect, compounds of this invention may be used in preventing or treating tissue damage or organ failure, acute and chronic, resulting from oxidative stress exacerbated by inflammation. Examples of diseases that fall in this category include: heart failure, liver failure, transplant failure and rejection, renal failure, pancreatitis, fibrotic lung diseases (cystic fibrosis, COPD, and idiopathic pulmonary fibrosis, among others), diabetes (including complications), atherosclerosis, ischemia-reperfusion injury, glaucoma, stroke, autoimmune disease, autism, macular degeneration, and muscular dystrophy. For example, in the case of autism, studies suggest that increased oxidative stress in the central nervous system may contribute to the development of the disease (Chauhan and Chauhan, 2006).

Evidence also links oxidative stress and inflammation to the development and pathology of many other disorders of the central nervous system, including psychiatric disorders such as psychosis, major depression, and bipolar disorder; seizure disorders such as epilepsy; pain and sensory syndromes such as migraine, neuropathic pain or tinnitus; and behavioral syndromes such as the attention deficit disorders. See, e.g., Dickerson et al., 2007; Hanson et al., 2005; Kendall-Tackett, 2007; Lencz et al., 2007; Dudhgaonkar et al., 2006; Lee et al., 2007; Morris et al., 2002; Ruster et al., 2005; McIver et al., 2005; Sarchielli et al., 2006; Kawakami et al., 2006; Ross et al., 2003, which are all incorporated by reference herein. For example, elevated levels of inflammatory cytokines, including TNF, interferon-γ, and IL-6, are associated with major mental illness (Dickerson et al., 2007). Microglial activation has also been linked to major mental illness. Therefore, downregulating inflammatory cytokines and inhibiting excessive activation of microglia could be beneficial in patients with schizophrenia, major depression, bipolar disorder, autism-spectrum disorders, and other neuropsychiatric disorders.

Accordingly, in pathologies involving oxidative stress alone or oxidative stress exacerbated by inflammation, treatment may comprise administering to a subject a therapeutically effective amount of a compound of this invention, such as those described above or throughout this specification. Treatment may be administered preventively, in advance of a predictable state of oxidative stress (e.g., organ transplantation or the administration of radiation therapy to a cancer patient), or it may be administered therapeutically in settings involving established oxidative stress and inflammation.

The compounds disclosed herein may be generally applied to the treatment of inflammatory conditions, such as sepsis, dermatitis, autoimmune disease and osteoarthritis. In one aspect, the compounds of this invention may be used to treat inflammatory pain and/or neuropathic pain, for example, by inducing Nrf2 and/or inhibiting NF-κB.

In some embodiments, the compounds disclosed herein may be used in the treatment and prevention of diseases such as cancer, inflammation, Alzheimer's disease, Parkinson's disease, multiple sclerosis, autism, amyotrophic lateral sclerosis, Huntington's disease, autoimmune diseases such as rheumatoid arthritis, lupus, Crohn's disease and psoriasis, inflammatory bowel disease, all other diseases whose pathogenesis is believed to involve excessive production of either nitric oxide or prostaglandins, and pathologies involving oxidative stress alone or oxidative stress exacerbated by inflammation.

Another aspect of inflammation is the production of inflammatory prostaglandins such as prostaglandin E. These molecules promote vasodilation, plasma extravasation, localized pain, elevated temperature, and other symptoms of inflammation. The inducible form of the enzyme COX-2 is associated with their production, and high levels of COX-2 are found in inflamed tissues. Consequently, inhibition of COX-2 may relieve many symptoms of inflammation, and a number of important anti-inflammatory drugs (e.g., ibuprofen and celecoxib) act by inhibiting COX-2 activity. Recent research, however, has demonstrated that a class of cyclopentenone prostaglandins (cyPGs) (e.g., 15-deoxy prostaglandin J2, a.k.a. PGJ2) plays a role in stimulating the orchestrated resolution of inflammation (e.g., Rajakariar et al., 2007). COX-2 is also associated with the production of cyclopentenone prostaglandins. Consequently, inhibition of COX-2 may interfere with the full resolution of inflammation, potentially promoting the persistence of activated immune cells in tissues and leading to chronic, "smoldering" inflammation. This effect may be responsible for the increased incidence of cardiovascular disease in patients using selective COX-2 inhibitors for long periods of time.

In one aspect, the compounds disclosed herein may be used to control the production of pro-inflammatory cytokines within the cell by selectively activating regulatory cysteine residues (RCRs) on proteins that regulate the activity of redox-sensitive transcription factors. Activation of RCRs by cyPGs has been shown to initiate a pro-resolution program in which the activity of the antioxidant and cytoprotective transcription factor Nrf2 is potently induced and the activities of the pro-oxidant and pro-inflammatory transcription factors NF-κB and the STATs are suppressed. In some embodiments, this increases the production of antioxidant and reductive molecules (NQO1, HO-1, SOD1, γ-GCS) and decreases oxidative stress and the production of pro-oxidant and pro-inflammatory molecules (iNOS, COX-2, TNF-α). In some embodiments, the compounds of this invention may cause the cells that host the inflammatory event to revert to a non-inflammatory state by promoting the resolution of inflammation and limiting excessive tissue damage to the host.

IV. Pharmaceutical Formulations and Routes of Administration

In another aspect, for administration to a patient in need of such treatment, pharmaceutical formulations (also referred to as a pharmaceutical preparations, pharmaceutical compositions, pharmaceutical products, medicinal products, medicines, medications, or medicaments) comprise a therapeutically effective amount of a compound disclosed herein formulated with one or more excipients and/or drug carriers appropriate to the indicated route of administration. In some embodiments, the compounds disclosed herein are formulated in a manner amenable for the treatment of human and/or veterinary patients. In some embodiments, formulation comprises admixing or combining one or more of the compounds disclosed herein with one or more of the following excipients: lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol. In some embodiments, e.g., for oral administration, the pharmaceutical formulation may be tableted or encapsulated. In some embodiments, the compounds may be dissolved or slurried in water, polyethylene glycol, propylene glycol, ethanol, corn oil, cottonseed oil, peanut oil, sesame oil, benzyl alcohol, sodium chloride, and/or various buffers. In some embodiments, the pharmaceutical formulations may be subjected to pharmaceutical operations, such as sterilization, and/or may contain drug carriers and/or excipients such as preservatives, stabilizers, wetting agents, emulsifiers, encapsulating agents such as lipids, dendrimers, polymers, proteins such as albumin, nucleic acids, and buffers.

Pharmaceutical formulations may be administered by a variety of methods, e.g., orally or by injection (e.g. subcutaneous, intravenous, and intraperitoneal). Depending on the route of administration, the compounds disclosed herein may be coated in a material to protect the compound from the action of acids and other natural conditions which may inactivate the compound. To administer the active compound by other than parenteral administration, it may be necessary to coat the compound with, or co-administer the compound with, a material to prevent its inactivation. In some embodiments, the active compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes.

The compounds disclosed herein may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

The compounds disclosed herein can be administered orally, for example, with an inert diluent or an assimilable edible carrier. The compounds and other ingredients may also be enclosed in a hard or soft-shell gelatin capsule, compressed into tablets, or incorporated directly into the patient's diet. For oral therapeutic administration, the compounds disclosed herein may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such pharmaceutical formulations is such that a suitable dosage will be obtained.

The therapeutic compound may also be administered topically to the skin, eye, ear, or mucosal membranes. Administration of the therapeutic compound topically may include formulations of the compounds as a topical solution, lotion, cream, ointment, gel, foam, transdermal patch, or tincture. When the therapeutic compound is formulated for topical administration, the compound may be combined with one or more agents that increase the permeability of the compound through the tissue to which it is administered. In other embodiments, it is contemplated that the topical administration is administered to the eye. Such administration may be applied to the surface of the cornea, conjunctiva, or sclera. Without wishing to be bound by any theory, it is believed that administration to the surface of the eye allows the therapeutic compound to reach the posterior portion of the eye. Ophthalmic topical administration can be formulated as a solution, suspension, ointment, gel, or emulsion. Finally, topical administration may also include administration to the mucosa membranes such as the inside of the mouth. Such administration can be directly to a particular location within the mucosal membrane such as a tooth, a sore, or an ulcer. Alternatively, if local delivery to the lungs is desired the therapeutic compound may be administered by inhalation in a dry-powder or aerosol formulation.

In some embodiments, it may be advantageous to formulate parenteral compositions in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical carrier. In some embodiments, the specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient. In some embodiments, active compounds are administered at a therapeutically effective dosage sufficient to treat a condition associated with a condition in a patient. For example, the efficacy of a compound can be evaluated in an animal model system that may be predictive of efficacy in treating the disease in a human or another animal.

In some embodiments, the effective dose range for the therapeutic compound can be extrapolated from effective doses determined in animal studies for a variety of different animals. In some embodiments, the human equivalent dose (HED) in mg/kg can be calculated in accordance with the following formula (see, e.g., Reagan-Shaw et al., *FASEB J.,* 22(3):659-661, 2008, which is incorporated herein by reference):

$$\text{HED (mg/kg)} = \text{Animal dose (mg/kg)} \times (\text{Animal } K_m / \text{Human } K_m)$$

Use of the $K_m$ factors in conversion results in HED values based on body surface area (BSA) rather than only on body mass. $K_m$ values for humans and various animals are well known. For example, the $K_m$ for an average 60 kg human (with a BSA of 1.6 $m^2$) is 37, whereas a 20 kg child (BSA 0.8 $m^2$) would have a $K_m$ of 25. $K_m$ for some relevant animal models are also well known, including: mice $K_m$ of 3 (given a weight of 0.02 kg and BSA of 0.007); hamster $K_m$ of 5 (given a weight of 0.08 kg and BSA of 0.02); rat $K_m$ of 6 (given a weight of 0.15 kg and BSA of 0.025) and monkey $K_m$ of 12 (given a weight of 3 kg and BSA of 0.24).

Precise amounts of the therapeutic composition depend on the judgment of the practitioner and are specific to each individual. Nonetheless, a calculated HED dose provides a general guide. Other factors affecting the dose include the physical and clinical state of the patient, the route of administration, the intended goal of treatment and the potency, stability and toxicity of the particular therapeutic formulation.

The actual dosage amount of a compound of the present disclosure or composition comprising a compound of the present disclosure administered to a patient may be determined by physical and physiological factors such as type of animal treated, age, sex, body weight, severity of condition, the type of disease being treated, previous or concurrent therapeutic interventions, idiopathy of the patient and on the route of administration. These factors may be determined by a skilled artisan. The practitioner responsible for administration will typically determine the concentration of active ingredient(s) in a composition and appropriate dose(s) for the individual patient. The dosage may be adjusted by the individual physician in the event of any complication.

In some embodiments, the therapeutically effective amount typically will vary from about 0.001 mg/kg to about 1000 mg/kg, from about 0.01 mg/kg to about 750 mg/kg, from about 100 mg/kg to about 500 mg/kg, from about 1 mg/kg to about 250 mg/kg, from about 10 mg/kg to about 150 mg/kg in one or more dose administrations daily, for one or several days (depending of course of the mode of administration and the factors discussed above). Other suitable dose ranges include 1 mg to 10,000 mg per day, 100 mg to 10,000 mg per day, 500 mg to 10,000 mg per day, and 500 mg to 1,000 mg per day. In some embodiments, the amount is less than 10,000 mg per day with a range of 750 mg to 9,000 mg per day.

In some embodiments, the amount of the active compound in the pharmaceutical formulation is from about 2 to about 75 weight percent. In some of these embodiments, the amount if from about 25 to about 60 weight percent.

Single or multiple doses of the agents are contemplated. Desired time intervals for delivery of multiple doses can be determined by one of ordinary skill in the art employing no more than routine experimentation. As an example, patients may be administered two doses daily at approximately 12-hour intervals. In some embodiments, the agent is administered once a day.

The agent(s) may be administered on a routine schedule. As used herein a routine schedule refers to a predetermined designated period of time. The routine schedule may encompass periods of time which are identical, or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may be taken orally and that the timing of which is or is not dependent upon food intake. Thus, for example, the agent can be taken every morning and/or every evening, regardless of when the patient has eaten or will eat.

V. Combination Therapy

In addition to being used as a monotherapy, the compounds of the present disclosure may also be used in combination therapies. In some embodiments, compounds of the present disclosure may be combined with one or more agents that promote proper folding or assembly of CFTR. (correctors) or that enhance the function of CFTR (potentiators). For example, combinations can include a compound of the invention combined with one or more correctors, one or more potentiators, a corrector and a potentiator. In other examples, the combination includes an amplifier either with just one of the compounds of the present invention or in combination with a compound of the present invention and the above described combinations of correctors and potentiators.

In some embodiments, there are provided combination therapies, wherein a compound disclosed herein is combined with another CF treatment, for example, a compound designed to improve function of CFTR that has reached the cell membrane and is capable of at least partial function. Such compounds are known as CFTR potentiators, and the first disease-specific therapy for CF, ivacaftor, has been clinically demonstrated to improve CFTR function in patients with several of the significant mutations. Compounds that prevent misfolding of CFTR are known as correctors. In some embodiments the compounds of the present invention may be used to function as correctors. The enhanced efficacy for the treatment of CF from combining two correctors, or a corrector with a potentiator, is well understood in the art and such combinations have been approved for marketing or are currently being studied in clinical trials. Combinations of three agents are also being studied in clinical trials. It is recognized that that polytherapies are or may soon become the standard of care. In some embodiments, other classes of CFTR modulators, such as "amplifiers" that increase the steady-state levels of CFTR, may become available and may also be used as part of a polytherapy.

Other potential combinations will be apparent to the skilled practitioner. In some embodiments, effective combination therapy is achieved with a single composition or pharmacological formulation that includes multiple agents, or with two or more distinct compositions or formulations, administered at the same time, wherein one composition includes a compound of this invention, and the other(s) include(s) the additional agent(s), formulated together or separately. Alternatively, in other embodiments, the therapy precedes or follows the other agent treatment by intervals ranging from minutes to months.

VI. DEFINITIONS

When used in the context of a chemical group: "hydrogen" means —H; "hydroxy" means —OH; "oxo" means =O; "carbonyl" means —C(=O)—; "carboxy" means —C(=O)OH (also written as —COOH or —$CO_2$H); "halo" means independently —F, —Cl, —Br or —I; "amino" means —$NH_2$; "hydroxyamino" means —NHOH; "nitro" means —$NO_2$; imino means =NH; "cyano" means —CN; "isocyanyl" means —N=C=O; "azido" means —$N_3$; in a monovalent context "phosphate" means —OP(O)$(OH)_2$ or a deprotonated form thereof; in a divalent context "phosphate" means —OP(O)(OH)O— or a deprotonated form thereof;

"mercapto" means —SH; and "thio" means ═S; "thiocarbonyl" means —C(═S)—; "sulfonyl" means —$S(O)_2$—; and "sulfinyl" means —S(O)—.

In the context of chemical formulas, the symbol "—" means a single bond, "═" means a double bond, and "≡" means triple bond. The symbol "----" represents an optional bond, which if present is either single or double. The symbol "═══" represents a single bond or a double bond. Thus, the formula

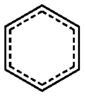

covers, for example,

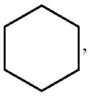, 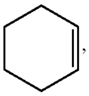, 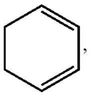, 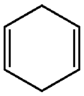 and 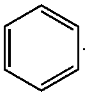.

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "∿∿", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◀" means a single bond where the group attached to the thick end of the wedge is "out of the page." The symbol "ıııııı" means a single bond where the group attached to the thick end of the wedge is "into the page". The symbol "∿∿" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

A bold dot on a carbon atom indicates that the hydrogen attached to that carbon is oriented out of the plane of the paper. For example, the following two depictions are equivalent:

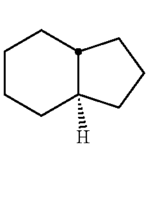 and 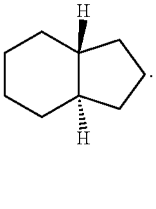.

When a variable is depicted as a "floating group" on a ring system, for example, the group "R" in the formula:

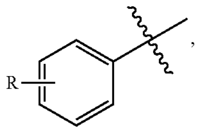, then the variable may replace any hydrogen atom attached to any of the ring atoms, including a depicted, implied, or expressly defined hydrogen, so long as a stable structure is formed. When a variable is depicted as a "floating group" on a fused ring system, as for example the group "R" in the formula:

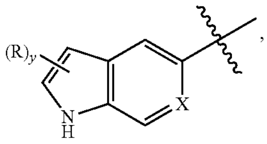, then the variable may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the R enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" or "C=n" defines the exact number (n) of carbon atoms in the group/class. "C≤n" defines the maximum number (n) of carbon atoms that can be in the group/class, with the minimum number as small as possible for the group/class in question. For example, it is understood that the minimum number of carbon atoms in the groups "$alkyl_{(C≤8)}$", "$alkanediyl_{(C≤8)}$", "$heteroaryl_{(C≤8)}$", and "$acyl_{(C≤8)}$" is one, the minimum number of carbon atoms in the groups "$alkenyl_{(C≤8)}$", "$alkynyl_{(C≤8)}$", and "$heterocycloalkyl_{(C≤8)}$" is two, the minimum number of carbon atoms in the group "$cycloalkyl_{(C≤8)}$" is three, and the minimum number of carbon atoms in the groups "$aryl_{(C≤8)}$" and "$arenediyl_{(C≤8)}$" is six. "Cn-n'" defines both the minimum (n) and maximum number (n') of carbon atoms in the group. Thus, "$alkyl_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "$olefin_{C5}$", and "$olefin_{C5}$" are all synonymous. Except as noted below, every carbon atom is counted to determine whether the group or compound falls with the specified number of carbon atoms. For example, the group dihexylamino is an example of a dialkylamino$_{(C=12)}$ group; however, it is not an example of a dialkylamino$_{(C=6)}$ group. Likewise, phenylethyl is an example of an aralkyl$_{(C=8)}$ group. When any of the chemical groups or compound classes defined herein is modified by the term "substituted", any carbon atom in the moiety replacing the hydrogen atom is not counted. Thus methoxyhexyl, which has a total of seven carbon atoms, is an example of a substituted alkyl$_{(C1-6)}$ Unless specified otherwise, any chemical group or compound class listed in a claim set without a carbon atom limit has a carbon atom limit of less than or equal to twelve.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" signifies that the compound or chemical group so modified is an acyclic or cyclic, but non-aromatic compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" signifies that the compound or chemical group so modified has a planar unsaturated ring of atoms with 4n+2 electrons in a fully conjugated cyclic π system. An aromatic compound or chemical group may be depicted as a single resonance structure; however, depiction of one resonance structure is taken to also refer to any other resonance structure. For example:

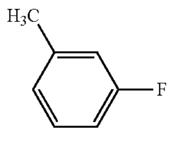

is also taken to refer to.

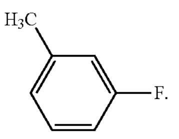

Aromatic compounds may also be depicted using a circle to represent the delocalized nature of the electrons in the fully conjugated cyclic π system, two non-limiting examples of which are shown e below:

and

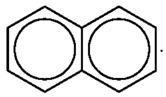

The term "alkyl" refers to a monovalent saturated aliphatic group with a carbon atom as the point of attachment, a linear or branched acyclic structure, and no atoms other than carbon and hydrogen. The groups —$CH_3$ (Me), —$CH_2CH_3$ (Et), —$CH_2CH_2CH_3$ (n-Pr or propyl), —$CH(CH_3)_2$ (i-Pr, $^i$Pr or isopropyl), —$CH_2CH_2CH_2CH_3$ (n-Bu), —$CH(CH_3)CH_2CH_3$ (sec-butyl), —$CH_2CH(CH_3)_2$ (isobutyl), —$C(CH_3)_3$ (tert-butyl, t-butyl, t-Bu or $^t$Bu), and —$CH_2C(CH_3)_3$ (neo-pentyl) are non-limiting examples of alkyl groups. The term "alkanediyl" refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —$CH_2$— (methylene), —$CH_2CH_2$—, —$CH_2C(CH_3)_2CH_2$—, and —$CH_2CH_2CH_2$— are non-limiting examples of alkanediyl groups. The term "alkylidene" refers to the divalent group =CRR' in which R and R' are independently hydrogen or alkyl. Non-limiting examples of alkylidene groups include: =$CH_2$, =$CH(CH_2CH_3)$, and =$C(CH_3)_2$. An "alkane" refers to the class of compounds having the formula H—R, wherein R is alkyl as this term is defined above.

The term "cycloalkyl" refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —$CH(CH_2)_2$ (cyclopropyl), cyclobutyl, cyclopentyl, or cyclohexyl (Cy). As used herein, the term does not preclude the presence of one or more alkyl groups (carbon number limitation permitting) attached to a carbon atom of the non-aromatic ring structure. The term "cycloalkanediyl" refers to a divalent saturated aliphatic group with two carbon atoms as points of attachment, no carbon-carbon double or triple bonds, and no atoms other than carbon and hydrogen. The group

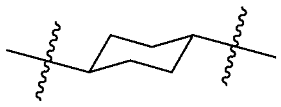 [SMILES: *C1CCC(*)CC1]

is a non-limiting example of cycloalkanediyl group. A "cycloalkane" refers to the class of compounds having the formula H—R, wherein R is cycloalkyl as this term is defined above.

The term "alkenyl" refers to a monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH=$CH_2$ (vinyl), —CH=$CHCH_3$, —CH=$CHCH_2CH_3$, —$CH_2CH$=$CH_2$ (allyl), —$CH_2CH$=$CHCH_3$, and —CH=CHCH=$CH_2$. The term "alkenediyl" refers to a divalent unsaturated aliphatic group, with two carbon atoms as points of attachment, a linear or branched acyclic structure, at least one nonaromatic carbon-carbon double bond, no carbon-carbon triple bonds, and no atoms other than carbon and hydrogen. The groups —CH═CH—, —CH═C($CH_3$)$CH_2$—, —CH═$CHCH_2$—, and —$CH_2CH$═$CHCH_2$— are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula H—R, wherein R is alkenyl as this term is defined above. Similarly, the terms "terminal alkene" and "α-olefin" are synonymous and refer to an alkene having just one carbon-carbon double bond, wherein that bond is part of a vinyl group at an end of the molecule.

The term "alkynyl" refers to a monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups —C≡CH, —C≡$CCH_3$, and —$CH_2C$≡$CCH_3$ are non-limiting examples of alkynyl groups. An "alkyne" refers to the class of compounds having the formula H—R, wherein R is alkynyl.

The term "aryl" refers to a monovalent unsaturated aromatic group with an aromatic carbon atom as the point of attachment, said carbon atom forming part of a one or more aromatic ring structures, each with six ring atoms that are all carbon, and wherein the group consists of no atoms other than carbon and hydrogen. If more than one ring is present, the rings may be fused or unfused. Unfused rings are connected with a covalent bond. As used herein, the term aryl does not preclude the presence of one or more alkyl groups (carbon number limitation permitting) attached to the first aromatic ring or any additional aromatic ring present. Non-limiting examples of aryl groups include phenyl (Ph), methylphenyl, (dimethyl)phenyl, —$C_6H_4CH_2CH_3$ (ethylphenyl), naphthyl, and a monovalent group derived from biphenyl (e.g., 4-phenylphenyl).

The term "arenediyl" refers to a divalent aromatic group with two aromatic carbon atoms as points of attachment, said carbon atoms forming part of one or more six-membered aromatic ring structures, each with six ring atoms that are all carbon, and wherein the divalent group consists of no atoms other than carbon and hydrogen. As used herein, the term arenediyl does not preclude the presence of one or more alkyl groups (carbon number limitation permitting) attached to the first aromatic ring or any additional aromatic ring present. If more than one ring is present, the rings may be fused or unfused. Unfused rings are connected with a covalent bond. Non-limiting examples of arenediyl groups include:

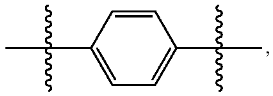,
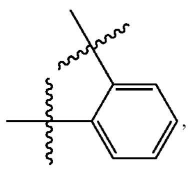,
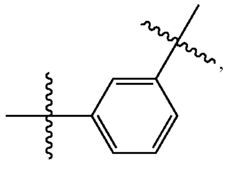,
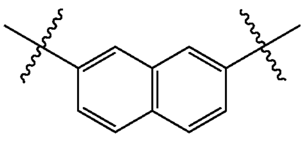

-continued

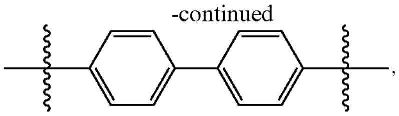, and

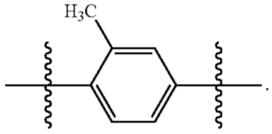.

An "arene" refers to the class of compounds having the formula H—R, wherein R is aryl as that term is defined above. Benzene and toluene are non-limiting examples of arenes.

The term "aralkyl" refers to the monovalent group-alkanediyl-aryl, in which the terms alkanediyl and aryl are each used in a manner consistent with the definitions provided above. Non-limiting examples are: phenylmethyl (benzyl, Bn) and 2-phenyl-ethyl.

The term "heteroaryl" refers to a monovalent aromatic group with an aromatic carbon atom or nitrogen atom as the point of attachment, said carbon atom or nitrogen atom forming part of one or more aromatic ring structures, each with three to eight ring atoms, wherein at least one of the ring atoms of the aromatic ring structure(s) is nitrogen, oxygen or sulfur, and wherein the heteroaryl group consists of no atoms other than carbon, hydrogen, aromatic nitrogen, aromatic oxygen and aromatic sulfur. If more than one ring is present, the rings are fused; however, the term heteroaryl does not preclude the presence of one or more alkyl or aryl groups (carbon number limitation permitting) attached to one or more ring atoms. Non-limiting examples of heteroaryl groups include benzoxazolyl, benzimidazolyl, furanyl, imidazolyl (Im), indolyl, indazolyl, isoxazolyl, methylpyridinyl, oxazolyl, oxadiazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. A "heteroarene" refers to the class of compounds having the formula H—R, wherein R is heteroaryl. Pyridine and quinoline are non-limiting examples of heteroarenes.

The term "heterocycloalkyl" refers to a monovalent non-aromatic group with a carbon atom or nitrogen atom as the point of attachment, said carbon atom or nitrogen atom forming part of one or more non-aromatic ring structures, each with three to eight ring atoms, wherein at least one of the ring atoms of the non-aromatic ring structure(s) is nitrogen, oxygen or sulfur, and wherein the heterocycloalkyl group consists of no atoms other than carbon, hydrogen, nitrogen, oxygen and sulfur. If more than one ring is present, the rings are fused or spirocyclic. As used herein, the term does not preclude the presence of one or more alkyl groups (carbon number limitation permitting) attached to one or more ring atoms. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. Non-limiting examples of N-heterocycloalkyl groups include N-pyrrolidinyl and

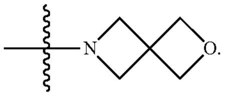 [SMILES: *N1CC2(COC2)C1]

When the term "heterocycloalkyl" is used with the "substituted" modifier, one or more hydrogen atom has been replaced, independently at each instance, by oxo, —OH, —F, —Cl, —Br, —I, —$NH_2$, —$NO_2$, —$CO_2H$, —$CO_2CH_3$, —$CO_2CH_2CH_3$, —CN, —SH, —$OCH_3$, —$OCH_2CH_3$, —C(O)$CH_3$, —$NHCH_3$, —$NHCH_2CH_3$, —N$(CH_3)_2$, —C(O)$NH_2$, —C(O)$NHCH_3$, —C(O)N$(CH_3)_2$, —OC(O)$CH_3$, —NHC(O)$CH_3$, —S$(O)_2$OH, or —S$(O)_2NH_2$. For example, the following groups are non-limiting examples of substituted heterocycloalkyl groups (more specifically, substituted N-heterocycloalkyl groups):

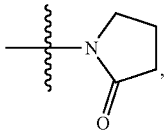,
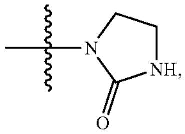,
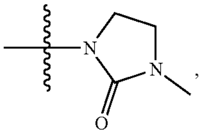,
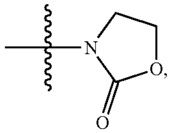,
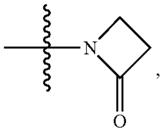, and
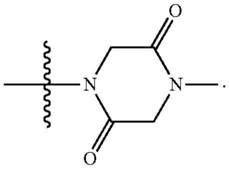.

The term "acyl" refers to the group —C(O)R, in which R is a hydrogen, alkyl, cycloalkyl, or aryl as those terms are defined above. The groups, —CHO, —C(O)$CH_3$ (acetyl, Ac), —C(O)$CH_2CH_3$, —C(O)CH$(CH_3)_2$, —C(O)CH$(CH_2)_2$, —C(O)$C_6H_5$, and —C(O)$C_6H_4CH_3$ are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkyl group, as defined above, attached to a —CHO group.

The term "alkoxy" refers to the group —OR, in which R is an alkyl, as that term is defined above. Non-limiting examples include: —$OCH_3$ (methoxy), —$OCH_2CH_3$ (ethoxy), —$OCH_2CH_2CH_3$, —OCH$(CH_3)_2$ (isopropoxy), or —OC$(CH_3)_3$ (tert-butoxy). The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkylthio" and "acylthio" refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group.

The term "alkylamino" refers to the group —NHR, in which R is an alkyl, as that term is defined above. Non-limiting examples include: —$NHCH_3$ and —$NHCH_2CH_3$. The terms "cycloalkylamino" and "heterocycloalkylamino", when used without the "substituted" modifier, refers to groups, defined as —NHR, in which R is cycloalkyl and heterocycloalkyl, respectively. The term "dialkylamino" refers to the group —NRR', in which R and R' can be the same or different alkyl groups. Non-limiting examples of dialkylamino groups include: —N$(CH_3)_2$ and —N$(CH_3)$$(CH_2CH_3)$. The term "amido" (acylamino), when used without the "substituted" modifier, refers to the group —NHR, in which R is acyl, as that term is defined above. A non-limiting example of an amido group is —NHC(O)$CH_3$.

An "amine protecting group" or "amino protecting group" is well understood in the art. An amine protecting group is a group which modulates the reactivity of the amine group during a reaction which modifies some other portion of the molecule. Amine protecting groups can be found at least in Greene and Wuts, 1999, which is incorporated herein by reference. Some non-limiting examples of amino protecting groups include formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxycarbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethyl-silylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyl-oxycarbonyl, phenylthiocarbonyl and the like; alkylaminocarbonyl groups (which form ureas with the protect amine) such as ethylaminocarbonyl and the like; aralkyl groups such as benzyl, triphenylmethyl, benzyloxymethyl and the like; and silyl groups such as trimethylsilyl and the like. Additionally, the "amine protecting group" can be a divalent protecting group such that both hydrogen atoms on a primary amine are replaced with a single protecting group. In such a situation the amine protecting group can be phthalimide (phth) or a substituted derivative thereof wherein the term "substituted" is as defined above. In some embodiments, the halogenated phthalimide derivative may be tetrachlorophthalimide (TCphth). When used herein, a "protected amino group", is a group of the formula $PG_{MA}$NH— or $PG_{DA}$N— wherein $PG_{MA}$ is a monovalent amine protecting group, which may also be described as a "monovalently protected amino group" and $PG_{DA}$ is a divalent amine protecting group as described above, which may also be described as a "divalently protected amino group".

With the exception of the term "heterocycloalkyl", when a chemical group is used with the "substituted" modifier, one or more hydrogen atom has been replaced, independently at each instance, by —OH, —F, —Cl, —Br, —I, —$NH_2$, —$NO_2$, —$CO_2H$, —$CO_2CH_3$, —$CO_2CH_2CH_3$, —CN, —SH, —$OCH_3$, —$OCH_2CH_3$, —C(O)$CH_3$, —$NHCH_3$, —$NHCH_2CH_3$, —$N(CH_3)_2$, —$C(O)NH_2$, —$C(O)NHCH_3$, —$C(O)N(CH_3)_2$, —$OC(O)CH_3$, —$NHC(O)CH_3$, —$S(O)_2OH$, or —$S(O)_2NH_2$. For example, the following groups are non-limiting examples of substituted alkyl groups: —$CH_2OH$, —$CH_2Cl$, —$CF_3$, —$CH_2CN$, —$CH_2C(O)OH$, —$CH_2C(O)OCH_3$, —$CH_2C(O)NH_2$, —$CH_2C(O)CH_3$, —$CH_2OCH_3$, —$CH_2OC(O)CH_3$, —$CH_2NH_2$, —$CH_2N(CH_3)_2$, and —$CH_2CH_2Cl$. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —$CH_2Cl$ is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —$CH_2F$, —$CF_3$, and —$CH_2CF_3$ are non-limiting examples of fluoroalkyl groups. Non-limiting examples of substituted aralkyls are: (3-chlorophenyl)-methyl, and 2-chloro-2-phenyl-eth-1-yl. The groups, —$C(O)CH_2CF_3$, —$CO_2H$ (carboxyl), —$CO_2CH_3$ (methylcarboxyl), —$CO_2CH_2CH_3$, —$C(O)NH_2$ (carbamoyl), and —$CON(CH_3)_2$, are non-limiting examples of substituted acyl groups. The groups —$NHC(O)OCH_3$ and —$NHC(O)NHCH_3$ are non-limiting examples of substituted amido groups.

Some of the abbreviations used herein are as follows: Ac indicates an acetyl group (—$C(O)CH_3$) Boc refers to tert-butyloxycarbonyl; COX-2, cyclooxygenase-2; cyPGs refers to cyclopentenone prostaglandins; DBDMH refers to 1,3-Dibromo-5,5-dimethylhydantoin; DIBAL-H is diisobutylaluminium hydride; DMAP refers to 4-dimethylaminopyridine; DMF is dimethylformamide; DMSO is dimethyl sulfoxide; EDC refers to 1-ethyl-3-(3-dimethylaminopropyl)carbodiimide; $Et_2O$, diethyl ether; HO-1 stands for inducible heme oxygenase IFNγ or IFN-γ stand for interferon-γ; IL-1β stands for interleukin-1β; iNOS stands for inducible nitric oxide synthase; NCS refers to N-Chlorosuccinimide; NMO refers to N-methylmorpholine N-oxide; NO stands for nitric oxide; Py stands for Pyridine; T3P refers to propylphosphonic anhydride; TFA is trifluoroacetic acid; THF is tetrahydrofuran; TNFα or TNF-α, tumor necrosis factor-α; TPAP is tetrapropylammonium perruthenate; Ts stands for tosyl; TsOH or p-TsOH is p-toluenesulfonic acid.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects or patients.

An "active ingredient" (AI) or active pharmaceutical ingredient (API) (also referred to as an active compound, active substance, active agent, pharmaceutical agent, agent, biologically active molecule, or a therapeutic compound) is the ingredient in a pharmaceutical drug that is biologically active.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to the patient or subject, is sufficient to effect such treatment or prevention of the disease as those terms are defined below.

An "excipient" is a pharmaceutically acceptable substance formulated along with the active ingredient(s) of a medication, pharmaceutical composition, formulation, or drug delivery system. Excipients may be used, for example, to stabilize the composition, to bulk up the composition (thus often referred to as "bulking agents," "fillers," or "diluents" when used for this purpose), or to confer a therapeutic enhancement on the active ingredient in the final dosage form, such as facilitating drug absorption, reducing viscosity, or enhancing solubility. Excipients include pharmaceutically acceptable versions of antiadherents, binders, coatings, colors, disintegrants, flavors, glidants, lubricants, preservatives, sorbents, sweeteners, and vehicles. The main excipient that serves as a medium for conveying the active ingredient is usually called the vehicle. Excipients may also be used in the manufacturing process, for example, to aid in the handling of the active substance, such as by facilitating powder flowability or non-stick properties, in addition to aiding in vitro stability such as prevention of denaturation or aggregation over the expected shelf life. The suitability of an excipient will typically vary depending on the route of administration, the dosage form, the active ingredient, as well as other factors.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "$IC_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human patients are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds disclosed herein which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

A "pharmaceutically acceptable carrier," "drug carrier," or simply "carrier" is a pharmaceutically acceptable substance formulated along with the active ingredient medication that is involved in carrying, delivering and/or transporting a chemical agent. Drug carriers may be used to improve the delivery and the effectiveness of drugs, including for example, controlled-release technology to modulate drug bioavailability, decrease drug metabolism, and/or reduce drug toxicity. Some drug carriers may increase the effectiveness of drug delivery to the specific target sites. Examples of carriers include: liposomes, microspheres (e.g., made of poly(lactic-co-glycolic) acid), albumin microspheres, synthetic polymers, nanofibers, protein-DNA complexes, protein conjugates, erythrocytes, virosomes, and dendrimers.

A "pharmaceutical drug" (also referred to as a pharmaceutical, pharmaceutical preparation, pharmaceutical composition, pharmaceutical formulation, pharmaceutical product, medicinal product, medicine, medication, medicament, or simply a drug, agent, or preparation) is a composition used to diagnose, cure, treat, or prevent disease, which comprises an active pharmaceutical ingredient (API) (defined above) and optionally contains one or more inactive ingredients, which are also referred to as excipients (defined above).

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an active pharmaceutical ingredient of the present invention. The prodrug itself may or may not also have activity with respect in a given indication. For example, a compound comprising a hydroxy group may be administered as an ester that is converted by hydrolysis in vivo to the hydroxy compound. Non-limiting examples of suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, and esters of amino acids. Similarly, a compound comprising an amine group may be administered as an amide that is converted by hydrolysis in vivo to the amine compound.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease or symptom thereof in a subject or patient that is experiencing or displaying the pathology or symptomatology of the disease.

The term "unit dose" refers to a formulation of the compound or composition such that the formulation is prepared in a manner sufficient to provide a single therapeutically effective dose of the active ingredient to a patient in a single administration. Such unit dose formulations that may be used include but are not limited to a single tablet, capsule, or other oral formulations, or a single vial with a syringeable liquid or other injectable formulations.

The above definitions supersede any conflicting definition in any reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: Experimental Procedures and Characterization Data

A. General Information

Unless otherwise stated, commercially reagents were used as received, and all reactions were run under nitrogen atmosphere. All solvents were of HPLC or ACS grade. Nuclear magnetic resonance (NMR) spectra were recorded on a Varian Inova-400 spectrometer at operating frequencies of 400 MHz ($^1$H NMR) or 100 MHz ($^{13}$C NMR). Chemical shifts (6) are given in ppm relative to residual solvent (usually chloroform δ 7.26 ppm for $^1$H NMR) and coupling constants (J) in Hz. Multiplicity is tabulated as s for singlet, d for doublet, t for triplet, q for quadruplet, and m for multiplet. Mass spectra were recorded on Waters Micromass ZQ or Agilent 6120 mass spectrometer. The compounds of the present disclosure may be prepared according to the methods outlined in Example 1 as well as methods known to a skilled artisan, including those disclosed in Honda et al., 2002, Sharma et al., 2004, and van Berkel et al., 2012, which are incorporated by reference herein.

B. Synthetic Routes to Compounds of the Present Disclosure

Scheme 1.

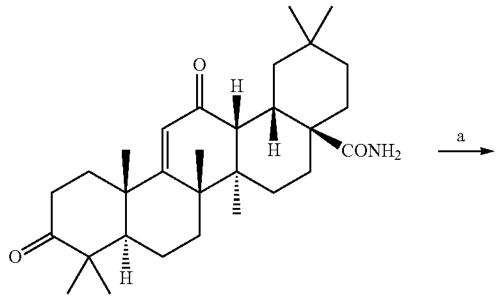

1

-continued

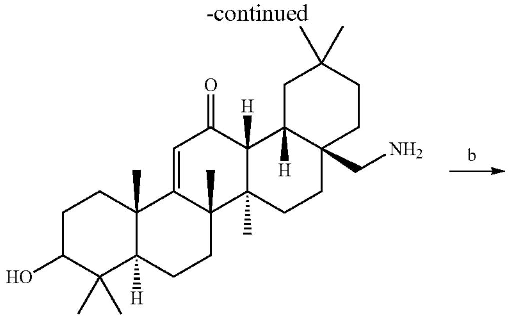

2

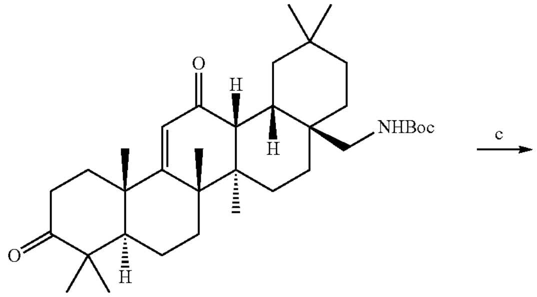

3

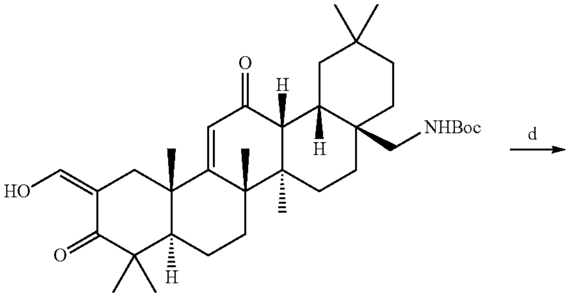

4

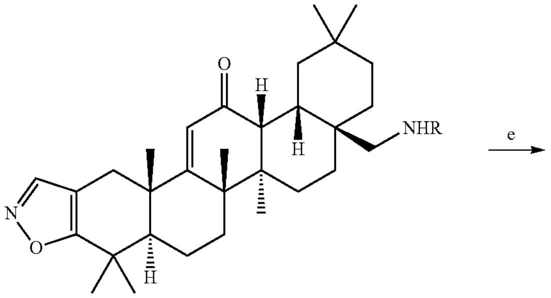

5 R = Boc
6 R = H

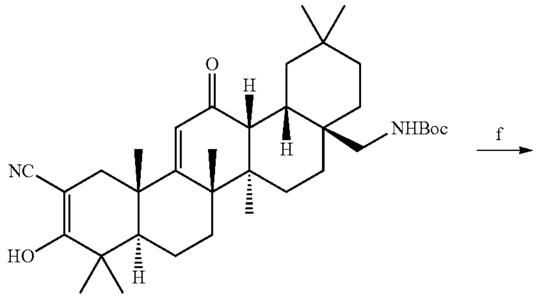

7

-continued

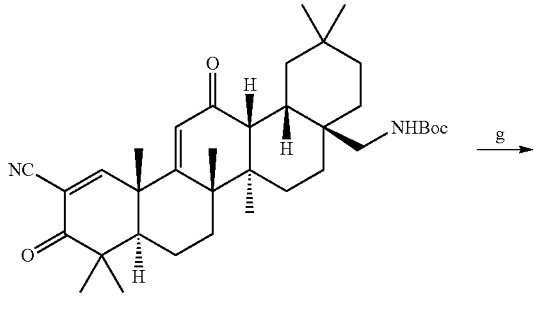

CC1

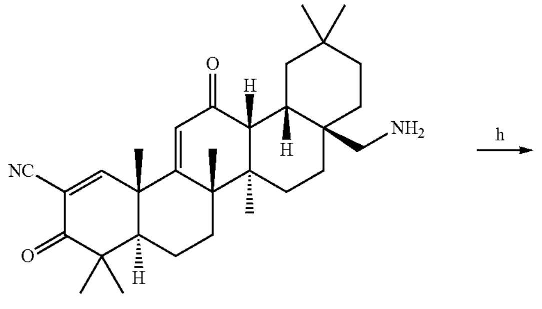

CC2

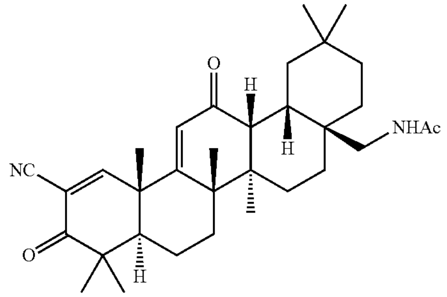

T3

Reagents and conditions:
a) $LiAlH_4$, THF, reflux, 88%;
b) 1) $Boc_2O$, $NaHCO_3$, THF, $H_2O$, rt; 2) Jones' reagent, acetone, 0° C., 55%;
c) $HCO_2Et$, NaOMe, MeOH, 0° C.-rt;
d) $NH_2OH$•HCl, EtOH, $H_2O$, 60° C., 56% for 5; 23% for 6;
e) NaOMe, MeOH, 55° C., 91%;
f) 1,3-dibromo-5,5-dimethylhydantoin, DMF, 0° C.; pyridine, 55° C., 86%;
g) TFA, $CH_2Cl_2$, 0° C., 65%;
h) $Ac_2O$, $Et_3N$, $CH_2Cl_2$, 0° C., 71%.

Scheme 2.

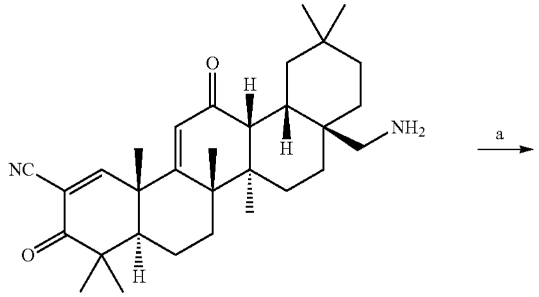

CC2

-continued

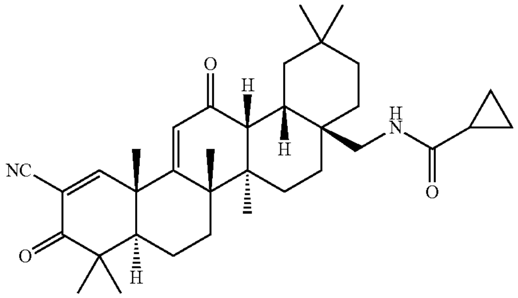

T4

Reagents and conditions:
a) cyclopropanecarbonyl chloride, $Et_3N$, $CH_2Cl_2$, 0° C., 60%.

Scheme 3.

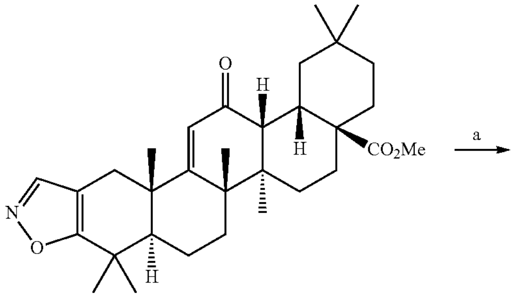

8

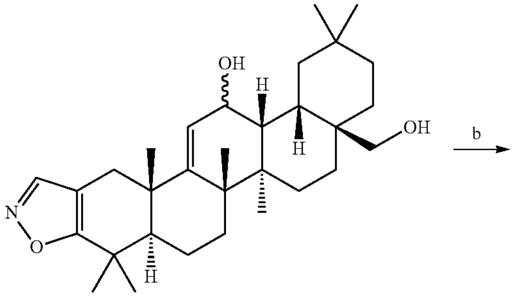

9

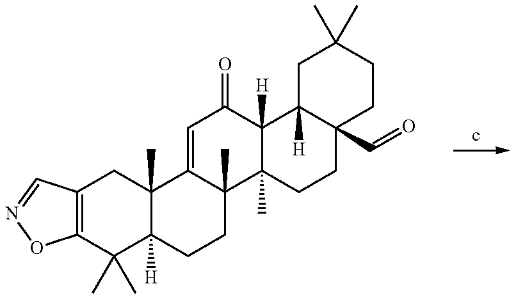

10

-continued

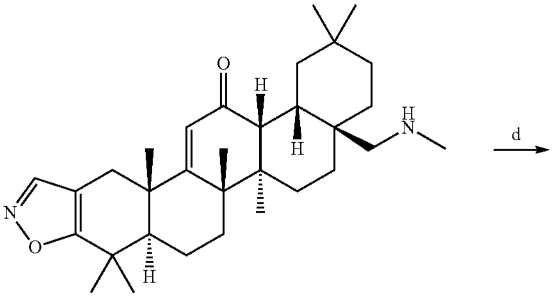

11

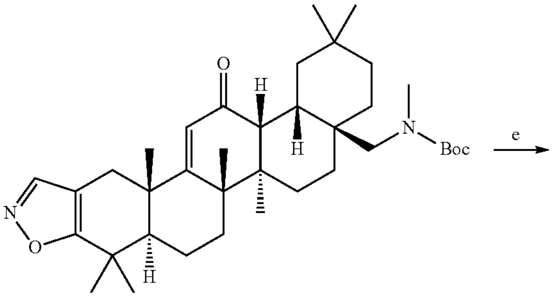

12

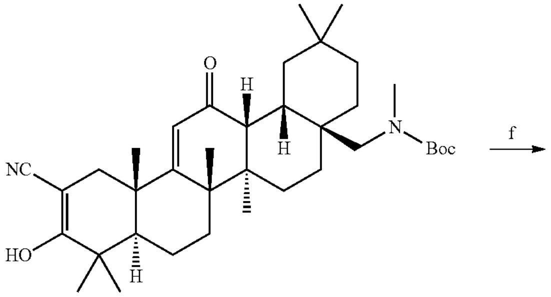

13

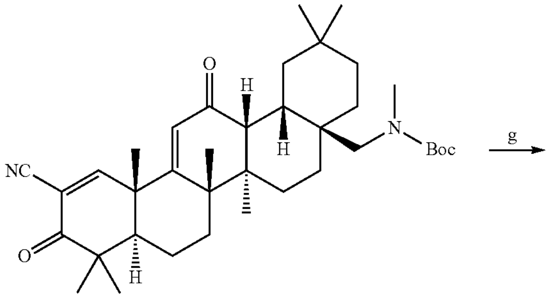

T5

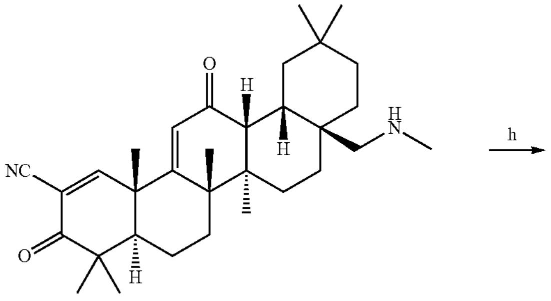

T6

-continued

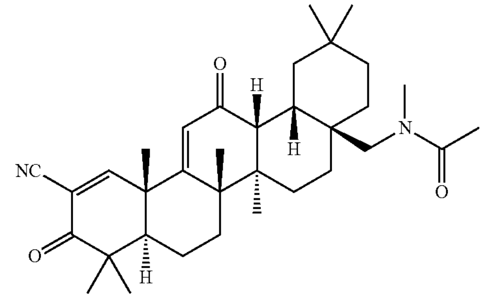

T7

Reagents and conditions:
a) DIBAL-H, toluene, THF, 0° C.-rt;
b) NMO, TPAP, 4Å MS, $CH_2Cl_2$, rt, 68% from 8;
c) methylamine, AcOH, $NaBH_3CN$, MeOH, THF, rt, 80%;
d) $(Boc)_2O$, $NaHCO_3$, THF, $H_2O$, rt, 93%;
e) NaOMe, MeOH, 55° C., 92%;
f) 1,3-dibromo-5,5-dimethylhydantoin, DMF, 0° C.; pyridine, 55° C., 82%;
g) TFA, $CH_2Cl_2$, 0° C., 89%;
h) $Ac_2O$, $Et_3N$, $CH_2Cl_2$, 0° C., 74%.

Scheme 4.

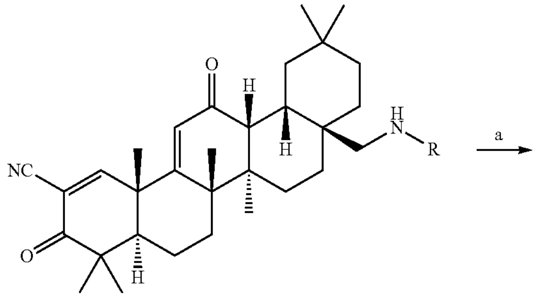

CC2 R = H
T6 R = Me

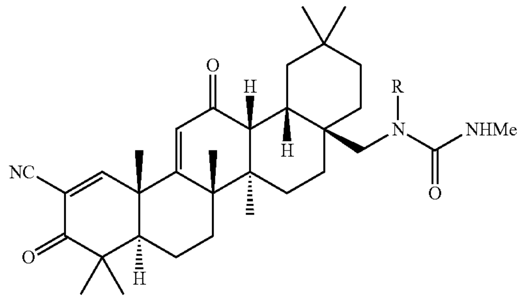

T8 R = H
T9 R = Me

Reagents and conditions:
a) N-methylcarbamoyl chloride, $Et_3N$, $CH_2Cl_2$, 0° C., 73% for T8; 43% for T9.

Scheme 5
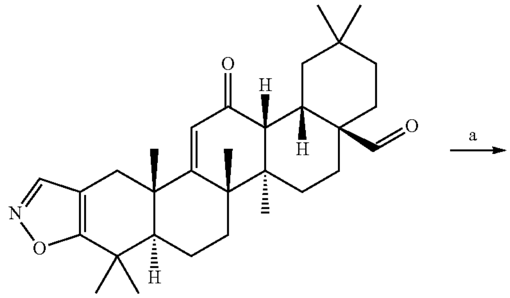
10
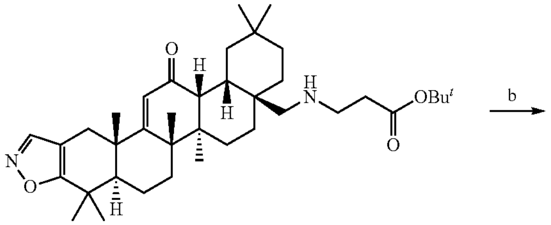
14
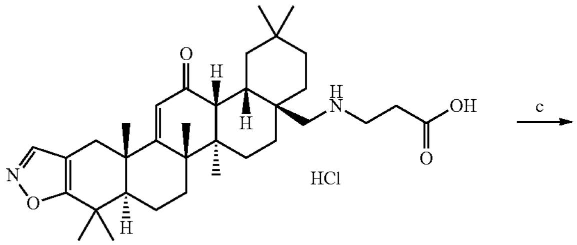
15
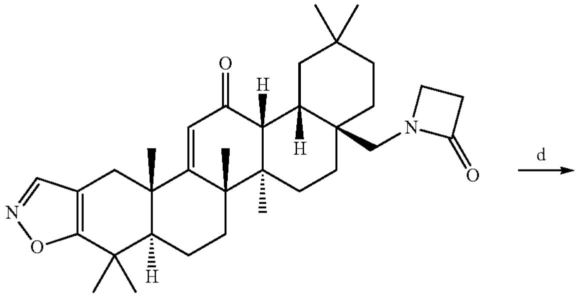
16
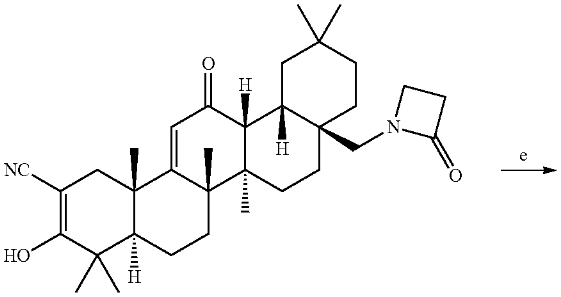
17
-continued
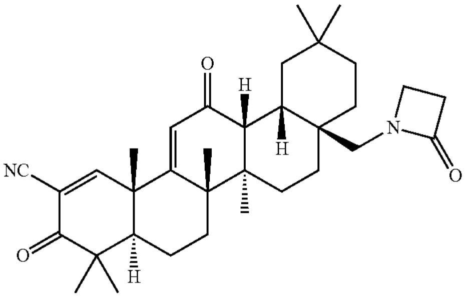
T10
Reactions and conditions:
a) tert-butyl 3-aminopropanoate hydrochloride, $Et_3N$, THF, rt; $NaBH_4$, EtOH, rt, 83%;
b) HCl in 1,4-dioxane, rt, 85%;
c) $POCl_3$, $Et_3N$, $CH_2Cl_2$, 0° C., 68%;
d) NaOMe, MeOH, 55° C., 94%;
e) 1,3-Dibromo-5,5-dimethylhydantoin, DMF, 0° C.; pyridine, 60° C., 77%.
Scheme 6
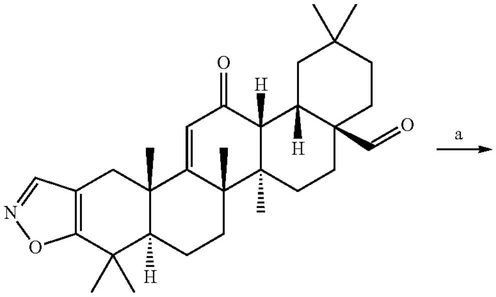
10
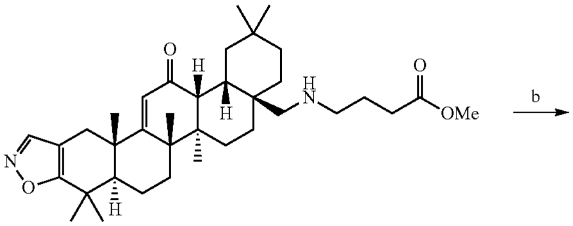
18
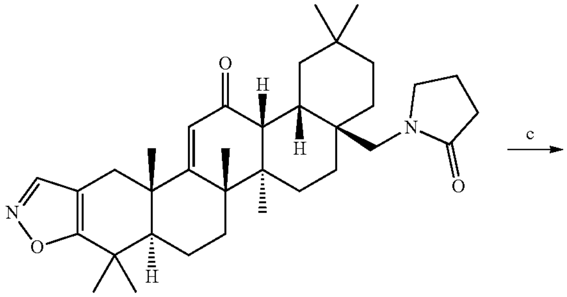
19

-continued

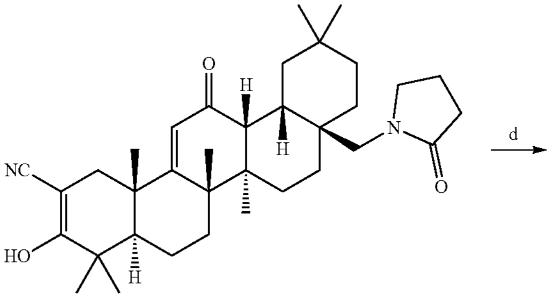

20

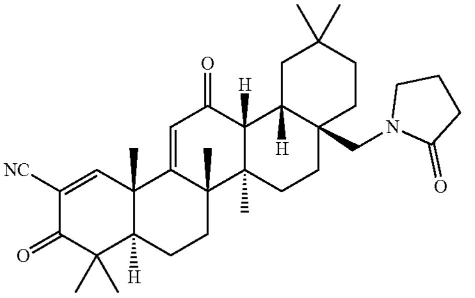

T11

Reagents and conditions:
a) methyl 4-aminobutanoate hydrochloride, $Et_3N$, $NaBH(OAc)_3$, THF, rt; $NaBH_4$, MeOH, rt, 99%;
b) toluene, 140° C., 75%;
c) NaOMe, MeOH, 55° C., 96%;
d) 1,3-Dibormo-5,5-dimethylhydantoin, DMF, 0° C.; pyridine, 55° C., 70%.

Scheme 7

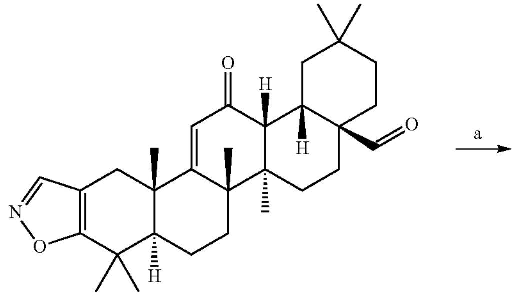

10

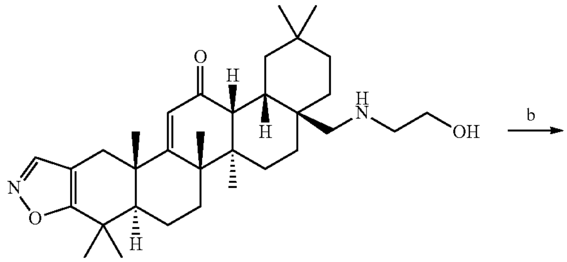

21

-continued

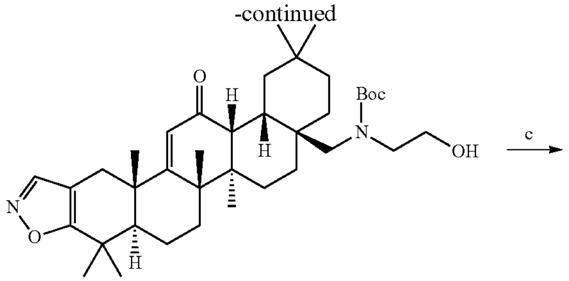

22

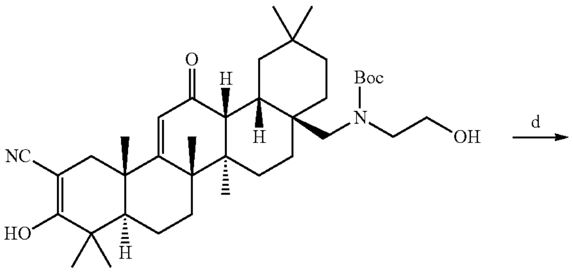

23

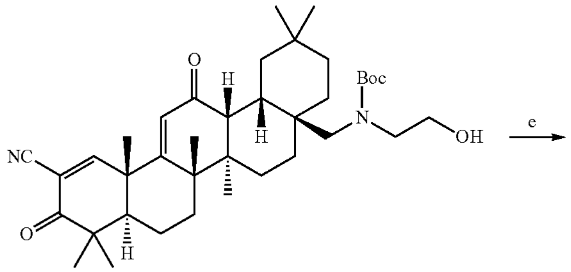

24

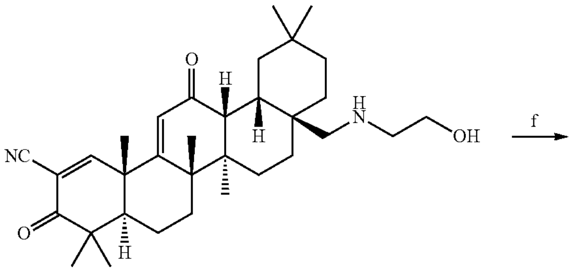

T12

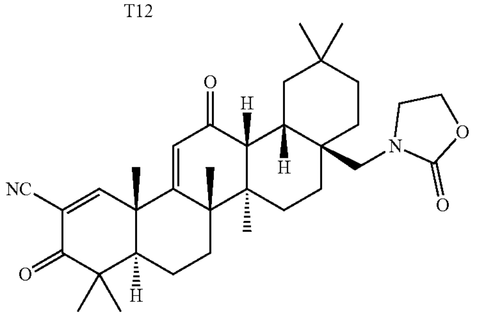

T13

Reagents and conditions:
a) ethanolamine, HOAc, $NaBH_3CN$, MeOH, THF, rt, 63%;
b) $Boc_2O$, $Et_3N$, $CH_2Cl_2$, rt, 78%;
c) $K_2CO_3$, MeOH, rt, 74%;
d) 1,3-Dibromo-5,5-dimethylhydantoin, DMF, 0° C.; pyridine, 60° C., 71%;
e) TFA, $CH_2Cl_2$, rt, 39%;
f) CDI, $CH_2Cl_2$, rt, 43%.

Scheme 8
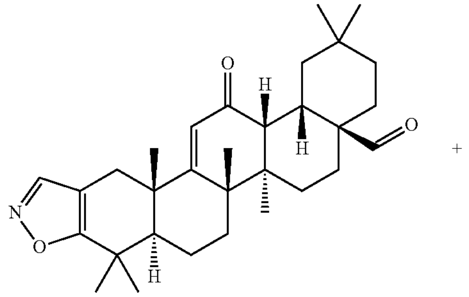
10
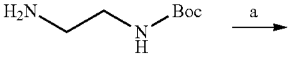
25
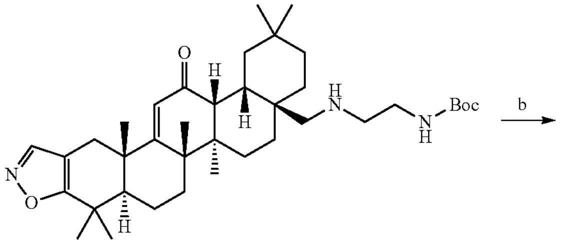
26
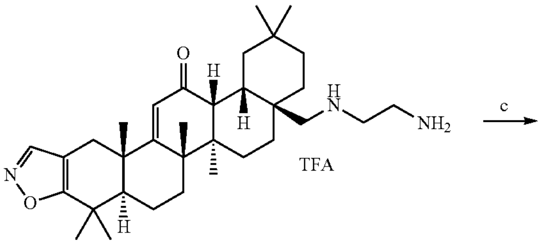
27
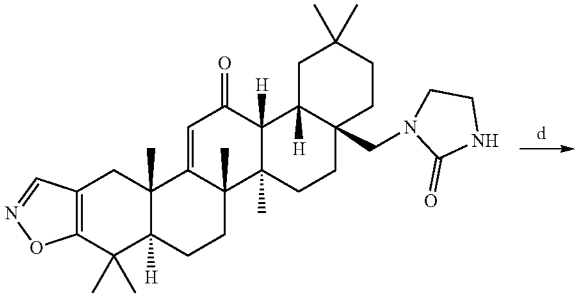
28
-continued
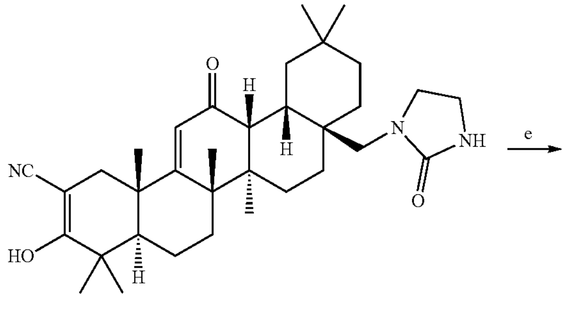
29
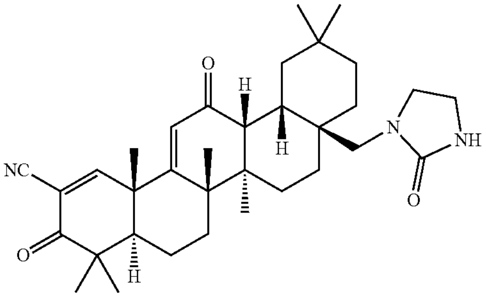
T14
Reagents and conditions:
a) $NaBH_3CN$, AcOH, MeOH, THF, rt, 94%;
b) TFA, $CH_2Cl_2$, rt;
c) CDI, Hunig's base, 1,4-dioxane, 80° C., 27% from 26;
d) $K_2CO_3$, MeOH, rt, 77%;
e) 1,3-Dibromo-5,5-dimethylhydantoin, DMF, 0° C.; pyridine, 60° C., 64%.
Scheme 9
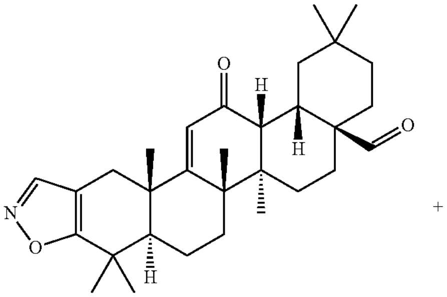
10
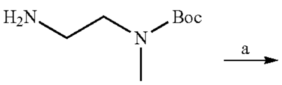
30
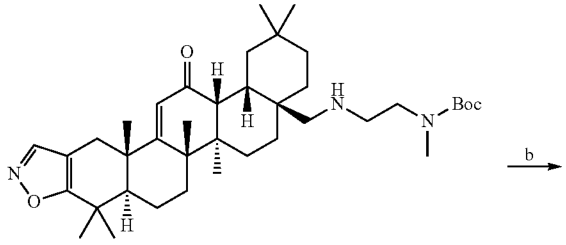
31

-continued
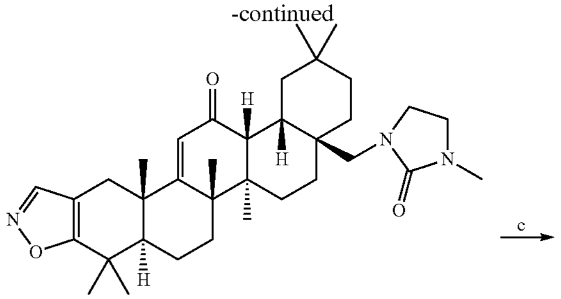
32
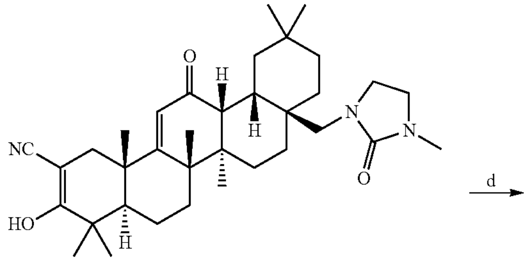
33
-continued
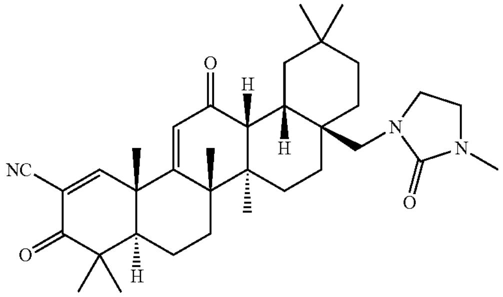
T15
Reagents and conditions: a) $NaBH_3CN$, AcOH, MeOH, THF, RT, 82%; b) 1) TFA, $CH_2Cl_2$, rt; 2) Phosgene, toluene, $CH_2Cl_2$, rt, 49%; c) $K_2CO_3$, MeOH, rt, 74%; d) 1,3-Dibromo-5,5-dimethylhydantoin, DMF, 0° C.; pyridine, 60° C., 90%.
Scheme 10
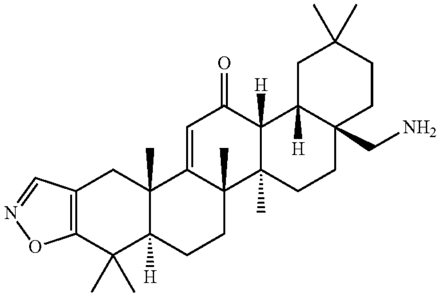
6
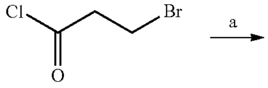
34
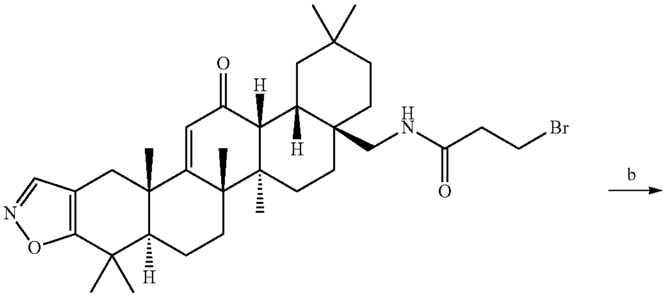
35

-continued
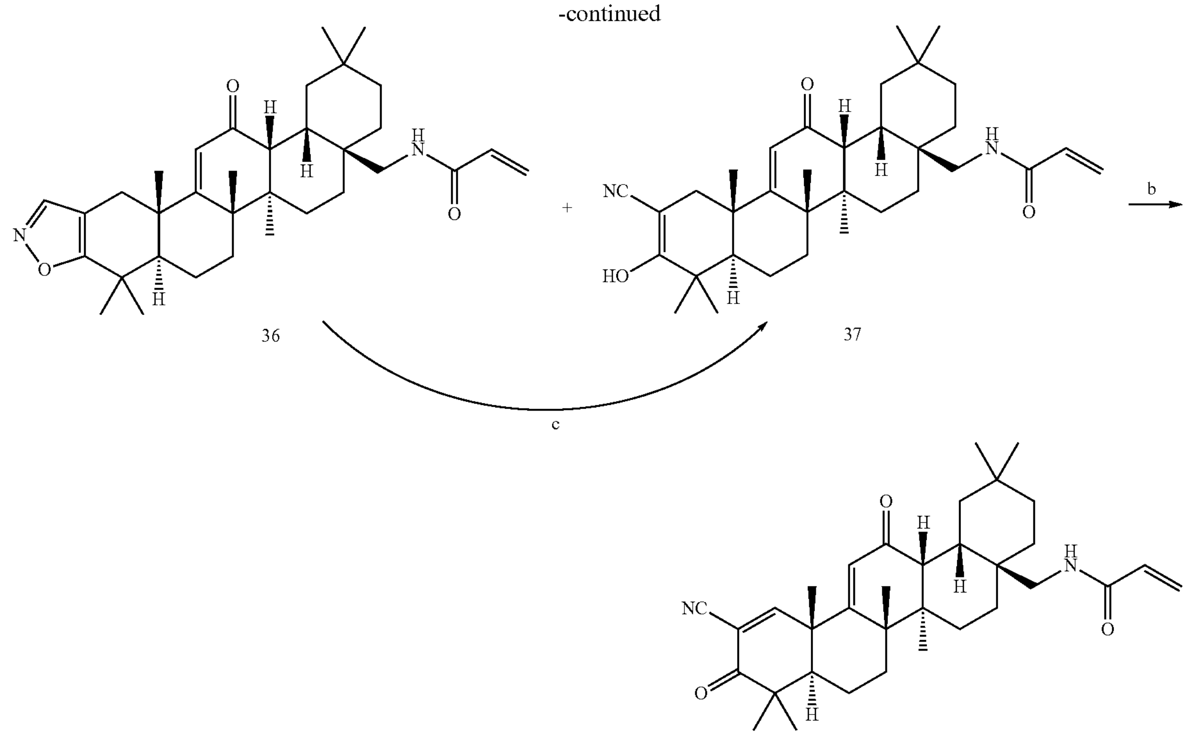
36 + 37 → T16
Reagents and conditions: a) $Et_3N$, $CH_2Cl_2$, 0° C., quantitative yield; b) NaH, THF, 0° C.-rt; c) NaOMe, MeOH, 55° C., 58% from 6; d) 1,3-dibromo-5,5-dimethylhydantoin, DMF, 0° C.; pyridine, 55° C., 36%.
Scheme 11
-continued
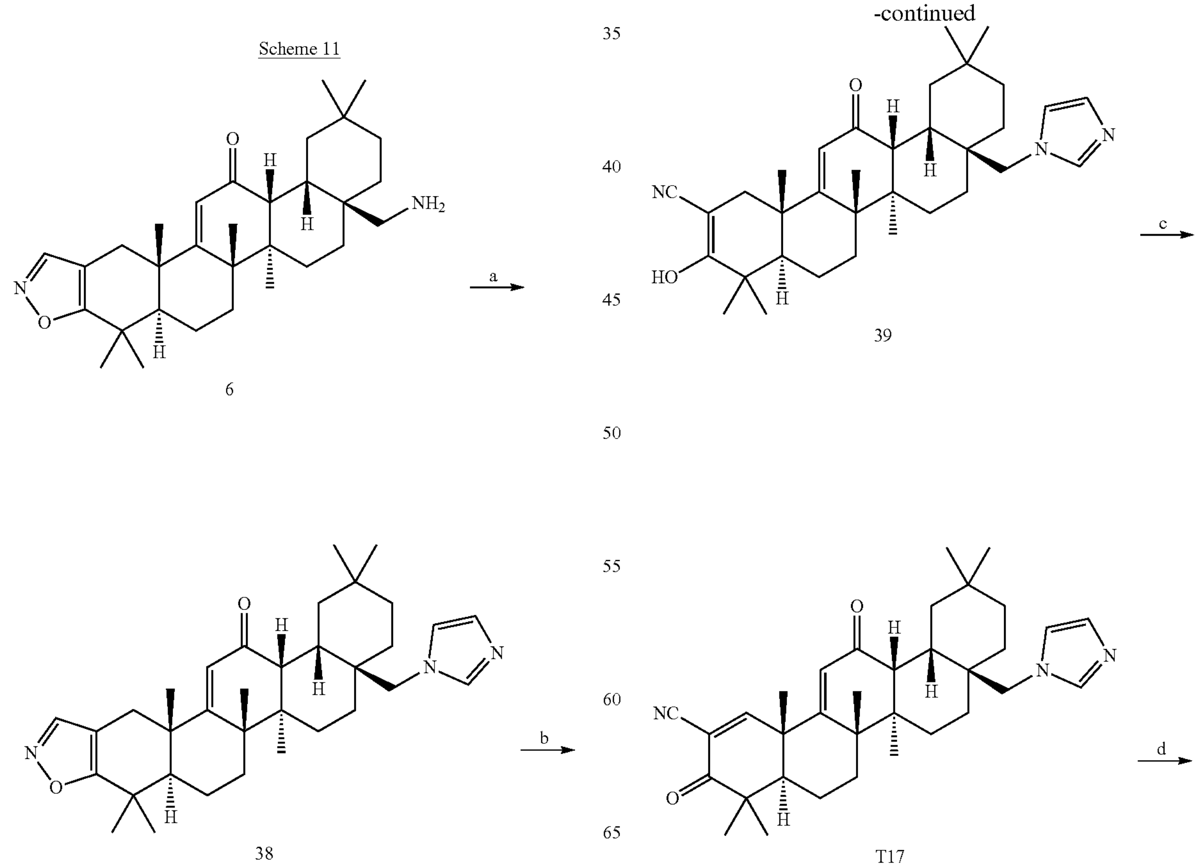
6
39
38
T17

-continued
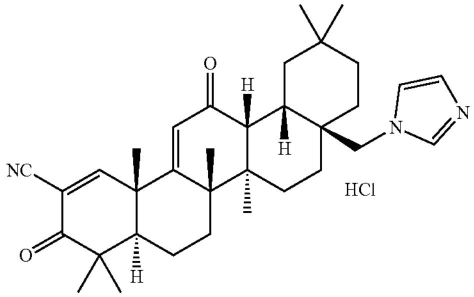
T17-HCl
Reagents and conditions: a) $(HCHO)_n$, trimeric glyoxal dihydrage, $(NH_4)_2CO_3$, MeOH, rt, 89%; b) NaOMe, MeOH, 55° C., 73%; c) 1,3-Dibromo-5,5-dimethylhydantoin, DMF, 0° C.; pyridine, 60° C., 36%; d) HCl in 1,4-dioxane, 0° C. to rt, 94%.
Scheme 12
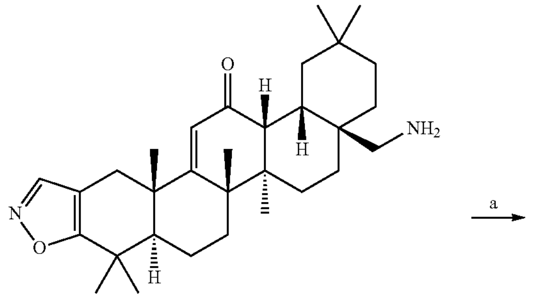
6
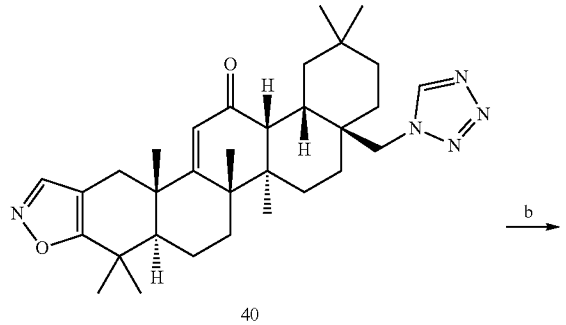
40
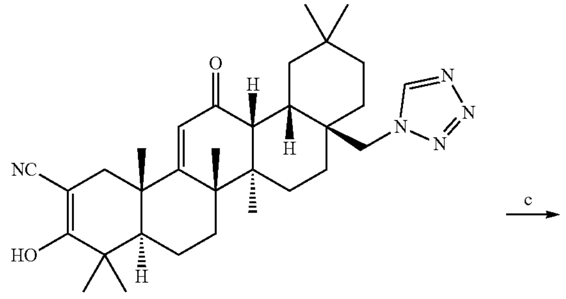
41
-continued
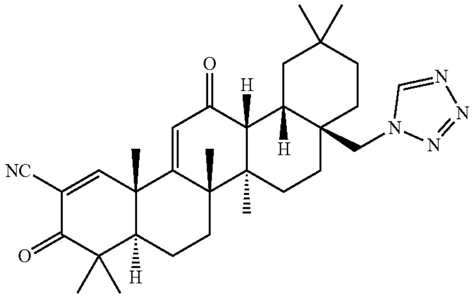
T18
Reagents and conditions: a) trimethyl orthoformate, $NaN_3$, AcOH, rt-80° C., 75%; b) NaOMe, MeOH, 55° C., 71%; c) 1,3-Dibromo-5,5-dimethylhydantoin, DMF, 0° C.; pyridine, 60° C., 38%.
Scheme 13
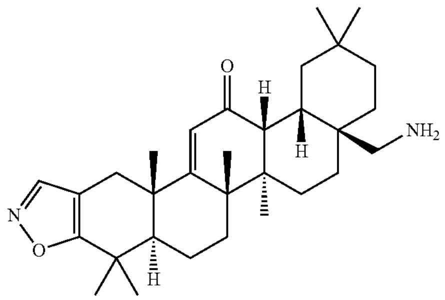
6
+
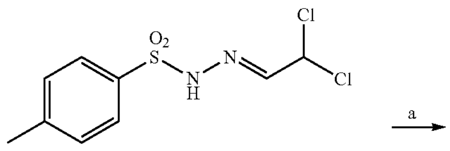
42
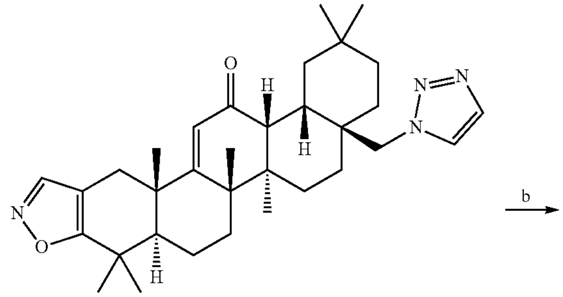
43
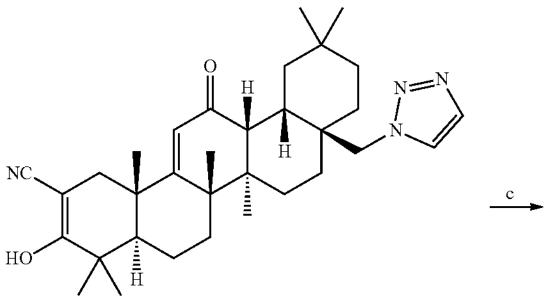
44

-continued

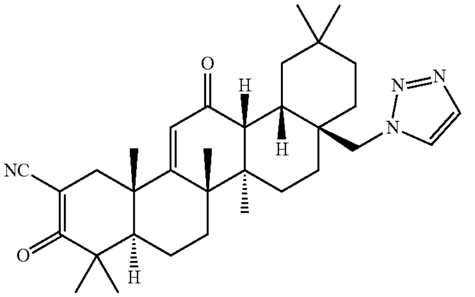

T19

Reagents and conditions: a) Hunig's base, EtOH, MeCN, 0° C.-rt, 82%; b) NaOMe, MeOH, 55° C., 79%; c) 1,3-Dibromo-5,5-dimethylhydantoin, DMF, 0° C.; pyridine, 60° C., 72%.

Scheme 14

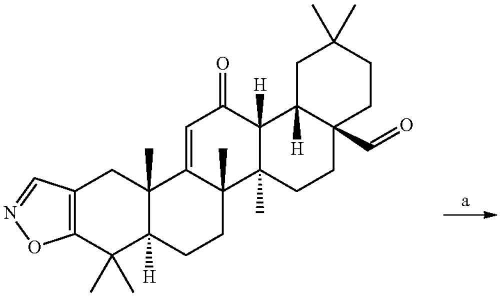

10

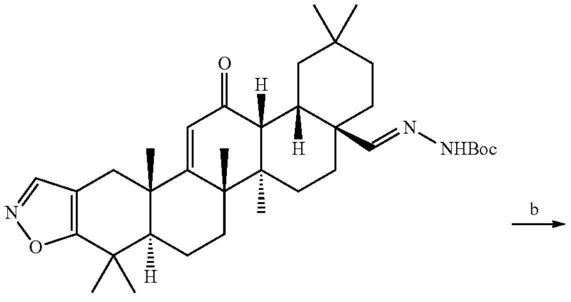

45

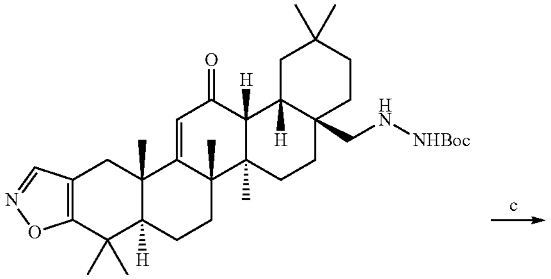

46

-continued

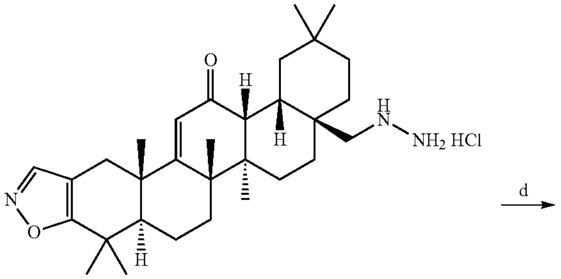

47

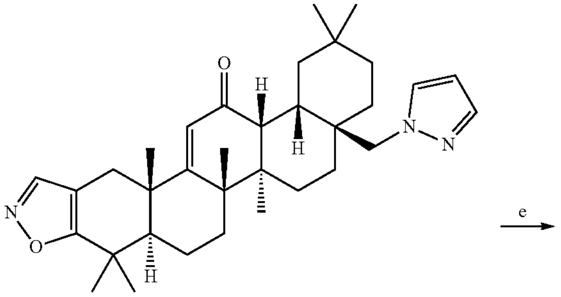

48

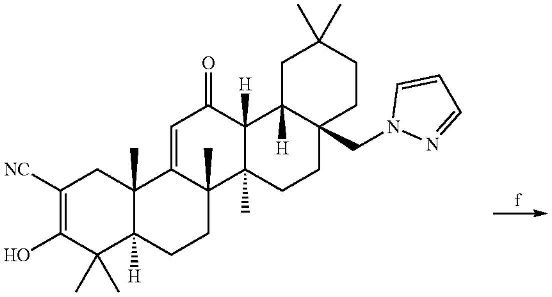

49

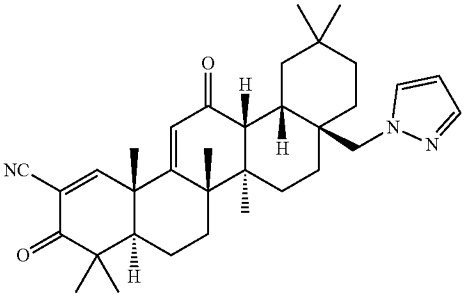

T20

Reagents and conditions: a) tert-Butyl carbazate, THF, 70° C., 95%; b) $NaCNBH_3$, acetic acid, THF, 70° C., 84%; c) 4M HCl in 1,4-dioxane, THF, 70° C., 79%; d) 1,1,3,3-Tetramethoxypropane, 12N, HCl, EtOH, rt-reflux, 63%; e) NaOMe, MeOH, 55° C.; f) 1,3-Dibromo-5,5-dimethylhydantoin, DMF, 0° C.; pyridine, 60° C., 64% from 48.

Scheme 15
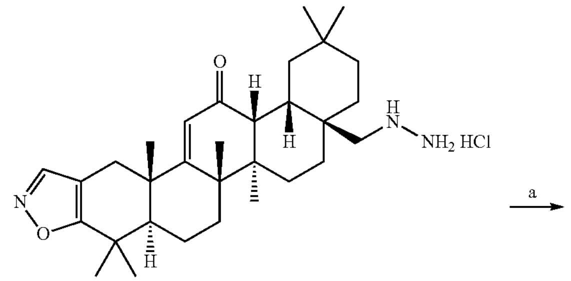
47
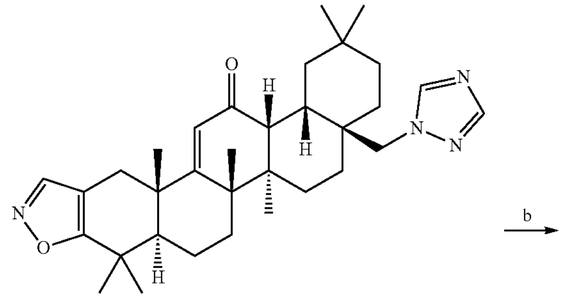
50
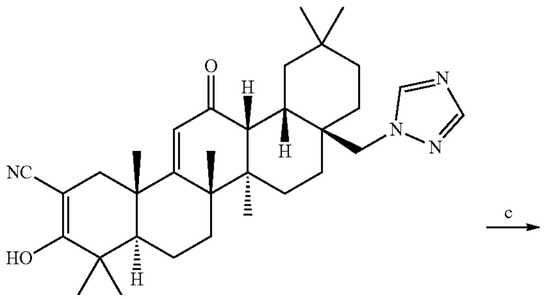
51
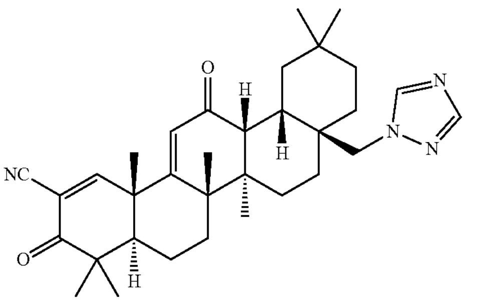
T21
Reagents and conditions: a) 1,3,5-triazine, HCOOH, rt, 64%; b) NaOMe, MeOH, 55° C.; c) 1,3-Dibromo-5,5-dimethylhydantoin, DMF, 0° C.; pyridine, 60° C., 66% from 50.
Scheme 16
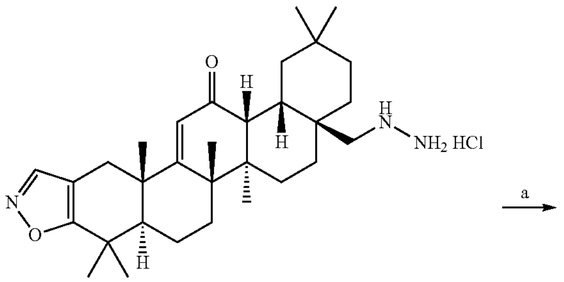
47
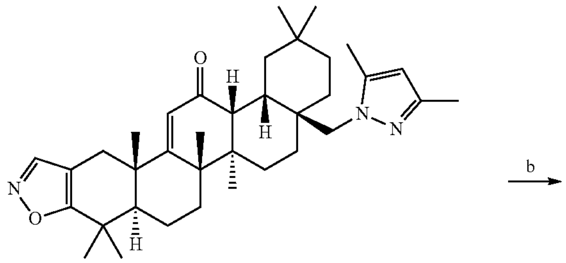
52
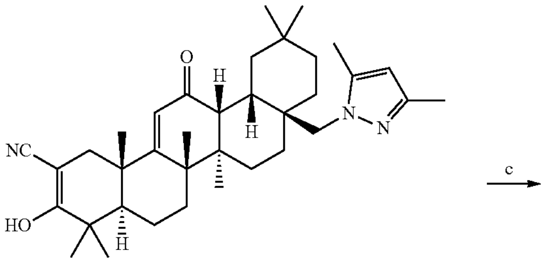
53
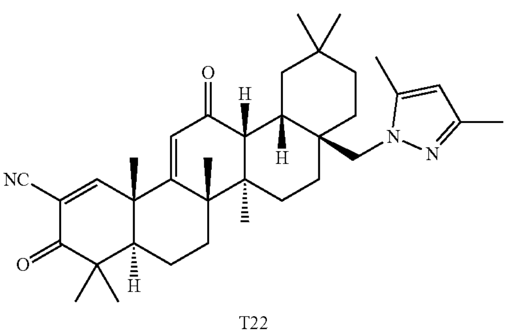
T22
Reagents and conditions: a) acetylacetone, 12N aq. HCl, EtOH, 80° C., 87%; b) NaOMe, MeOH, 55° C., 84%; c) DDQ, toluene, 85° C., 25%.

Scheme 17
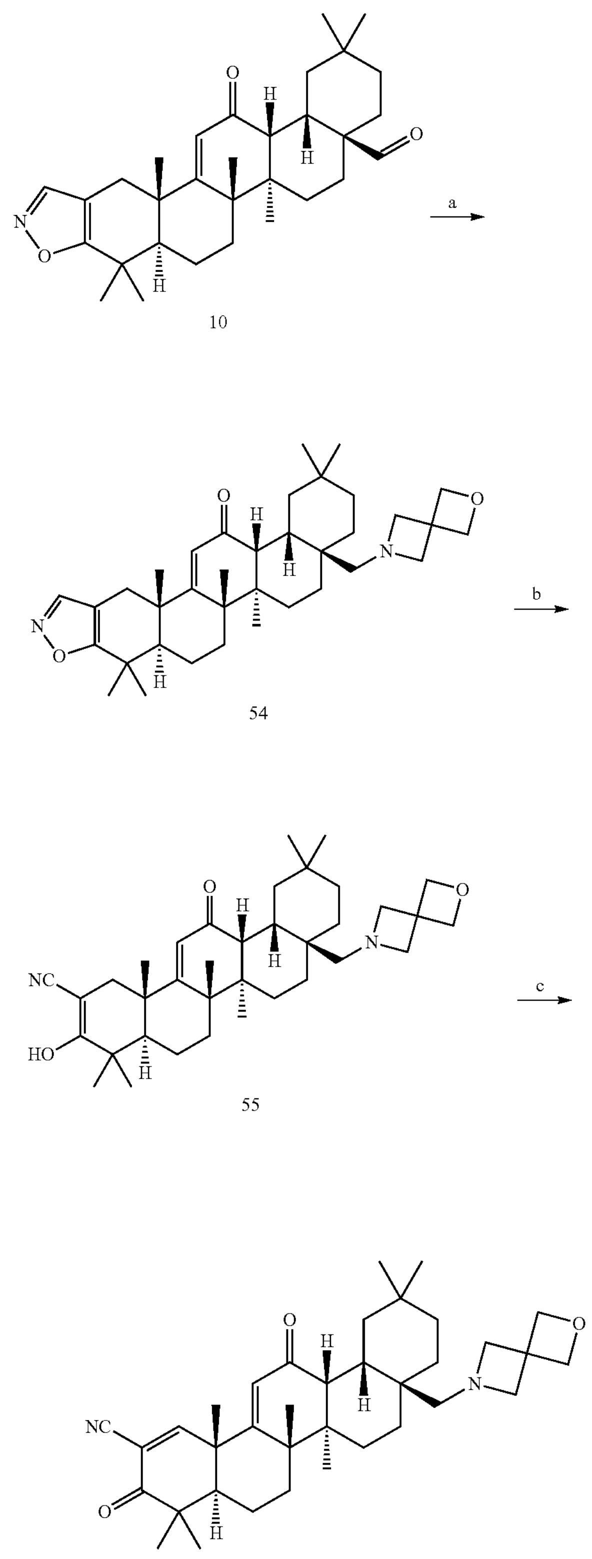
10, 54, 55, T23
Reagents and conditions: a) 2-oxa-6-azaspiro[3.3]heptane, AcOH, $NaBH_3CN$, MeOH, THF, rt, 51%; b) $K_2CO_3$, MeOH, rt, quantitative yield; c) 1,3-Dibromo-5,5-dimethylhydantoin, DMF, 0° C.; pyridine, 60° C., 8%.
Scheme 18
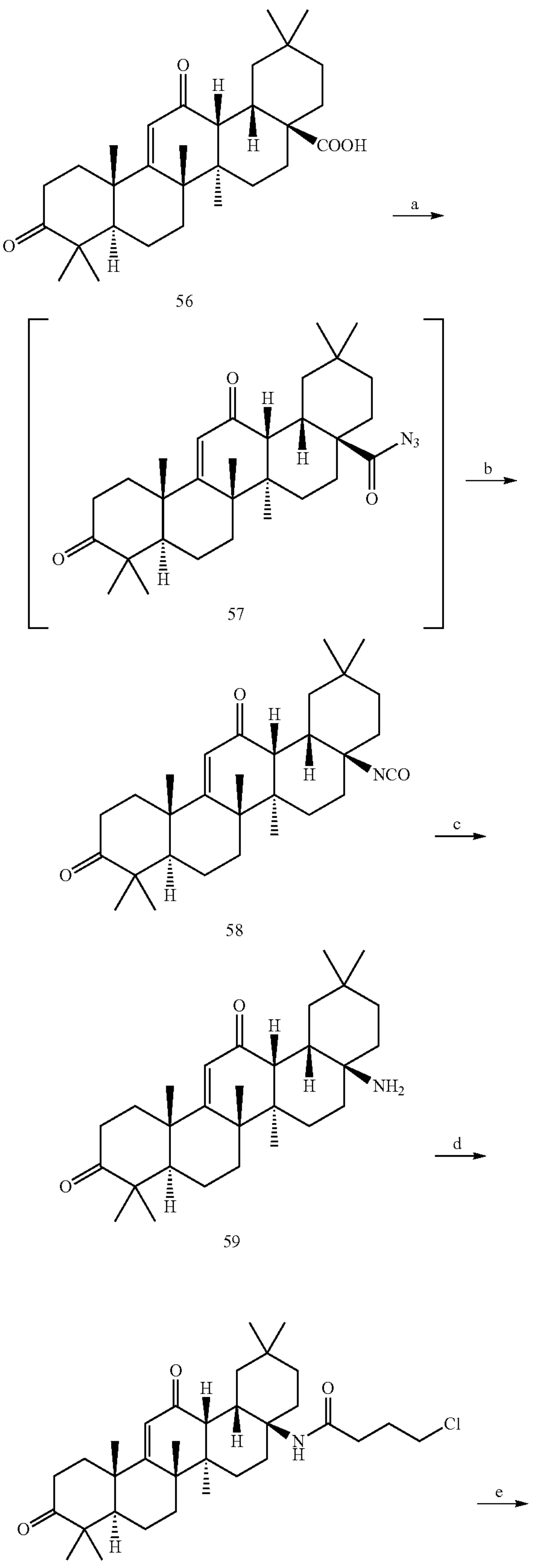
56, 57, 58, 59, 60

-continued

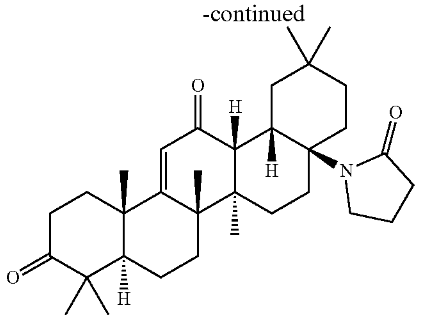

61 f

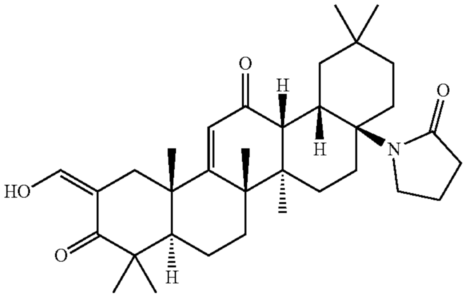

62 g

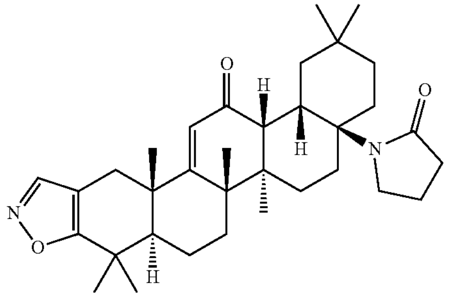

63 h

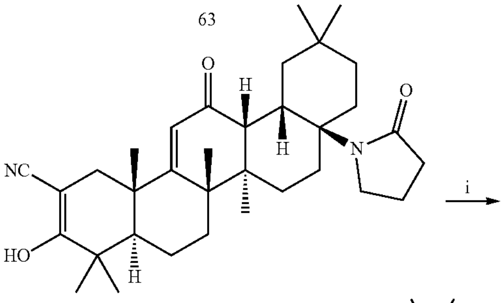

64 i

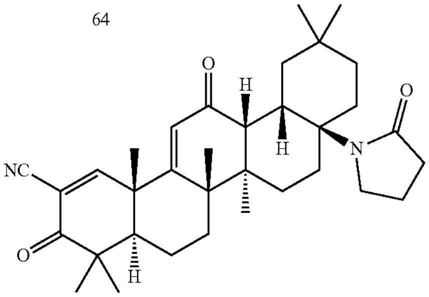

T24

Reagents and conditions: a) diphenyl phosphorazide, $Et_3N$, toluene, 0° C. to rt; b) toluene, 80° C., 88% from 56; c) aq. HCl, MeCN, rt, 95%; d) 4-chlorobutanoyl chloride, $Et_3N$, $CH_2Cl_2$, rt, 95%; e) NaH, DMF, 0° C. to rt; f) $HCO_2Et$, NaOMe, MeOH, rt; g) $NH_2OH$•HCl, EtOH, water, 55° C., 22% from 60; h) $K_2CO_3$, MeOH, rt, quant.; i) 1,3-dibromo-5,5-dimethylhydatoin, DMF, 0° C. to rt; pyridine, 55° C., 21%.

Scheme 19

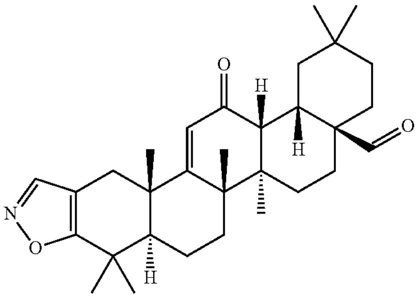

10 a

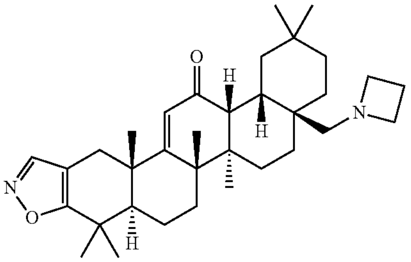

65 b

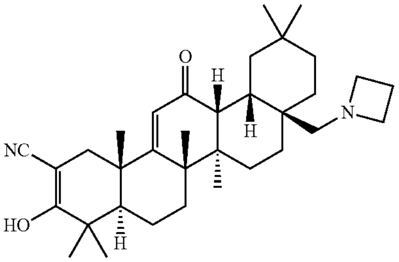

66 c

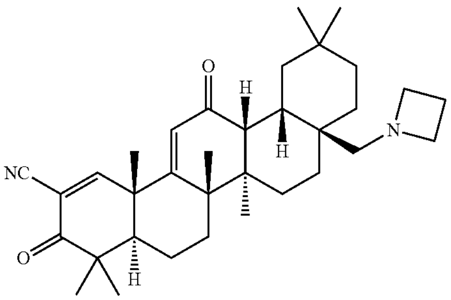

T25

Reagents and conditions: a) azetidine hydrochloride, N,N-diisopropylethylamine, AcOH, THF, rt; $NaBH_3CN$, MeOH, rt, 31%; b) NaOMe, MeOH, 50° C., 98%; c) DDQ, toluene, 50° C., 26%.

Scheme 20
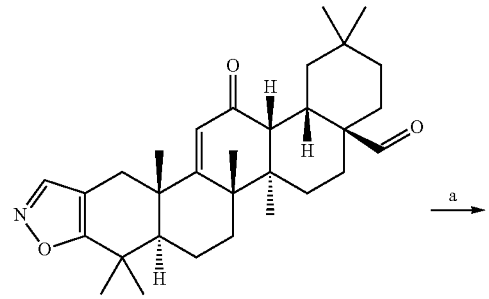
10
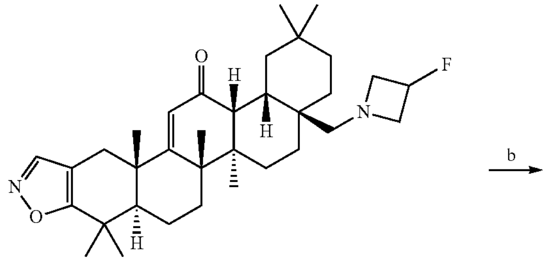
67
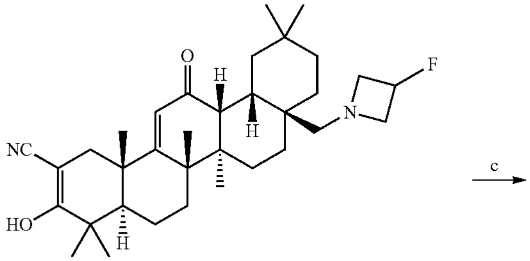
68
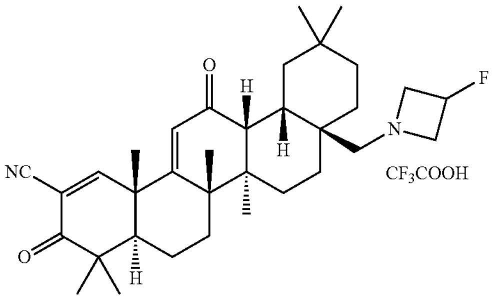
T26
Reagents and conditions: a) 3-fluoroazetidine hydrochloride, N,N-diisopropylethylamine, AcOH, THF, rt; $NaBH_3CN$, MeOH, rt, 61%; b) NaOMe, MeOH, 55° C., 90%; c) DDQ, toluene, 50° C., 14%.
Scheme 21
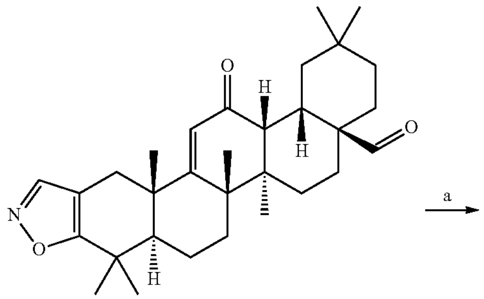
10
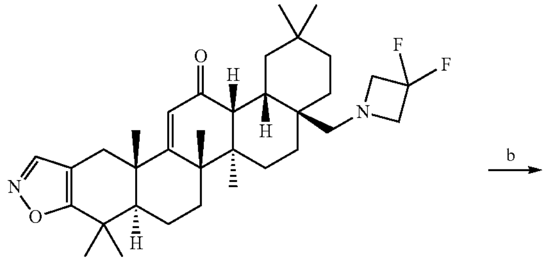
69
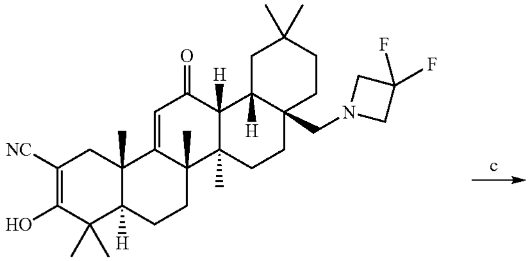
70
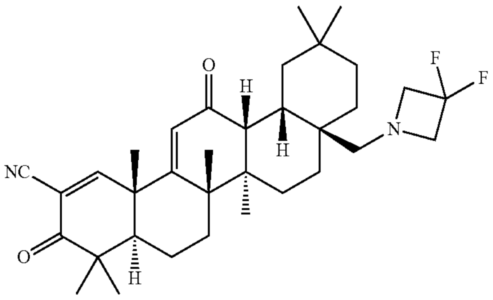
T27
Reagents and conditions: a) 3,3-difluorazetidine hydrochloride, N,N-diisopropylethylamine, AcOH, THF, rt; $NaBH_3CN$, MeOH, rt, 47%; b) NaOMe, MeOH, 55° C., 94%; c) DDQ, toluene, 50° C., 37%.

Scheme 20
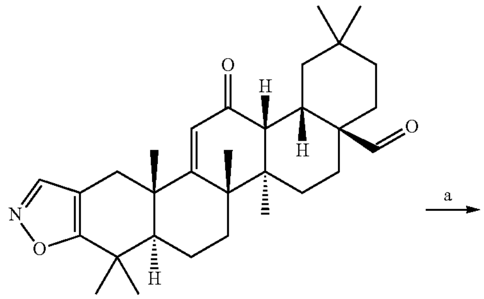
10
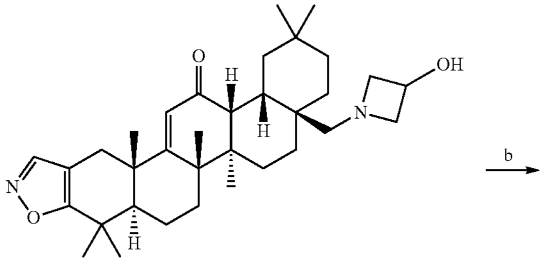
71
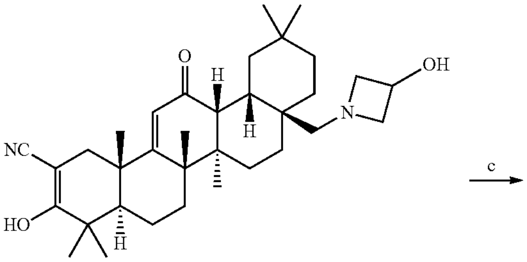
72
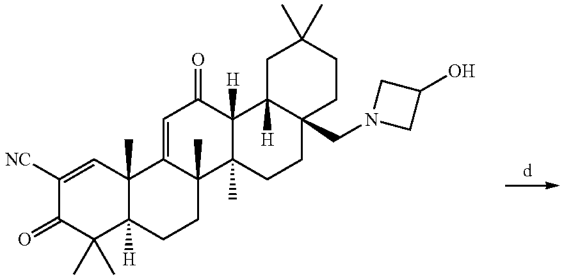
T28
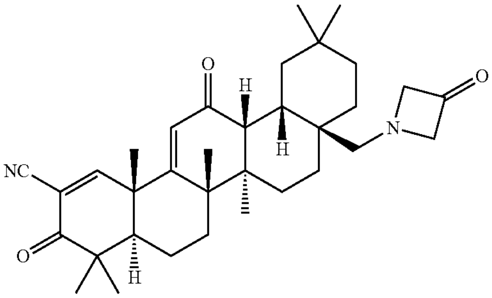
T29
Reagents and conditions: a) azetidin-3-ol hydrochloride, N,N-diisopropylethylamine, THF, rt; AcOH, $NaBH_3CN$, MeOH, rt, 40%; b) NaOMe, MeOH, 55° C., 83%; c) DDQ, toluene, 50° C., 22%; d) oxalyl chloride, DMSO, $CH_2Cl_2$, -78° C.; $Et_3N$, -78° C. to rt, 68%.
Scheme 23
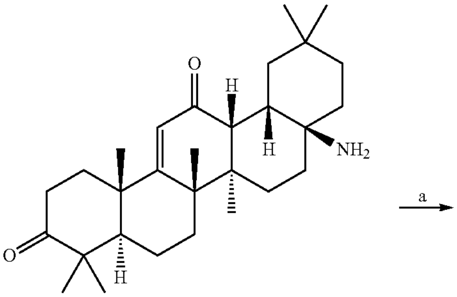
59
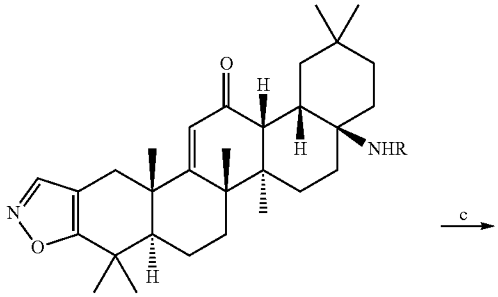
b 73 R = CHO
74 R = H
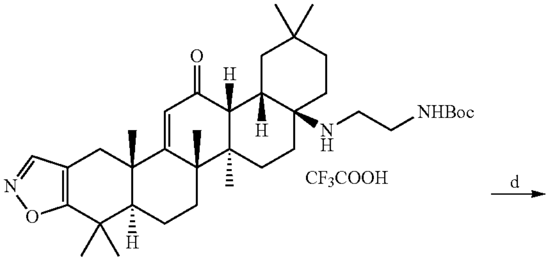
75
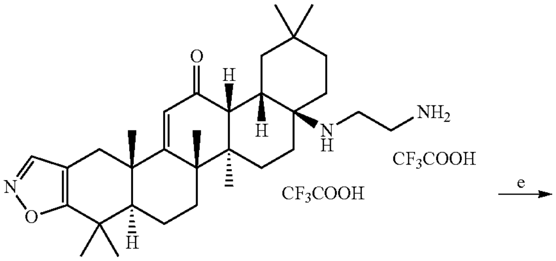
76
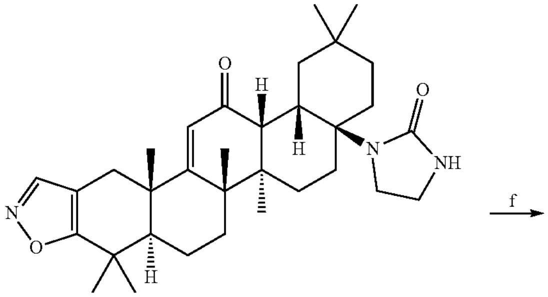
77

-continued

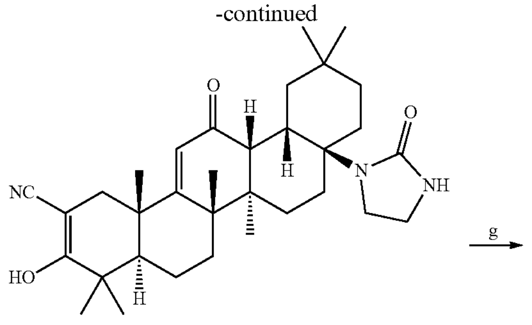

78

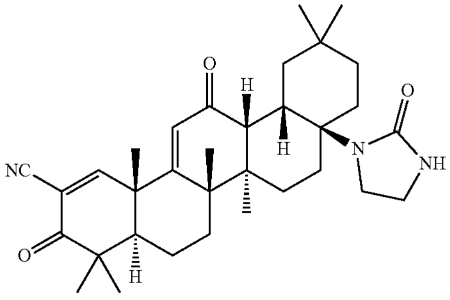

T30

Reagents and conditions: a) 1) $HCO_2Et$, NaOMe, MeOH, 0° C. to rt; 2) $NH_2OH$•HCl, EtOH, water, 55° C.; b) 12M aq. HCl, MeOH, 60° C., 99% from 59; c) N-Boc-2-aminoacetaldehyde, $NaB(OAc)_3H$, $ClCH_2CH_2Cl$, 65° C., 32%; d) $CF_3CO_2H$, $CH_2Cl_2$, rt, 41%; e) Phosgene, N,N-diisopropylethylamine, toluene, $CH_2Cl_2$, rt, 94%; f) $K_2CO_3$, MeOH, rt, 91%; g) 1,3-Dibromo-5,5-dimethylhydantoin, DMF, 0° C.; pyridine, 60° C., 16%.

Scheme 24

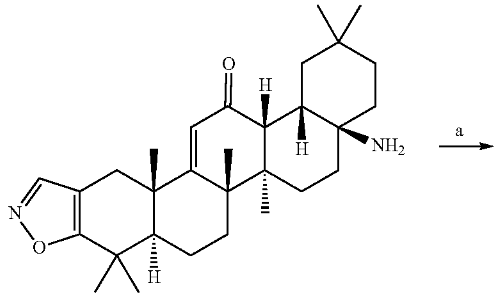

74

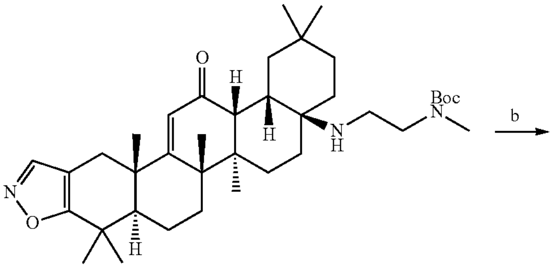

79

-continued

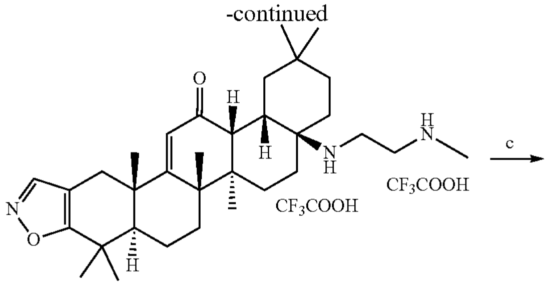

80

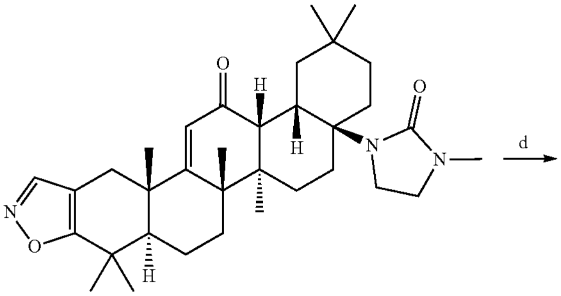

81

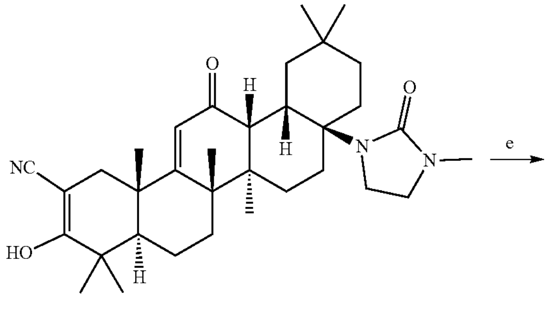

82

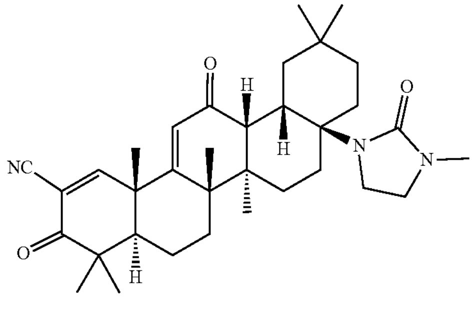

T31

Reagents and conditions:
a) t-butyl methyl(2-oxoethyl)carbamate, $NaBH(OAc)_3$, $ClCH_2CH_2Cl$, 65° C. to rt, 73%;
b) $CF_3CO_2H$, $CH_2Cl_2$, rt, 61%;
c) Phosgene, N-N-diisopropylethylamine, toluene, $CH_2Cl_2$, rt, 89%;
d) $K_2CO_3$, MeOH, rt, 78%;
e) 1,3-Dibromo-5,5-dimethylhydantoin, DMF, 0° C., pyridine, 60° C., 28%.

Scheme 25
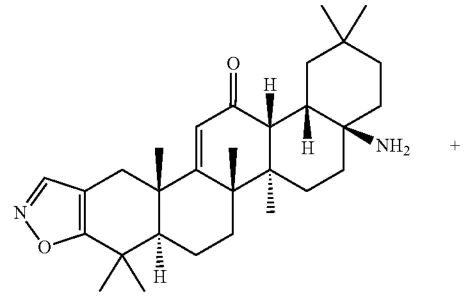
74
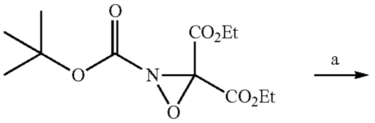
83
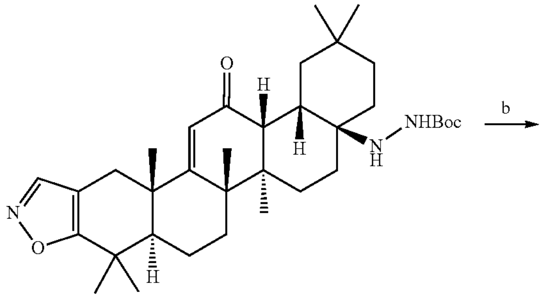
84
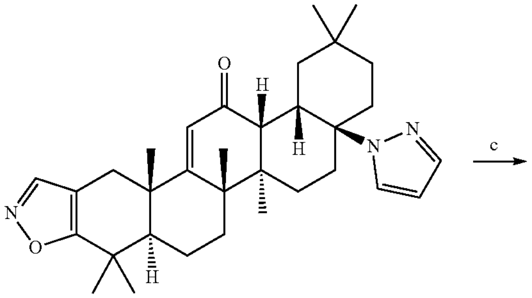
85
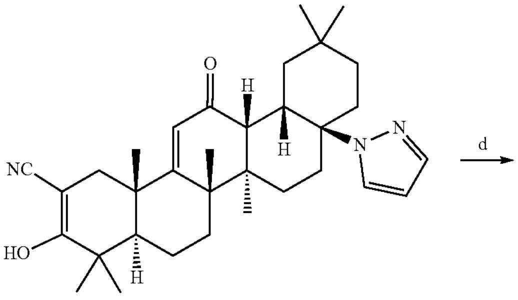
86
-continued
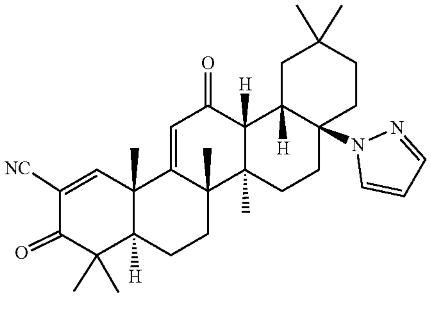
T32
Reagents and conditions:
a) $CH_2Cl_2$, 0° C., 51%;
b) 1) 4M HCl in 1,4-dioxane, $CH_2Cl_2$, 0° C. to 60° C.; $CF_3CO_2H$, $CH_2Cl_2$, rt; 2) 1,1,3,3- tetramethoxy-propane, 12M aq. HCl, EtOH, 80° C. to rt, 60%;
c) $K_2CO_3$, MeOH, rt, 88%;
e) 1,3-Dibromo-5,5-dimethylhydantoin, DMF, rt; pyridine, 60° C., 41%.
Scheme 26
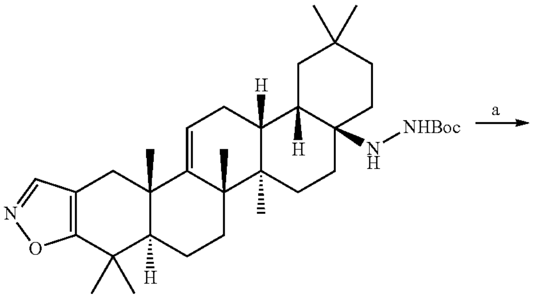
84
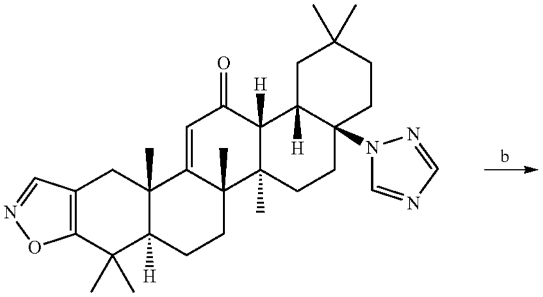
87
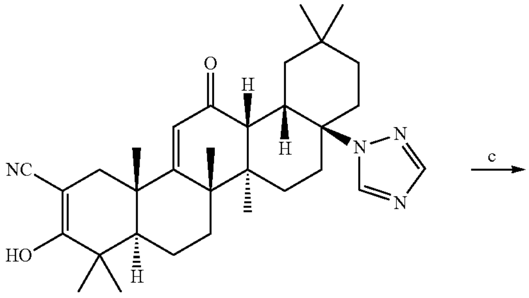
88

-continued

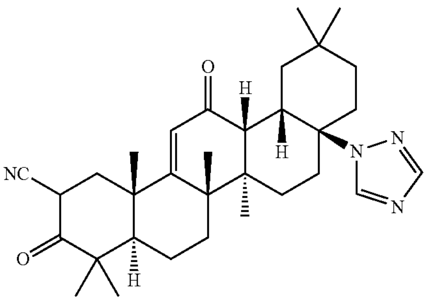

T33

Reagents and conditions: a) 1) $CF_3CO_2H$, $CH_2Cl_2$, rt; 2) 1,3,5-triazine, $HCO_2H$, rt, 59%; b) $K_2CO_3$, MeOH, rt, 86%; c) 1,3-dibromo-5,5-dimethylhydantoin, DMF, rt; pyridine, 60° C., 87%

Scheme 27

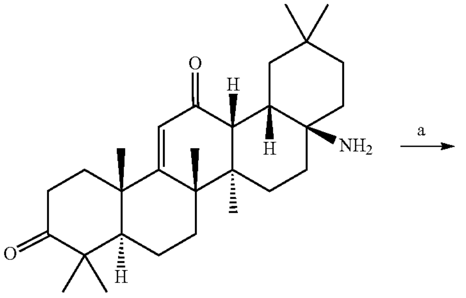

59

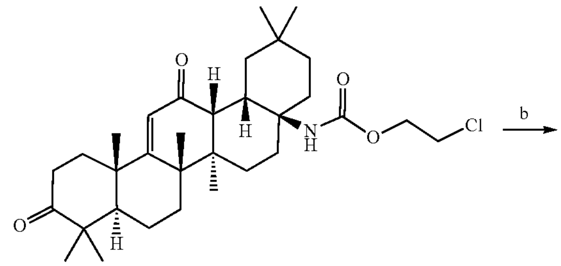

89

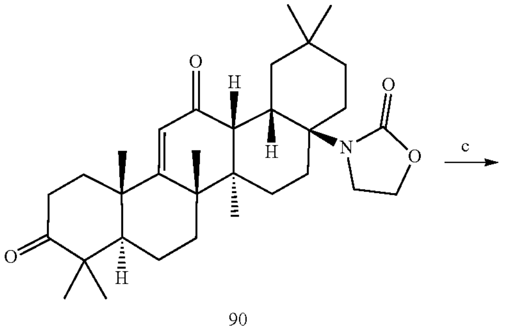

90

-continued

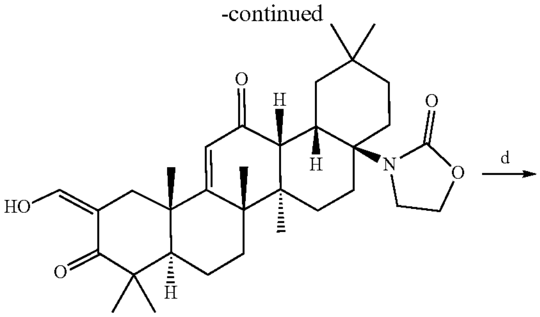

91

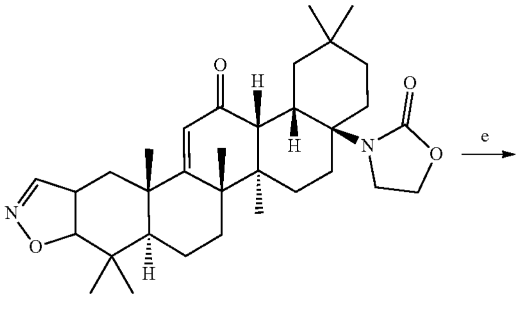

92

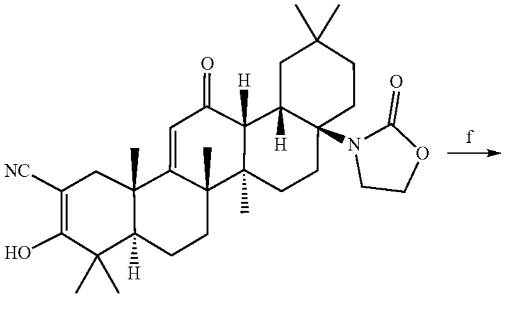

93

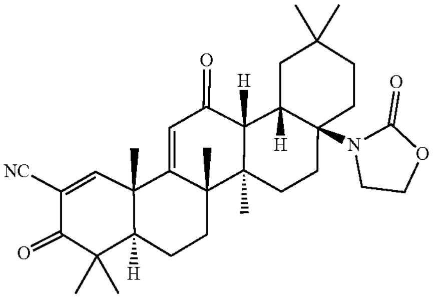

T34

Reagents and conditions:
a) 2-Chloroethyl chloroformate, $Et_3N$, $CH_2Cl_2$, 0° C., 58%;
b) $KOBu^t$, THF, 0° C., 80%;
c) $HCO_2Et$, NaOMe, MeOH, rt, 97%;
d) $NH_2OH$•HCl, EtOH, water, 60° C., 98%;
e) $K_2CO_3$, MeOH, rt to 50° C., 89%;
f) 1,3-dibromo-5,5-dimethylhydantoin, DMF, 0° C., pyridine, 60° C., 58%.

Scheme 28
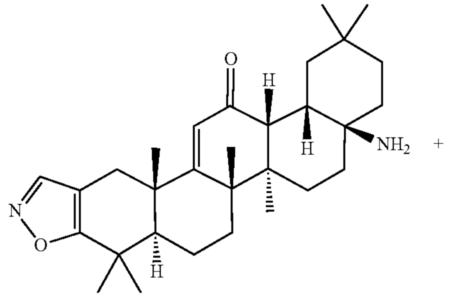
74
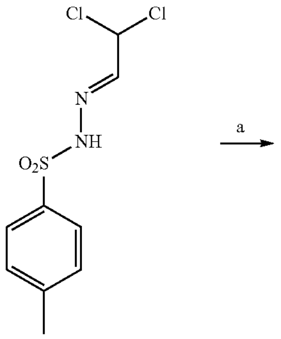
42
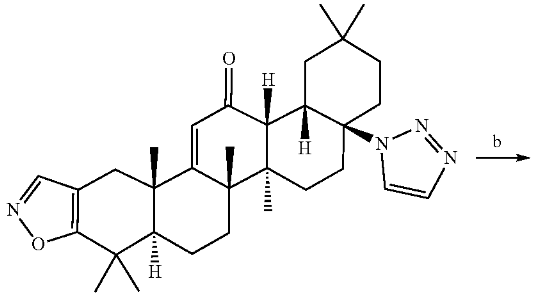
94
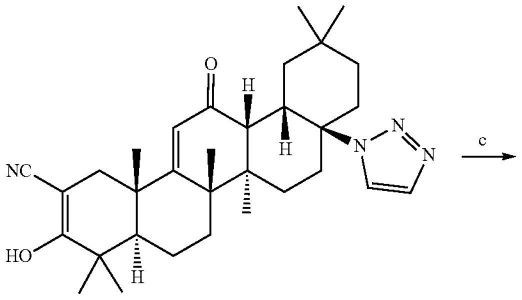
95
-continued
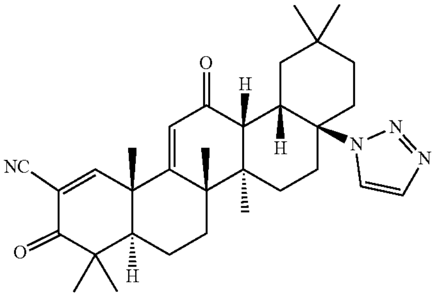
T35
Reagents and conditions:
a) N,N-diidopropylethylamine, EtOH, MeCN, 0° C. to 50° C., 47%;
b) $K_2CO_3$, MeOH, rt to 40° C., 92%;
c) 1,3-dibromo-5,5-dimethylhydantoin, DMF, rt, pyridine, 60° C., 44%.
Scheme 29
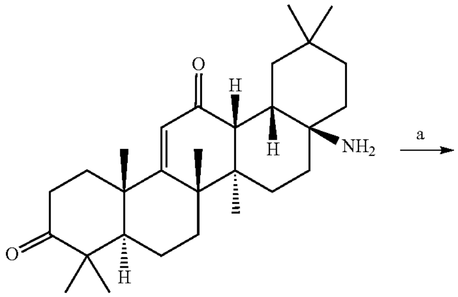
59
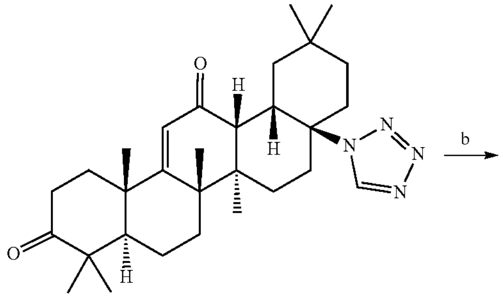
96
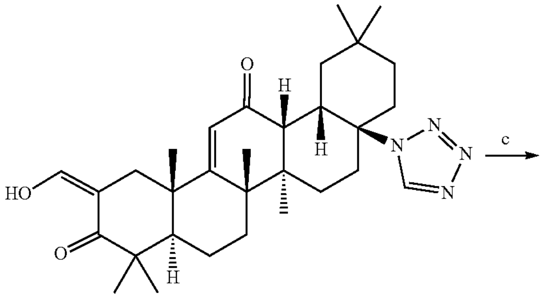
97

-continued

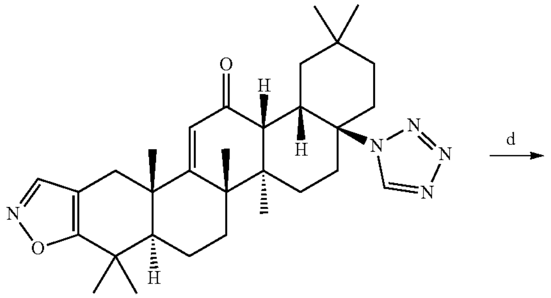

98

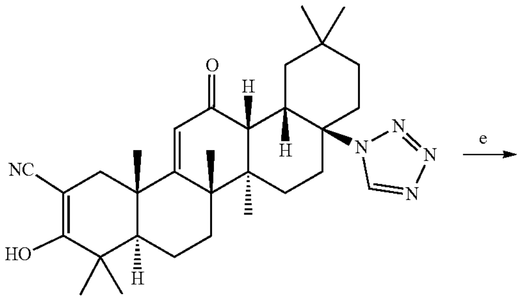

99

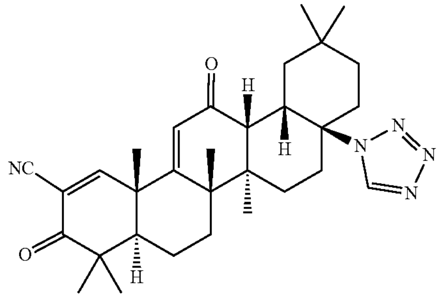

T36

Reagents and conditions:
a) $NaN_3$, trimethoxymethane, AcOH, 80° C. to rt, 85%;
b) $HCO_2Et$, NaOMe, MeOH, rt;
c) $NH_2OH$•HCl, EtOH, water, 60° C. to rt, 52% from 96;
d) NaOMe, MeOH, rt, 97%;
e) 1,3-dibromo-5,5-dimethylhydantoin, DMF, 0° C., pyridine, 55° C., 80%.

Scheme 30

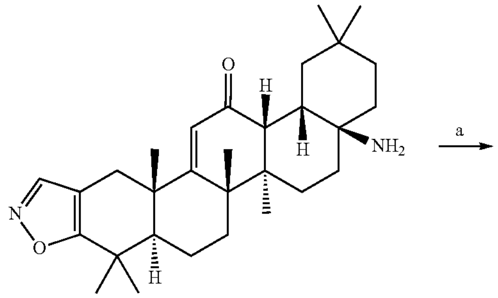

74

-continued

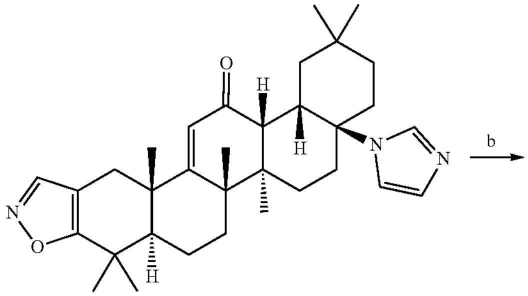

100

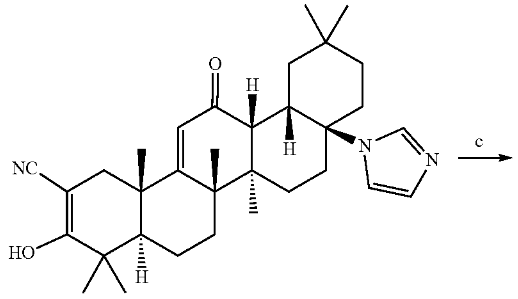

101

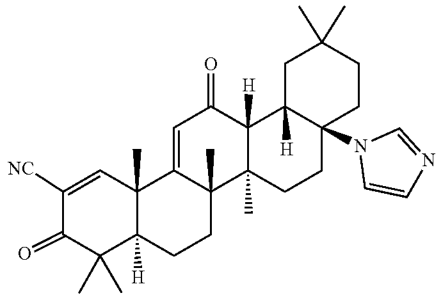

T37

Reagents and conditions:
a) paraformaldehyde, trimeric glyoxal dihydrate, $(NH_4)_2CO_3$, MeOH, 60° C., 23%;
b) $K_2CO_3$, MeOH, rt, quantitative yield;
c) DDQ, toluene, 50° C., 45%.

Scheme 31

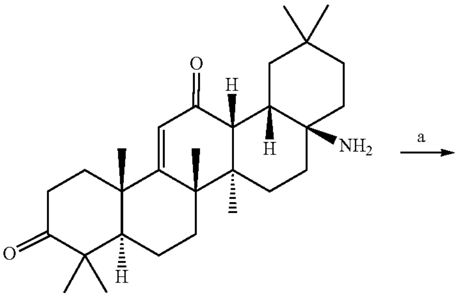

59

-continued
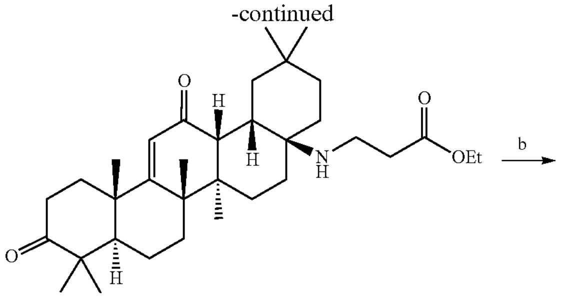
102
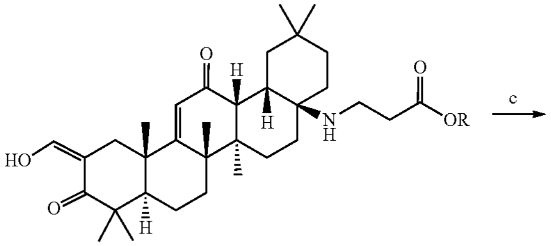
103 (R = Me and Et)
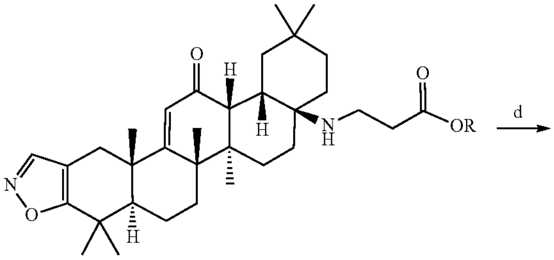
104 (R = Me and Et)
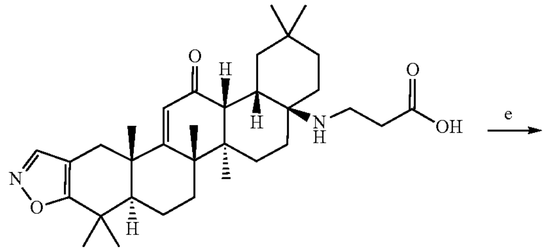
105
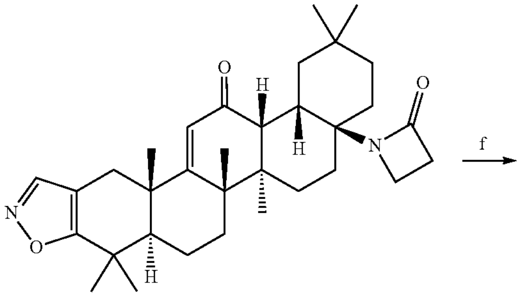
106
-continued
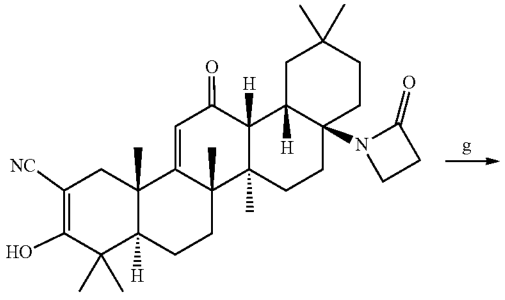
107
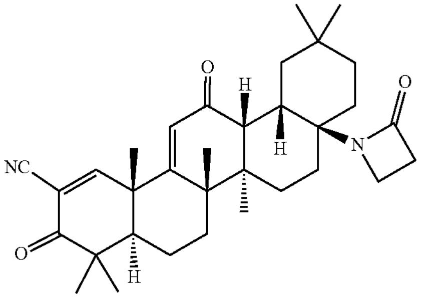
T38
Reagents and conditions:
a) ethyl acrylate, KOH, 60° C. to 100° C., 87%;
b) $HCO_2Et$, NaOMe, MeOH, 0° C. to rt;
c) $NH_2OH$•HCl, EtOH, water, 55° C., 61% from 102;
d) 4M HCl in 1,4-dioxane, water, 12N HCl, MeCN, rt, 86%;
e) $POCl_3$, $Et_3N$, $CH_2Cl_2$, 0° C. to rt, 40%;
f) $K_2CO_3$, MeOH, rt, quantitive yield;
g) 1,3-dibromo-5,5-dimethylhydantoin, DMF, 0° C.; pyridine, 60° C., 41%.
Scheme 32
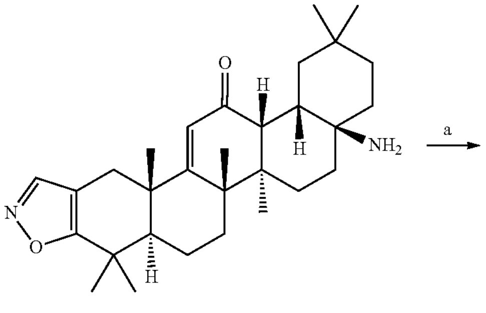
74
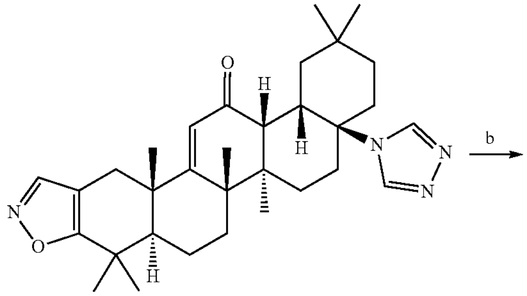
108

-continued
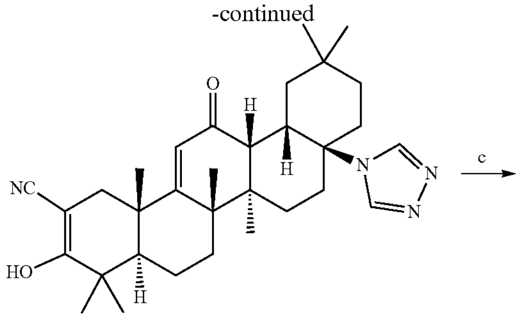
109
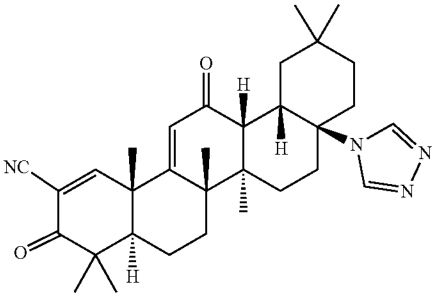
T39
Reagents and conditions:
a) 1,2-diformylhydrazine, ethyl orthoformate, MeOH, 60° C. to 75° C., 40%;
b) $K_2CO_3$, MeOH, rt, quantitive yield;
c) 1,3-dibromo-5,5-dimethylhydantoin, DMF, rt, pyridine, 60° C., 50%.
Scheme 33
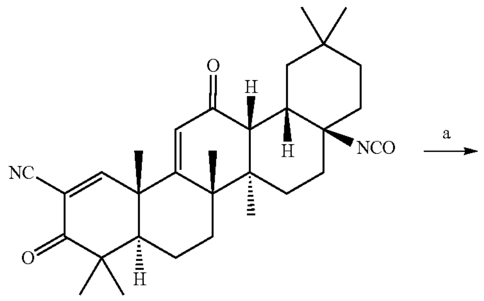
110
-continued
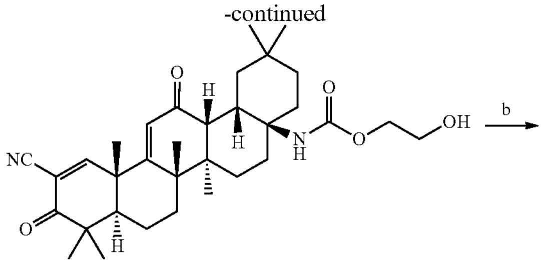
111
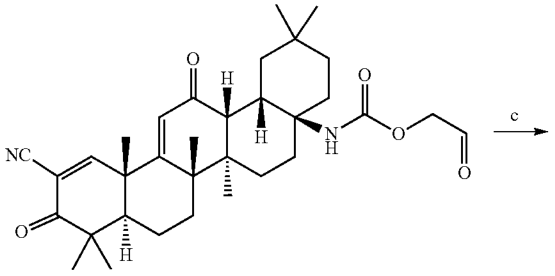
112
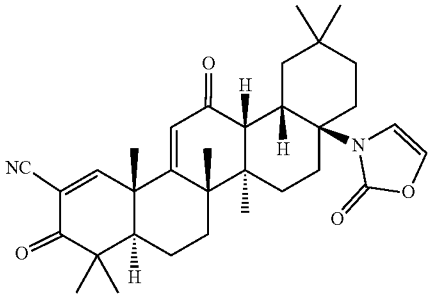
T40
Reagents and conditions:
a) ethylene glycol, 130° C., 89%;
b) oxalyl chloride, DMSO, $CH_2Cl_2$, -78° C.; $Et_3N$, -78° C. to rt, quantitive yield;
c) AcOH, 100° C., 52%.
Scheme 34
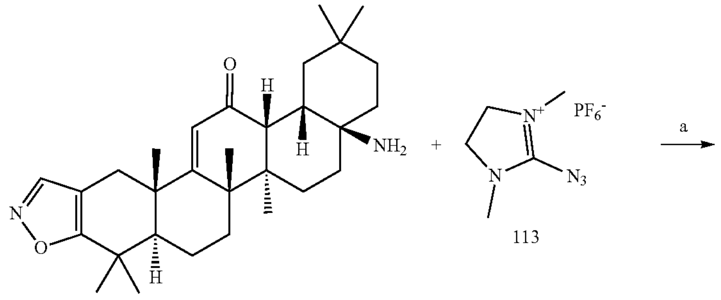
74
113

-continued
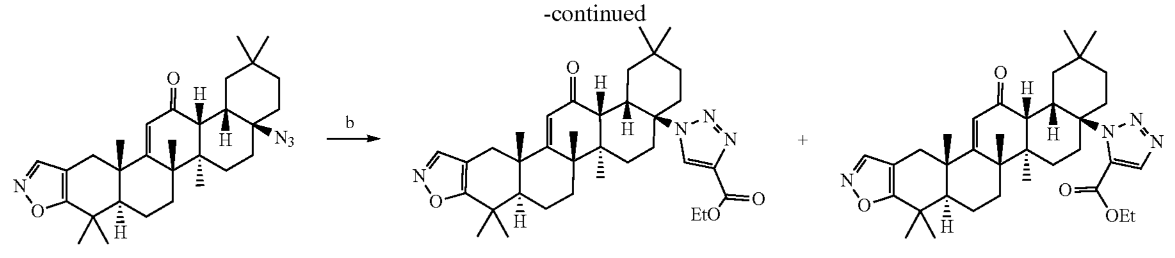
114 115a 115b
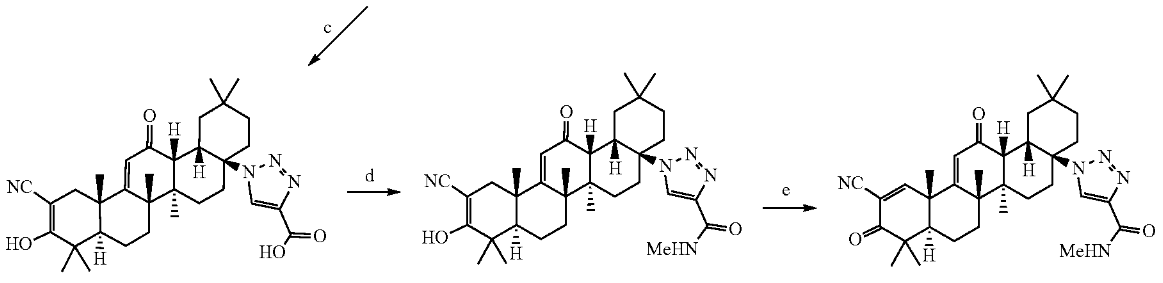
116 117 T41
Reagents and conditions:
a) DMAP, MeCH, 30° C., 83%;
b) ethyl propiolate, EtOH, 60° C. to 80° C., 68% for 115a, 10% for 115b;
c) LiOH, $H_2O$, MeOH, rt, 91%;
d) 33% $MeNH_2$ in EtOH, N,N-carbonyldiimidazole, $CH_2Cl_2$, rt, 61%;
e) 1,3-dibromo-5,5-dimethylhydantoin, DMF, rt; pyridine, 60° C., 86%.
Scheme 35
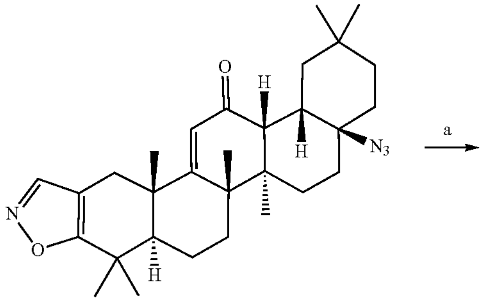
114
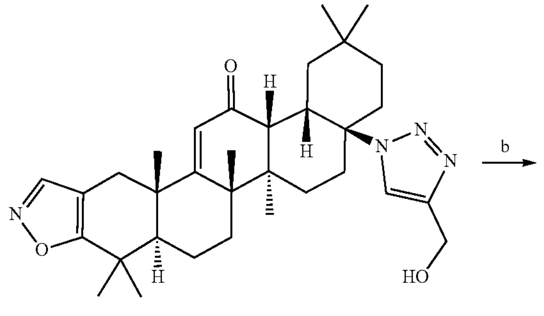
118
-continued
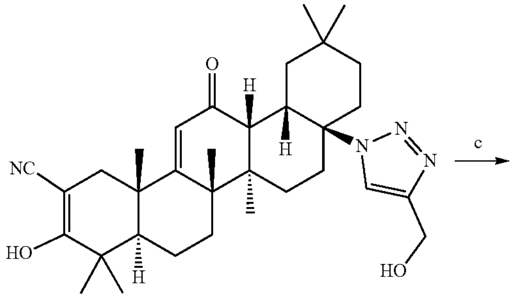
119
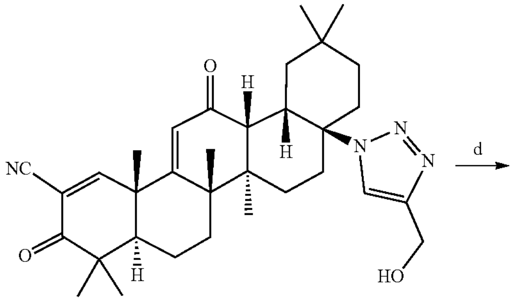
T42

-continued

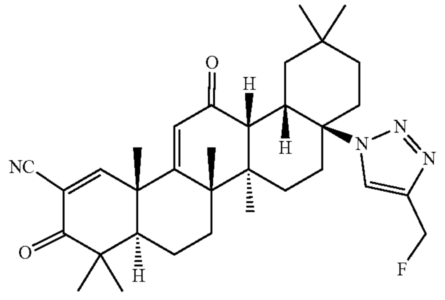

T43

Reagents and conditions:
a) 2-propyn-1-ol, EtOH, 90° C., 73%;
b) $K_2CO_3$, MeOH, rt, 96%;
c) 1,3-dibromo-5,5-dimethylhydantoin, DMF, rt; pyridine, 60° C., 77%;
d) perfluoro-1-butanesulfonyl fluoride, $Et_3N•3HF$, N,N-diisopropylethylamine, MeCN, 45° C., 24%.

Scheme 36

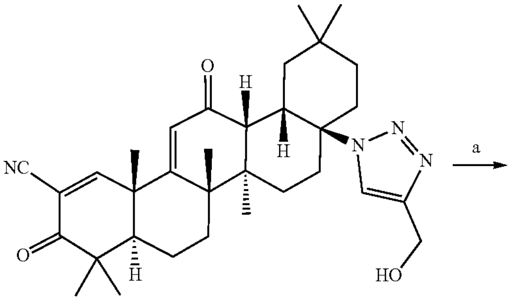

T42

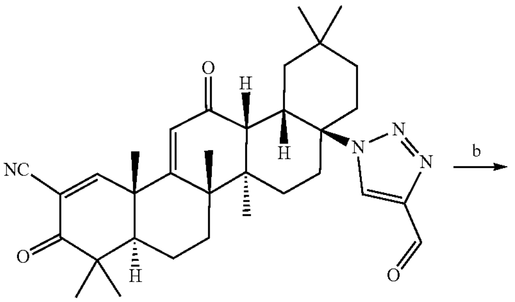

120

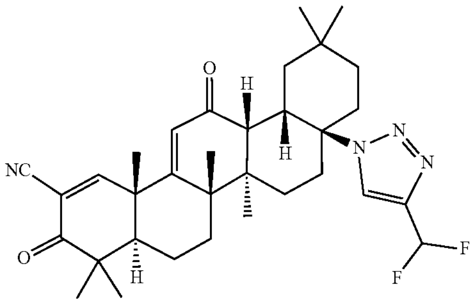

T44

Reagents and conditions:
a) oxalyl chloride, DMSO, $CH_2Cl_2$, -78° C.; $Et_3N$, -78° C. to rt, quantitive yield;
b) DAST, $CH_2Cl_2$, -78° C. to 0° C., 59%.

Scheme 37

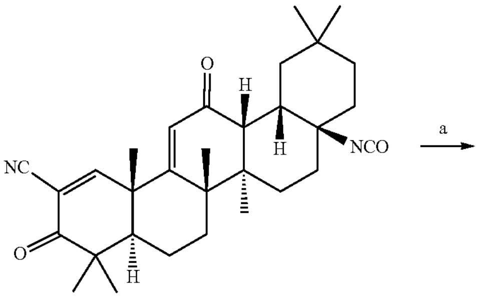

110

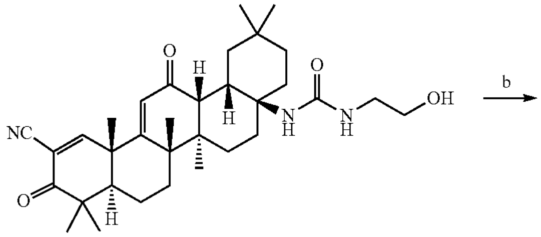

121

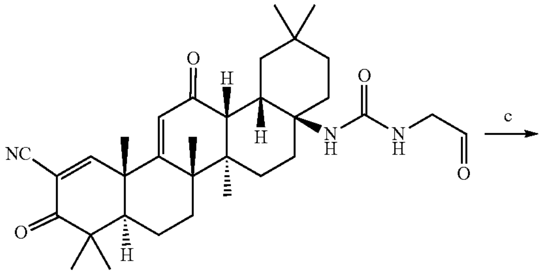

122

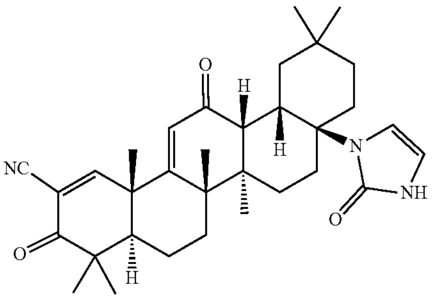

T45

Reagents and conditions:
a) ethanolamine, THF, rt, 96%;
b) oxalyl chloride, DMSO, $CH_2Cl_2$, -78° C.; $Et_3N$, -78° C. to rt, 18%;
c) AcOH, 70° C., 45%.

Scheme 38

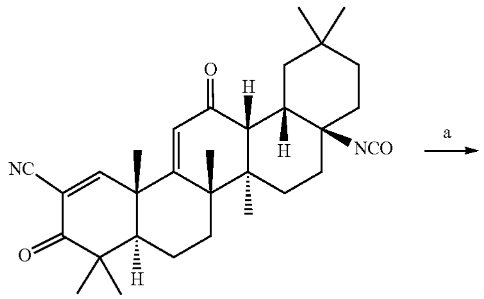

110

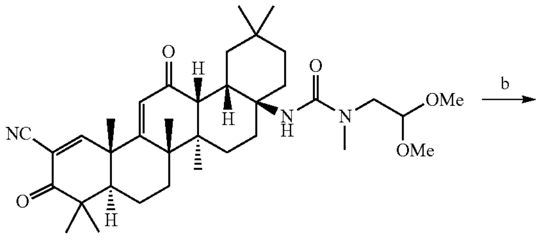

123

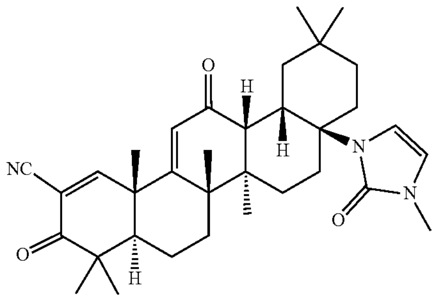

T46

Reagents and conditions:
a) 2-2-dimethoxy-N-methyl-ethanamine, N-methylpyrrolidinone, rt, quantitative yield;
b) AcOH, $H_2O$, 60° C., 36%.

Scheme 39

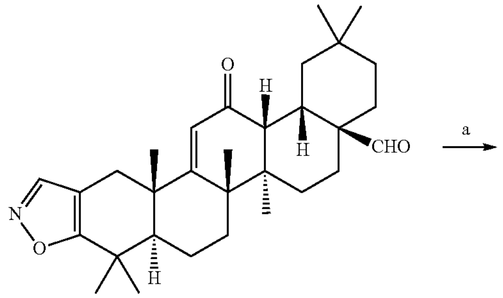

10

-continued

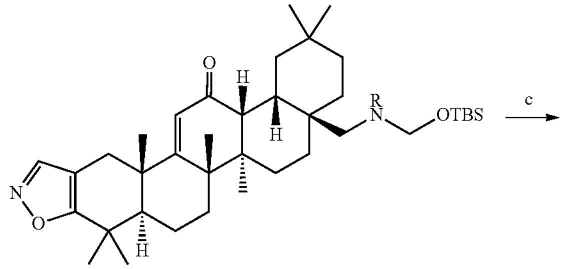

b
124 R = H
125 R = Boc

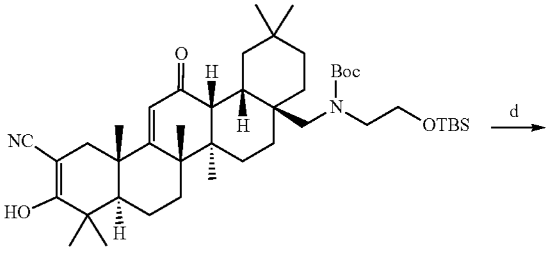

126

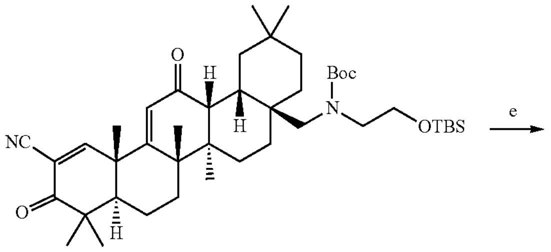

127

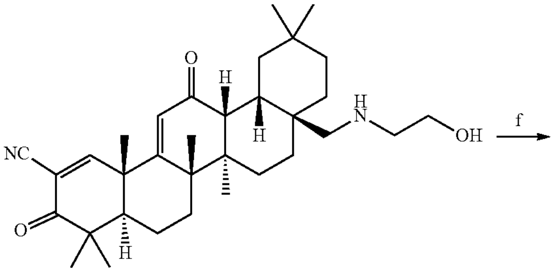

128

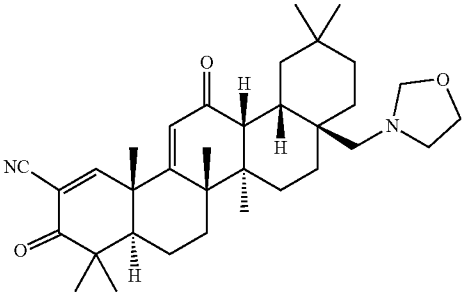

T47

Reagents and conditions:
a) 2-(tert-butyldimethylsilyloxy)ethylamine, THF, rt, HOAc, $NaBH_3CN$, MeOH, rt, 82%;
b) $Boc_2O$, $NaHCO_3$, THF, $H_2O$, 0° C. to rt, quantitative yield;
c) $K_2CO_3$, MeOH, rt, 63%;
d) 1,3-dibromo-5,5-dimethylhydantoin, DMF, 0° C.; pyridine, 60° C., 45%;
e) $CF_3CO_2H$, $CH_2Cl_2$, rt, 96%;
f) paraformaldehyde, THF, 75° C., 43%.

Scheme 40
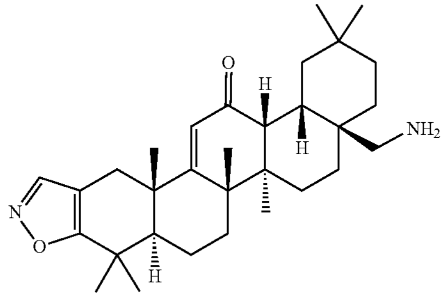
6
+
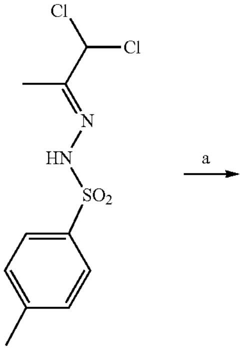
129
-continued
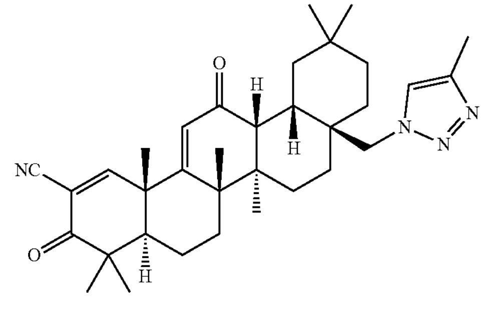
T48
Reagents and conditions:
a) N,N-diisopropylethylamine, EtOH, MeCN, 0° C. to rt, 70%;
b) NaOMe, MeOH, 55° C., 92%;
c) 1,3-dibromo-5,5-dimethylhydantoin, DMF, 0° C.; pyridine, 60° C., 56%.
Scheme 41
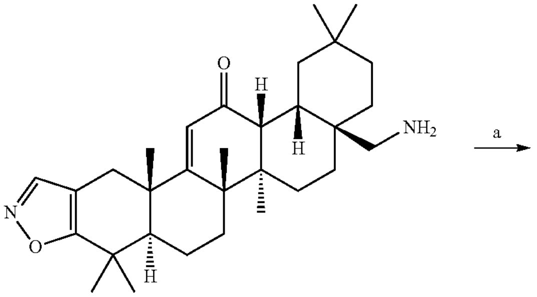
6
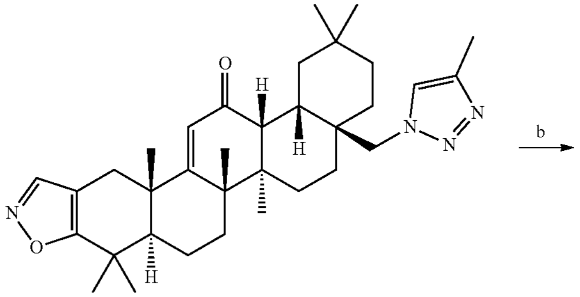
130
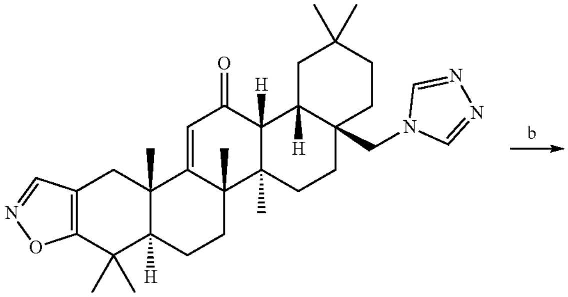
132
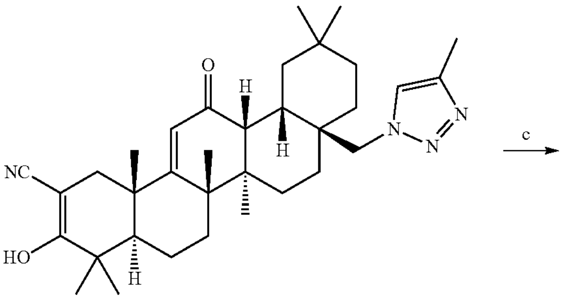
131
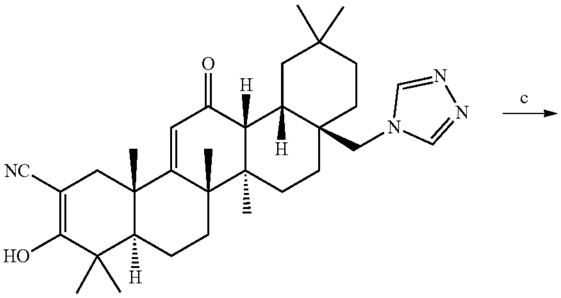
133

-continued

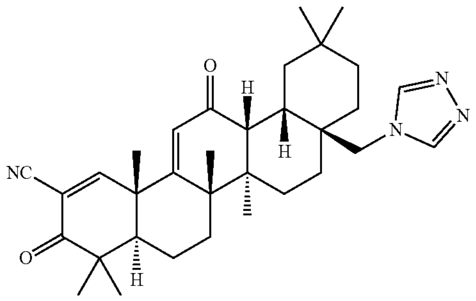

T49

Reagents and conditions:
a) formic hydrazine, triethyl orthoformate, MeOH, 65° C., 34%;
b) NaOMe, MeOH, 55° C.;
c) 1,3-Dibromo-5,5-dimethylhydantoin, DMF, 0° C.; pyridine, 60° C., 29% from 132.

Scheme 42

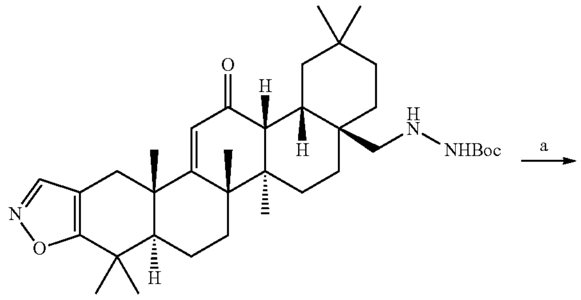

46

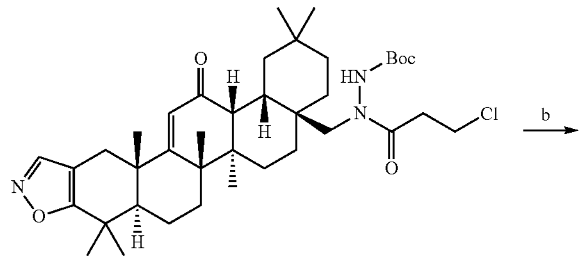

134

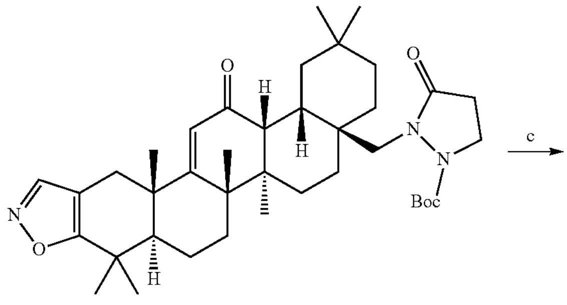

135

-continued

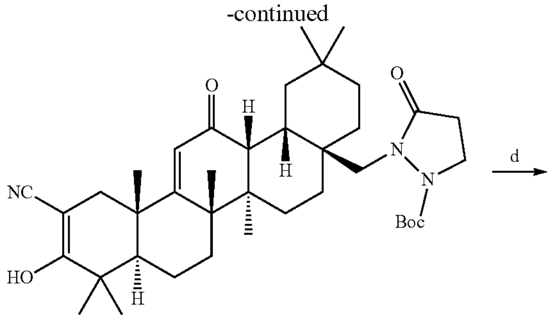

136

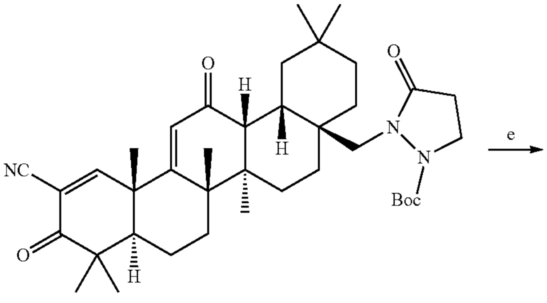

T50

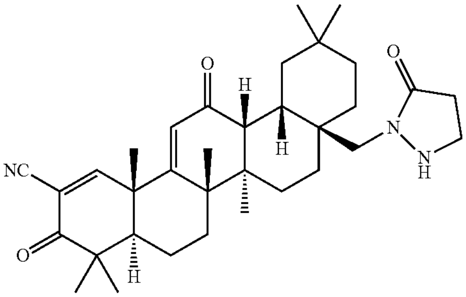

T51

Reagents and conditions:
a) 3-chloropropionyl chloride, $CH_2Cl_2$, rt, 73%;
b) $K_2CO_3$, DMF, rt, quantitative yield;
c) NaOMe, MeOH, 55° C., 96%;
d) 1,3-dibromo-5,5-dimethylhydantoin, DMF, 0° C.; pyridine, 60° C., 73%;
e) $CF_3CO_2H$, $CH_2Cl_2$, rt, 68%.

Scheme 43

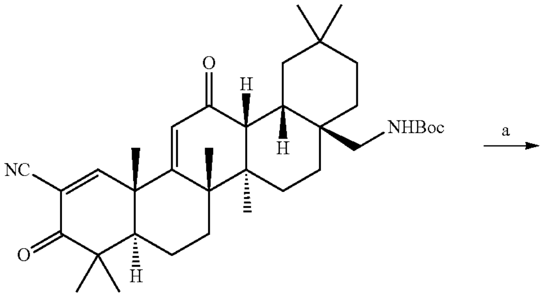

CC1

-continued
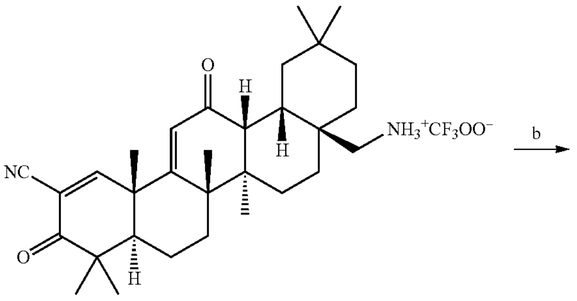
137
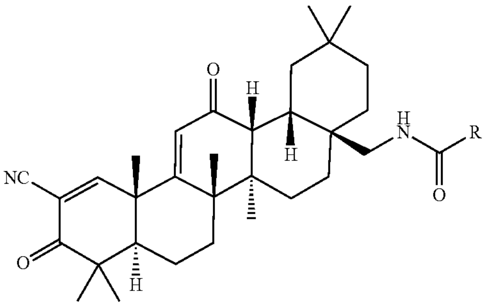
T52 R = $CD_3$
T53 R = Et
Reagents and conditions:
a) $CF_3CO_3H$, $CH_2Cl_2$, 0° C., quantitative yield;
b) RCOCl, $Et_3N$, $CH_2Cl_2$, 0° C., 52% for T52; 62% for T53.
Scheme 44
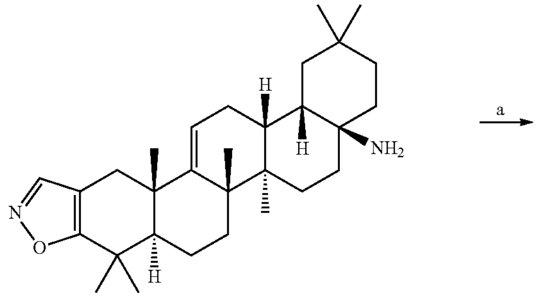
74
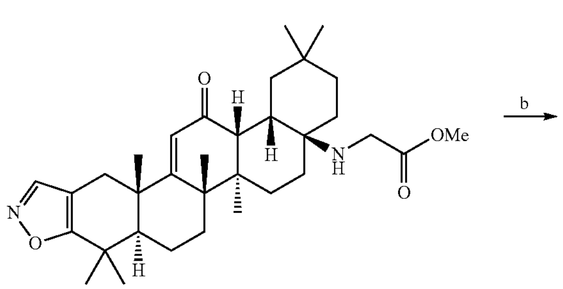
138
-continued
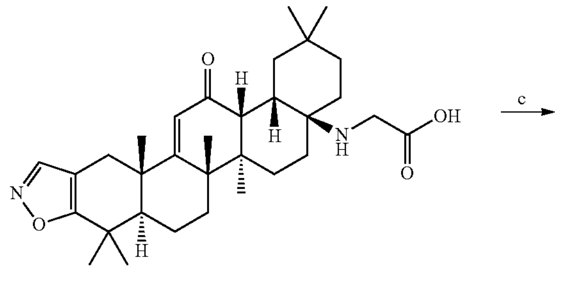
139
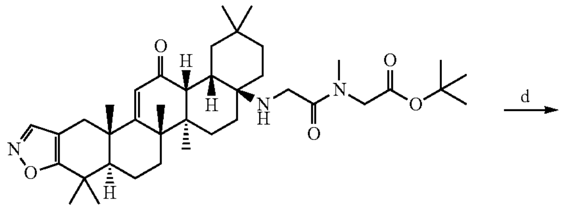
140
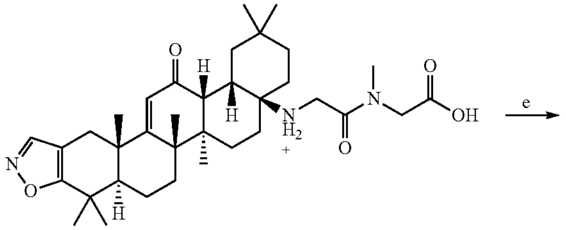
141
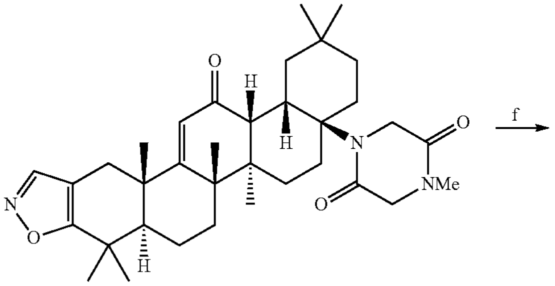
142
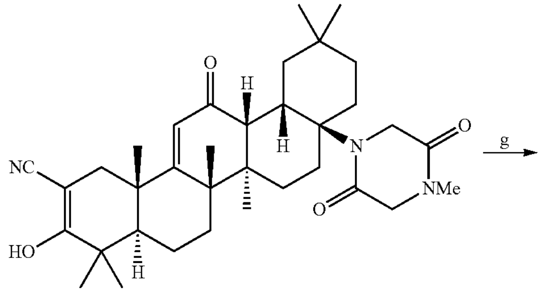
143

-continued

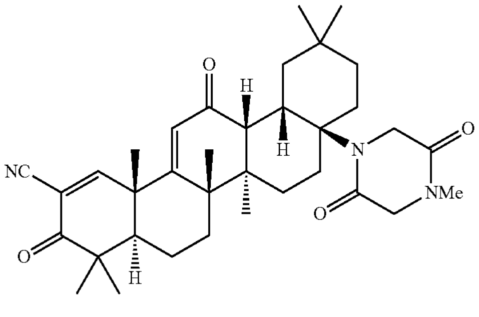

T54

Reagents and conditions: a) KI, N,N-Diisopropylethylamine, $BrCH_2CO_2Me$, rt to 60° C., 77%; b) 4 M HCl in 1,4-dioxane, $H_2O$, rt to 50° C, 66%; c) t-butyl N-methylglycinate hydrochloride, N,N-diisopropylethylamine, HATU, DMF, 0° C. to rt, 80%; d) $CF_3CO_2H$, $CH_2Cl_2$, rt, 69%; e) N,N-diisopropylethylamine, HATU, DMF, rt, 90%; f) $K_2CO_3$, MeOH, rt, 96%; g) 1,3-dibromo-5,5-dimethylhydrantoin, DMF, 0° C.; pyridine, rt to 60° C., 59%.

Scheme 45

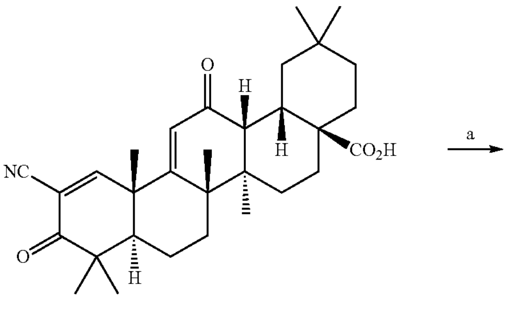

144

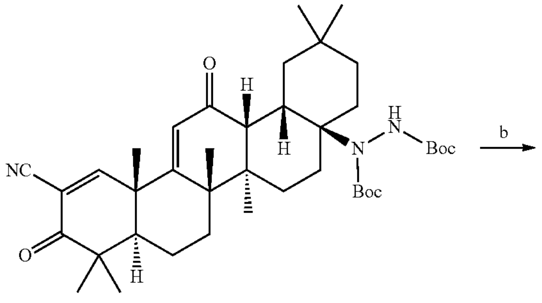

T55

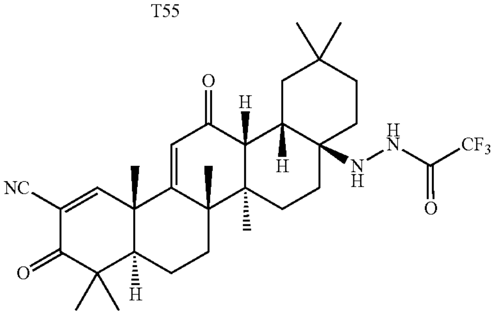

T56

Reagents and conditions:
a) di-tert-butyl azodicarboxylate, 9-mesityl-10-methylacridinium perchlorate, DBU, 1,2-dichloroethane, LED light, rt, 39%;
b) $CF_3CO_2H$, $CH_2Cl_2$, rt, 42%.

Scheme 46

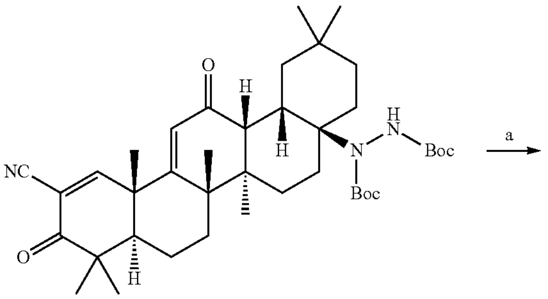

T55

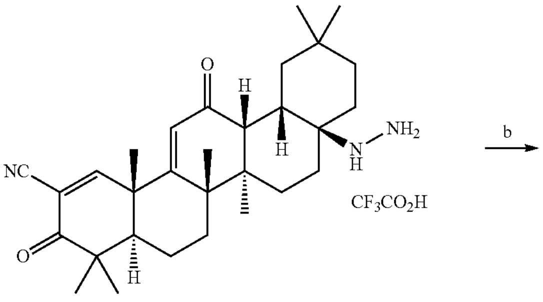

T57

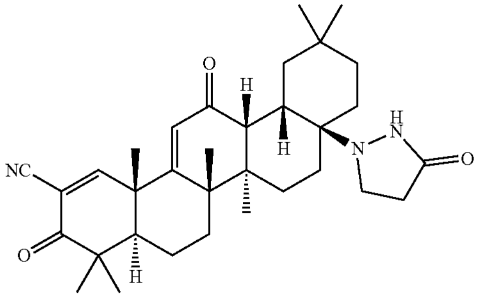

T58

Reagents and conditions:
a) $CF_3CO_2H$, $CH_2Cl_2$, rt, 69%;
b) 3-chloropropionyl chloride, $Et_3N$, MeCN, rt to 50° C., 57%.

Scheme 47

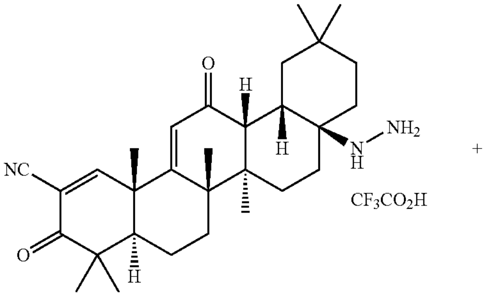

T57

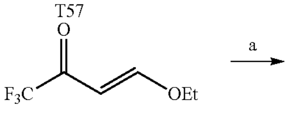

145

-continued
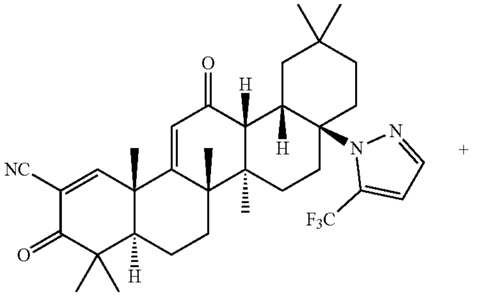
T59
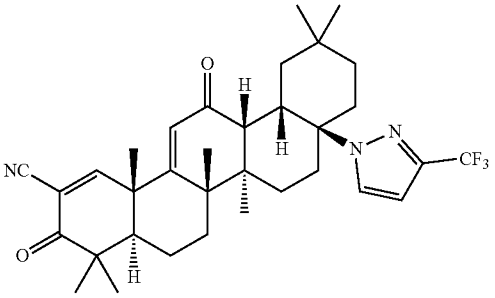
T60
Reagents and conditions:
a) EtOH, 70° C., 74% for T59; 7% for T60.
Scheme 48
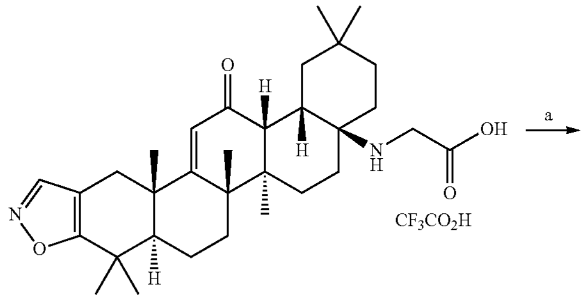
139
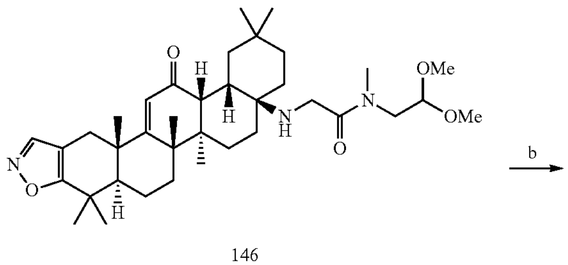
146
-continued
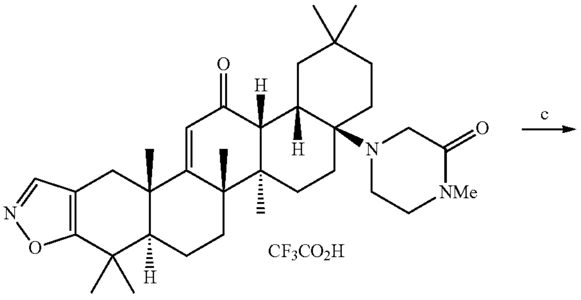
147
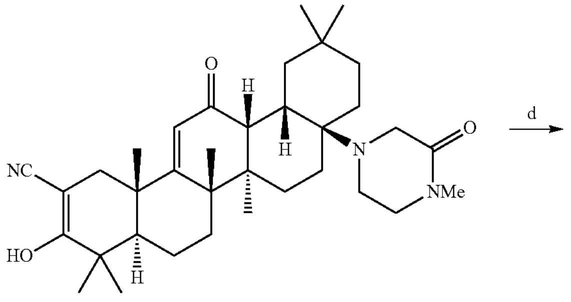
148
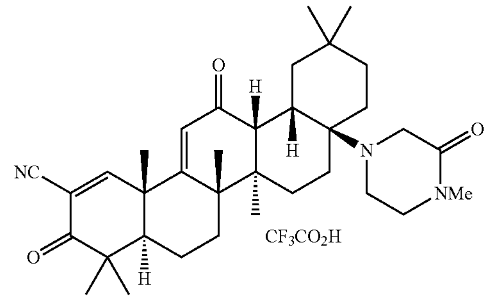
T61
Reagents and conditions:
a) N,N-diisopropylethylamine, HATU, DMF, 2-dimethoxy-N-methyl-ethanamine, DMF, 0° C. to rt, 67%;
b) 2M aq. HCl, $NaBH_3CN$, THF, rt, 56%;
c) $K_2CO_3$, MeOH, rt, 82%;
d) DDQ, toluene, rt to 50° C., 9%.
Scheme 49
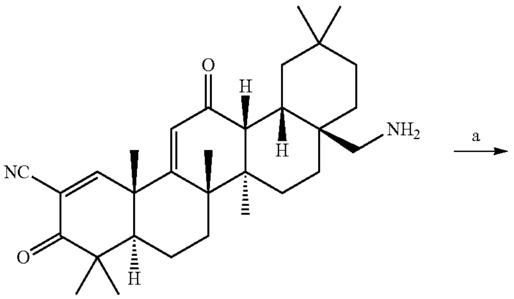
CC2

-continued
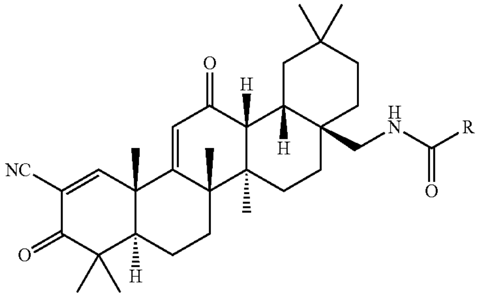
T62 R = $MeCF_2$
T63 R = $CHF_2$
Reagents and conditions:
a) $RCO_2H$, T3P, $Et_3N$, $CH_2Cl_2$, rt, 45% for T62; 61% for T63.
Scheme 50
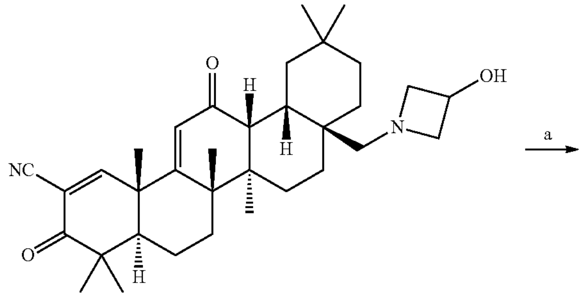
T28
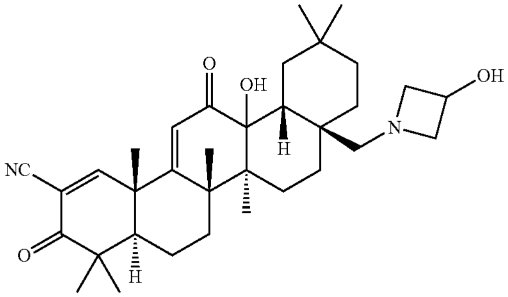
T64
Reagents and conditions:
a) Dess-Martin periodinane, $CH_2Cl_2$, 0° C. to rt, 35%.
Scheme 51
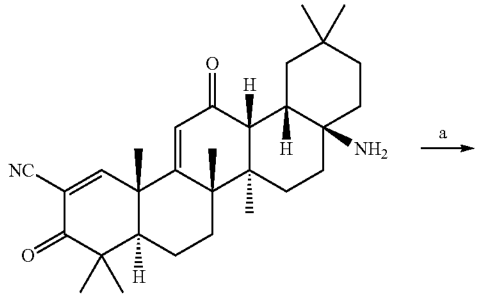
CC4
-continued
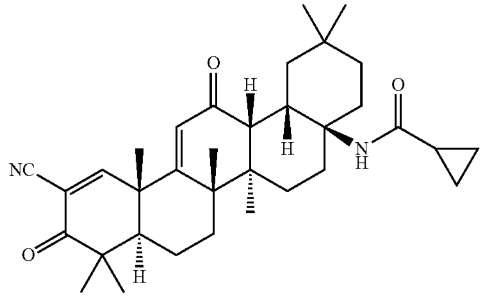
T68
Reagents and conditions:
a) Cyclopropanecarbonyl chloride, $Et_3N$, $CH_2Cl_2$, 0° C., 75%.
Scheme 52
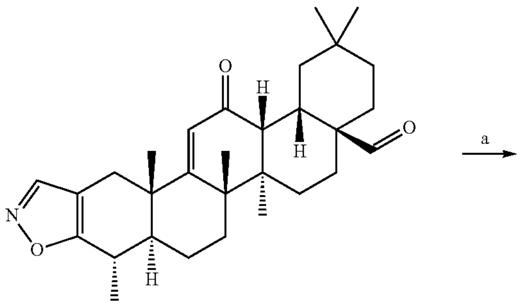
149
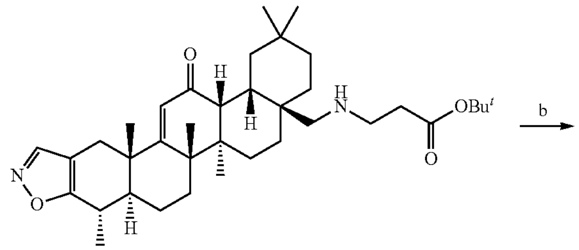
150
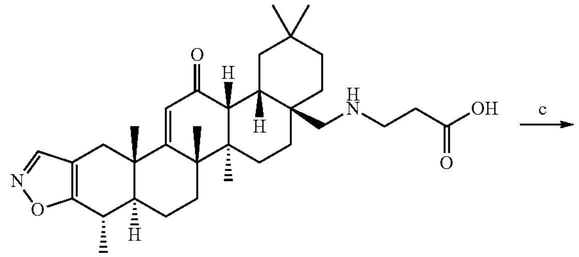
151

-continued

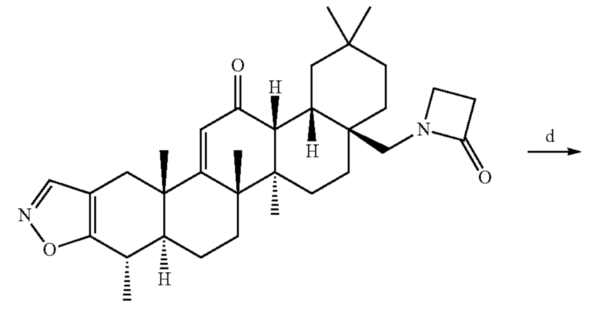

152

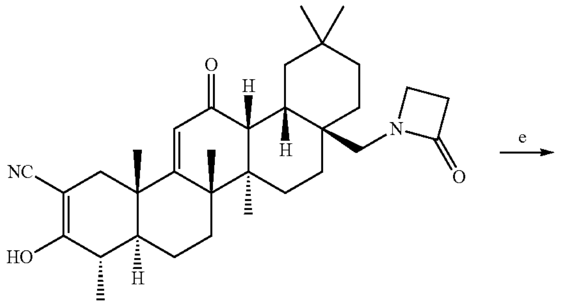

153

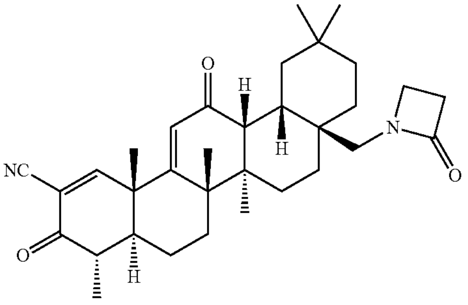

T65

Reagents and conditions:
a) tert-butyl 3-aminopropanoate hydrochloride, $Et_3N$, $NaBH(OAc)_3$, THF, rt; $NaBH_4$, EtOH, rt, 82%;
b) HCl in 1,4-dioxane, rt; TFA, $CH_2Cl_2$, 0° C. to rt, quantitative yield;
c) $POCl_3$, $Et_3N$, $CH_2Cl_2$, 0° C., 44%;
d) NaOMe, MeOH, 55° C., 98%;
e) 1,3-Dibromo-5,5-dimethylhydantoin, DMF, 0° C.; pyridine, 60° C., 62%.

Scheme 53

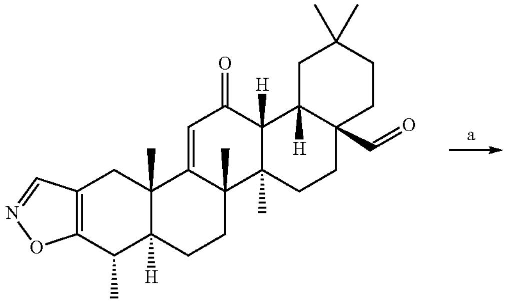

149

-continued

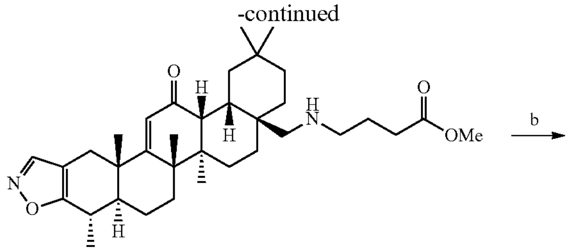

154

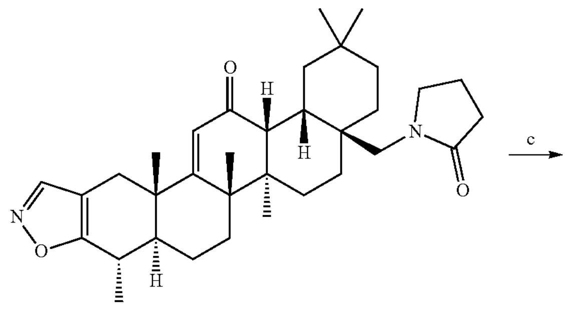

155

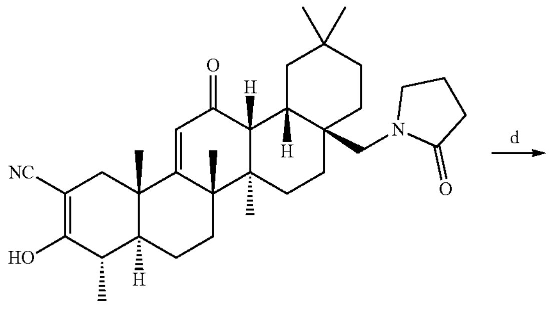

156

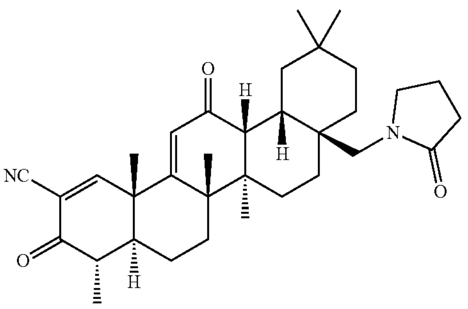

T66

Reagents and conditions:
a) methyl 4-aminobutanoate hydrochloride, $Et_3N$, $NaBH(OAc)_3$, THF, rt; $NaBH_4$, MeOH, rt, 93%;
b) toluene, reflux, 88%;
c) NaOMe, MeOH, 55° C., 96%;
d) 1,3-Dibromo-5,5-dimethylhydantoin, DMF, 0° C.; pyridine, 60° C., 71%.

Scheme 54

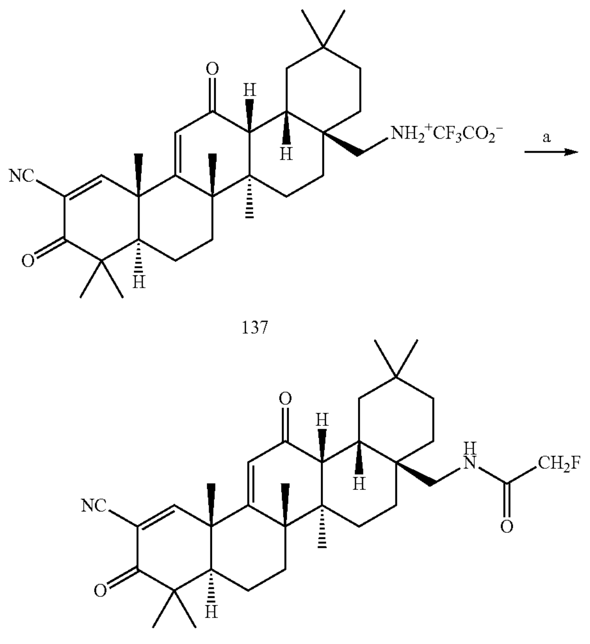

137

T67

Reagents and conditions:
a) 2-fluoroacetic acid, T3P, $Et_3N$, $CH_2Cl_2$, rt, 45%.

C. Characterization Data

Compound 2: Compound 1 (2.00 g, 4.28 mmol) in THF (70 mL) was cooled to 0° C. under $N_2$. Lithium aluminum hydride (2 M solution in THF, 12.8 mL) was added. The mixture was stirred at room temperature for 10 min; refluxed for 3 h; and then cooled to 0° C. Water (1.85 mL, 1.85 mmol) was added dropwise. After addition, the mixture was refluxed for 5 min, and filtered through a pad of celite while hot. The filter cake was washed with hot THE (2×100 mL). The filter cake was mixed with THE (100 mL); refluxed for 5 min; and filtered hot again. The combined filtrate was concentrated to give crude compound 2 (1.73 g, 88% yield) as a white solid. The crude product was used in the next step directly. m/z=440 (M−OH).

Compound 3: A mixture of compound 2 (1.437 g, 3.14 mmol) and $NaHCO_3$ (316.5 mg, 3.77 mmol) in THE (25 mL) and water (5.8 mL) were cooled to 0° C. Di-t-butyl dicarbonate (1.028 g, 4.71 mmol) was added via syringe. The syringe was rinsed with THE (4 mL), and added to the reaction mixture. The mixture was stirred at room temperature for 40 min. Sat. aq. $NaHCO_3$ (50 mL) was added. The mixture was stirred at room temperature for 5 min; and extracted with EtOAc (100 mL+50 mL). The combined organic extracts were washed with brine (30 mL); dried with $MgSO_4$; filtered; and concentrated. The crude product was dissolved in acetone (29 mL), and cooled to 0° C. Jones' reagent (2.67 M, ~1.6 mL) was added until the orange color persisted. The reaction mixture was stirred at 0° C. for 10 min, and then quenched with i-PrOH (2 mL). The mixture was stirred for 5 min; diluted with water (50 mL); and extracted with EtOAc (3×50 mL). The combined organic extracts were washed with water (30 mL); brine (30 mL); dried with $MgSO_4$; filtered; and concentrated. The residue was purified by column chromatography (silica gel, eluting with 0-40% EtOAc in hexanes) to give compound 3 (961 mg, 55% yield) as a white solid. m/z=498 (M−$C_4H_7$).

Compound 4: Compound 3 (1.060 g, 1.91 mmol) was dissolved in ethyl formate (4.70 mL, 57.7 mmol) and cooled to 0° C. Sodium methoxide solution (25 wt. % in MeOH, 4.40 mL, 19.2 mmol) was added under $N_2$. After stirring at room temperature for 2 h, the mixture was cooled to 0° C., and diluted with MTBE (30 mL). HCl (12N aqueous solution, 1.675 mL, 20.10 mmol) and 10% aq. $NaH_2PO_4$ (30 mL) were added sequentially. The mixture was extracted with EtOAc (3×30 mL). The combined organic extracts were washed with water (30 mL); dried with $MgSO_4$; filtered; and concentrated to give crude compound 4 (1.114 g) as a white solid, which was used in the next step directly. m/z=526 (M−$C_4H_7$).

Compound 5 and 6: A mixture of compound 4 (1.114 g, ≤1.91 mmol) and hydroxylamine hydrochloride (200 mg, 2.88 mmol) in EtOH (18 mL) and water (1.8 mL) were heated at 60° C. for 4 h. The mixture was concentrated. The residue was treated with sat. aq. $NaHCO_3$ (30 mL), and extracted with EtOAc (3×30 mL). The combined organic extracts were dried with $MgSO_4$; filtered; and concentrated. The residue was purified by column chromatography (silica gel, eluting with 0-50% EtOAc in hexanes, and then 0-30% [1% $Et_3N$ in MeOH] in $CH_2Cl_2$) to give compound 5 (white solid, 616 mg, 56% yield) and compound 6 (light brown solid, 210 mg, 23% yield). Compound 5: m/z=523 (M−$C_4H_7$); Compound 6: m/z=479 (M+1).

Compound 7: Compound 5 (200 mg, 0.38 mmol) in MeOH (3.8 mL) was treated with sodium methoxide solution (25 wt. % in MeOH, 130 μL, 0.57 mmol) at room temperature under $N_2$. The mixture was heated at 55° C. for 1 h, and then cooled to 0° C. The mixture was treated with 10% aq. $NaH_2PO_4$ (15 mL); and extracted with EtOAc (2×20 mL). The combined organic extracts were washed with water; dried with $MgSO_4$; filtered and concentrated to give compound 7 (200 mg, 91% yield) as a white solid. Compound 7 was used in the next step without further purification. m/z=523 (M−$C_4H_7$).

Compound CC1: A mixture of compound 7 (200 mg, 0.346 mmol) and 1,3-dibromo-5,5-dimethylhydantoin (52.4 mg, 0.183 mmol) were treated with DMF (1.7 mL) at 0° C. under $N_2$. The mixture was stirred at 0° C. for 2 h. Pyridine (110 μL, 1.38 mmol) was added. The mixture was heated at 55° C. for 4 h, and then cooled to room temperature. The mixture was diluted with EtOAc (30 mL), and washed with 1N aq. HCl (2×15 mL), water (15 mL) and brine (15 mL). The organic extract was dried with $MgSO_4$; filtered; and concentrated. The residue was purified by column chromatography (silica gel, eluting with 0-50% EtOAc in hexanes) to give compound CC1 (171 mg, 86% yield) as a white solid. m/z=521 (M−$C_4H_7$); $^1H$ NMR (400 MHz, $CDCl_3$) δ 8.04 (s, 1H), 5.96 (s, 1H), 4.63 (t, J=6.7 Hz, 1H), 3.27 (dd, J=13.9, 7.3 Hz, 1H), 3.17 (d, J=4.7 Hz, 1H), 3.06 (dd, J=13.9, 6.0 Hz, 1H), 2.24 (m, 1H), 1.97 (m, 1H), 1.55 (s, 3H), 1.50 (s, 3H), 1.43 (s, 9H), 1.26 (s, 3H), 1.18 (s, 3H), 1.01-1.90 (m, 14H), 1.00 (s, 3H), 0.92 (s, 3H), 0.88 (s, 3H).

Compound CC2: Compound CC1 (156 mg, 0.270 mmol) was dissolved in $CH_2Cl_2$ (5.4 mL), and cooled to 0° C. under $N_2$. Trifluoroacetic acid (1.04 mL, 13.5 mmol) was added. The mixture was stirred at 0° C. for 3 h, and then concentrated. The residue was diluted with $CH_2Cl_2$ (20 mL), and washed with sat. aq. $NaHCO_3$ (15 mL). The aqueous phase was separated, and extracted with $CH_2Cl_2$ (2×15 mL) and EtOAc (15 mL). The combined organic extracts were dried with $MgSO_4$; filtered; and concentrated to give crude compound CC2 (130 mg, quantitative yield) as a white solid. Crude compound CC2 (43 mg) was purified by column chromatography (silica gel, eluting with 0-50% EtOAc in hexanes, and then 0-20% [1% $Et_3N$ in MeOH] in $CH_2Cl_2$) to give compound CC2 (28 mg, 65% yield) as an off-white solid. m/z=477 (M+1); $^1H$ NMR (400 MHz, $CDCl_3$) δ 8.04 (s, 1H), 5.98 (s, 1H), 2.94 (d, J=4.7 Hz, 1H), 2.79 (d, J=13.5 Hz, 1H), 2.59 (d, J=13.1 Hz, 1H), 2.26 (m, 1H), 1.49 (s, 3H), 1.46 (s, 3H), 1.26 (s, 3H), 1.17 (s, 3H), 1.06-1.89 (m, 17H), 1.02 (s, 3H), 0.94 (s, 3H), 0.88 (s, 3H).

Compound T3: To a solution of crude compound CC2 (43 mg, 0.090 mmol) in $CH_2Cl_2$ (0.8 mL) at 0° C. was added $Et_3N$ (25 μL, 0.18 mmol) and acetic anhydride (13 μL, 0.14 mmol) sequentially. The mixture was stirred at 0° C. for 30 min, and then quenched with sat. aq. $NaHCO_3$ (1 mL). After stirring at ambient temperature for 5 min, the mixture was diluted with EtOAc (30 mL); and washed with sat. aq. $NaHCO_3$ (10 mL) and water (10 mL). The organic extract was dried with $MgSO_4$; filtered and concentrated. The residue was purified by column chromatography (silica gel, eluting with 0-70% acetone in hexanes) to give compound T3 (33 mg, 71% yield) as a white solid. m/z=519 (M+1); $^1H$ NMR (400 MHz, $CDCl_3$) δ 8.04 (s, 1H), 5.96 (s, 1H), 5.56 (t, J=6.8 Hz, 1H), 3.50 (dd, J=13.8, 7.4 Hz, 1H), 3.23 (d, J=4.7 Hz, 1H), 3.14 (dd, J=13.8, 5.7 Hz, 1H), 2.22 (m, 1H), 2.05 (m, 1H), 2.01 (s, 3H), 1.58 (s, 3H), 1.50 (s, 3H), 1.25 (s, 3H), 1.17 (s, 3H), 1.00 (s, 3H), 0.95-1.90 (m, 14H), 0.92 (s, 3H), 0.88 (s, 3H).

Compound T4: To a solution of compound CC2 (13 mg, 0.027 mmol) in $CH_2Cl_2$ (0.6 mL) at 0° C. was added $Et_3N$ (7.6 μL, 0.055 mmol) and the solution of cyclopropanecarbonyl chloride (3.7 mg, 0.035 mmol) in $CH_2Cl_2$ (0.1 mL) sequentially. The reaction was stirred at 0° C. for 30 min. The mixture was diluted with EtOAc (20 mL), and washed with sat. aq. $NaHCO_3$ (15 mL).

The organic extract was dried with $MgSO_4$; filtered and concentrated. The residue was purified by column chromatography (silica gel, eluting with 0-100% EtOAc in hexanes) to give compound T4 (9 mg, 60% yield) as a white solid. m/z=545 (M+1); $^1H$ NMR (400 MHz, $CDCl_3$) δ 8.04 (s, 1H), 5.96 (s, 1H), 5.72 (t, J=6.7 Hz, 1H), 3.60 (dd, J=13.8, 7.6 Hz, 1H), 3.18 (d, J=4.7 Hz, 1H), 3.08 (dd, J=13.8, 5.6 Hz, 1H), 2.23 (dt, J=13.6, 4.0 Hz, 1H), 2.05 (td, J=14.0, 13.5, 4.6 Hz, 1H), 1.56 (s, 3H), 1.49 (s, 3H), 1.25 (s, 3H), 1.17 (s, 3H), 1.00 (s, 3H), 0.94 (s, 3H), 0.91-1.89 (m, 17H), 0.89 (s, 3H), 0.75 (m, 2H).

Compound 9: Compound 8 (10.00 g, 19.71 mmol) in THF (200 mL) was cooled to 0° C. under $N_2$. DIBAL-H (1.0 M in toluene, 100 mL, 100 mmol, 5 equiv.) was added. The mixture was stirred at 0° C. for 30 min, and then at room temperature for 2 h. The reaction was cooled to 0° C., and quenched with water (20 mL) carefully, followed by 1N aq. HCl (300 mL). The mixture was extracted with EtOAc (4×150 mL). The combined organic extracts were washed with water (100 mL) and brine (100 mL); dried with $Na_2SO_4$; filtered and concentrated to give crude compound 9 (9.5 g, quantitative yield) as a white solid. Compound 9 was used in the next step without further purification.

Compound 10: Compound 9 (9.5 g, <19.71 mmol) was dissolved in $CH_2Cl_2$ (200 mL). 4 Å MS (20 g) and 4-methylmorpholine N-oxide (5.10 g, 43.53 mmol, 2.2 equiv.) were added. The mixture was stirred at room temperature for 10 min under $N_2$. TPAP (690 mg, 1.96 mmol, 0.1 equiv.) was added. The mixture was stirred at room temperature for 1.5 h, and then quenched with 10% $Na_2SO_3$ (50 mL). The mixture was stirred for 5 min at room temperature, and then filtered through a pad of celite. The celite was eluted with $CH_2Cl_2$ (50 mL). The aqueous phase from the filtrate was extracted with $CH_2Cl_2$ (2×50 mL), and EtOAc (2×50 mL). The combined organic extracts were washed with water (100 mL); dried with $Na_2SO_4$; and filtered through a pad of silica gel, which was eluted with EtOAc (100 mL). The filtrate was concentrated. The residue was purified by column chromatography (silica gel, eluting with 0-35% EtOAc in hexanes) to give compound 10 (6.39 g, 68% yield) as a white solid. m/z=478 (M+1).

Compound 11: Compound 10 (110 mg, 0.230 mmol) was dissolved in THE (2.3 mL) at room temperature under $N_2$. Methylamine (2.0 M solution in THF, 1.73 mL, 3.46 mmol) was added. The mixture was stirred at room temperature for 2 h, and then acetic acid (198 μL, 3.45 mmol) was added. The mixture was stirred at room temperature for 5 min, and then treated with a solution of sodium cyanoborohydride (217 mg, 3.45 mmol) in MeOH (2.3 mL). The mixture was stirred at room temperature for another 2 h, and then was partitioned between EtOAc (30 mL) and sat. aq. $NaHCO_3$ (20 mL). The aqueous phase was separated, and extracted with EtOAc (20 mL). The combined organic extracts were washed with water; dried with $MgSO_4$; filtered and concentrated. The residue was purified by column chromatography (silica gel, eluting with 0-20% MeOH in $CH_2Cl_2$) to give compound 11 (91 mg, 80% yield) as a white solid. m/z=493 (M+1).

Compound 12: To a mixture of compound 11 (90 mg, 0.18 mmol) and $NaHCO_3$ (18 mg, 0.22 mmol) in THE (1 mL) and water (0.36 mL) was added a solution of di-t-butyl dicarbonate (60 mg, 0.27 mmol) in THE (0.8 mL) at room temperature under $N_2$. The mixture was stirred at room temperature for 30 min, and then quenched with sat. aq. $NaHCO_3$ (20 mL). The mixture was extracted with EtOAc (2×30 mL). The combined organic extracts were washed with brine (20 mL); dried with $MgSO_4$; filtered; and concentrated. The residue was purified by column chromatography (silica gel, eluting with 0-40% EtOAc in hexanes) to give compound 12 (101 mg, 93% yield) as a white solid. m/z=593 (M+1).

Compound 13: Compound 12 (210 mg, 0.354 mmol) in MeOH (3.5 mL) was treated with sodium methoxide solution (25 wt. % in MeOH, 122 μL, 0.531 mmol) at room temperature under $N_2$. The mixture was heated at 55° C. for 1 h, and then cooled to 0° C. The mixture was treated with 10% aq. $NaH_2PO_4$ (15 mL); and extracted with EtOAc (2×20 mL). The combined organic extracts were washed with water; dried with $MgSO_4$; filtered and concentrated. The residue was purified by column chromatography (silica gel, eluting with 0-40% EtOAc in hexanes) to give compound 13 (193 mg, 92% yield) as a white solid. m/z=537 ($M-C_4H_7$).

Compound T5: A mixture of compound 13 (181 mg, 0.305 mmol) and 1,3-dibromo-5,5-dimethylhydantoin (48 mg, 0.168 mmol) were treated with DMF (1.5 mL) at 0° C. under $N_2$. The mixture was stirred at 0° C. for 2 h. Pyridine (99 μL, 1.22 mmol) was added. The mixture was heated at 55° C. for 4 h, and then cooled to room temperature. The mixture was diluted with EtOAc (30 mL), and washed with 1N aq. HCl (2×15 mL), water (15 mL) and brine (15 mL). The organic extract was dried with $MgSO_4$; filtered; and concentrated. The residue was purified by column chromatography (silica gel, eluting with 0-50% EtOAc in hexanes) to give compound T5 (148 mg, 82% yield) as a white solid. m/z=535 ($M-C_4H_7$); $^1H$ NMR (400 MHz, $CDCl_3$) δ 8.04 (s, 1H), 5.97 (s, 1H), 3.33 (m, 2H), 2.94 (s, 3H), 2.30 (m, 1H), 1.56 (s, 3H), 1.50 (s, 3H), 1.44 (s, 9H), 1.26 (s, 3H), 1.18 (s, 3H), 1.01 (s, 3H), 0.98-2.12 (m, 16H), 0.93 (s, 3H), 0.86 (s, 3H).

Compound T6: Compound T5 (138 mg, 0.234 mmol) was dissolved in $CH_2Cl_2$ (5 mL), and cooled to 0° C. under $N_2$. Trifluoroacetic acid (0.90 mL, 11.7 mmol) was added. The mixture was stirred at 0° C. for 4 h, and then concentrated. The residue was diluted with $CH_2Cl_2$ (20 mL), and washed with sat. aq. $NaHCO_3$ (15 mL). The aqueous phase was separated, and extracted with $CH_2Cl_2$ (2×15 mL) and EtOAc (15 mL). The combined organic extracts were dried with $MgSO_4$; filtered; and concentrated to give crude compound T6 (117 mg, quantitative yield) as a white solid. Crude T6 (39 mg) was purified by column chromatography (silica gel, eluting with 0-50% EtOAc in hexanes, and then 0-30% [1% $Et_3N$ in MeOH] in $CH_2Cl_2$) to give T6 (34 mg, 89% yield) as an off-white solid. m/z=491 (M+1); $^1H$ NMR (400 MHz, $CDCl_3$) δ 8.04 (s, 1H), 5.98 (s, 1H), 2.99 (d, J=4.8 Hz, 1H), 2.70 (d, J=11.6 Hz, 1H), 2.47 (s, 3H), 2.39 (d, J=11.7 Hz, 1H), 2.28 (m, 1H), 1.50 (s, 3H), 1.47 (s, 3H), 1.26 (s, 3H), 1.18 (s, 3H), 1.05-1.88 (m, 16H), 1.02 (s, 3H), 0.93 (s, 3H), 0.87 (s, 3H).

Compound T7: To a solution of crude compound T6 (39 mg, 0.079 mmol) in $CH_2Cl_2$ (0.8 mL) at 0° C. was added $Et_3N$ (22 μL, 0.16 mmol) and acetic anhydride (11 μL, 0.12 mmol) sequentially. The mixture was stirred at 0° C. for 30 min, and then quenched with sat. aq. $NaHCO_3$ (1 mL). After stirring at ambient temperature for 5 min, the mixture was diluted with EtOAc (30 mL); and washed with sat. aq. $NaHCO_3$ (10 mL) and water (10 mL). The organic extract was dried with $MgSO_4$; filtered and concentrated. The residue was purified by column chromatography (silica gel, eluting with 0-100% EtOAc in hexanes) to give partially purified product, which was purified again by column chromatography (silica gel, eluting with 0-40% acetone in hexanes) to give compound T7 (31 mg, 74% yield) as a white solid. m/z=533 (M+1); $^1H$ NMR (400 MHz, $CDCl_3$) δ 8.04 (s, 1H), 5.96 (s, 1H), 3.61 (d, J=13.8 Hz, 1H), 3.44 (d, J=4.6 Hz, 1H), 3.26 (d, J=13.8 Hz, 1H), 3.10 (s, 3H), 2.18-2.30 (m, 2H), 2.12 (s, 3H), 1.57 (s, 3H), 1.49 (s, 3H), 1.25 (s, 3H), 1.17 (s, 3H), 1.00 (s, 3H), 0.98-1.92 (m, 14H), 0.93 (s, 3H), 0.87 (s, 3H).

Compound T8: To a solution of crude compound CC2 (43 mg, 0.090 mmol) in $CH_2Cl_2$ (0.8 mL) at 0° C. was added $Et_3N$ (25 μL, 0.18 mmol) and N-methylcarbamoyl chloride (13 mg, 0.14 mmol) sequentially. The mixture was stirred at 0° C. for 30 min, and then quenched with sat. aq. $NaHCO_3$ (1 mL). After stirring at ambient temperature for 5 min, the mixture was diluted with EtOAc (30 mL); and washed with sat. aq. $NaHCO_3$ (10 mL) and water (10 mL). The organic extract was dried with $MgSO_4$; filtered and concentrated. The residue was purified by column chromatography (silica gel, eluting with 0-90% acetone in hexanes) to give compound T8 (35 mg, 73% yield) as a white solid. m/z=534 (M+1); $^1H$ NMR (400 MHz, $CDCl_3$) δ 8.05 (s, 1H), 5.96 (s, 1H), 4.34 (t, J=6.5 Hz, 1H), 4.19 (q, J=5.2 Hz, 1H), 3.46 (dd, J=13.8, 7.3 Hz, 1H), 3.22 (d, J=4.7 Hz, 1H), 3.11 (dd, J=13.8, 5.6 Hz, 1H), 2.78 (d, J=4.9 Hz, 3H), 2.24 (m, 1H), 2.08 (td, J=13.3, 4.5 Hz, 1H), 1.58 (s, 3H), 1.50 (s, 3H), 1.25 (s, 3H), 1.17 (s, 3H), 1.00 (s, 3H), 0.98-1.89 (m, 14H), 0.92 (s, 3H), 0.88 (s, 3H).

Compound T9: To a solution of crude compound T6 (39 mg, 0.079 mmol) in $CH_2Cl_2$ (0.8 mL) at 0° C. was added $Et_3N$ (22 μL, 0.16 mmol) and a suspension of N-methylcarbamoyl chloride (11 mg, 0.12 mmol) in $CH_2Cl_2$ (0.1 mL) sequentially. The mixture was stirred at 0° C. for 30 min, and then quenched with sat. aq. $NaHCO_3$ (1 mL). After stirring at ambient temperature for 5 min, the mixture was diluted with EtOAc (30 mL); and washed with sat. aq. $NaHCO_3$ (10 mL) and water (10 mL). The organic extract was dried with $MgSO_4$; filtered and concentrated. The residue was purified by column chromatography (silica gel, eluting with 0-100% EtOAc in hexanes) to give partially purified product, which was purified again by column chromatography (silica gel, eluting with 0-60% acetone in hexanes) to give compound T9 (19 mg, 43% yield) as a white solid. m/z=548 (M+1); $^1H$ NMR (400 MHz, $CDCl_3$) δ 8.04 (s, 1H), 5.96 (s, 1H), 4.36 (q, J=4.7 Hz, 1H), 3.68 (d, J=14.3 Hz, 1H), 3.34 (d, J=4.6 Hz, 1H), 3.12 (d, J=14.4 Hz, 1H), 2.97 (s, 3H), 2.81 (d, J=4.6 Hz, 3H), 2.20-2.32 (m, 2H), 1.58 (s, 3H), 1.50 (s, 3H), 1.25 (s, 3H), 1.17 (s, 3H), 1.02-1.88 (m, 14H), 1.00 (s, 3H), 0.93 (s, 3H), 0.86 (s, 3H).

Compound 14: A mixture of compound 10 (500 mg, 1.05 mmol) and tert-butyl 3-aminopropanoate hydrochloride (380 mg, 2.09 mmol) in THF (10.5 mL) was stirred at room temperature for 1 h. $Et_3N$ (0.29 mL, 2.09 mmol) was added. The mixture was stirred at room temperature for 5.5 h. $NaBH_4$ (80 mg, 2.11 mmol) and EtOH (10.5 mL) were added. The mixture was stirred at room temperature for 2 h. Additional amount of $NaBH_4$ (10 mg, 0.26 mmol) was added. The mixture was stirred for another 10 min. The mixture was treated with sat. aq. $NaHCO_3$ (50 mL), and extracted with EtOAc (2×50 mL). The combined organic extracts were washed with water (50 mL), and brine (25 mL). The aqueous washes were extracted with EtOAc (50 mL). The combined organic extracts were dried with $MgSO_4$, filtered, and concentrated. The residue was purified by column chromatography (silica gel, eluting with 0-100% EtOAc in hexanes) to give compound 14 (525 mg, 83% yield) as a white solid. m/z=607 (M+1).

Compound 15: Compound 14 (525 mg, 0.87 mmol) was treated with HCl (4.0 M in 1,4-dioxane, 2.16 mL, 8.65 mmol) at room temperature under $N_2$. The mixture was stirred at room temperature for 5.5 h, and then concentrated. The residue was azeotroped with toluene (10 mL, and then 20 mL), and concentrated. The residue was dried under vacuum to give compound 15 (431 mg, 85% yield) as a white solid. m/z=551 (M+1 of free amine).

Compound 16: Compound 15 (50 mg, 0.085 mmol) was dissolved in $CH_2Cl_2$ (1.7 mL), and cooled to 0° C. $Et_3N$ (35 μL, 0.26 mmol) and $POCl_3$ (12 μL, 0.13 mmol) were added sequentially. The mixture was stirred at 0° C. for 20 min. Sat. aq. $NaHCO_3$ (10 mL) was added. The mixture was stirred at ambient temperature for 5 min, and then extracted with EtOAc (2×15 mL). The combined organic extracts were washed with sat. aq. $NaHCO_3$ (10 mL) and water (10 mL); dried with $MgSO_4$; filtered and concentrated. The residue was purified by column chromatography (silica gel, eluting with 0-100% EtOAc in hexanes) to give compound 16 (31 mg, 68% yield) as a white solid. m/z=533 (M+1).

Compound 17: Compound 16 (57 mg, 0.11 mmol) was mixed with MeOH (1.5 mL) at room temperature. Sodium methoxide (25 wt. % solution in MeOH, 49 μL, 0.21 mmol) was added at room temperature. The mixture was stirred at 55° C. for 1 h. After cooled to 0° C., 10% aq. $NaH_2PO_4$ (15 mL) was added. The mixture was extracted with EtOAc (2×20 mL). The combined organic extracts were dried with $MgSO_4$, filtered and concentrated. The crude product was combined with the product obtained from compound 16 (12 mg, 0.023 mmol) using the same protocol to give compound 17 (65 mg, 94% yield) as a white solid. Compound 17 was used in the next step without further purification. m/z=533 (M+1).

Compound T10: Compound 17 (65 mg, 0.12 mmol) was dissolved in DMF (0.6 mL), and cooled to 0° C. under $N_2$. 1,3-Dibromo-5,5-dimethylhydantoin (18 mg, 0.063 mmol) was added. The mixture was stirred at 0° C. for 1 h. Pyridine (39 μL, 0.49 mmol) was added. The mixture was heated at 60° C. for 3 h. After cooled to room temperature, the mixture was diluted with EtOAc (25 mL), and washed with 1N aq.

HCl (10 mL), water (2×15 mL) and brine (10 mL). The organic extract was dried with $MgSO_4$; filtered; and concentrated. The residue was purified by column chromatography (silica gel, eluting with 0-50% acetone in hexanes) to give compound T10 (50 mg, 77% yield) as a white solid. m/z=531 (M+1); $^1$H NMR (400 MHz, $CDCl_3$) δ 8.04 (s, 1H), 5.97 (s, 1H), 3.44 (d, J=14.3 Hz, 1H), 3.38 (m, 2H), 3.11 (d, J=4.7 Hz, 1H), 3.00 (t, J=4.2 Hz, 2H), 2.96 (d, J=14.6 Hz, 1H), 2.27 (m, 1H), 2.04 (m, 1H), 1.55 (s, 3H), 1.50 (s, 3H), 1.26 (s, 3H), 1.18 (s, 3H), 1.02-1.93 (m, 14H), 1.01 (s, 3H), 0.93 (s, 3H), 0.88 (s, 3H).

Compound 18: To a suspension of methyl 4-aminobutanoate hydrochloride (64 mg, 0.42 mmol) in THE (1 mL) was added $Et_3N$ (58 μL, 0.42 mmol). After the mixture was stirred at room temperature for 10 min, a solution of compound 10 (100 mg, 0.21 mmol) in THE (1 mL) was added at room temperature. The mixture was stirred at room temperature for 1.5 h; treated with sodium triacetoxyborohydride (177 mg, 0.84 mmol); and stirred at room temperature for another 4 h. MeOH (2 mL) and sodium borohydride (18 mg, 0.48 mmol) were added sequentially, and the mixture was stirred at room temperature for 20 min. Sat. aq. $NaHCO_3$ (20 mL) was added. The mixture was extracted with EtOAc (3×20 mL). The combined organic extracts were washed with brine, dried with $MgSO_4$, filtered and concentrated to give compound 18 (120 mg, 99% yield) as a white solid, which was used in the next step without further purification. m/z=579 (M+1).

Compound 19: A mixture of compound 18 (120 mg, 0.19 mmol) in toluene (6 mL) was heated in a microwave synthesizer at 140° C. until compound 18 was completely consumed (2-3 h). The mixture was purified by column chromatography (silica gel, eluting with 0-100% EtOAc in hexanes) to give compound 19 (85 mg, 75% yield) as a white solid. m/z=547 (M+1).

Compound 20: A solution of compound 19 (83 mg, 0.15 mmol) in MeOH (1.5 mL) and THE (0.5 mL) was treated with sodium methoxide (25 wt. % solution in MeOH, 52 μL, 0.23 mmol) at room temperature. The mixture was heated at 55° C. for 1 h, and then cooled to room temperature. The mixture was treated with 10% aq. $NaH_2PO_4$ (15 mL), and extracted with EtOAc (2×15 mL). The combined organic extracts were dried with $MgSO_4$, filtered and concentrated to give compound 20 (80 mg, 96% yield) as a white solid, which was used in the next step without further purification. m/z=547 (M+1).

Compound T11: Compound 20 (80 mg, 0.15 mmol) in DMF (0.4 mL) was cooled to 0° C. A solution of 1,3-dibromo-5,5-dimethylhydantoin (23 mg, 0.080 mmol) in DMF (0.4 mL) was added. The mixture was stirred at 0° C. for 1 h. Pyridine (47 μL, 0.59 mmol) was added. The mixture was heated at 55° C. for 4 h. The mixture was cooled to room temperature; diluted with EtOAc (25 mL); and washed with 1N aq. HCl (10 mL) and water (2×15 mL) sequentially. The organic extract was dried with $MgSO_4$; filtered and concentrated. The residue was purified by column chromatography (silica gel, eluting with 0-100% EtOAc in hexanes) to give compound T11 (56 mg, 70% yield) as a white foam. m/z=545 (M+1); $^1$H NMR (400 MHz, $CDCl_3$) δ 8.04 (s, 1H), 5.97 (s, 1H), 3.42-3.62 (m, 3H), 3.36 (d, J=4.6 Hz, 1H), 3.05 (d, J=13.9 Hz, 1H), 2.37 (t, J=8.0 Hz, 2H), 2.18-2.32 (m, 2H), 2.02 (m, 2H), 1.59 (s, 3H), 1.50 (s, 3H), 1.25 (s, 3H), 1.17 (s, 3H), 1.01 (s, 3H), 0.97-1.91 (m, 14H), 0.93 (s, 3H), 0.87 (s, 3H).

Compound 21: Compound 10 (300 mg, 0.628 mmol) was dissolved in anhydrous THE (8 mL) at ambient temperature under nitrogen. To this solution was added ethanolamine (0.19 mL, 3.14 mmol). The mixture was stirred for 2 h. Glacial acetic acid (0.18 mL, 3.14 mmol) was added. After the mixture was stirred for 5 min, a solution of sodium cyanoborohydride (197 mg, 3.14 mmol) in MeOH (8 mL) was added. The mixture was stirred at ambient temperature for an additional 2 h. The reaction mixture was partitioned between EtOAc and sat. aq. $NaHCO_3$. The aqueous phase was separated, and extracted with EtOAc. The combined organic extracts were washed with water, and sat. aq. NaCl; dried with $Na_2SO_4$; filtered and concentrated. The residue was purified by column chromatography (silica gel, eluting with 15% MeOH in EtOAc) to give compound 21 (207 mg, 63% yield) as a white glass. m/z=523 (M+1).

Compound 22: A solution of compound 21 (207 mg, 0.395 mmol) in $CH_2Cl_2$ (10 mL) was treated with di-t-butyl dicarbonate (95 mg, 0.435 mmol) and triethylamine (0.11 mL, 0.790 mmol). The reaction was stirred at ambient temperature for 17 h. The mixture was washed with water and sat. aq. NaCl. The organic extract was dried with $Na_2SO_4$; filtered and concentrated. The residue was purified by column chromatography (silica gel, eluting with 50% EtOAc in hexanes) to give compound 22 (193 mg, 78% yield) as a white glass. m/z=623 (M+1).

Compound 23: A solution of compound 22 (193 mg, 0.309 mmol) in MeOH (10 mL) was treated with potassium carbonate (86 mg, 0.619 mmol). The reaction mixture was stirred at ambient temperature for 20 h. The solvent was removed in vacuo and the residue was partitioned between EtOAc and sat. aq. $KH_2PO_4$. The separated organic layer was washed with sat. aq. NaCl; dried with $Na_2SO_4$; filtered and concentrated. The residue was purified by column chromatography (silica gel, eluting with 60% EtOAc in hexanes) to give compound 23 (142 mg, 74% yield) as a white glass. m/z=567 (M−$C_4H_7$).

Compound 24: A solution of compound 23 (142 mg, 0.228 mmol) in anhydrous DMF (3 mL) was cooled to 0° C. under nitrogen, and treated dropwise with a solution of 1,3-dibromo-5,5-dimethylhydantoin (36 mg, 0.125 mmol) in anhydrous DMF (0.50 mL). The mixture was stirred at 0° C. for 1 h, and then treated with anhydrous pyridine (0.18 mL, 2.23 mmol). The mixture was heated at 60° C. for 4 h, and then cooled to room temperature. The solution was partitioned between EtOAc and sat. aq. $KH_2PO_4$. The aqueous layer was separated, and extracted with EtOAc. The combined organic extracts were washed with water and sat. aq. NaCl; dried with $Na_2SO_4$; filtered and concentrated. The residue was purified by column chromatography (silica gel, eluting with 60% EtOAc in hexanes) to give compound 24 (100 mg, 71% yield) as a white glass. m/z=621 (M+1).

Compound T12: A solution of compound 24 (73 mg, 0.117 mmol) in $CH_2Cl_2$ (10 mL) was treated with trifluoroacetic acid (1 mL, 13 mmol) and the reaction mixture was stirred at ambient temperature for 4 h. The solution was diluted with $CH_2Cl_2$, and washed with sat. aq. $NaHCO_3$, water, and sat. aq. NaCl. The organic extract was dried with $Na_2SO_4$; filtered and concentrated. The residue was purified by column chromatography (silica gel, eluting with 30% MeOH in EtOAc). The product was collected; dissolved in $CH_2Cl_2$; and filtered to remove silica gel. The filtrate was concentrated to give compound T12 (24 mg, 39% yield) as a light yellow solid. m/z=521 (M+1); $^1$H NMR (400 MHz, $CDCl_3$) δ 8.03 (s, 1H), 5.98 (s, 1H), 3.64-3.73 (m, 2H), 2.78-2.99 (m, 4H), 2.55 (d, J=11.9 Hz, 1H), 2.30 (m, 1H), 1.50 (s, 3H), 1.47 (s, 3H), 1.26 (s, 3H), 1.18 (s, 3H), 1.06-1.92 (m, 15H), 1.02 (s, 3H), 0.94 (s, 3H), 0.88 (s, 3H).

Compound T13: A solution of compound T12 (42 mg, 0.081 mmol) in anhydrous $CH_2Cl_2$ (3 mL) was treated with 1,1'-carbonyldiimidazole (13 mg, 0.081 mmol). The reaction mixture was stirred at ambient temperature for 4 h, and then diluted with $CH_2Cl_2$. The mixture was washed with water. The organic extract was dried with $Na_2SO_4$, filtered and concentrated. The residue was purified by column chromatography (silica gel, eluting with 70% EtOAc in hexanes) to give compound T13 (19 mg, 43% yield) as a white solid. m/z=547 (M+1); $^1$H NMR (400 MHz, $CDCl_3$) δ 8.04 (s, 1H), 5.97 (s, 1H), 4.26-4.38 (m, 2H), 3.75 (td, J=8.4, 5.9 Hz, 1H), 3.57-3.65 (m, 2H), 3.19 (d, J=4.7 Hz, 1H), 2.92 (d, J=14.3 Hz, 1H), 2.29 (m, 1H), 2.19 (m, 1H), 1.87 (td, J=14.2, 4.6 Hz, 1H), 1.56 (s, 3H), 1.50 (s, 3H), 1.26 (s, 3H), 1.18 (s, 3H), 1.02 (s, 3H), 0.99-1.82 (m, 13H), 0.94 (s, 3H), 0.88 (s, 3H).

Compound 26: To a solution of compound 10 (500 mg, 1.05 mmol) in anhydrous THF (15 mL) was added t-butyl-N-(2-aminoethyl)carbamate 25 (838 mg, 5.23 mmol) at room temperature under nitrogen. The mixture was stirred for 2 h. Acetic acid (0.30 mL, 5.25 mmol) was added. The mixture was stirred for another 5 min, and then a solution of sodium cyanoborohydride (329 mg, 5.24 mmol) in MeOH (15 mL) was added. The reaction mixture was stirred for an additional 2 h, and then partitioned between EtOAc and sat. aq. $NaHCO_3$. The aqueous phase was separated, and extracted with EtOAc. The combined organic extracts were washed with water and sat. aq. NaCl; dried with $Na_2SO_4$; filtered and concentrated. The residue was purified by column chromatography (silica gel, eluting with EtOAc) to give compound 26 (611 mg, 94% yield) as a white glass. m/z=622 (M+1).

Compound 27: A solution of compound 26 (374 mg, 0.601 mmol) in $CH_2Cl_2$ (10 mL) was treated with trifluoroacetic acid (2 mL, 26.0 mmol) at ambient temperature. After stirring for 2 h, the reaction mixture was concentrated. The residue was azeotroped with toluene to give compound 27 as a clear glass. m/z=522 (M of free amine+1).

Compound 28: To the mixture of compound 27 (all from the last step) in 1,4-dioxane (10 mL) was added Hunig's base (0.31 mL, 1.78 mmol) and 1,1'-carbonyldiimidazole (107 mg, 0.661 mmol) sequentially. The reaction mixture was heated at 80° C. for 30 h, and then concentrated. The residue was diluted with EtOAc, and washed with sat. aq. NaCl. The organic extract was dried with $Na_2SO_4$, filtered and concentrated. The residue was purified by column chromatography (silica gel, eluting with 3% MeOH in EtOAc) to give compound 28 (90 mg, 27% yield from 26) as a white glass. m/z=548 (M+1).

Compound 29: A solution of 28 (90 mg, 0.16 mmol) in MeOH (10 mL) was treated with potassium carbonate (45 mg, 0.33 mmol). The reaction mixture was stirred at ambient temperature for 21 h. The solvent was removed in vacuo and the residue was partitioned between EtOAc and sat. aq. $KH_2PO_4$. The organic layer was separated; washed with sat. aq. NaCl; dried with $Na_2SO_4$; filtered and concentrated. The residue was purified by column chromatography (silica gel, eluting with 5% MeOH in EtOAc) to give compound 29 (69 mg, 77% yield) as a white solid. m/z=548 (M+1).

Compound T14: A solution of compound 29 (69 mg, 0.13 mmol) in anhydrous DMF (3 mL) was cooled to 0° C. under nitrogen. A solution of 1,3-dibromo-5,5-dimethylhydantoin (19 mg, 0.066 mmol) in anhydrous DMF (0.50 mL) was added dropwise. The mixture was stirred at 0° C. for 1 h, and then anhydrous pyridine (0.10 mL, 1.24 mmol) was added. The mixture was heated at 60° C. for 4 h. Upon cooling, the mixture was partitioned between EtOAc and sat. aq. $KH_2PO_4$. The aqueous phase was separated, and extracted with EtOAc. The combined organic extracts were washed with water and sat. aq. NaCl; dried with $Na_2SO_4$; filtered and concentrated. The residue was purified by column chromatography (silica gel, eluting with EtOAc) to give compound T14 (44 mg, 64% yield) as a yellow solid. m/z=546 (M+1); $^1$H NMR (400 MHz, $CDCl_3$) δ 8.05 (s, 1H), 5.97 (s, 1H), 4.31 (s, 1H), 3.60 (q, J=7.5 Hz, 1H), 3.51 (q, J=8.0 Hz, 1H), 3.30-3.44 (m, 4H), 2.96 (d, J=14.2 Hz, 1H), 2.32 (m, 1H), 2.19 (dt, J=4.5, 13.4 Hz, 1H), 1.57 (s, 3H), 1.49 (s, 3H), 1.25 (s, 3H), 1.17 (s, 3H), 1.01 (s, 3H), 0.94 (s, 3H), 0.87 (s, 3H), 0.77-1.91 (m, 14H).

Compound 31: To a solution of compound 10 (500 mg, 1.05 mmol) in anhydrous THF (15 mL) was added 1-Boc-1-methyl-ethylenediamine 30 (911 mg, 5.23 mmol) at room temperature under nitrogen. The mixture was stirred for 2 h. Acetic acid (0.30 mL, 5.25 mmol) was added. The mixture was stirred for another 5 min, and then a solution of sodium cyanoborohydride (329 mg, 5.24 mmol) in MeOH (15 mL) was added. The reaction mixture was stirred for an additional 2 h, and then partitioned between EtOAc and sat. aq. $NaHCO_3$. The aqueous phase was separated, and extracted with EtOAc. The combined organic extracts were washed with water and sat. aq. NaCl; dried with $Na_2SO_4$; filtered and concentrated. The residue was purified by column chromatography (silica gel, eluting with 70% EtOAc in hexanes) to give compound 31 (546 mg, 82% yield) as a white glass. m/z=636 (M+1).

Compound 32: A solution of compound 31 (419 mg, 0.658 mmol) in $CH_2Cl_2$ (20 mL) was treated with trifluoroacetic acid (3 mL, 38.9 mmol) at ambient temperature. After stirring for 2 h, the reaction mixture was concentrated. The residue was azeotroped with toluene, and then partitioned between $CH_2Cl_2$ and sat. aq. $NaHCO_3$. The aqueous layer was separated, and extracted with $CH_2Cl_2$. The combined organic extracts were dried with $Na_2SO_4$, filtered and concentrated. The crude product was dissolved in $CH_2Cl_2$ (20 mL). The solution was treated with phosgene (20% solution in toluene, 0.70 mL, 1.32 mmol). The mixture was stirred at ambient temperature for 18 h, and then washed with sat. aq. $NaHCO_3$. The organic extract was dried with $Na_2SO_4$, filtered and concentrated. The residue was purified by column chromatography (silica gel, eluting with EtOAc) to give compound 32 (181 mg, 49% yield) as a white glass. m/z=562 (M+1).

Compound 33: A solution of 32 (181 mg, 0.322 mmol) in MeOH (10 mL) was treated with potassium carbonate (89 mg, 0.644 mmol). The reaction mixture was stirred at ambient temperature for 20 h. The solvent was removed in vacuo and the residue was partitioned between EtOAc and sat. aq. $KH_2PO_4$. The organic layer was separated; washed with sat. aq. NaCl; dried with $Na_2SO_4$; filtered and concentrated. The residue was purified by column chromatography (silica gel, eluting with EtOAc) to give compound 33 (134 mg, 74% yield) as a white solid. m/z=562 (M+1).

Compound T15: A solution of compound 33 (129 mg, 0.229 mmol) in anhydrous DMF (3 mL) was cooled to 0° C. under nitrogen. A solution of 1,3-dibromo-5,5-dimethylhydantoin (36 mg, 0.126 mmol) in anhydrous DMF (0.50 mL) was added dropwise. The mixture was stirred at 0° C. for 1 h, and then anhydrous pyridine (0.185 mL, 2.29 mmol) was added. The mixture was heated at 60° C. for 4 h. Upon cooling, the mixture was partitioned between EtOAc and sat. aq. $KH_2PO_4$. The aqueous phase was separated, and extracted with EtOAc. The combined organic extracts were washed with water and sat. aq. NaCl; dried with $Na_2SO_4$; filtered and concentrated. The residue was purified by column chromatography (silica gel, eluting with EtOAc) to give compound T15 (115 mg, 90% yield) as a yellow solid.

m/z=560 (M+1); $^1$H NMR (400 MHz, $CDCl_3$) δ 8.04 (s, 1H), 5.96 (s, 1H), 3.45-3.56 (m, 2H), 3.25-3.36 (m, 4H), 2.80 (s, 3H), 2.77 (d, J=14.2 Hz, 1H), 2.23-2.33 (m, 2H), 1.59 (s, 3H), 1.49 (s, 3H), 1.25 (s, 3H), 1.17 (s, 3H), 1.00 (s, 3H), 0.98-1.89 (m, 14H), 0.93 (s, 3H), 0.87 (s, 3H).

Compound 35: To a solution of compound 6 (31 mg, 0.065 mmol) in $CH_2Cl_2$ (0.65 mL) at 0° C. was added $Et_3N$ (13 μL, 0.097 mmol) and compound 34 (14 mg, 0.079 mmol) sequentially under $N_2$. The mixture was stirred at 0° C. for 20 min; diluted with EtOAc (20 mL); and washed with sat. aq. $NaHCO_3$ (10 mL) and water (10 mL). The aqueous washes were combined, and extracted with EtOAc (20 mL). The combined organic extracts were dried with $MgSO_4$, filtered and concentrated. The residue was azeotroped with toluene, and dried in vacuo to give compound 35 (40 mg, quantitative yield) as a yellow solid. m/z=613, 615 (M+1).

Compound 37: To a solution of compound 35 (19.9 mg, 0.0325 mmol) was in THF (0.5 mL) was added sodium hydride (60 wt. % in mineral oil, 6.0 mg, 0.15 mmol) at 0° C. The mixture was slowly warmed to room temperature over 3 h, and then quenched with 10% aq. $NaH_2PO_4$ (10 mL). The mixture was extracted with EtOAc (2×20 mL). The combined organic extracts were washed with water (10 mL); dried with $MgSO_4$; filtered and concentrated to give a mixture of compound 36 and compound 37. The mixture was dissolved in MeOH (0.5 mL), and treated with sodium methoxide (25 wt. % solution in MeOH, 14.9 μL, 0.065 mmol) at room temperature. The mixture was heated at 55° C. for 1 h. After cooled to room temperature, the reaction mixture was quenched with 10% aq. $NaH_2PO_4$ (10 mL), and was extracted with EtOAc (2×20 mL). The combined organic extracts were washed with water (10 mL); dried with $MgSO_4$; filtered and concentrated. The residue was purified by column chromatography (silica gel, eluting with 0-100% EtOAc in hexanes) to give compound 37 (10 mg, 58% yield from compound 6) as a white solid. m/z=533 (M+1).

Compound T16: To a solution of compound 37 (28 mg, 0.053 mmol) in DMF (0.3 mL) at 0° C. was added a solution of 1,3-dibromo-5,5-dimethylhydantoin (7.5 mg, 0.026 mmol) in DMF (0.2 mL) under $N_2$. The mixture was stirred at 0° C. for 1 h, and then treated with pyridine (17 μL, 0.21 mmol). The mixture was heated at 55° C. for 14 h, and then cooled to room temperature. The mixture was diluted with EtOAc (25 mL), and washed with 1N aq. HCl (10 mL) and water (2×15 mL). The organic extract was dried with $MgSO_4$, filtered and concentrated. The residue was purified by column chromatography (silica gel, eluting with 0-100% EtOAc in hexanes) to give compound T16 (10 mg, 36% yield) as a white solid. m/z=531 (M+1); $^1$H NMR (400 MHz, $CDCl_3$) δ 8.04 (s, 1H), 6.29 (dd, J=16.9, 1.4 Hz, 1H), 6.11 (dd, J=16.9, 10.2 Hz, 1H), 5.97 (s, 1H), 5.67 (dd, J=10.3, 1.4 Hz, 1H), 5.63 (m, 1H), 3.74 (dd, J=13.7, 7.9 Hz, 1H), 3.21 (d, J=4.7 Hz, 1H), 3.10 (dd, J=13.7, 5.4 Hz, 1H), 2.25 (m, 1H), 2.10 (m, 1H), 1.60 (s, 3H), 1.51 (s, 3H), 1.26 (s, 3H), 1.18 (s, 3H), 1.02-1.90 (m, 14H), 1.01 (s, 3H), 0.93 (s, 3H), 0.89 (s, 3H).

Compound 38: To a mixture of paraformaldehyde (47 mg, 1.57 mmol), ammonium carbonate (73 mg, 0.75 mmol) and trimeric glyoxal dihydrate (132 mg, 0.63 mmol) in MeOH (6 mL) was added compound 6 (100 mg, 0.21 mmol). The mixture was stirred at room temperature for 9 h, and treated with additional amount of paraformaldehyde (47 mg, 1.57 mmol), ammonium carbonate (73 mg, 0.75 mmol) and trimeric glyoxal dihydrate (132 mg, 0.63 mmol). The mixture was stirred at room temperature for overnight; and then was diluted with EtOAc (20 mL). The mixture was washed with water (2×10 mL), and brine (10 mL). The organic extract was dried with $Na_2SO_4$, filtered, and concentrated. The residue was purified by column chromatography [silica gel, eluting with 0-10% (1% $Et_3N$ in MeOH) in $CH_2Cl_2$] to give compound 38 (99 mg, 89% yield) as a white solid. m/z=530 (M+1).

Compound 39: Compound 38 (99 mg, 0.19 mmol) in MeOH (2 mL) was treated with sodium methoxide (25 wt. % in MeOH, 86 μL, 0.37 mmol) at room temperature. The reaction was heated at 55° C. for 2.5 h. After cooled to 0° C., 10% aq. $NaH_2PO_4$ (10 mL) was added and the mixture was extracted with EtOAc (2×20 mL). The combined organic extracts were washed with brine, dried with $Na_2SO_4$, filtered and concentrated. The residue was purified by column chromatography [silica gel, eluting with 0-10% (1% $Et_3N$ in MeOH) in $CH_2Cl_2$] to give compound 39 (72 mg, 73% yield) as a white solid. m/z=530 (M+1).

Compound T17 and T17-HCl: Compound 39 (72 mg, 0.14 mmol) was dissolved in DMF (2 mL) and cooled to 0° C. under $N_2$. 1,3-Dibromo-5,5-dimethylhydantoin (21 mg, 0.075 mmol) in DMF (0.5 mL) was added dropwise. The mixture was stirred at 0° C. for 2 h. Pyridine (33 μL, 0.41 mmol) was then added and the reaction was heated at 60° C. for 4 h. After cooled to room temperature, the mixture was diluted with EtOAc (20 mL), washed with water (2×15 mL) and brine (10 mL). The organic extract was dried with $Na_2SO_4$, filtered, and concentrated. The residue was purified by column chromatography (silica gel, eluting with 0-10% (1% $Et_3N$ in MeOH) in $CH_2Cl_2$] to give compound T17 (26 mg, 36% yield) as a white solid. m/z=528 (M+1); $^1$H NMR (400 MHz, $CDCl_3$) δ 8.04 (s, 1H), 7.43 (s, 1H), 7.06 (t, J=1.1 Hz, 1H), 6.87 (t, J=1.3 Hz, 1H), 6.04 (s, 1H), 4.15 (d, J=14.3 Hz, 1H), 3.74 (d, J=14.2 Hz, 1H), 3.05 (d, J=4.7 Hz, 1H), 2.36 (m, 1H), 1.54 (s, 3H), 1.53 (s, 3H), 1.28 (s, 3H), 1.20 (s, 3H), 1.07 (s, 3H), 1.01-1.97 (m, 15H), 0.87 (s, 6H). Compound T17 (10 mg, 0.019 mmol) was dissolved in MeOH (1 mL) was cooled to 0° C. HCl (4 M in 1,4-dioxane, 9 μL, 0.036 mmol) was added. The mixture was sonicated for a few minutes at room temperature. The solution was concentrated and dried under vacuum to give compound T17 HCl (10 mg, 94% yield). m/z=528 (M of free base+1); $^1$H NMR (400 MHz, $CDCl_3$) δ 9.41 (s, 1H), 8.04 (s, 1H), 7.39 (s, 1H), 7.07 (s, 1H), 6.04 (s, 1H), 4.61 (d, J=14.0 Hz, 1H), 4.00 (d, J=14.0 Hz, 1H), 3.03 (d, J=4.6 Hz, 1H), 2.39 (m, 1H), 1.63 (s, 3H), 1.53 (s, 3H), 1.27 (s, 3H), 1.19 (s, 3H), 1.08 (s, 3H), 0.94-2.13 (m, 15H), 0.88 (s, 3H), 0.88 (s, 3H).

Compound 40: Compound 6 (74 mg, 0.15 mmol) was dissolved in glacial acetic acid (2 mL). At room temperature, trimethyl orthoformate (0.19 mL, 1.7 mmol) was added and the reaction was stirred for 20 min. Sodium azide (150 mg, 2.31 mmol) was then added and the reaction was heated at 80° C. for 2 h. After cooled to room temperature, EtOAc (30 mL) was added and the reaction mixture was washed with water (2×10 mL), sat. aq. $NaHCO_3$ (10 mL), and brine (10 mL). The organic extract was dried with $Na_2SO_4$, filtered and concentrated. The residue was purified by column chromatography (silica gel, eluting with 0-100% EtOAc in hexanes) to give compound 40 (62 mg, 75% yield) as a white solid. m/z=532 (M+1).

Compound 41: Compound 40 (77 mg, 0.14 mmol) in MeOH (2 mL) was treated with sodium methoxide (25 wt. % in MeOH, 66 μL, 0.29 mmol) at room temperature. The reaction was heated at 55° C. for 2.5 h, and then cooled to 0° C. 10% aq. $NaH_2PO_4$ (10 mL) was added. The mixture was extracted with EtOAc. The combined organic extracts were washed with brine, dried with $Na_2SO_4$, filtered and concentrated. The residue was purified by column chromatography (silica gel, eluting with 0-100% EtOAc in hexanes) to give compound 41 (55 mg, 71% yield) as a white solid. m/z=532 (M+1).

Compound T18: Compound 41 (55 mg, 0.10 mmol) was dissolved in DMF (1.5 mL) and cooled to 0° C. under $N_2$. 1,3-Dibromo-5,5-dimethylhydantoin (16 mg, 0.057 mmol) in DMF (0.5 mL) was added dropwise. The mixture was stirred at 0° C. for 2 h. Pyridine (25 μL, 0.31 mmol) was then added and the reaction was heated at 60° C. for 4 h. After cooled to room temperature, the mixture was diluted with EtOAc (20 mL) and washed with 1N aq. HCl (10 mL), water (2×15 mL) and brine (10 mL). The organic extract was dried with $Na_2SO_4$, filtered, and concentrated. The residue was purified by column chromatography (silica gel, eluting with 0-50% EtOAc in $CH_2Cl_2$) to give compound T18 (21 mg, 38% yield) as a white solid. m/z=530 (M+1); $^1$H NMR (400 MHz, $CDCl_3$) δ 8.59 (s, 1H), 8.04 (s, 1H), 6.04 (s, 1H), 4.79 (d, J=14.1 Hz, 1H), 4.09 (d, J=14.0 Hz, 1H), 3.12 (d, J=4.7 Hz, 1H), 2.33 (m, 1H), 2.20 (td, J=13.6, 4.3 Hz, 1H), 1.59 (s, 3H), 1.53 (s, 3H), 1.28 (s, 3H), 1.20 (s, 3H), 1.07 (s, 3H), 0.91 (s, 3H), 0.90-1.95 (m, 14H), 0.89 (s, 3H).

Compound 43: A solution of compound 6 (1.0 g, 2.09 mmol) in EtOH (40 mL) was treated with Hunig's base (2.07 mL, 11.88 mmol) at 0° C. The mixture was stirred for 10 min, and then treated with a solution of compound 42 (880 mg, 3.13 mmol) in acetonitrile (25 mL) dropwise over 10 min. After addition was complete, the reaction was stirred at ambient temperature for 16 hours. The mixture was concentrated and the residue was diluted with EtOAc. The mixture was washed with sat. aq. $NaHCO_3$ and sat. aq. NaCl. The organic extract was dried with $Na_2SO_4$; filtered and concentrated. The residue was purified by column chromatography (silica gel, eluting with 50-100% EtOAc in hexanes) to give compound 43 (915 mg, 82% yield) as a reddish-brown glass. m/z=531 (M+1).

Compound 44: A solution of compound 43 (4.52 g, 8.52 mmol) in MeOH (50 mL) was treated with sodium methoxide (5.4 M solution in MeOH, 3.41 mL, 18.41 mmol) at room temperature. The mixture was heated at 55° C. for 2 h, and then concentrated. The residue was partitioned between EtOAc and sat. aq. $KH_2PO_4$. The organic extract was washed with sat. aq. NaCl; dried with $Na_2SO_4$; filtered and concentrated. The residue was purified by column chromatography (silica gel, eluting with 30-100% EtOAc in hexanes) to give compound 44 (3.59 g, 79% yield) as an orange solid. m/z=531 (M+1).

Compound T19: A solution of compound 44 (3.59 g, 6.76 mmol) in anhydrous DMF (35 mL) was treated portionwise with 1,3-dibromo-5,5-dimethylhydantoin (966 mg, 3.38 mmol) at 0° C. under $N_2$. After addition was complete, the mixture was stirred at 0° C. for 2 h, and then treated with anhydrous pyridine (1.64 mL, 20.28 mmol). The cold bath was removed and the reaction was heated at 60° C. for 4 h. The reaction mixture was poured into a mixture of EtOAc (200 mL) and water (200 mL) at room temperature. The mixture was stirred for a few minutes. The precipitated solid was collected by filtration; washed with water, EtOAc, and MeOH sequentially; and dried in vacuo at 25° C. to give compound T19 (3.30 g, 92% yield) as an off-white solid. m/z=529 (M+1); $^1$H NMR (400 MHz, $CDCl_3$) δ 8.05 (s, 1H), 7.71 (d, J=0.9 Hz, 1H), 7.55 (d, J=1.0 Hz, 1H), 6.02 (s, 1H), 4.76 (d, J=13.9 Hz, 1H), 4.05 (d, J=13.9 Hz, 1H), 3.19 (d, J=4.7 Hz, 1H), 2.20-2.35 (m, 2H), 1.60 (s, 3H), 1.53 (s, 3H), 1.27 (s, 3H), 1.19 (s, 3H), 1.06 (s, 3H), 0.96-1.92 (m, 14H), 0.89 (s, 3H), 0.88 (s, 3H).

Compound 45: Compound 10 (1 g, 2 mmol) and tert-butyl carbazate (0.4 g, 3 mmol) were combined and dissolved in THE (20 mL) at room temperature. The reaction was heated at 70° C. for 16 h. After cooled to room temperature, THF was removed by rotovap and the residue was purified by column chromatography (silica gel, eluting with 0-60% EtOAc in hexanes) to give compound 45 (1.18 g, 95% yield) as a white solid. m/z=536 ($M-C_4H_7$).

Compound 46: Compound 45 (5.8 g, 9.8 mmol) was dissolved in THF (40 mL). Sodium cyanoborohydride (1.8 g, 29 mmol) and acetic acid (0.56 mL, 9.8 mmol) were added at room temperature sequentially. The reaction was heated at 70° C. for 6 h, and then cooled to room temperature. Sat. aq. $NaHCO_3$ (30 mL) was added. The mixture was extracted with EtOAc (2×30 mL). The combined organic extracts were washed with brine (20 mL), dried with $Na_2SO_4$, filtered and concentrated. The residue was purified by column chromatography (silica gel, eluting with 0-60% EtOAc in hexanes) to give compound 46 (4.9 g, 84% yield) as a white solid. m/z=538 ($M-C_4H_7$).

Compound 47: Compound 46 (5 g, 8.4 mmol) was dissolved in THE (250 mL) and HCl (4 M in 1,4-dioxane, 30 mL, 120 mmol) was added at room temperature. The reaction was heated at 70° C. for 16 h, and then cooled to room temperature. The precipitates was collected by filtration, and washed with cold THE (50 mL) to give compound 47 (3.3 g, 79% yield) as a white solid. m/z=494 (M+1 of free base).

Compound 48: Compound 47 (150 mg, 0.28 mmol) was dissolved in EtOH (9 mL). 1,1,3,3-Tetramethoxypropane (52 μL, 0.31 mmol) and 12N aq. HCl (71 μL, 0.85 mmol) were added sequentially. The reaction was heated at 80° C. for 4 h, and then additional amount of 1,1,3,3-tetramethoxypropane (52 μL, 0.31 mmol) and 12N aq. HCl (71 μL, 0.85 mmol) were added. The reaction was heated at 80° C. for another 2 h, and then cooled to room temperature. The reaction mixture was concentrated, and the residue was diluted with EtOAc (30 mL). The mixture was washed with sat. aq. $NaHCO_3$ (2×20 mL), water (20 mL) and brine (20 mL). The organic extract was dried with $Na_2SO_4$, filtered, and concentrated. The residue was purified by column chromatography (silica gel, eluting with 0-60% EtOAc in hexanes) to give compound 48 (94 mg, 63% yield) as a white solid. m/z=530 (M+1).

Compound 49: Compound 48 (94 mg, 0.18 mmol) in MeOH (2 mL) was treated with sodium methoxide (25 wt. % in MeOH, 81 μL, 0.35 mmol) at room temperature. The reaction was heated at 55° C. for 1.5 h, and then cooled to 0° C. 10% aq. $NaH_2PO_4$ (10 mL) was added. The mixture was extracted with EtOAc (2×20 mL). The combined organic extracts were washed with brine, dried with $Na_2SO_4$, filtered and concentrated to give crude product 49 (90 mg), which was used in the next step without purification. m/z=530 (M+1).

Compound T20: Crude compound 49 (90 mg, 0.17 mmol) was dissolved in DMF (2 mL) and cooled to 0° C. under $N_2$. 1,3-Dibromo-5,5-dimethylhydantoin (24 mg, 0.085 mmol) in DMF (0.5 mL) was added dropwise. The mixture was stirred at 0° C. for 2 h. Pyridine (41 μL, 0.51 mmol) was then added and the reaction was heated at 60° C. for 4 h. After cooled to room temperature, the mixture was diluted with EtOAc (20 mL) and washed with 1N aq. HCl (10 mL), water (2×15 mL) and brine (10 mL). The organic extract was dried with $Na_2SO_4$, filtered, and concentrated. The residue was purified by column chromatography (silica gel, eluting with 0-100% EtOAc in hexanes) to give compound T20 (60 mg, 64% yield from compound 48) as a white solid. m/z=528 (M+1); $^1$H NMR (400 MHz, $CDCl_3$) δ 8.05 (s, 1H), 7.51 (dd, J=1.6 Hz, 1H), 7.37 (dd, J=2.0 Hz, 1H), 6.25 (t, J=2.1 Hz, 1H), 6.01 (s, 1H), 4.35 (d, J=14.0 Hz, 1H), 3.95 (d, J=14.0 Hz, 1H), 3.25 (d, J=4.7 Hz, 1H), 2.29 (m, 1H), 2.20 (dt, J=4.0, 14.0 Hz, 1H), 1.59 (s, 3H), 1.52 (s, 3H), 1.27 (s, 3H), 1.19 (s, 3H), 1.06 (s, 3H), 0.98-1.94 (m, 14H), 0.86 (s, 3H), 0.85 (s, 3H).

Compound 50: Compound 47 (33 mg, 0.062 mmol) and 1,3,5-triazine (30 mg, 0.37 mmol) were combined and dissolved in formic acid (0.5 mL) at room temperature. After stirring for 2 h, the reaction mixture was diluted with EtOAc (30 mL), and was washed with water (2×15 mL), sat. aq. $NaHCO_3$ (15 mL), and brine (15 mL). The organic extract was dried with $Na_2SO_4$, filtered and concentrated. The residue was purified by column chromatography (silica gel, eluting with 0-10% MeOH in $CH_2Cl_2$) to give compound 50 (21 mg, 64% yield) as a white solid. m/z=531 (M+1).

Compound 51: Compound 50 (122 mg, 0.23 mmol) in MeOH (2 mL) was treated with sodium methoxide (25 wt. % in MeOH, 105 μL, 0.46 mmol) at room temperature. The reaction was heated at 55° C. for 1.5 h, and then cooled to 0° C. 10% aq. $NaH_2PO_4$ (10 mL) was added. The mixture was extracted with EtOAc (2×20 mL). The combined organic extracts were washed with brine, dried with $Na_2SO_4$, filtered and concentrated to give crude compound 51 (115 mg), which was used in the next step without purification. m/z=531 (M+1).

Compound T21: Crude compound 51 (115 mg, 0.22 mmol) was dissolved in DMF (2 mL) and cooled to 0° C. under $N_2$. 1,3-Dibromo-5,5-dimethylhydantoin (31 mg, 0.11 mmol) in DMF (0.5 mL) was added dropwise. The mixture was stirred at 0° C. for 2 h. Pyridine (53 μL, 0.65 mmol) was then added and the reaction was heated at 60° C. for 4 h. After cooled to room temperature, the mixture was diluted with $CH_2Cl_2$ (20 mL) and washed with water (2×15 mL) and brine (10 mL). The organic extract was dried with $Na_2SO_4$, filtered, and concentrated. The residue was purified by column chromatography (silica gel, eluting with 0-10% MeOH in $CH_2Cl_2$) to give compound T21 (80 mg, 66% yield from compound 50) as a white solid. m/z=529 (M+1); $^1H$ NMR (400 MHz, $CDCl_3$) δ 8.05 (s, 2H), 7.93 (s, 1H), 6.02 (s, 1H), 4.37 (d, J=14.1 Hz, 1H), 4.00 (d, J=14.1 Hz, 1H), 3.20 (d, J=4.7 Hz, 1H), 2.32 (m, 1H), 2.16 (td, J=13.6, 4.4 Hz, 1H), 1.58 (s, 3H), 1.53 (s, 3H), 1.27 (s, 3H), 1.19 (s, 3H), 1.06 (s, 3H), 0.99-1.96 (m, 14H), 0.87 (s, 3H), 0.86 (s, 3H).

Compound 52: Compound 47 (108 mg, 0.20 mmol) was dissolved in EtOH (3 mL). Acetylacetone (23 μL, 0.22 mmol) and 12N aq. HCl (51 μL, 0.61 mmol) were added. The reaction was heated at 80° C. for 2 h, and then concentrated. The residue was diluted with EtOAc (30 mL), and the mixture was washed sat. aq. $NaHCO_3$ (2×20 mL). The combined aqueous extracts were extracted again with EtOAc (20 mL). The combined organic extracts were washed with brine (15 mL), dried with $Na_2SO_4$, filtered and concentrated. The residue was purified by column chromatography (silica gel, eluting with 0-100% EtOAc in hexanes) to give compound 52 (99 mg, 87% yield) as a white solid. m/z=558 (M+1).

Compound 53: Compound 52 (117 mg, 0.21 mmol) in MeOH (3 mL) was treated with sodium methoxide (25 wt. % solution in MeOH, 96 μL, 0.42 mmol) at room temperature. The reaction was heated at 55° C. for 1.5 h. After cooled to 0° C., the reaction mixture was treated with 10% aq. $NaH_2PO_4$ (4 mL), and was extracted with EtOAc (2×20 mL). The combined organic extracts were washed with brine, dried with $Na_2SO_4$, filtered and concentrated. The residue was purified by column chromatography (silica gel, eluting with 0-100% EtOAc in hexanes) to give compound 53 (98 mg, 84% yield) as a white solid. m/z=558 (M+1).

Compound T22: Compound 53 (56 mg, 0.10 mmol) was dissolved in toluene (2 mL). 2,3-Dichloro-5,6-dicyano-1,4-benzoquinone (27 mg, 0.12 mmol) in toluene (1 mL) was added. The reaction was heated at 85° C. for 1.5 h. After cooled to 0° C., the reaction mixture was treated with sat. aq. $NaHCO_3$ (20 mL) and was extracted with EtOAc (2×30 mL). The combined organic extracts were washed with brine (20 mL), dried with $Na_2SO_4$, filtered, and concentrated. The residue was purified by column chromatography (silica gel, eluting with 60% EtOAc in hexanes) to give compound T22 (14 mg, 25% yield) as a white solid. m/z=556 (M+1); $^1H$ NMR (400 MHz, $CDCl_3$) δ 8.06 (s, 1H), 6.01 (s, 1H), 5.77 (s, 1H), 4.05 (d, J=14.2 Hz, 1H), 3.78 (d, J=14.0 Hz, 1H), 3.22 (d, J=4.6 Hz, 1H), 2.49 (dt, J=13.4, 4.3 Hz, 1H), 2.22 (s, 3H), 2.18 (s, 3H), 2.16 (m, 1H), 1.53 (s, 3H), 1.51 (s, 3H), 1.27 (s, 3H), 1.18 (s, 3H), 1.05 (s, 3H), 0.98-1.92 (m, 13H), 0.87 (m, 1H), 0.85 (s, 6H).

Compound 54: To a solution of compound 10 (0.40 g, 0.84 mmol) in anhydrous THF (10 mL) was added 2-oxa-6-azaspiro[3.3]heptane (0.42 g, 4.24 mmol). After the solution was stirred at room temperature for overnight, acetic acid (0.25 g, 4.16 mmol) was added. The solution was stirred for another 10 min, and then treated with a solution of sodium cyanoborohydride (0.26 g, 4.14 mmol) in MeOH (10 mL). The mixture was stirred at room temperature for overnight, and then concentrated. The residue was partitioned between EtOAc (50 mL) and sat. aq. $NaHCO_3$ (50 mL). The aqueous phase was separated, and extracted with EtOAc (25 mL). The combined organic extracts were washed with sat. aq. NaCl (25 mL); dried over $Na_2SO_4$; filtered and concentrated. The residue was dissolved in $CH_2Cl_2$, and purified by column chromatography (silica gel, eluting with EtOAc) to give compound 54 (0.24 g, 51% yield) as a white solid. m/z=561 (M+1).

Compound 55: To a mixture of compound 54 (0.24 g, 0.43 mmol) in MeOH (15 mL) was added potassium carbonate (0.24 g, 1.74 mmol). The reaction mixture was stirred at room temperature for overnight, and then was concentrated in vacuo. The residue was partitioned between EtOAc and sat. aq. $KH_2PO_4$. The organic extract was dried with $Na_2SO_4$; filtered and concentrated to give compound 55 (0.24 g, quantitative yield) as a beige solid. m/z=561 (M+1).

Compound T23: Compound 55 (0.24 g, 0.44 mmol) in DMF (9 mL) was cooled to 0° C. A solution of 1,3-dibromo-5,5-dimethylhydantoin (62 mg, 0.22 mmol) in DMF (1 mL) was added. The mixture was stirred at 0° C. for 30 min. Pyridine (400 μL, 4.95 mmol) was added. The mixture was heated at 50° C. for 4 h, and then stirred at room temperature for overnight. DMF was removed in vacuo, and the residue was partitioned between EtOAc and sat. aq. $KH_2PO_4$. The aqueous phase was extracted with EtOAc (2×25 mL). The combined organic extracts were washed with water (2×20 mL); dried with $Na_2SO_4$; filtered and concentrated. The residue was purified by column chromatography (silica gel, eluting with EtOAc) to give partially purified compound T23, which was purified again by column chromatography (silica gel, eluting with 2% MeOH in $CHCl_3$) to give compound T23 (20 mg, 8% yield) as a light yellow solid. m/z=559 (M+1); $^1H$ NMR (400 MHz, $CDCl_3$) δ 8.03 (s, 1H), 5.97 (s, 1H), 4.72 (s, 4H), 3.40 (s, 4H), 2.88 (m, 1H), 2.40 (m, 1H), 2.20-2.32 (m, 2H), 1.49 (s, 3H), 1.44 (s, 3H), 1.26 (s, 3H), 1.18 (s, 3H), 0.99 (s, 3H), 0.92 (s, 3H), 0.85 (s, 3H), 0.76-1.83 (m, 15H).

Compound 58: Diphenyl phosphorazide (13.8 mL, 64.0 mmol) was added to a 0° C. solution of compound 56 (20.03 g, 42.74 mmol) and triethylamine (18.0 mL, 130 mmol) in toluene (425 mL). The resultant mixture was warmed to room temperature and stirred overnight, concentrated to a thick oil, loaded directly onto silica gel, and purified by column chromatography (silica gel, eluting with 0 to 20% EtOAc in hexanes) to give a mixture of compounds 57 and 58 as a white solid that was briefly dried and used without further purification.

The mixture of compounds 57 and 58 (all above obtained, ≤42.74 mmol) was dissolved in toluene (280 mL), and heated to 80° C. for 3 h, then dried to give compound 58 (17.52 g, 88% yield from 56) as a white solid. m/z=466 (M+1).

Compound 59: Hydrochloric acid (12N aq., 90 mL, 1.08 mol) was added to a room temperature solution of compound 58 (17.52 g, 37.62 mmol) in MeCN (400 mL) and stirred for 3 h. The resultant mixture was concentrated to approximately 150 mL, basified with NaOH (4 M aq., ~300 mL) and extracted with EtOAc (400 mL, then 2×200 mL). The combined organic fractions were washed with sat. aq. $NaHCO_3$ (100 mL) and brine (100 mL), dried with $Na_2SO_4$ and concentrated to give compound 59 (15.68 g, 95% yield) as a white solid. m/z=440 (M+1).

Compound 60: 4-Chlorobutanoyl chloride (0.77 mL, 6.9 mmol) was added to a room temperature solution of compound 59 (1.001 g, 2.277 mmol) and triethylamine (3.2 mL, 23 mmol) in $CH_2Cl_2$ (23 mL), and stirred for 1.5 h. The resultant mixture was diluted with EtOAc (150 mL), washed with HCl (1 M aq., 2×50 mL) and brine (50 mL), dried with $MgSO_4$, concentrated and purified by column chromatography (silica gel, eluting with 0 to 100% EtOAc in hexanes) to compound 60 (1.182 g, 95% yield) as a white solid. m/z=544.

Compound 61: Sodium hydride (60% w/w in mineral oil, 275 mg, 6.9 mmol) was added to a 0° C. solution of compound 60 (1.182 g, 2.172 mmol) in DMF (44 mL). After 2.5 h the reaction was quenched by the careful addition of HCl (1 M aq., 50 mL). The resultant mixture was extracted with EtOAc (200 mL), washed with water (2×30 mL) and brine (20 mL). The organic extract was dried with $MgSO_4$, concentrated, and azeotroped with heptane (2×50 mL). The residue was purified by column chromatography (silica gel, eluting with 0 to 100% EtOAc in hexanes) to give partially purified compound 61 (468 mg, ~70% pure) as an off-white solid that was used without further purification.

Compound 63: Sodium methoxide (30% w/w in MeOH, 5 mL) was added to a room temperature solution of impure compound 61 (468 mg, ~70% pure) in ethyl formate (20 mL). The resultant mixture was stirred at room temperature for 4 h, then diluted with HCl (1 M aq., 50 mL), and extracted EtOAc (150 mL, then 50 mL). The combined organic fractions were washed with brine (50 mL), dried with $MgSO_4$, and concentrated to give compound 62 that was used without further purification.

A solution of compound 62 (all above obtained) and hydroxylamine hydrochloride (85.2 mg, 1.23 mmol) in a mixture of ethanol (20 mL) and water (3 mL) was heated to 55° C. overnight with stirring. The resultant mixture was concentrated to approximately 5 mL, diluted with EtOAc (150 mL), washed with HCl (1 M aq., 25 mL) and brine (25 mL). The organic extract was dried with $MgSO_4$, and concentrated. The residue was purified by column chromatography (silica gel, eluting with 0 to 100% EtOAc in hexanes) to give compound 63 (251.4 mg, 22% from compound 60) as a white solid. m/z=533 (M+1).

Compound 64: A mixture of compound 63 (251.4 mg, 0.472 mmol) and potassium carbonate (978 mg, 7.1 mmol) in methanol (50 mL) was stirred at room temperature overnight under nitrogen. The resultant mixture was concentrated to approximately 5 mL, diluted with HCl (1 M aq., 50 mL) and extracted with EtOAc (2×100 mL). The combined organic fractions were washed with brine (25 mL), dried with $MgSO_4$ and concentrated to give crude compound 64 (253 mg) as a white solid that was used without further purification.

Compound T24: 1,3-Dibromo-5,5-dimethylhydantoin (68.7 mg, 0.24 mmol) in DMF (2 mL) was added to a 0° C. solution of compound 64 (all above obtained, ≤0.472 mmol) in DMF (6 mL), and the residue was washed into the reaction with DMF (2 mL). After 5 min, the ice bath was removed, and the reaction allowed to warm to room temperature. Pyridine (0.19 mL, 2.4 mmol) was added after 3 h. The reaction was heated to 55° C. for 4 h, and then cooled to room temperature. The resultant mixture was diluted with HCl (1 M aq., 50 mL) and extracted with EtOAc (50 mL, then 2×25 mL). The combined organic fractions were washed with brine (25 mL), dried with $MgSO_4$, concentrated, and azeotroped with heptane (25 mL). The residue was purified by column chromatography (silica gel, eluting with 0 to 100% EtOAc in hexanes) to give compound T24 (53.6 mg, 21% yield from compound 63) as a white solid. m/z=531 (M+1). $^1H$ NMR (400 MHz, $CDCl_3$) δ 8.03 (s, 1H), 5.97 (s, 1H), 3.42 (dt, J=9.7, 7.5 Hz, 1H), 3.32 (m, 1H), 2.80 (d, J=4.3 Hz, 1H), 2.28-2.44 (m, 2H), 1.49 (s, 3H), 1.40 (s, 3H), 1.26 (s, 3H), 1.17 (s, 3H), 1.04 (s, 3H), 1.02 (s, 3H), 0.95-2.02 (m, 18H), 0.90 (s, 3H).

Compound 65: N,N-diisopropylethylamine (0.39 mL, 2.2 mmol) was added to a solution of compound 10 (285 mg, 0.45 mmol) and azetidine hydrochloride (210 mg, 2.2 mmol) in THF (6 mL) at room temperature under $N_2$. The mixture was stirred at room temperature for 4 h, then acetic acid (0.13 mL, 2.2 mmol) was added. The resultant mixture was stirred at room temperature for another 16 h, then a solution of sodium cyanoborohydride (0.14 g, 2.2 mmol) in MeOH (6 mL) was added dropwise over a period of 10 min. The reaction mixture was stirred at room temperature for additional 4 h, and then partitioned between EtOAc (50 mL) and sat. aq. $NaHCO_3$ (50 mL). The aqueous layer was separated and extracted with EtOAc (3×50 mL). The combined organic extracts were dried with $Na_2SO_4$, filtered and concentrated. The residue was purified by column chromatography [Agela Technologies AQ C18 spherical 20-35 μm 100 Å silica gel column, eluting with 0-80% (0.07% $CF_3CO_2H$ in acetonitrile) in (0.1% $CF_3CO_2H$ in water)] to give compound 65 trifluoroacetic acid salt. The compound was partitioned between EtOAc (40 mL) and sat. aq. $NaHCO_3$ (40 mL). The aqueous layer was separated and extracted with EtOAc (3×40 mL). The combined organic extracts were dried with $Na_2SO_4$, filtered and concentrated to give compound 65 (72 mg, 31% yield) as a solid. m/z=519.3 (M+1).

Compound 66: Sodium methoxide (0.5 M in MeOH, 2.29 mL, 1.14 mmol) was added dropwise to a solution of compound 65 (220 mg, 0.42 mmol) in MeOH (5.4 mL) at room temperature under $N_2$. The mixture was then heated to 50° C. and stirred for 40 min. The reaction mixture was diluted with water (20 mL); neutralized to pH 7 with 1N aq. HCl; and then extracted with EtOAc (3×30 mL). The combined organic extracts were washed with brine, dried with $Na_2SO_4$, filtered, and concentrated in vacuo to give compound 66 (215 mg, 98% yield) as a white solid, which was used in the next step without further purification. m/z=519.3 (M+1).

T25: A slurry of compound 65 (200 mg, 0.39 mmol) in toluene (5.0 mL) was sparged with argon at room temperature for 5 min, then DDQ (96.3 mg, 0.42 mmol) was then added. The mixture was heated at 50° C. for 40 min under argon. The reaction mixture was cooled to room temperature, and then partitioned between EtOAc (30 mL) and sat. aq. $NaHCO_3$ (30 mL). The aqueous phase was separated and extracted with EtOAc (3×30 mL). The combined organic extracts were dried with $Na_2SO_4$, filtered, and concentrated. The residue was purified by column chromatography [Agela Technologies AQ C18 spherical 20-35 μm 100 k silica gel column, eluting with 0-65% (0.07% $CF_3CO_2H$ in acetonitrile) in (0.1% $CF_3CO_2H$ in water)] to give compound T25 trifluoroacetic acid salt. The compound was partitioned between EtOAc (20 mL) and 13% aq. NaCl (20 mL). The aqueous layer was separated and extracted with EtOAc (3×20 mL). The combined organic extracts were dried with $Na_2SO_4$, filtered and concentrated to give compound T25 (52 mg, 26% yield) as a solid. m/z=517.4 (M+1); $^1$H NMR (400 MHz, DMSO-$d_6$) δ 8.66 (s, 1H), 6.22 (s, 1H), 3.22-3.14 (m, 4H), 2.84 (d, J=4.7 Hz, 1H), 2.39 (d, J=13.3 Hz, 1H), 2.29-2.19 (m, 2H), 1.95 (p, J=6.8 Hz, 2H), 1.90-0.94 (m, 15H), 1.44 (s, 3H), 1.42 (s, 3H), 1.17 (s, 3H), 1.07 (s, 3H), 0.91 (s, 3H), 0.87 (s, 3H), 0.82 (s, 3H).

Compound 67: A mixture of compound 10 (0.28 g, 0.59 mmol), 3-fluoroazetidine hydrochloride (0.24 g, 2.2 mmol), N,N-diisopropylethylamine (0.38 mL, 2.2 mmol) in THF (6 mL) was stirred for 2 h at room temperature under $N_2$. Acetic acid (0.12 mL, 2.2 mmol) was then added. The resultant mixture was stirred at room temperature for another 16 h. A solution of sodium cyanoborohydride (0.14 g, 2.2 mmol) in methanol (6 mL) was added dropwise. The reaction mixture was stirred at room temperature for additional 4 h, and then partitioned between EtOAc (30 mL) and sat. aq. $NaHCO_3$ (10 mL). The aqueous phase was separated and extracted with EtOAc (2×30 mL). The combined organic extracts were washed with brine (10 mL), dried with $Na_2SO_4$, filtered, and concentrated. The residue was purified by column chromatography [Agela Technologies AQ C18 spherical 20-35 m 100 Å silica gel column, eluting with 0-100% (0.07% $CF_3CO_2H$ in acetonitrile) in (0.1% $CF_3CO_2H$ in water)]. The purified fractions were combined; basified with aq. $NaHCO_3$ (30 mL); and was extracted with EtOAc (3×25 mL). The combined organic extracts were dried with $Na_2SO_4$, filtered and concentrated to give compound 67 (0.19 g, 61% yield) as a white solid. m/z=535.3 (M+1);

Compound 68: Sodium methoxide (25 wt. % in MeOH, 0.21 mL, 0.92 mmol) was added dropwise to a solution of compound 67 (0.183 g, 0.34 mmol) in MeOH (4.2 mL) at room temperature under $N_2$. The mixture was then heated at 55° C. for 60 min. The reaction mixture was cooled to room temperature and concentrated. The residue was diluted with water (20 mL) and then neutralized to pH 7 with 1N aq. HCl. The precipitated solid was collected by filtration and dried in vacuo to give compound 68 (165 mg, 90% yield) as a white solid. m/z=537.4 (M+1).

T26: A mixture of compound 68 (79 mg, 0.15 mmol) and DDQ (36.8 mg, 0.16 mmol) in toluene (2 mL) was stirred at 50° C. for 5 h under argon. The reaction mixture was concentrated. The residue was diluted with sat. aq. $NaHCO_3$ (1 mL) and then extracted with EtOAc (3×1 mL). The combined organic extracts were washed with sat. aq. $NaHCO_3$ (4×1 mL) and brine (1 mL); dried with $Na_2SO_4$; filtered and concentrated. The residue was purified by column chromatography [Agela Technologies AQ C18 spherical 20-35 μm 100 k silica gel column, eluting with 0-100% (0.07% $CF_3CO_2H$ in acetonitrile) in (0.1% $CF_3CO_2H$ in water)] to give T26 (13 mg, 14% yield) as a white solid. m/z=535.3 (M+1); $^1$H NMR (400 MHz, $CDCl_3$) δ 8.00 (s, 1H), 5.99 (s, 1H), 5.39 (dt, J=56.8, 5.4 Hz, 1H), 5.15-4.79 (m, 2H), 4.22-3.85 (m, 2H), 3.61 (d, J=13.1 Hz, 1H), 2.94 (d, J=12.9 Hz, 1H), 2.78 (d, J=4.7 Hz, 1H), 2.26 (m, 1H), 2.20-1.15 (m, 15H), 1.50 (s, 3H), 1.46 (s, 3H), 1.26 (s, 3H), 1.18 (s, 3H), 1.02 (s, 3H), 0.94 (s, 3H), 0.90 (s, 3H).

Compound 69: A mixture of compound 10 (0.30 g, 0.63 mmol), 3,3-difluoroazetidine hydrochloride (0.30 g, 2.4 mmol), and N,N-diisopropylethylamine (0.41 mL, 2.4 mmol) in THF (6 mL) was stirred at room temperature for 2 h under $N_2$. Acetic acid (0.13 mL, 2.4 mmol) was then added. The resultant mixture was stirred at room temperature for another 16 h. A solution of sodium cyanoborohydride (0.15 g, 2.4 mmol) in MeOH (6 mL) was added dropwise. The reaction mixture was stirred at room temperature for additional 16 h, and then partitioned between EtOAc (50 mL) and sat. aq. $NaHCO_3$ (30 mL). The aqueous phase was separated and extracted with EtOAc (2×30 mL). The combined organic extracts were washed with brine (10 mL), dried with $Na_2SO_4$, filtered, and concentrated. The residue was purified by column chromatography [Agela Technologies AQ C18 spherical 20-35 μm 100 Å silica gel column, eluting with 0-100% (0.07% $CF_3CO_2H$ in acetonitrile) in (0.1% $CF_3CO_2H$ in water)]. The purified fractions were combined; basified with aq. $NaHCO_3$ (30 mL); and was extracted with EtOAc (2×40 mL). The combined organic extracts were washed with brine, dried with $Na_2SO_4$, filtered and concentrated to give compound 69 (0.165 g, 47% yield) as a white solid. m/z=555.3 (M+1).

Compound 70: Sodium methoxide (25 wt. % in MeOH, 0.17 mL, 0.75 mmol) was added dropwise to a solution of compound 69 (0.153 g, 0.28 mmol) in MeOH (3.4 mL) at room temperature under $N_2$. The mixture was then heated to 55° C. and stirred for 1 h. The reaction mixture was concentrated. The residue was diluted with water (6 mL) and then neutralized to pH 7 with 1N aq. HCl. Precipitation happened. The precipitated solid was collected by filtration and dried in vacuo to give compound 70 (0.144 g, 94% yield) as a white solid. m/z=555.4 (M+1).

T27: A mixture of compound 70 (135 mg, 0.24 mmol) and DDQ (60.8 g, 0.27 mmol) in toluene (3.2 mL) was stirred at 50° C. for 2 h under argon. The reaction mixture was concentrated. The residue was diluted with sat. aq. $NaHCO_3$ (1 mL) and extracted with EtOAc (3×1 mL). The combined organic extracts were washed with sat. aq. $NaHCO_3$ (4×1 mL) and brine (1 mL), dried with $Na_2SO_4$, filtered and concentrated. The residue was purified by column chromatography [Agela Technologies AQ C18 spherical 20-35 μm 100 Å silica gel column, eluting with 0-100% (0.07% $CF_3CO_2H$ in acetonitrile) in (0.1% $CF_3CO_2H$ in water)]. The purified fractions were combined, and partitioned between $CH_2Cl_2$ (10 mL) and sat. aq. $NaHCO_3$ (10 mL). The organic extract was dried with $Na_2SO_4$, filtered and concentrated to give compound T27 (50 mg, 37% yield) as a light yellow solid. m/z=553.3 (M+1); $^1$H NMR (400 MHz, DMSO-$d_6$) δ 8.66 (s, 1H), 6.23 (s, 1H), 3.66 (td, J=12.4, 2.8 Hz, 4H), 2.82 (d, J=4.7 Hz, 1H), 2.56 (dd, J=13.3, 13.3 Hz, 2H), 2.22-2.15 (m, 1H), 1.90-0.95 (m, 15H), 1.44 (s, 3H), 1.42 (s, 3H), 1.17 (s, 3H), 1.07 (s, 3H), 0.92 (s, 3H), 0.86 (s, 3H), 0.83 (s, 3H).

Compound 71: To a mixture of compound 10 (538.0 mg, 1.126 mmol), azetidin-3-ol hydrochloride (616.9 mg, 5.631 mmol) in tetrahydrofuran (10 mL) was added N,N-diisopropylethylamine (0.981 mL, 5.631 mmol) at room temperature under $N_2$. The mixture was stirred at room temperature for 18 h. Acetic acid (0.320 mL, 5.63 mmol) was added. The mixture was stirred at room temperature for 4 h. A solution of sodium cyanoborohydride (372.5 mg, 5.631 mmol) in methanol (10 mL) was added dropwise over a period of 10 min. The mixture was stirred for 4 h, and then partitioned between EtOAc (50 mL) and sat. aq. $NaHCO_3$ (50 mL). The aqueous layer was separated and extracted with EtOAc (3×50 mL). The combined organic extracts were dried with $Na_2SO_4$, filtered and concentrated. The residue was purified by column chromatography [Agela Technologies AQ C18 spherical 20-35 μm 100 k silica gel column, eluting with 0-80% (0.07% $CF_3CO_2H$ in acetonitrile) in (0.1% $CF_3CO_2H$ in water)] to give compound 71 (242 mg, 40% yield) as a solid. m/z=535.4 (M+1).

Compound 72: Sodium methoxide (25 wt. % in MeOH, 0.152 mL, 0.67 mmol) was added dropwise to a solution of compound 71 (132 mg, 0.247 mmol) in MeOH (3.0 mL) at room temperature under $N_2$. The mixture was then heated at 55° C. for 60 min. The reaction mixture was concentrated. The residue was diluted with water (4 mL) and neutralized to pH 7 with 1N aq. HCl. The precipitated solid was collected by filtration and dried in vacuo to give compound 72 (0.110 g, 83% yield). m/z=535.7 (M+1).

T28: A mixture of compound 72 (80 mg, 0.15 mmol) and DDQ (37.4 mg, 0.16 mmol) was stirred at 50° C. for 2 h under argon. The reaction mixture was concentrated. The residue was diluted with sat. aq. $NaHCO_3$ (10 mL) and extracted with EtOAc (2×20 mL). The combined organic extracts were washed with sat. aq. $NaHCO_3$ (30 mL), water (4×10 mL) and brine (10 mL); dried with $Na_2SO_4$; filtered and concentrated. The residue was first purified by column chromatography [Agela Technologies AQ C18 spherical 20-35 μm 100 Å silica gel column, eluting with 0-100% (0.07% $CF_3CO_2H$ in acetonitrile) in (0.1% $CF_3CO_2H$ in water)] to give partially purified product, which was further purified by preparative TLC (silica gel, eluting with 50% acetone in hexanes with 1% N,N-Diisopropylethylamine) to give compound T28 (18 mg, 22% yield). m/z=533.3 (M+1); $^1H$ NMR (400 MHz, $CDCl_3$) δ 8.04 (s, 1H), 5.97 (s, 1H), 4.42 (p, J=5.8 Hz, 1H), 3.75-3.68 (m, 2H), 3.00-2.86 (m, 3H), 2.50 (d, J=13.1 Hz, 1H), 2.35 (d, J=12.9 Hz, 1H), 2.33-2.25 (m, 1H), 1.85-1.00 (m, 15H), 1.50 (s, 3H), 1.46 (s, 3H), 1.26 (s, 3H), 1.18 (s, 3H), 0.99 (s, 3H), 0.93 (s, 3H), 0.85 (s, 3H).

T29: Dimethyl sulfoxide (32 μL, 0.45 mmol) was slowly added to a solution of oxalyl chloride (19 μL, 0.22 mmol) in $CH_2Cl_2$ (4 mL) at −78° C. The mixture was stirred for 5 min at −78° C. A solution of compound T28 (50 mg, 0.094 mmol) in $CH_2Cl_2$ (1.0 mL) was then added dropwise. The resultant mixture was stirred at −78° C. for another 15 min. Triethylamine (131 μL, 0.94 mmol) was added dropwise. The reaction mixture was stirred at −78° C. for 30 min, and then allowed to slowly warm up to room temperature. The mixture was stirred at room temperature for 60 min, and then was partitioned between EtOAc (30 mL) and brine (30 mL). The aqueous layer was separated and extracted with EtOAc (3×30 mL). The combined organic extracts were dried with $Na_2SO_4$, filtered and concentrated. The residue was purified by column chromatography (silica gel, eluting with 0-100% EtOAc in hexanes) to give compound T29 (34 mg, 68% yield) as a solid. m/z=531.3 (M+1); $^1H$ NMR (400 MHz, $CDCl_3$) δ 8.04 (s, 1H), 5.99 (s, 1H), 4.18 (s, 4H), 2.92 (d, J=4.7 Hz, 1H), 2.85 (d, J=13.0 Hz, 1H), 2.66 (d, J=13.0 Hz, 1H), 2.41-2.33 (m, 1H), 1.92-1.07 (m, 15H), 1.50 (s, 3H), 1.46 (s, 3H), 1.26 (s, 3H), 1.18 (s, 3H), 1.03 (s, 3H), 0.95 (s, 3H), 0.88 (s, 3H).

Compound 74: To a solution of compound 59 (2.0 g, 4.5 mmol) in ethyl formate (10 mL, 120 mmol) at 0° C. was added sodium methoxide (25 wt. % in MeOH, 10.4 mL, 45.5 mmol) dropwise under $N_2$. The mixture was stirred at room temperature for 2 h, then diluted with t-butyl methyl ether (20 mL) and washed with aq. HCl (2.0 M, 25.0 mL). The aqueous phase was separated; neutralized with sat. aq. $NaHCO_3$ (20 mL); and then extracted with t-butyl methyl ether (20 mL). The combined organic extracts were washed with water (20 mL) and brine (20 mL), dried with $Na_2SO_4$, filtered and concentrated. The crude product (2.2 g) was dissolved in a mixture of ethanol (40 mL) and water (4 mL) at room temperature, and treated with hydroxylamine hydrochloride (0.49 g, 7.0 mmol). The resultant mixture was stirred at 55° C. for 16 h. The mixture was partitioned between EtOAc (50 mL) and sat. aq. $NaHCO_3$ (20 mL). The aqueous phase was separated and extracted with EtOAc (20 mL). The combined organic extracts were washed with water (20 mL) and brine (20 mL); dried with $Na_2SO_4$; filtered; and concentrated to give a mixture of compound 73 and 74 (2.3 g).

To a solution of the above mixture of compound 73 and 74 (2.3 g) in methanol (30 mL) was added HCl (12 M in water, 3.3 mL, 39 mmol) at room temperature. The mixture was stirred at 60° C. for 7 h and let stand at room temperature overnight. The mixture was treated with aq. $KHCO_3$ (2.0 M, 30.0 mL, 60.0 mmol) dropwise and diluted with water (30 mL). After the mixture was stirred for 30 min, the precipitated solid was collected by filtration, washed with water (2×10 mL) and dried in vacuo to give compound 74 (2.09 g, 99% yield for compound 59) as a white solid. m/z=465.4 (M+1).

Compound 75: To a well-stirred slurry of compound 74 (142 mg, 0.31 mmol) in 1,2-dichloroethane (5.0 mL) at room temperature under $N_2$ was added a solution of N-Boc-2-aminoacetaldehyde (99.4 mg, 0.62 mmol) in 1,2-dichloroethane (1.5 mL). The mixture was stirred at 65° C. for 4 h, and then cooled to room temperature. Sodium triacetoxyborohydride (130 mg, 0.611 mmol) was added. The resultant mixture was stirred at room temperature for 18 h, and then heated at 65° C. for 6 h. The reaction mixture was cooled to room temperature and stirred for additional 72 h. The mixture was partitioned between EtOAc (30 mL) and sat. aq. $NaHCO_3$ (30 mL). The aqueous phase was separated and extracted with EtOAc (3×30 mL). The combined organic extracts were dried with $Na_2SO_4$, filtered, concentrated. The residue was purified by column chromatography [Agela Technologies AQ C18 spherical 20-35 μm 100 Å silicagel column, eluting with 0-100% (0.07% $CF_3CO_2H$ in acetonitrile) in (0.1% $CF_3CO_2H$ in water)] to give partially purified compound 75 (70 mg, 32% yield), which was used in next step without further purification. m/z=608.4 (M+1).

Compound 76: To a solution of compound 75 (79.4 mg, 0.11 mmol) in $CH_2Cl_2$ (3.0 mL) at room temperature was added trifluoroacetic acid (1.0 mL, 13 mmol) in one portion. The mixture was stirred at room temperature for 30 min, and then concentrated. The residue was purified by column chromatography [Agela Technologies AQ C18 spherical 20-35 μm 100 Å silica gel column, eluting with 0-70% (0.07% $CF_3CO_2H$ in acetonitrile) in (0.1% $CF_3CO_2H$ in water)] to give compound 76 (33 mg, 41% yield). m/z=508.3 (M+1).

Compound 77: To a solution of compound 76 (38.0 mg, 0.052 mmol) in $CH_2Cl_2$ (4.0 mL) at room temperature was added N,N-diisopropylethylamine (45.0 μL, 0.26 mmol). The mixture was stirred at room temperature for 2.5 h. Phosgene (1.4 M in toluene, 44.2 μL, 0.062 mmol) was then added dropwise. This reaction mixture was stirred at room temperature for 1 h, and then concentrated. The residue was purified by column chromatography [Agela Technologies AQ C18 spherical 20-35 μm 100 Å silica gel column, eluting with 0-80% (0.07% $CF_3CO_2H$ in acetonitrile) in (0.1%

$CF_3CO_2H$ in water)] to give compound 77 (26 mg, 94% yield) as a solid. m/z=534.3 (M+1).

Compound 78: A slurry of compound 77 (55.0 mg, 0.103 mmol) and potassium carbonate (57.0 mg, 0.412 mmol) in methanol (5.0 mL) was stirred at room temperature for 18 h. The reaction mixture was diluted with water (10 mL); neutralized to pH 7 with aq. HCl (2 M, 0.40 mL); and then partitioned between water (30 mL) and EtOAc (30 mL). The aqueous phase was separated and extracted with EtOAc (2×30 mL). The combined organic extracts were dried with $Na_2SO_4$, filtered, and concentrated to give compound 78 (50 mg, 91% yield) as a white solid, which was used in the next step without further purification. m/z=534.3 (M+1).

T30: To a solution of compound 78 (50.0 mg, 0.094 mmol) in DMF (3.0 mL) at 0° C. was added 1,3-dibromo-5,5-dimethylhydantoin (13.7 mg, 0.048 mmol) in one portion under $N_2$. The mixture was stirred 0° C. for 30 min. Pyridine (30.3 μL, 0.38 mmol) was added. The resultant mixture was stirred at 60° C. for 135 min, and then at room temperature for 16 h. The reaction mixture was diluted with water (40 mL); stirred for 30 min at room temperature; and then partitioned between EtOAc (40 mL) and water (40 mL). The aqueous phase was separated and extracted with EtOAc (3×30 mL). The combined organic extracts were dried with $Na_2SO_4$, filtered and concentrated. The residue was first purified by column chromatography (silica gel, eluting with 0-100% EtOAc in hexanes) to give partially purified product, which was further purified by column chromatography [Agela Technologies AQ C18 spherical 20-35 μm 100 Å silica gel column, eluting with 0-80% (0.07% $CF_3CO_2H$ in acetonitrile) in (0.1% $CF_3CO_2H$ in water)]. The obtained impure product was purified again with column chromatography (silica gel, eluting with 0-10% ethanol in $CH_2Cl_2$) to give compound T30 (7.8 mg, 16% yield) as a white solid. m/z=532.3 (M+1); $^1H$ NMR (400 MHz, $CDCl_3$) δ 8.04 (s, 1H), 5.98 (s, 1H), 4.22 (bs, 1H), 3.22-3.51 (m, 5H), 2.98 (m, 1H), 1.49 (s, 3H), 1.45 (s, 3H), 1.26 (s, 3H), 1.18 (s, 3H), 1.06-1.99 (m, 15H), 1.04 (s, 3H), 1.02 (s, 3H), 0.90 (s, 3H).

Compound 79: To a solution of compound 74 (200.0 mg, 0.43 mmol) in 1,2-dichloroethane (6.0 mL) at room temperature was added a solution of t-butyl methyl(2-oxoethyl) carbamate (152 mg, 0.879 mmol) in 1,2-dichloroethane (2.2 mL) under $N_2$. The mixture was stirred at 65° C. for 5.5 h, and then cooled to room temperature. Sodium triacetoxyborohydride (182 mg, 0.86 mmol) was added in one portion. The resultant mixture was stirred at room temperature for 18 h, and then partitioned between sat. aq. $NaHCO_3$ (30 mL) and EtOAc (30 mL). The aqueous phase was separated and extracted with EtOAc (3×30 mL). The combined organic extracts were dried with $Na_2SO_4$, filtered and concentrated. The residue was purified by column chromatography [Agela Technologies AQ C18 spherical 20-35 μm 100 k silica gel column, eluting with 0-100% (0.07% $CF_3CO_2H$ in acetonitrile) in (0.1% $CF_3CO_2H$ in water)]. The purified fractions were combined and concentrated. The residue was partitioned between EtOAc (40 mL) and brine (40 mL). The aqueous layer was separated and extracted with EtOAc (2×30 mL). The combined organic extracts were dried with $Na_2SO_4$, filtered and concentrated to give compound 79 (195 mg, 73% yield) as a solid. m/z=622.4 (M+1).

Compound 80: To a solution of compound 79 (170.0 mg, 0.27 mmol) in $CH_2Cl_2$ (6 mL) at room temperature was added trifluoroacetic acid (1.5 mL, 19 mmol). The mixture was stirred at room temperature for 45 min, and then concentrated. The residue was purified by column chromatography [Agela Technologies AQ C18 spherical 20-35 μm 100 k silica gel column, eluting with 0-75% (0.07% $CF_3CO_2H$ in acetonitrile) in (0.1% $CF_3CO_2H$ in water)] to give compound 80 (125 mg, 61% yield) as a solid. m/z=522.4 (M+1).

Compound 81: To a solution of compound 80 (120.0 mg, 0.16 mmol) in $CH_2Cl_2$ (13 mL) at room temperature was added N,N-diisopropylethylamine (139 μL, 0.80 mmol). The mixture was stirred at room temperature for 2.5 h. Phosgene (1.40 M in toluene, 137 μL, 0.19 mmol) was added dropwise. This resultant mixture was stirred at room temperature for 1 h, and then concentrated. The residue was purified by column chromatography [Agela Technologies AQ C18 spherical 20-35 μm 100 Å silica gel column, eluting with 0-100% (0.07% $CF_3CO_2H$ in acetonitrile) in (0.1% $CF_3CO_2H$ in water)] to give compound 81 (78 mg, 89% yield) as a solid. m/z=548.3 (M+1).

Compound 82: A mixture of compound 81 (130.0 mg, 0.24 mmol) and potassium carbonate (130.3 mg, 0.94 mmol) in methanol (4.0 mL) was stirred at room temperature for 16 h. The reaction mixture was neutralized to pH 7 with 2 M aq. HCl, and then partitioned between EtOAc (50 mL) and water (50 mL). The aqueous phase was separated and extracted with EtOAc (3×30 mL). The combined organic extracts were dried with $Na_2SO_4$, filtered, and concentrated in vacuo to give compound 82 (102 mg, 78% yield). m/z=548.3 (M+1).

T31: To a solution of compound 82 (102.0 mg, 0.19 mmol) in DMF (3.6 mL) at 0° C. was added 1,3-dibromo-5,5-dimethylhydantoin (27.2 mg, 0.095 mmol) under $N_2$. The mixture was stirred at 0° C. for 20 min, then pyridine (60.2 μL, 0.74 mmol) was added. The resultant mixture was stirred at 60° C. for 90 min; cooled to room temperature; diluted with water (40 mL); and stirred for 30 min. The mixture was partitioned between EtOAc (40 mL) and water (40 mL). The aqueous phase was separated and extracted with EtOAc (3×30 mL). The combined organic extracts were dried with $Na_2SO_4$, filtered and concentrated. The residue was purified by column chromatography (silica gel, eluting with 0-100% EtOAc in hexanes) to give purified compound T31 (15 mg, 15% yield). The partially purified compound T31 was purified again by column chromatography (silica gel, eluting with 30-100% EtOAc in hexanes) to give a $2^{nd}$ crop of compound T31 (13 mg, 13% yield) as an off-white solid. m/z=546.3 (M+1); $^1H$ NMR (400 MHz, $CDCl_3$) δ 8.04 (s, 1H), 5.97 (s, 1H), 3.36-3.24 (m, 2H), 3.19-3.05 (m, 2H), 3.00 (d, J=4.7 Hz, 1H), 2.75 (s, 3H), 2.00-1.00 (m, 16H), 1.49 (s, 3H), 1.43 (s, 3H), 1.26 (s, 3H), 1.18 (s, 3H), 1.03 (s, 3H), 1.01 (s, 3H), 0.90 (s, 3H).

Compound 84: A solution of compound 74 (111.3 mg, 0.24 mmol) in $CH_2Cl_2$ (1 mL) was sparged with argon at 0° C. A solution of compound 83 (63 mg, 0.22 mmol) in $CH_2Cl_2$ (1 mL) was sparged with argon at 0° C., and was added to the above solution dropwise over a period of 20 min. The resultant mixture was stirred at 0° C. for 60 min, and then directly loaded onto a silica gel column, eluting with EtOAc in hexanes to give compound 84 (64 mg, 51% yield) as a white solid. m/z=580.4 (M+1).

Compound 85: To a solution of compound 84 (64 mg, 0.11 mmol) in $CH_2Cl_2$ (1 mL) at 0° C. was added HCl (4 M in 1,4-dioxane, 0.55 mL, 2.2 mmol) in one portion. The mixture was stirred at 0° C. for 5 min; at room temperature for 1 h; and at 60° C. for 40 min. LCMS indicated incomplete deprotection of Boc group. The mixture was concentrated under reduced pressure. The residue was dissolved in $CH_2Cl_2$ (1 mL), and was treated with trifluoroacetic acid (0.5 mL, 6.5 mmol) at room temperature. The mixture was stirred at room temperature for 30 min, and then concentrated to give the crude hydrazine trifluoroacetic acid salt.

The compound was dissolved in ethanol (4 mL). A solution of 1,1,3,3-tetramethoxy-propane (21.8 mg, 0.13 mmol) in EtOH (0.5 mL) and catalytic amount of HCl (12 M in water, 1 drop) were added sequentially at room temperature. The mixture was stirred at 80° C. for 4 h; at room temperature for overnight; and then concentrated. The residue was partitioned between EtOAc and sat. aq. $NaHCO_3$. The organic phase was separated and washed with brine, dried with $Na_2SO_4$, filtered and concentrated. The residue was purified by column chromatography (silica gel, eluting with EtOAc in hexanes) to give compound 85 (34 mg, 60% yield) as a cream color solid. m/z=516.2 (M+1).

Compound 86: Potassium carbonate (29 mg, 0.21 mmol) was added to a solution of compound 85 (34 mg, 0.066 mmol) in methanol (1 mL) at room temperature. The mixture was stirred at room temperature for 2.5 h, and then partitioned between EtOAc (25 mL) and sat. aq. $KH_2PO_4$ (25 mL). The organic phase was separated; washed with brine (10 mL); dried with $Na_2SO_4$; filtered; and concentrated in vacuo to give compound 86 (30 mg, 88% yield) as a colorless solid.

T32: 1,3-Dibromo-5,5-dimethylhydantoin (9.8 mg, 0.034 mmol) was added to a solution of compound 86 (34 mg, 0.066 mmol) in DMF (0.3 mL) at room temperature. The mixture was stirred at room temperature for 1 h, then pyridine (22 μL, 0.27 mmol) was added. The resultant mixture was sparged with nitrogen, and stirred at 60° C. in a sealed tube for 18 h. After cooled to room temperature, the reaction mixture was diluted with water (2 mL) and EtOAc (2 mL), and stirred for 10 min at room temperature. The mixture was partitioned between EtOAc (20 mL) and 1N aq. HCl (10 mL). The organic extract was separated; washed with water (3×10 mL) and brine (10 mL); dried with $Na_2SO_4$; filtered; and concentrated. The residue was purified by preparative TLC (silica gel, eluting with 40% EtOAc in hexanes) to give compound T32 (14 mg, 41% yield) as a white solid. m/z=514.3 (M+1); $^1H$ NMR (400 MHz, $CDCl_3$) δ 8.01 (s, 1H), 7.59 (d, J=2.4 Hz, 1H), 7.53 (d, J=1.7 Hz, 1H), 6.30 (t, J=2.1 Hz, 1H), 5.94 (s, 1H), 3.47 (m, 1H), 3.02 (d, J=4.6 Hz, 1H), 2.32 (m, 1H), 2.20 (m, 1H), 1.91-0.87 (m, 13H), 1.41 (s, 3H), 1.24 (s, 3H), 1.14 (s, 3H), 1.10 (s, 3H), 1.07 (s, 3H), 0.96 (s, 3H), 0.95 (s, 3H).

Compound 87: Trifluoroacetic acid (0.6 mL, 8 mmol) was added to a solution of compound 84 (0.080 g, 0.14 mmol) in $CH_2Cl_2$ (1 mL) at room temperature under $N_2$. The mixture was stirred at room temperature for 1 h, and then concentrated in vacuo to give the crude hydrazine trifluoroacetic acid salt. Formic acid (1 mL, 30 mmol) and 1,3,5-Triazine (67 mg, 0.83 mmol) were added sequentially. The resultant mixture was stirred at room temperature for 2 h, and then diluted with EtOAc (20 mL). The mixture was washed with water (2×10 mL), sat. aq. $NaHCO_3$ (10 mL) and brine (10 mL). The organic extract was dried with $Na_2SO_4$, filtered, and concentrated. The residue was purified by column chromatography (silica gel, 0-100% EtOAc in hexanes) to give compound 87 (42 mg, 59% yield) as a light-yellow solid. m/z=517.3 (M+1).

Compound 88: Potassium carbonate (36 mg, 0.26 mmol) was added to a solution of compound 87 (0.035 g, 0.068 mmol) in methanol (1 mL) at room temperature. The mixture was stirred for 5 h at room temperature, and then partitioned between EtOAc (25 mL) and sat. aq. $KH_2PO_4$ (25 mL). The organic extract was washed with brine (10 mL), dried with $Na_2SO_4$, filtered, and concentrated in vacuo to give compound 88 (30 mg; 86% yield) as white solid.

T33: 1,3-Dibromo-5,5-dimethylhydantoin (8.6 mg, 0.030 mmol) was added to a solution of compound 88 (30 mg, 0.058 mmol) in DMF (0.3 mL) at room temperature. The mixture was stirred at room temperature for 2.5 h. Trace amount of 1,3-Dibromo-5,5-dimethylhydantoin was added, and the mixture was stirred at room temperature until compound 88 was completely consumed (~1 h). Pyridine (19 μL, 0.24 mmol) was then added. The mixture was sparged with nitrogen, and stirred in a sealed tube at 60° C. for 1 h; and at room temperature for 3 days. The reaction mixture was diluted with water (2 mL) and EtOAc (2 mL); stirred at room temperature for 10 min; and then partitioned between EtOAc (20 mL) and 1N aq. HCl (10 mL). The organic extract was washed with water (3×10 mL) and brine (10 mL), dried with $Na_2SO_4$, filtered, and concentrated. The residue was purified by column chromatography (silica gel, 0-100% EtOAc in hexanes) to give compound T33 (26 mg, 87% yield) as a white solid. m/z 515.3 (M+1); $^1H$ NMR (400 MHz, $CDCl_3$) δ 8.24 (s, 1H), 8.00 (s, 1H), 7.96 (s, 1H), 5.96 (s, 1H), 3.55-3.47 (m, 1H), 2.89 (d, J=4.7 Hz, 1H), 2.41 (td, J=14.2, 13.7, 4.3 Hz, 1H), 2.14 (d, J=15.0 Hz, 1H), 1.93 (td, J=13.5, 5.5 Hz, 1H), 1.86-1.00 (m, 12H), 1.43 (s, 3H), 1.24 (s, 3H), 1.15 (s, 3H), 1.11 (s, 3H), 1.08 (s, 3H), 0.98 (s, 3H), 0.97 (s, 3H).

Compound 89: A solution of compound 59 (436 mg, 0.99 mmol) and triethylamine (0.55 mL, 3.97 mmol) in $CH_2Cl_2$ (8 mL) at 0° C. was treated with 2-chloroethyl chloroformate (307 μL, 2.97 mmol) under $N_2$. The reaction was stirred for 1 h at 0° C. Sat. aq. $NH_4Cl$ solution (5 mL) was added. The mixture was partitioned between EtOAc (40 mL) and water (40 mL). The layers were separated, and the aqueous layer was extracted with EtOAc (3×40 mL). The combined organic extracts were dried with $Na_2SO_4$, filtered and concentrated. The residue was purified by column chromatography (silica gel, eluting with 0-100% EtOAc in hexanes) to give compound 89 (316 mg, 58% yield) as a solid. m/z=546 (M+1).

Compound 90: Compound 89 (167 mg, 0.306 mmol) in anhydrous THF (5 mL) at 0° C. under $N_2$ was treated with potassium t-butoxide (1 M solution in THF, 0.37 mL, 0.37 mmol) dropwise. The reaction was stirred at 0° C. for 10 min, and then was quenched with sat. aq. $NH_4Cl$ solution (5 mL). The mixture was partitioned between EtOAc (30 mL) and 13% aq. NaCl (30 mL). The layers were separated, and the aqueous layer was extracted with EtOAc (3×30 mL). The combined organic extracts were dried with $Na_2SO_4$, filtered and concentrated. The residue was purified by column chromatography [Agela Technologies AQ C18 spherical 20-35 μm 100 Å silica gel column, eluting with 0-80% (0.07% $CF_3CO_2H$ in acetonitrile) in (0.1% $CF_3CO_2H$ in water)] to give compound 90 (125 mg, 80% yield) as a solid. m/z=510 (M+1).

Compound 91: Compound 90 (120 mg, 0.235 mmol) in ethyl formate (0.6 mL, 7.4 mmol) at room temperature under $N_2$ was treated with sodium methoxide (25 wt. % in MeOH, 0.54 mL, 2.37 mmol). The reaction was stirred at room temperature until compound 90 was completely consumed (~30 min). The mixture was diluted with EtOAc (10 mL), cooled at 0° C., and neutralized with 12 M aq. HCl. The mixture was partitioned between EtOAc (30 mL) and water (30 mL). The layers were separated, and the aqueous layer was extracted with EtOAc (3×30 mL). The combined organic extracts were washed with brine, dried with $Na_2SO_4$, filtered and concentrated to give compound 91 (123 mg, 97% yield), which was used in the next step without further purification. m/z=538 (M+1).

Compound 92: Compound 91 (123 mg, 0.23 mmol) and $NH_2OH$ HCl (23.8 mg, 0.343 mmol) were dissolved in ethanol (4 mL) and $H_2O$ (0.4 mL). The reaction was heated at 60° C. for 90 min; cooled to rt; and partitioned between EtOAc (40 mL) and sat. aq. $NaHCO_3$ solution (40 mL). The layers were separated, and the aqueous layer was extracted with EtOAc (3×30 mL). The combined organic extracts were dried with $Na_2SO_4$, filtered and concentrated. The residue was purified by column chromatography (silica gel, eluting with 0-100% EtOAc in hexanes) to give compound 92 (120 mg, 98% yield) as a solid. m/z=535 (M+1).

Compound 93: Compound 92 (126 mg, 0.236 mmol) in MeOH (4 mL) was treated with $K_2CO_3$ (130 mg, 0.943 mmol) at room temperature. The reaction was stirred at room temperature for 3.5 h, and then heated at 50° C. until compound 92 was completely consumed. The mixture was cooled to rt; neutralized with 2 M aq. HCl to pH 7; and then partitioned between EtOAc (50 mL) and $H_2O$ (50 mL). The layers were separated, and the aqueous layer was extracted with EtOAc (3×30 mL). The combined organic extracts were dried with $Na_2SO_4$, filtered and concentrated to give compound 93 (112 mg, 89% yield), which was used in the next step without further purification. m/z=535 (M+1).

T34: Compound 93 (112 mg, 0.209 mmol) in DMF (4 mL) at 0° C. under $N_2$ was treated with 1,3-dibromo-5,5-dimethylhydantoin (30.5 mg, 0.107 mmol). The mixture was stirred at 0° C. for 20 min. Pyridine (67.8 μL, 0.84 mmol) was then added. The reaction was heated at 60° C. for 6 h, and then cooled to room temperature. The mixture was diluted with water (40 mL) and was stirred for 10 min. The precipitated solid was collected by filtration; washed with water (2×15 mL); and dried in vacuo. The solid was purified by column chromatography (silica gel, eluting with 0-100% EtOAc in hexanes) to give compound T34 (65 mg, 58% yield) as an off-white solid. m/z=533 (M+1); $^1H$ NMR (400 MHz, $CDCl_3$) δ 8.03 (s, 1H), 5.99 (s, 1H), 4.29 (td, J=8.7, 3.8 Hz, 1H), 4.15 (q, J=8.7 Hz, 1H), 3.64 (q, J=9.0 Hz, 1H), 3.42 (td, J=8.6, 3.8 Hz, 1H), 2.88 (d, J=4.3 Hz, 1H), 2.02-1.10 (m, 16H), 1.50 (s, 3H), 1.44 (s, 3H), 1.27 (s, 3H), 1.18 (s, 3H), 1.05 (s, 3H), 1.02 (s, 3H), 0.91 (s, 3H).

Compound 94: A solution of compound 42 (0.17 g, 0.59 mmol) in EtOH (5 mL) was treated with N,N-diisopropylethylamine (0.47 mL, 2.7 mmol) at 0° C. The mixture was stirred for 10 min, and then treated with a mixture of compound 74 (0.25 g, 0.54 mmol) in acetonitrile (5 mL) dropwise over 10 min. The reaction mixture was stirred at room temperature for 3 days. Additional amount of N,N-diisopropylethylamine (1.5 mL, 8.6 mmol) and compound 42 (0.5 g, 1.8 mmol) were added sequentially. The mixture was stirred at room temperature for 1 day; heated at 50° C. for 8 h; cooled to room temperature; and concentrated. The residue was diluted with EtOAc (50 mL) and was washed with sat. aq. $NaH_2PO_4$ (25 mL), sat. aq. $NaHCO_3$ (25 mL) and brine (20 mL). The organic extract was dried with $Na_2SO_4$, filtered and concentrated. The residue was purified by column chromatography (silica gel, 0-80% EtOAc in hexanes) to give compound 94 (130 mg, 47% yield) as a brown solid. m/z=517 (M+1).

Compound 95: Compound 94 (130 mg, 0.25 mmol) in MeOH (1 mL) was treated with $K_2CO_3$ (110 mg, 0.79 mmol) at room temperature. The reaction was stirred at room temperature for 4 h, and then heated at 40° C. for 45 min. After cooled to rt, the mixture was partitioned between EtOAc (25 mL) and sat. aq. $KH_2PO_4$ solution (25 mL). The organic extract was washed with brine (10 mL), dried with $Na_2SO_4$, filtered and concentrated to give compound 95 (120 mg, 92% yield) as an orange solid, which was used in the next step without further purification. m/z=517 (M+1).

T35: Compound 95 (114 mg, 0.221 mmol) in DMF (1 mL) at 0° C. under $N_2$ was treated with 1,3-dibromo-5,5-dimethylhydantoin (31 mg, 0.11 mmol). The mixture was stirred at room temperature for 1 h. Pyridine (70 μL, 0.86 mmol) was then added. The mixture was sparged with $N_2$, and heated in a sealed vial at 60° C. for 2.75 h. After cooled to room temperature, the mixture was partitioned between EtOAc (22 mL), water (2 mL), and 1 M aq. HCl (10 mL). The organic extract was washed with water (3×10 mL) and brine (10 mL); dried with $Na_2SO_4$; filtered and concentrated. The product obtained contains small amount of DMF. The product was dissolved in MTBE (50 mL) and $CH_2Cl_2$ (10 mL), and was washed with water (4×20 mL) and brine (20 mL). The organic extract was dried with $Na_2SO_4$; filtered and concentrated. The residue was purified by column chromatography (silica gel, 0-85% EtOAc in hexanes) to give compound T35 (50 mg, 44% yield) as a white solid. m/z=515 (M+1); $^1H$ NMR (400 MHz, $CDCl_3$) δ 8.00 (s, 1H), 7.76 (s, 1H), 7.71 (s, 1H), 5.95 (s, 1H), 3.48-3.40 (m, 1H), 2.88 (d, J=4.5 Hz, 1H), 2.49-2.31 (m, 2H), 2.00-1.15 (m, 13H), 1.42 (s, 3H), 1.24 (s, 3H), 1.14 (s, 3H), 1.11 (s, 3H), 1.09 (s, 3H), 0.99 (s, 3H), 0.94 (s, 3H).

Compound 96: To a mixture of compound 59 (100 mg, 0.23 mmol) in acetic acid (2.7 mL) at room temperature under $N_2$ were added trimethoxymethane (0.26 mL, 2.3 mmol) and sodium azide (203 mg, 3.12 mmol) sequentially. The reaction was heated at 80° C. for 1 h. The reaction was cooled to room temperature and stirred overnight. The reaction was partitioned between EtOAc (50 mL) and $H_2O$ (25 mL). The organic extract was washed with water (2×25 mL), sat. aq. $NaHCO_3$ (2×25 mL) and brine (25 mL); dried with $Na_2SO_4$; filtered and concentrated. The residue was purified by column chromatography (silica gel, eluting with 0-100% EtOAc in hexanes) to give compound 96 (95 mg, 85% yield) as a white solid. m/z=493 (M+1).

Compound 97: To a mixture of compound 96 (385 mg, 0.78 mmol) in ethyl formate (2 mL, 25 mmol) at room temperature under $N_2$ was added sodium methoxide (25 wt. % in MeOH, 1.80 mL, 7.86 mmol). After stirring at room temperature for 3 h, the reaction mixture was diluted with EtOAc; cooled at 0° C.; and neutralized with 12 M aq. HCl. The mixture was partitioned between EtOAc (50 mL) and $H_2O$ (50 mL). The layers were separated, and the aqueous layer was extracted with EtOAc (3×30 mL). The combined organic extracts were washed with brine, dried with $Na_2SO_4$, filtered and concentrated to give compound 97 (510 mg), which was used in the next step without further purification. m/z=543 (M+Na).

Compound 98: Compound 97 (407 mg, 0.78 mmol) and hydroxylamine hydrochloride (81.5 mg, 1.17 mmol) were dissolved in ethanol (10 mL) and $H_2O$ (1 mL). The reaction was heated at 60° C. for 1 h, and then stirred at room temperature overnight. The mixture was partitioned between EtOAc (50 mL) and sat. $NaHCO_3$ solution (50 mL). The layers were separated, and the aqueous layer was extracted with EtOAc (3×30 mL). The combined organic extracts were dried with $Na_2SO_4$, filtered and concentrated. The residue was purified by column chromatography (silica gel, eluting with 0-100% EtOAc in hexanes) to give compound 98 (210 mg, 52% from compound 96) as a solid. m/z=518.4 (M+1).

Compound 99: Compound 98 (200 mg, 0.39 mmol) in MeOH (5 mL) was treated with sodium methoxide (0.5 M in MeOH, 2.1 mL, 1.05 mmol) dropwise at room temperature. The reaction was stirred at room temperature for 6 h, and then was neutralized with 1 M aq. HCl to pH 7. The mixture was concentrated, and the residue was partitioned between EtOAc (50 mL) and brine (50 mL). The layers were separated, and the aqueous layer was extracted with EtOAc (3×30 mL). The combined organic extracts were dried with $Na_2SO_4$, filtered and concentrated to give compound 99 (194 mg, 97% yield) as an off-white solid, which was used in the next step without further purification. m/z=518 (M+1).

T36: To a solution of compound 99 (120 mg, 0.232 mmol) in DMF (4 mL) at 0° C. under $N_2$ was added 1,3-dibromo-5,5-dimethylhydantoin (33.8 mg, 0.12 mmol). The mixture was stirred at 0° C. for 50 min. Pyridine (75 μL, 0.927 mmol) was then added and the reaction was heated at 55° C. for 5 h. After cooled to room temperature, the mixture was partitioned between EtOAc (50 mL) and brine (50 mL). The layers were separated, and the aqueous layer was extracted with EtOAc (3×40 mL). The combined organic extracts were dried with $Na_2SO_4$, filtered and concentrated. The residue was purified by column chromatography (silica gel, eluting with 0-100% EtOAc in hexanes) to give compound T36 as an oil. The oil was dissolved in $CH_2Cl_2$ and MeOH, and the mixture was concentrated. The off-white solid precipitated from MeOH was collected and dried under vacuum to give compound T36 (96 mg, 80% yield). m/z=538 (M+Na). $^1H$ NMR (400 MHz, $CDCl_3$) δ 8.71 (s, 1H), 7.99 (s, 1H), 5.98 (s, 1H), 3.52-3.43 (m, 1H), 2.77 (d, J=4.7 Hz, 1H), 2.55-2.44 (m, 1H), 2.31-2.23 (m, 1H), 2.00-1.02 (m, 13H), 1.43 (s, 3H), 1.24 (s, 3H), 1.15 (s, 3H), 1.12 (s, 3H), 1.10 (s, 3H), 1.00 (s, 3H), 0.97 (s, 3H).

Compound 100: To a mixture of paraformaldehyde (113 mg, 3.77 mmol), ammonium carbonate (181 mg, 1.88 mmol) and trimeric glyoxal dihydrate (339 mg, 1.61 mmol) in MeOH (7 mL) was added compound 74 (125 mg, 0.269 mmol). The reaction was heated at 60° C. over the weekend. Compound 74 was completely consumed. The reaction was partitioned between EtOAc (50 mL) and $H_2O$ (50 mL). The layers were separated, and the aqueous layer was extracted with EtOAc (50 mL). The combined organic extracts were washed with water (20 mL) and brine (20 mL); dried with $Na_2SO_4$; filtered and concentrated. The residue was purified by column chromatography (silica gel, 0-100% acetone in hexanes) to give compound 100 (32 mg, 23% yield) as a white solid. m/z=516 (M+1).

Compound 101: Compound 100 (27 mg, 0.052 mmol) in MeOH (1 mL) was treated with potassium carbonate (31 mg, 0.22 mmol) at room temperature. The reaction was stirred at room temperature for 3 h. Compound 100 was completely consumed. The reaction mixture was concentrated, and the residue was partitioned between EtOAc (20 mL) and sat. aq. $KH_2PO_4$ (20 mL). The organic extract was washed with brine (10 mL); dried with $Na_2SO_4$; filtered and concentrated to give compound 101 (27 mg, quantitative yield), which was used in the next step without further purification. m/z=516 (M+1).

T37: Compound 101 (27 mg, 0.052 mmol) was dissolved in toluene (0.7 mL). 2,3-Dichloro-5,6-dicyano-1,4-benzoquinone (13 mg, 0.058 mmol) was added. The reaction was heated at 50° C. for 2 h. After cooled, the reaction mixture was diluted with sat. aq. $NaHCO_3$ (10 mL) and was extracted with EtOAc (2×20 mL). The combined organic extracts were washed with sat. aq. $NaHCO_3$, water and brine; dried with $Na_2SO_4$; filtered; concentrated; and dried under high vacuum. The residue was purified by preparative TLC (silica gel, eluting with 50% acetone in hexanes containing 1% triethylamine) to give compound T37 (12 mg, 45% yield) as an off-white solid. m/z=514 (M+1); $^1H$ NMR (400 MHz, $CDCl_3$) δ 8.00 (s, 1H), 7.69 (s, 1H), 7.10 (s, 1H), 7.08 (s, 1H), 5.96 (s, 1H), 3.18 (d, J=12.9 Hz, 1H), 2.93 (d, J=4.5 Hz, 1H), 2.49-2.37 (m, 1H), 1.85-1.00 (m, 14H), 1.43 (s, 3H), 1.24 (s, 3H), 1.15 (s, 3H), 1.09 (s, 3H), 1.08 (s, 3H), 1.00 (s, 3H), 0.97 (s, 3H).

Compound 102: To a mixture of compound 59 (100 mg, 0.23 mmol) and KOH (15 mg, 0.23 mmol) was added ethyl acrylate (1 mL, 9.2 mmol). The reaction was heated at 60° C. for overnight, then at 100° C. for 3 days for a full conversion. After cooled to room temperature, the reaction mixture was partitioned between EtOAc (25 mL) and water (25 mL). The layers were separated, and the aqueous layer was extracted with EtOAc (25 mL). The combined organic extracts were washed with water (2×20 mL) and brine (2×10 mL); dried with $Na_2SO_4$; filtered, and concentrated. The residue was purified by column chromatography [silica gel, eluting with 0-100% (1% triethylamine in acetone) in (1% triethylamine in hexanes)] to give compound 102 (107 mg, 87% yield) as a gum. m/z=540 (M+1).

Compound 103: To a mixture of compound 102 (107 mg, 0.198 mmol) in ethyl formate (0.432 mL, 5.35 mmol) at 0° C. under $N_2$ was added sodium methoxide (25 wt. % in MeOH, 0.453 mL, 1.98 mmol). After stirring at room temperature for 3.5 h, the reaction mixture was diluted with t-butyl methyl ether (5 mL) and $H_2O$ (5 mL), and treated with 2 M aq. HCl (1.09 mL) to adjust pH to ~1. The mixture was stirred for 10 min and the layers were separated. The aqueous layer was extracted with EtOAc (50 mL). The combined organic extracts were washed with brine (10 mL); dried with $Na_2SO_4$; filtered and concentrated to give compound 103 (mixture of R=methyl and ethyl, 130 mg), which was used in the next step without further purification. m/z=554 (R=Me, M+1); 568 (R=Et, M+1).

Compound 104: Compound 103 (112 mg, 0.202 mmol) in ethanol (2 mL) and $H_2O$ (0.2 mL) was treated with $NH_2OH$ HCl (21 mg, 0.30 mmol). The reaction was heated at 55° C. for overnight. After cooled down to room temperature, the mixture was partitioned between EtOAc (20 mL) and sat. aq. $NaHCO_3$ (20 mL). The organic extract was washed with water (10 mL) and brine (10 mL); dried with $Na_2SO_4$; filtered and concentrated. The residue was purified by column chromatography [silica gel, eluting with 0-60% (1% triethylamine in acetone) in (1% triethylamine in hexanes)] to give compound 104 (mixture of R=methyl and ethyl, 68 mg, 61% from compound 102) as a white solid. m/z=551 (R=Me, M+1); 565 (R=Et, M+1).

Compound 105: To compound 104 (68 mg, 0.12 mmol) was added HCl (4 M in 1,4-dioxane, 1 mL, 4 mmol) and the reaction was stirred at room temperature for overnight. One drop of water was added, and the reaction was stirred at room temperature over the weekend. 80% conversion was achieved. MeCN (2 mL) and HCl (12 M aqueous, 0.2 mL) were added and the reaction was stirred at room temperature for overnight. Additional amount of HCl (12 M aqueous, 2 mL) was added, and the reaction was stirred at room temperature for overnight. Compound 104 was completely consumed. The reaction mixture was diluted with water (5 mL), and 2 M aq. $KHCO_3$ and sat. aq. $KH_2PO_4$ were added to adjust pH to 6-7. The precipitated solid was collected by filtration; washed with water (2×5 mL); and dried under high vacuum to give compound 105 (57 mg, 86% yield). m/z=537 (M+1).

Compound 106: To a solution of compound 105 (51 mg, 0.095 mmol) in $CH_2Cl_2$ (1.7 mL) was added triethylamine (40 μL, 0.28 mmol). The mixture was cooled to 0° C., and phosphorus (V) oxychloride (13 μL, 0.14 mmol) was added. The reaction was stirred at 0° C. for 1.5 h before additional amount of triethylamine (40 μL, 0.28 mmol) and phosphorus (V) oxychloride (13 μL, 0.14 mmol) were added. The mixture was stirred at 0° C. for 1.5 h, and at room temperature for 2.5 h. The reaction was quenched with sat. aq. $NaHCO_3$ (2 mL), and stirred for 5 min. The mixture was partitioned between EtOAc (25 mL) and $H_2O$ (10 mL). The layers were separated, and the aqueous layer was extracted with EtOAc (10 mL). The combined organic extracts were washed with sat. aq. $NaHCO_3$ (10 mL), water (10 mL), and brine (10 mL); dried with $Na_2SO_4$; filtered and concentrated. The residue was purified by column chromatography [silica gel, eluting with 0-60% (1% triethylamine in acetone) in (1% triethylamine in hexanes)] to give compound 106 (20 mg, 40% yield). m/z=519 (M+1).

Compound 107: Compound 106 (27 mg, 0.052 mmol) in MeOH (1 mL) was treated with potassium carbonate (31 mg, 0.22 mmol) at room temperature. The reaction was stirred at room temperature for 4 h. Compound 107 was completely consumed. The reaction was partitioned between EtOAc (20 mL) and sat. aq. $KH_2PO_4$ (20 mL). The organic extract was washed with brine (10 mL); dried with $Na_2SO_4$; filtered and concentrated to give compound 107 (27 mg, quantitative yield) was carried to the next step without purification. m/z=519 (M+1).

T38: Compound 107 (27 mg, 0.052 mmol) in DMF (0.26 mL) at 0° C. under $N_2$ was treated with 1,3-dibromo-5,5-dimethylhydantoin (7.8 mg, 0.027 mmol). The mixture was stirred at 0° C. for 1 h. Pyridine (17 μL, 0.21 mmol) was then added and the reaction was heated at 60° C. for 5 h, and stirred at room temperature for overnight. The mixture was diluted with EtOAc (25 mL); washed with 1N aq. HCl (10 mL), water (10 mL), and brine (10 mL). The organic extract was dried with $Na_2SO_4$, filtered and concentrated. The residue was purified by preparative TLC (silica gel, eluting with 30% acetone in hexane) to give compound T38 (11 mg, 41% yield) as an off-white solid. m/z=517 (M+1). $^1H$ NMR (400 MHz, $CDCl_3$) δ 8.03 (s, 1H), 5.99 (s, 1H), 3.26 (q, J=4.5 Hz, 1H), 3.04 (q, J=4.3 Hz, 1H), 2.93 (d, J=4.7 Hz, 1H), 2.81 (t, J=4.2 Hz, 2H), 2.65-2.58 (m, 1H), 2.00-1.10 (m, 15H), 1.50 (s, 3H), 1.42 (s, 3H), 1.26 (s, 3H), 1.18 (s, 3H), 1.03 (s, 3H), 1.01 (s, 3H), 0.90 (s, 3H).

Compound 108: A mixture of 1,2-diformylhydrazine (44 mg, 0.50 mmol) and triethyl orthoformate (120 μL, 0.72 mmol) in MeOH (0.2 mL) was heated at 60° C. for 1 h. Compound 74 (230 mg, 0.5 mmol) was then added. The reaction was heated at 60° C. for overnight. Additional amount of 1,2-diformylhydrazine (52 mg, 0.59 mmol) and triethyl orthoformate (120 μL, 0.72 mmol) were added and the reaction was heated at 60° C. for 4 h. A mixture of 1,2-diformylhydrazine (80 mg, 0.91 mmol) and triethyl orthoformate (250 μL, 1.50 mmol) in MeOH (0.4 mL) was heated at 60° C. for 2 h, and then was added to the reaction mixture. The reaction was heated at 60° C. for overnight, and then at 75° C. for overnight. A mixture of 1,2-diformylhydrazine (160 mg, 1.82 mmol) and triethyl orthoformate (600 μL, 3.60 mmol) in MeOH (0.3 mL) was heated at 65° C. for 2 h, and then was added to the reaction mixture. The reaction was heated at 65° C. over the weekend. The reaction was concentrated, and the residue was diluted with EtOAc (3 mL) and $H_2O$ (3 mL). Some solid precipitated and was removed by filtration. The filtrate was acidified with 1N aq. HCl, and was extracted with EtOAc (2×25 mL). The organic extracts were washed with 1N aq. HCl (2×10 mL), water (2×10 mL), and brine (10 mL); dried with $Na_2SO_4$; filtered; and concentrated. The residue was purified by column chromatography (silica gel, eluting with 0-100% acetone in hexanes) to give compound 108 (104 mg, 40% yield) as a white solid. m/z=517 (M+1).

Compound 109: Compound 108 (100 mg, 0.19 mmol) in MeOH (2 mL) was treated with potassium carbonate (110 mg, 0.77 mmol) at room temperature. The reaction was stirred at room temperature for 4 h, and then was partitioned between EtOAc (20 mL) and sat. aq. $KH_2PO_4$ (20 mL). The layers were separated, and the aqueous layer was extracted with EtOAc (20 mL). The combined organic extracts were washed with brine, dried with $Na_2SO_4$, filtered and concentrated to give compound 109 (100 mg, quantitative yield) as a white solid, which was used in the next step without further purification. m/z=517 (M+1).

T39: To a solution of compound 109 (100 mg, 0.19 mmol) in DMF (1 mL) under $N_2$ was added 1,3-dibromo-5,5-dimethylhydantoin (29 mg, 0.10 mmol). The mixture was attired at room temperature for 1 h. Pyridine (64 μL, 0.79 mmol) was then added and the reaction was heated at 60° C. for 3 h. After cooled to room temperature, the mixture was diluted with water (5 mL). The precipitated solid was collected by filtration, and was washed with water (3×5 mL). The filtrate was extracted with EtOAc (2×20 mL). The combined organic extracts were washed with 1N aq. HCl (10 mL), water (10 mL), and brine (10 mL); dried with $Na_2SO_4$; filtered and concentrated. The residue was combined with solid and was purified column chromatography (silica gel, eluting with 25-100% acetone in hexanes) to give compound T39 (50 mg, 50% yield) as a white solid. m/z=515 (M+1). $^1H$ NMR (400 MHz, $CDCl_3$) δ 8.32 (s, 2H), 8.00 (s, 1H), 5.99 (s, 1H), 3.22-3.12 (m, 1H), 2.80 (d, J=4.5 Hz, 1H), 2.55-2.42 (m, 1H), 2.00-1.20 (m, 14H), 1.45 (s, 3H), 1.25 (s, 3H), 1.15 (s, 3H), 1.10 (s, 3H), 1.09 (s, 3H), 1.02 (s, 3H), 0.98 (s, 3H).

Compound 111: A mixture of compound 110 (100 mg, 0.205 mmol) and ethylene glycol (1 mL, 18 mmol) was stirred at 130° C. for 1 h, at room temperature for overnight, at 100° C. for 1 h, and at 130° C. for 3.5 h. The mixture was cooled to 50° C., and treated with water (2 mL) dropwise. The mixture was stirred at 50° C. for 30 min, and then cooled to room temperature over 1 h. The precipitated solid was collected by filtration; washed with water (3×5 mL); and dried under high vacuum to give compound 111 (100 mg, 89% yield). m/z=549 (M-1).

Compound 112: To a solution of oxalyl chloride (37 μL, 0.44 mmol) in $CH_2Cl_2$ (4 mL) at −78° C. was added DMSO (62 μL, 0.87 mmol). The reaction was stirred for 10 min. A solution of compound 111 (100 mg, 0.18 mmol) in $CH_2Cl_2$ (3 mL) was then added dropwise. The reaction was stirred for another 15 min, and triethylamine (0.253 mL, 1.82 mmol) was then added. The reaction was stirred at −78° C. for 20 min, and then allowed to warm to room temperature. The reaction mixture was diluted with EtOAc (25 mL) and was washed with brine (15 mL). The organic extract was washed with sat. aq. $KH_2PO_4$ (10 mL) and brine (10 mL); dried with $Na_2SO_4$; filtered; and concentrated to give compound 112 (105 mg, quantitative yield), which was used in the next step without further purification.

T40: Compound 112 (80 mg, 0.14 mmol) in acetic acid (1 mL) was heated at 100° C. for 1 h. The reaction mixture was concentrated. The residue was diluted with EtOAc (20 mL). The mixture was washed with water (2×10 mL), sat. $NaHCO_3$ (10 mL) and brine (10 mL). The organic extract was dried with $Na_2SO_4$, filtered and concentrated. The residue was purified by column chromatography (silica gel, eluting with 0-80% EtOAc in hexanes). The purified fractions were combined, concentrated, and washed with MeOH to give compound T40 (40 mg, 52% yield) as an off-white solid. m/z=531 (M+1); $^1H$ NMR (400 MHz, $CDCl_3$) δ 8.02 (s, 1H), 6.84 (d, J=2.2 Hz, 1H), 6.68 (d, J=2.2 Hz, 1H), 5.99 (s, 1H), 2.90 (d, J=4.5 Hz, 1H), 2.14-2.02 (m, 1H), 1.95-1.20 (m, 15H), 1.47 (s, 3H), 1.27 (s, 3H), 1.26 (s, 3H), 1.17 (s, 3H), 1.07 (s, 6H), 0.94 (s, 3H).

Compound 114: To a solution of compound 74 (250 mg, 0.54 mmol) in MeCN (2 mL) was added 4-(dimethylamino) pyridine (79 mg, 0.64 mmol). Compound 113 (180 mg, 0.64 mmol) in MeCN (1 mL) was then added. The reaction was heated at 30° C. for 4.5 h. The mixture was diluted with EtOAc (20 mL), washed with water (10 mL), sat. aq. $NaHCO_3$ solution (10 mL) and brine (10 mL). The organic extract was dried with $Na_2SO_4$, filtered and concentrated. The residue was purified by column chromatography (silica gel, eluting with 0-40% EtOAc in hexanes) to give compound 114 (220 mg, 83% yield) as a glass. m/z=491 (M+1).

Compound 115a and 115b: To a solution of compound 114 (220 mg, 0.45 mmol) in ethanol (1 mL) was added ethyl propiolate (68 μL, 0.67 mmol). The reaction was heated at 60° C. for 1 day, and at 80° C. for overnight. The mixture was concentrated, and the residue was purified by column chromatography (silica gel, eluting with 0-50% EtOAc in hexanes) to give compound 115a (180 mg, 68% yield) and compound 115b (30 mg, 10% yield). 115a: m/z=589 (M+1); 115b: m/z=589 (M+1).

Compound 116: To a mixture of compound 115a (150 mg, 0.25 mmol) in MeOH (2 mL) was added lithium hydroxide (1 M in $H_2O$, 1.3 mL, 1.3 mmol). The reaction was stirred at room temperature for 3 h. Additional amount of lithium hydroxide (1 M in $H_2O$, 0.2 mL, 0.2 mmol) was added and the reaction was stirred for another 1.5 h. The mixture was then neutralized with 1N aq. HCl 1 M and diluted with EtOAc (25 mL). The layers were separated, and the aqueous layer was extracted with EtOAc (20 mL). The combined organic extracts were washed with water (2×15 mL) and brine (10 mL); dried with $Na_2SO_4$; filtered and concentrated to give compound 116 (130 mg, 91% yield), which was used in the next step without further purification. m/z=561 (M+1).

Compound 117: To a solution of compound 116 (95 mg, 0.17 mmol) in $CH_2Cl_2$ (1 mL) was added N,N-carbonyldiimidazole (41 mg, 0.25 mmol). The mixture was stirred for 2 h at room temperature, and then methylamine (33% in ethanol, 0.5 mL, 4 mmol) was added. The reaction was stirred at room temperature for overnight. The mixture was partitioned between EtOAc (25 mL) and 1 M aq. HCl (10 mL). The organic extract was separated; washed with water (10 mL) and brine (10 mL); dried with $Na_2SO_4$, filtered and concentrated. The residue was purified by column chromatography (silica gel, eluting with 0-60% acetone in hexanes) to give compound 117 (59 mg, 61% yield) as a white solid. m/z=574 (M+1).

T41: To a mixture of compound 117 (70 mg, 0.12 mmol) in DMF (0.7 mL) under $N_2$ was added 1,3-dibromo-5,5-dimethylhydantoin (18 mg, 0.063 mmol) at room temperature. The mixture was stirred for 30 min, and pyridine (40 μL, 0.5 mmol) was then added. The reaction was heated at 60° C. for 2.5 h, and then was cooled to room temperature. The mixture was diluted with EtOAc (25 mL), and was washed with 1N aq. HCl (15 mL), water (2×15 mL), and brine (10 mL). The organic extract was dried with $Na_2SO_4$, filtered and concentrated. The residue was purified column chromatography (silica gel, eluting with 0-100% EtOAc in hexanes) to give compound T41 (60 mg, 86% yield) as a white solid. m/z=572 (M+1); $^1H$ NMR (400 MHz, $CDCl_3$) δ 8.22 (d, J=0.8 Hz, 1H), 8.00 (s, 1H), 7.14 (s, broad, 1H), 5.96 (s, 1H), 3.60-3.53 (m, 1H), 3.02 (d, J=5.1 Hz, 3H), 2.89 (d, J=4.7 Hz, 1H), 2.45 (td, J=14.3, 13.7, 4.3 Hz, 1H), 2.24-2.16 (m, 1H), 2.00-1.17 (m, 13H), 1.42 (s, 3H), 1.24 (s, 3H), 1.14 (s, 3H), 1.11 (s, 3H), 1.08 (s, 3H), 0.98 (s, 3H), 0.94 (s, 3H).

Compound 118: To a mixture of compound 114 (180 mg, 0.37 mmol) in ethanol (0.9 mL) was added 2-propyn-1-ol (32 μL, 0.55 mmol). The reaction was heated at 90° C. for overnight. Additional 2-propyn-1-ol (150 μL, 2.54 mmol) was then added and the reaction was heated at 90° C. over the weekend. The reaction was cooled; diluted with EtOAc (25 mL); and washed with water (2×10 mL) and brine (10 mL). The organic extract was dried with $Na_2SO_4$, filtered and concentrated. The residue was purified column chromatography (silica gel, eluting with 0-100% EtOAc in hexanes) to give compound 118 (146 mg, 73% yield). m/z=547 (M+1).

Compound 119: Compound 118 (146 mg, 0.267 mmol) in MeOH (5 mL) was treated with potassium carbonate (140 mg, 1.0 mmol) at room temperature. The reaction was stirred at room temperature for overnight. The reaction mixture was partitioned between EtOAc (25 mL) and sat. aq. $KH_2PO_4$ solution (25 mL). The organic extract was separated; washed with brine; dried with $Na_2SO_4$; filtered and concentrated to give compound 119 (140 mg, 96% yield) as a white solid, which was used in the next step without further purification.

T42: To a mixture of compound 119 (85 mg, 0.16 mmol) in DMF (0.85 mL) under $N_2$ was added 1,3-dibromo-5,5-dimethylhydantoin (23 mg, 0.081 mmol). The mixture was stirred at room temperature for 30 min, and then pyridine (52 μL, 0.64 mmol) was added. The reaction was heated at 60° C. for 3.5 h, and then was cooled to room temperature. The mixture was diluted with EtOAc (25 mL), and was washed with 1N aq. HCl (15 mL), water (2×15 mL), and brine (10 mL). The organic extract was dried with $Na_2SO_4$, filtered and concentrated. The residue was purified by column chromatography (silica gel, eluting with 0-100% EtOAc in hexanes) to give compound T42 (65 mg, 77% yield) as a white solid. m/z=545 (M+1); $^1H$ NMR (400 MHz, $CDCl_3$) δ 8.00 (s, 1H), 7.68 (s, 1H), 5.96 (s, 1H), 4.81 (s, 2H), 3.47-3.39 (m, 1H), 2.90 (d, J=4.6 Hz, 1H), 2.48-2.29 (m, 2H), 1.91 (td, J=13.6, 5.1 Hz, 1H), 1.85-1.16 (m, 12H), 1.42 (s, 3H), 1.24 (s, 3H), 1.14 (s, 3H), 1.10 (s, 3H), 1.08 (s, 3H), 0.98 (s, 3H), 0.96 (s, 3H).

T43: Compound T42 (30 mg, 0.055 mmol) in MeCN (0.5 mL) was treated with N,N-diisopropylethylamine (43 μL, 0.25 mmol), triethylamine trihydrofluoride (13 μL, 0.083 mmol), and perfluoro-1-butanesulfonyl fluoride (20 μL, 0.11 mmol). The reaction was heated at 45° C. for 5 h. Two drops of perfluoro-1-butanesulfonyl fluoride were added and the reaction was stirred overnight. The reaction mixture was diluted with EtOAc (25 mL), washed with water (10 mL) and brine (10 mL). The organic extract was dried with $Na_2SO_4$, filtered and concentrated. The residue was purified by column chromatography (silica gel, eluting with 0-60% EtOAc in hexanes) to give compound T43 (7.2 mg, 24% yield) as a white solid. m/z=547 (M+1). $^1H$ NMR (400 MHz, $CDCl_3$) δ 8.00 (s, 1H), 7.80 (d, J=2.5 Hz, 1H), 5.96 (s, 1H), 5.51 (d, J=48.3 Hz, 2H), 3.47-3.39 (m, 1H), 2.88 (d, J=4.6 Hz, 1H), 2.48-2.29 (m, 2H), 1.92 (td, J=13.6, 5.1 Hz, 1H), 1.85-1.16 (m, 12H), 1.42 (s, 3H), 1.24 (s, 3H), 1.14 (s, 3H), 1.11 (s, 3H), 1.09 (s, 3H), 0.99 (s, 3H), 0.96 (s, 3H).

Compound 120: A solution of oxalyl chloride (0.019 mL, 0.22 mmol) in $CH_2Cl_2$ (2 mL) was cooled to −78° C. Dimethyl sulfoxide (0.032 mL, 0.45 mmol) was added slowly. The mixture was stirred for 15 min. A solution of compound T42 (51 mg, 0.094 mmol) in $CH_2Cl_2$ (2 mL) was then added dropwise. The mixture was stirred for 30 min. Triethylamine (0.130 mL, 0.933 mmol) was added dropwise. The mixture was stirred for 2 h at −78° C., and then allowed to warm to room temperature. The mixture was diluted with EtOAc (25 mL) and quenched with sat. aq. $KH_2PO_4$ (10 mL). The organic layer was separated; washed with brine (10 mL); dried with $Na_2SO_4$; filtered and concentrated to give compound 120 (58 mg, quantitative yield). Compound 120 was used in the next step without further purification.

T44: Diethylaminosulfur trifluoride (0.030 mL, 0.23 mmol) was added to a solution of compound 120 (55 mg, <0.10 mmol) in $CH_2Cl_2$ (1 mL) at −78° C. under nitrogen. The mixture was stirred at −78° C. for 1.5 h, at 0° C. for 4 h, and was kept in a freezer overnight. The reaction mixture was quenched with sat. aq. $NaHCO_3$ (10 mL). The organic layer was dried with $Na_2SO_4$, filtered and concentrated. The residue was purified by column chromatography (silica gel, eluting with 0-60% EtOAc in hexanes) to give compound T44 (34 mg, 59% yield) as a white solid. m/z=565.3 (M+1); $^1$H NMR (400 MHz, $CDCl_3$) δ 8.00 (s, 1H), 7.93 (s, 1H), 6.89 (t, J=54.8 Hz, 1H), 5.97 (s, 1H), 3.52-3.43 (m, 1H), 2.86 (d, J=4.7 Hz, 1H), 2.52-2.40 (m, 1H), 2.34-2.25 (m, 1H), 2.00-1.05 (m, 13H), 1.43 (s, 3H), 1.24 (s, 3H), 1.14 (s, 3H), 1.12 (s, 3H), 1.09 (s, 3H), 0.99 (s, 3H), 0.95 (s, 3H).

Compound 121: Ethanolamine (0.124 mL, 2.05 mmol) was added to a mixture of compound 110 (0.20 g, 0.41 mmol) in THF (2 mL) at room temperature. After stirring for 30 min, the mixture was concentrated under a stream of nitrogen. The residue was partitioned between EtOAc (22 mL), and water (12 mL) and sat. aq. $KH_2PO_4$ (10 mL). The organic layer was separated. The aqueous layer was extracted with EtOAc (20 mL). The combined organic extracts were washed with brine; dried with $Na_2SO_4$; filtered and concentrated. The residue was mixed with MeOH (15 mL), and concentrated. The residue was dried under vacuum to give compound 121 (215 mg, 96% yield) as a white solid. m/z=550.3 (M+1).

Compound 122: A solution of oxalyl chloride (0.078 mL, 0.89 mmol) in $CH_2Cl_2$ (8 mL) was cooled to −78° C. Dimethyl sulfoxide (0.13 mL, 1.83 mmol) was added slowly. The mixture was stirred for 15 min. A solution of compound 121 (0.212 g, 0.386 mmol) in $CH_2Cl_2$ (6 mL) was then added dropwise over 30 min. The mixture was stirred for 30 min. Triethylamine (0.537 mL, 3.85 mmol) was added dropwise. The mixture was stirred for 2 h at −78° C., and then allowed to warm to room temperature. The mixture was diluted with EtOAc (25 mL) and quenched with sat. aq. $KH_2PO_4$ (10 mL). The organic layer was separated; washed with brine (10 mL); dried with $Na_2SO_4$; filtered and concentrated. The residue was purified by column chromatography (silica gel) to give compound 122 (37 mg, 18% yield) as an off-white solid. m/z=548.3 (M+1).

T45: Acetic acid (1.0 mL, 18 mmol) was added to compound 122 (37 mg, 0.068 mmol). The mixture was heated at 70° C. for 1.5 h. The mixture was concentrated under a stream of nitrogen and dried under high vacuum for 1 h. The residue was purified by column chromatography (silica gel) to give compound T45 (16 mg, 45% yield) as an off-white solid. m/z=530.3 (M+1); $^1$H NMR (400 MHz, $CDCl_3$) δ 8.03 (s, 1H), 6.36 (dd, J=2.8, 2.8 Hz, 1H), 6.32 (dd, J=2.8, 2.8 Hz, 1H), 5.97 (s, 1H), 3.03 (d, J=4.5 Hz, 1H), 2.14-2.00 (m, 1H), 2.00-1.14 (m, 15H), 1.46 (s, 3H), 1.25 (s, 3H), 1.22 (s, 3H), 1.16 (s, 3H), 1.08 (s, 3H), 1.06 (s, 3H), 0.94 (s, 3H).

Compound 123: 2,2-Dimethoxy-N-methyl-ethanamine (0.131 mL, 1.02 mmol) was added to a mixture of compound 110 (100 mg, 0.205 mmol) in N-methylpyrrolidinone (1 mL). After stirring at room temperature for 2.5 h, the mixture was diluted with water (~2 mL). The mixture was stirred at room temperature for 30 min. The precipitated solid was collected by filtration; washed with water (2×10 mL); and dried under high vacuum overnight to give compound 123 (70 mg). The filtrate was diluted with sat. aq. $KH_2PO_4$ (20 mL), and extracted with EtOAc (25 mL). The organic extract was washed with water (3×10 mL) and brine (10 mL); dried with $Na_2SO_4$; filtered and concentrated to give the 2$^{nd}$ crop of compound 123. The two crops were combined to give compound 123 (130 mg, quantitative yield). m/z=608.4 (M+1).

T46: Water (0.020 mL, 1.1 mmol) was added to a mixture of compound 123 (75 mg, 0.12 mmol) in acetic acid (1 mL). The mixture was heated at 60° C. overnight. After cooled to room temperature, the mixture was purified by column chromatography (silica gel) to give compound T46 (24 mg, 36% yield) as a white solid. m/z=544.3 (M+1); $^1$H NMR (400 MHz, $CDCl_3$) 8.02 (s, 1H), 6.35 (d, J=3.1 Hz, 1H), 6.24 (d, J=3.0 Hz, 1H), 5.96 (s, 1H), 3.22 (s, 3H), 3.01 (d, J=4.5 Hz, 1H), 1.45 (s, 3H), 1.25 (s, 3H), 1.20 (s, 3H), 1.16 (s, 3H), 1.10-2.10 (m, 16H), 1.07 (s, 3H), 1.06 (s, 3H), 0.93 (s, 3H).

Compound 124: Compound 10 (500.0 mg, 1.047 mmol) was dissolved in anhydrous THF (10 mL) at ambient temperature under nitrogen. To this solution 2-(tert-butyldimethylsilyloxy)-ethylamine (917.7 mg, 5.233 mmol) was added and the mixture was stirred for 5 h. Glacial acetic acid (314.2 mg, 5.233 mmol) was added. The mixture was stirred for 1 hour. A solution of sodium cyanoborohydride (328.8 mg, 5.233 mmol) in methanol (12 mL) was added. The mixture was stirred at ambient temperature for an additional 18 h. The reaction mixture was partitioned between EtOAc and sat. aq. $NaHCO_3$. The layers were separated and the aqueous layer was extracted twice with EtOAc. The combined organic extracts were washed with water, sat. aq. NaCl; dried over $Na_2SO_4$; filtered and concentrated. The residue was purified by column chromatography (silica gel, eluting with 2.5% MeOH in $CHCl_3$) to give compound 124 (547.2 mg, 82% yield) as a white solid. m/z=637.5 (M+1).

Compound 125: A solution of 124 (742.0 mg, 1.165 mmol) in THF (12 mL) and $H_2O$ (2.5 mL) was cooled to 0° C. Di-t-butyl dicarbonate (381.3 mg, 1.747 mmol) and $NaHCO_3$ (117.4 mg, 1.398 mmol) were added. After the addition, the cold bath was removed, and the reaction mixture was stirred at ambient temperature for 18 h. The mixture was partitioned between EtOAc and sat. aq. $NaHCO_3$. The layers were separated, and the aqueous layer was extracted with twice with EtOAc. The combined organic extracts were washed with water and sat. aq. NaCl; dried over $Na_2SO_4$, filtered and concentrated. The residue was purified by column chromatography (silica gel, eluting with 2.5% MeOH in $CHCl_3$) to give compound 125 (858.8 mg, quantitative yield) as a white solid. m z=737.8 (M+1).

Compound 126: A solution of 125 (451.9 mg, 0.613 mmol) in methanol (10 mL) was treated with potassium carbonate (169.4 mg, 1.226 mmol). The reaction mixture was stirred at ambient temperature for 18 h. The solvent was removed in vacuo and the residue was partitioned between EtOAc and sat. aq. $KH_2PO_4$. The aqueous layer was separated, and extracted twice with EtOAc. The combined organic extracts were washed with sat. aq. NaCl; dried over $Na_2SO_4$; filtered and concentrated. The residue was purified by column chromatography (silica gel, eluting with 2.5% MeOH in $CHCl_3$) to give compound 126 (287.0 mg, 63% yield) as a white solid. m/z=737.7 (M+1).

Compound 127: A solution of compound 126 (287.0 mg, 0.389 mmol) in anhydrous DMF (12 mL) was cooled to 0° C. under nitrogen. A solution of 1,3-dibromo-5,5-dimethylhydantoin (55.6 mg, 0.195 mmol) in anhydrous DMF (3.0 mL) was added dropwise. The mixture was stirred at 0° C. for 1 hour. Anhydrous pyridine (307.1 mg, 3.882 mmol) was added. The mixture was heated at 60° C. for 4 h. Upon cooling, the solution was partitioned between EtOAc and sat. aq. $KH_2PO_4$. The layers were separated, and the aqueous layer was extracted twice with EtOAc. The combined organic extracts were washed with water and sat. aq. NaCl; dried over $Na_2SO_4$; filtered and concentrated. The residue was purified by column chromatography (silica gel, eluting with 25% EtOAc in hexanes) to give compound 127 (128 mg, 45% yield) as a white solid. m/z=735.7 (M+1).

Compound 128: A solution of 127 (115.0 mg, 0.156 mmol) in dichloromethane (4 mL) was treated with trifluoroacetic acid (1 mL). The reaction mixture was stirred at ambient temperature for 2 h. The mixture was partitioned between EtOAc and sat. aq. $NaHCO_3$. The layers were separated, and the aqueous layer was extracted twice with EtOAc. The combined organic extracts were washed with water and sat. aq. NaCl; dried over $Na_2SO_4$; filtered and concentrated. The residue was purified by column chromatography (silica gel, eluting with 2.5% MeOH in $CHCl_3$) to give compound 128 (78.2 mg, 96% yield) as a white solid. m/z=521.6 (M+1).

T47: A solution of 128 (100.0 mg, 0.192 mmol, 1.0 equiv.) in THE (2.0 mL) was treated with paraformaldehyde (6.9 mg, 0.23 mmol) in a sealable tube. The tube was sealed, and the reaction mixture was stirred at 75° C. for 18 h. The mixture was filtered through a sintered glass filter. The filter cake was washed with THF. The combined filtrate and wash were dried over $Na_2SO_4$, filtered and concentrated. The residue was purified by column chromatography (silica gel, eluting with 2.5% MeOH in $CHCl_3$) to give compound T47 (44.0 mg, 43% yield) as a yellow solid. m/z=533.3 (M+1); $^1$H NMR (400 MHz, $CDCl_3$) δ 8.02 (s, 1H), 5.86 (s, 1H), 3.77 (td, J=10.5, 10.1, 3.6 Hz, 1H), 3.57 (dt, J=11.3, 4.4 Hz, 1H), 3.32 (d, J=12.0 Hz, 1H), 2.93 (d, J=10.7 Hz, 1H), 2.74 (td, J=12.9, 6.0 Hz, 1H), 2.54 (ddd, J=12.7, 9.8, 5.0 Hz, 1H), 2.14 (dt, J=12.6, 3.5 Hz, 1H), 2.10-2.00 (m, 3H), 1.97-1.10 (m, 15H), 1.71 (s, 3H), 1.54 (s, 3H), 1.27 (s, 3H), 1.15 (s, 3H), 1.06 (s, 3H), 0.93 (s, 3H), 0.89 (s, 3H).

Compound 130: Compound 6 (50 mg, 0.10 mmol) in ethanol (3 mL) was cooled to 0° C. and N,N-diisopropylethylamine (0.11 mL, 0.63 mmol) was added. After stirring for 10 min at 0° C., a solution of compound 1291 (46 mg, 0.16 mmol) in MeCN (0.5 mL) was added dropwise. The reaction was stirred at room temperature overnight. The solvents were removed in vacuo and the residue was taken up in EtOAc (30 mL). The mixture was washed with sat. aq. $NaHCO_3$ (2×20 mL) and brine (20 mL). The organic extract was dried with $Na_2SO_4$, filtered and concentrated. The residue was purified by column chromatography (silica gel, eluting with 0-100% EtOAc in $CH_2Cl_2$) to give compound 130 (40 mg, 70% yield) as a white solid. m/z=545 (M+1).

Compound 131: Compound 130 (39 mg, 0.072 mmol) in MeOH (2 mL) was treated with sodium methoxide (25 wt. % in MeOH, 32 μL, 0.14 mmol) at room temperature. The reaction was heated at 55° C. for 2 h, and then was cooled to 0° C. 10% aq. $NaH_2PO_4$ (20 mL) was added. The mixture was extracted with EtOAc (2×20 mL). The combined organic extracts were washed with brine (15 mL), dried with $Na_2SO_4$, filtered and concentrated to give compound 131 (36 mg, 92% yield). Compound product 131 was carried to the next step without further purification. m/z=545 (M+1).

T48: Compound 131 (36 mg, 0.066 mmol) was dissolved in DMF (1 mL) and cooled to 0° C. under $N_2$. 1,3-Dibromo-5,5-dimethylhydantoin (9.4 mg, 0.033 mmol) in DMF (0.5 mL) was added dropwise. The mixture was stirred at 0° C. for 1 h. Pyridine (21 μL, 0.26 mmol) was then added. The reaction mixture was heated at 60° C. for 6 h. After cooled to room temperature, the mixture was diluted with EtOAc (20 mL) and washed with water (2×15 mL) and brine (10 mL). The organic extract was dried with $Na_2SO_4$, filtered, and concentrated. The residue was purified by column chromatography (silica gel, eluting with 0-100% EtOAc in dichloromethane) to give compound T48 (20 mg, 56% yield) as a white solid. m/z=543 (M+1). $^1$H NMR (400 MHz, $CDCl_3$) δ 8.03 (s, 1H), 7.25 (s, 1H), 6.00 (s, 1H), 4.65 (d, J=13.9 Hz, 1H), 3.93 (d, J=13.9 Hz, 1H), 3.14 (d, J=4.7 Hz, 1H), 3.72 (s, 3H), 2.14-2.30 (m, 4H), 1.86-0.95 (m, 12H), 1.56 (s, 3H), 1.50 (s, 3H), 1.24 (s, 3H), 1.16 (s, 3H), 1.03 (s, 3H), 0.87 (s, 3H), 0.85 (s, 3H).

Compound 132: Compound 6 (100 mg, 0.209 mmol) was dissolved in MeOH (2 mL). A mixture of formic hydrazine (25 mg, 0.42 mmol) and triethyl orthoformate (69 μL, 0.41 mmol) in MeOH (1 mL) was added at room temperature. The reaction was heated at 65° C. for overnight. The mixture was cooled, and another portion formic hydrazine (25 mg, 0.42 mmol) and triethyl orthoformate (69 μL, 0.41 mmol) in MeOH (1 mL) was added. The reaction was heated at 65° C. for 4 days. Additional amount of formic hydrazine (50 mg, 0.84 mmol) and triethyl orthoformate (138 μL, 0.82 mmol) in MeOH (2 mL) was added. The mixture was continued heating for overnight, and then concentrated. The residue was dissolved in $CH_2Cl_2$ (20 mL). The mixture was washed with water (2×20 mL) and brine (20 mL). The organic extract was dried with $Na_2SO_4$, filtered and concentrated. The residue was purified by column chromatography [silica gel, eluting with 0-10% (1% $Et_3N$ in MeOH) in $CH_2Cl_2$] to give compound 132 (38 mg, 34% yield). m/z=531 (M+1).

Compound 133: Compound 132 (38 mg, 0.072 mmol) in MeOH (2 mL) was treated with sodium methoxide (25 wt. % in MeOH, 33 μL, 0.14 mmol) at room temperature. The reaction was heated at 55° C. for 1.5 h, and then was cooled to 0° C. 10% aq. $NaH_2PO_4$ (10 mL) was added. The mixture was extracted with EtOAc (2×20 mL). The combined organic extracts were washed with brine (20 mL), dried with $Na_2SO_4$, filtered and concentrated to give compound 133 (41 mg), which was carried to the next step without further purification. m/z=531 (M+1).

T49: Compound 133 (41 mg, ≤0.072 mmol) was dissolved in DMF (2 mL) and cooled to 0° C. under $N_2$. 1,3-Dibromo-5,5-dimethylhydantoin (11 mg, 0.038 mmol) in DMF (0.5 mL) was added dropwise. The mixture was stirred at 0° C. for 1 h. Pyridine (25 μL, 0.31 mmol) was then added and the reaction was heated at 60° C. for 6 h. After cooled to room temperature, the mixture was diluted with EtOAc (20 mL) and washed with water (2×15 mL) and brine (10 mL). The organic extract was dried with $Na_2SO_4$, filtered, and concentrated. The residue was purified by column chromatography [silica gel, eluting with 0-10% (1% $Et_3N$ in MeOH) in $CH_2Cl_2$] to give compound T49 (11 mg, 29% yield from compound 132) as a white solid. m/z=529 (M+1). $^1$H NMR (400 MHz, $CDCl_3$) δ 8.11 (s, 2H), 8.04 (s, 1H), 6.05 (s, 1H), 4.28 (d, J=14.3 Hz, 1H), 3.78 (d, J=14.3 Hz, 1H), 3.00 (d, J=4.7 Hz, 1H), 2.38-2.30 (m, 1H), 2.00-1.94 (m, 15H), 1.55 (s, 3H), 1.53 (s, 3H), 1.27 (s, 3H), 1.19 (s, 3H), 1.08 (s, 3H), 0.89 (s, 3H), 0.88 (s, 3H).

Compound 134: Compound 46 (100 mg, 0.17 mmol) was dissolved in $CH_2Cl_2$ (3 mL), and cooled to 0° C. 3-Chloropropionyl chloride (32 μL, 0.34 mmol) was added. The reaction was stirred at room temperature for 1.5 h, and then concentrated. The residue was partitioned between EtOAc (20 mL) and sat. aq. $NaHCO_3$ (20 mL). The organic extract was separated. The aqueous layer was extracted with EtOAc (2×20 mL). The combined organic extracts were washed with brine (20 mL), dried with $Na_2SO_4$, filtered, and concentrated. The residue was purified by column chromatography (silica gel, eluting with 0-60% EtOAc in hexanes) to give compound 134 (84 mg, 73% yield). m/z=684 (M+1).

Compound 135: Compound 134 (200 mg, 0.29 mmol) was dissolved in DMF (10 mL). Potassium carbonate (162 mg, 1.17 mmol) was added at room temperature. The reaction was stirred for 1 h at room temperature. EtOAc (30 mL) and water (20 mL) were added. The organic extract was washed with water (2×20 mL) and brine (20 mL); dried with $Na_2SO_4$; filtered and concentrated. The residue was purified by column chromatography (silica gel, eluting with 0-100% EtOAc in hexanes) to give compound 135 (194 mg, quantitative yield). m/z=648 (M+1).

Compound 136: Compound 135 (163 mg, 0.25 mmol) was dissolved in MeOH (4 mL). Sodium methoxide (25 wt. % in MeOH, 115 μL, 0.50 mmol) was added at room temperature. The reaction was heated at 55° C. for 1.5 h, and then cooled to room temperature. 10% aq. $NaH_2PO_4$ (10 mL) was added. The mixture was extracted with EtOAc (2×20 mL). The combined organic extracts were washed with brine (20 mL), dried with $Na_2SO_4$, filtered and concentrated. The residue was purified by column chromatography (silica gel, eluting with 0-100% EtOAc in hexanes) to give compound 136 (157 mg, 96% yield). m/z=648 (M+1).

T50: Compound 136 (103 mg, 0.16 mmol) was dissolved in DMF (2 mL), and cooled to 0° C. A solution of 1,3-dibromo-5,5-dimethylhydantoin (23 mg, 0.080 mmol) in DMF (0.5 mL) was added. The syringe was rinsed with DMF (0.5 mL) and added to the reaction mixture. The reaction was stirred at 0° C. for 1 h. Pyridine (51 μL, 0.63 mmol) was added. The reaction was heated at 60° C. for 4 h, and then cooled to room temperature. The mixture was partitioned between EtOAc (20 mL) and water (20 mL). The organic extract was washed with water (2×10 mL). The combined aqueous layers were extracted with EtOAc. The combined organic extracts were washed with brine (20 mL), dried with $Na_2SO_4$, filtered and concentrated. The residue was purified by column chromatography (silica gel, eluting with 0-80% EtOAc in hexanes) to give compound T50 (84 mg, 73% yield). m/z=646 (M+1). $^1$H NMR (400 MHz, $CDCl_3$) δ 8.04 (s, 1H), 5.95 (s, 1H), 3.90-4.02 (m, 3H), 3.82 (d, J=14.9 Hz, 1H), 3.19 (d, J=4.6 Hz, 1H), 2.53 (t, J=7.4 Hz, 2H), 2.36 (dt, J=13.5, 4.2 Hz, 1H), 2.00-1.04 (m, 15H), 1.56 (s, 3H), 1.50 (s, 3H), 1.48 (s, 9H), 1.25 (s, 3H), 1.17 (s, 3H), 1.00 (s, 3H), 0.93 (s, 3H), 0.86 (s, 3H).

T51: Compound T50 (71 mg, 0.11 mmol) was dissolved in $CH_2Cl_2$ (1 mL) and cooled to 0° C. Trifluoroacetic acid (250 μL, 3.25 mmol) was added. The mixture was stirred at room temperature for 3 h, and then concentrated. The residue was dissolved in $CH_2Cl_2$ (20 mL), and washed with sat. aq. $NaHCO_3$ (2×10 mL) and brine (20 mL). The organic extract was dried with $Na_2SO_4$, filtered and concentrated. The residue was purified by column chromatography (silica gel, eluting with 0-10% MeOH in $CH_2Cl_2$) to give compound T51 (41 mg, 68% yield). m/z=546 (M+1). $^1$H NMR (400 MHz, $CDCl_3$) δ 8.05 (s, 1H), 5.98 (s, 1H), 4.51 (s, broad, 1H), 3.51 (d, J=14.2 Hz, 1H), 3.41-3.34 (m, 2H), 3.39 (d, J=14.2 Hz, 1H), 3.29 (d, J=4.7 Hz, 1H), 2.45-2.62 (m, 2H), 2.30 (dt, J=13.5, 4.2 Hz, 1H), 2.03-2.14 (m, 1H), 1.97-1.00 (m, 14H), 1.56 (s, 3H), 1.50 (s, 3H), 1.25 (s, 3H), 1.17 (s, 3H), 1.01 (s, 3H), 0.93 (s, 3H), 0.86 (s, 3H).

Compound 137: Compound CC1 (917 mg, 1.59 mmol) was dissolved in $CH_2Cl_2$ (16 mL) and cooled to 0° C. Trifluoroacetic acid (2.45 mL, 31.8 mmol) was added. The mixture was stirred at 0° C. for 3.5 h. After concentration, the residue was dissolved in $CH_2Cl_2$ (3×30 mL), and concentrated. The residue was then dissolved in toluene (2×30 mL), and concentrated. The residue was dried under vacuum to give compound 137 (1.03 g, quantitative yield) as a white solid, which was used in the next step without further purification. m/z=477.3 (M−$CF_3CO_2$).

T52: Compound 137 (99 mg, 0.17 mmol) was dissolved in $CH_2Cl_2$ (1.7 mL) and cooled to 0° C. Triethylamine (72 μL, 0.51 mmol) and acetyl-d3 chloride (13 μL, 0.19 mmol) were added sequentially. The mixture was stirred at 0° C. for 20 min. Toluene (10 mL) was added. The mixture was concentrated. The residue was purified by column chromatography (silica gel, eluting with 0-50% acetone in hexanes) to give compound T52 (46 mg, 52% yield) as a white solid. m/z=522.3 (M+1); $^1$H NMR (400 MHz, $CDCl_3$) δ 8.04 (s, 1H), 5.96 (s, 1H), 5.54 (t, J=6.6 Hz, 1H), 3.52 (dd, J=13.8, 7.5 Hz, 1H), 3.23 (d, J=4.7 Hz, 1H), 3.14 (dd, J=13.8, 5.7 Hz, 1H), 2.26-2.19 (m, 1H), 2.05 (td, J=13.5, 4.3 Hz, 1H), 1.90-0.95 (m, 14H), 1.58 (s, 3H), 1.50 (s, 3H), 1.26 (s, 3H), 1.18 (s, 3H), 1.00 (s, 3H), 0.93 (s, 3H), 0.89 (s, 3H).

T53: Compound 137 (95 mg, 0.16 mmol) was dissolved in $CH_2Cl_2$ (1.6 mL) and cooled to 0° C. Triethylamine (69 μL, 0.49 mmol) and propionyl chloride (16 μL, 0.18 mmol) were added sequentially. The mixture was stirred at 0° C. for 20 min. Toluene (10 mL) was added. The mixture was concentrated. The residue was purified by column chromatography (silica gel, eluting with 0-40% acetone in hexanes) to give compound T53 (54 mg, 62% yield) as a white solid. m/z=533.3 (M+1); $^1$H NMR (400 MHz, $CDCl_3$) δ 8.04 (s, 1H), 5.96 (s, 1H), 5.54 (t, J=6.6 Hz, 1H), 3.51 (dd, J=13.8, 7.4 Hz, 1H), 3.23 (d, J=4.7 Hz, 1H), 3.15 (dd, J=13.8, 5.8 Hz, 1H), 2.26-2.19 (m, 1H), 2.24 (q, J=7.6 Hz, 2H), 2.07 (td, J=13.5, 4.4 Hz, 1H), 1.90-0.94 (m, 14H), 1.59 (s, 3H), 1.50 (s, 3H), 1.26 (s, 3H), 1.18 (s, 3H), 1.17 (t, J=7.6 Hz, 3H), 1.00 (s, 3H), 0.92 (s, 3H), 0.88 (s, 3H).

Compound 138: To a stirring mixture of compound 74 (1.1 g, 2.4 mmol), potassium iodide (1.00 g, 6.02 mmol) and N,N-Diisopropylethylamine (10.00 mL, 57.41 mmol) in acetonitrile (100 mL) was added methyl bromoacetate (5.00 mL, 52.8 mmol) at room temperature. The reaction was heated at 60° C. for 90 min. Compound 74 was completely consumed. The mixture was cooled to room temperature and partitioned between EtOAc (40 mL) and sat. aq. $NaHCO_3$ (40 mL). The layers were separated, and the aqueous layer was extracted with EtOAc (3×30 mL). The combined organic extracts were washed with brine; dried with $Na_2SO_4$; filtered and concentrated. The residue was purified by column chromatography (silica gel, elution with 0-100% EtOAc in hexanes) to give compound 138 (984 mg, 77% yield) as a solid. m/z=537.3 (M+1).

Compound 139: To a stirring mixture of compound 138 (430 mg, 0.80 mmol) and HCl (4 M solution in 1,4-dioxane, 10 mL, 40 mmol) was added water (1 mL). The mixture was stirred at room temperature for 72 h, and then heated at 50° C. for 5.5 h. The mixture was concentrated. The residue was purified by column chromatography [C18, eluting with 0-80% (0.07% $CF_3CO_2H$ in acetonitrile) in (0.1% $CF_3CO_2H$ in water)] to give compound 139 (423 mg, 66% yield) as a glass. m/z=523.5 (M of free amine+1).

Compound 140: To a stirring solution of compound 139 (323 mg, 0.507 mmol) and N,N-Diisopropylethylamine (265 μL, 1.52 mmol) in DMF (8.6 mL) was added HATU (424 mg, 1.12 mmol) at 0° C. The mixture was stirred at 0° C. for 15 min, and then added to a stirring solution of t-butyl N-methylglycinate hydrochloride (194 mg, 1.06 mmol) and N,N-diisopropylethylamine (221 μL, 1.27 mmol) in DMF (4.3 mL, 56 mmol) at 0° C. The mixture was stirred at ambient temperature for 60 min, and then partitioned between EtOAc (30 mL) and sat. aq. $NaHCO_3$ (30 mL). The layers were separated, and the aqueous layer was extracted with EtOAc (3×30 mL). The combined organic extracts were washed with brine; dried with $Na_2SO_4$; filtered and concentrated. The residue was purified by column chromatography (silica gel, elution with 0-100% acetone in $CH_2Cl_2$) to give compound 140 (265 mg, 80% yield) as an oil. m/z=650.6 (M+1).

Compound 141: To a stirring solution of compound 140 (265 mg, 0.408 mmol) in $CH_2Cl_2$ (8.0 mL) was added trifluoroacetic acid (2.0 mL, 26 mmol) at room temperature under $N_2$. The reaction was stirred at room temperature for 3 h and then concentrated. The residue was purified by column chromatography [Agela Technologies AQ C18 spherical 20-35 μm 100 Å silica gel column, eluting with 0-90% (0.07% $CF_3CO_2H$ in acetonitrile) in (0.1% $CF_3CO_2H$ in water)] to give compound 141 (198 mg, 69% yield) as a solid. m/z=594.5 (M+1).

Compound 142: To a stirring solution of compound 141 (395 mg, 0.558 mmol) and N,N-diisopropylethylamine (310 μL, 1.8 mmol) in DMF (10 mL) was added HATU (440 mg, 1.2 mmol) at room temperature under $N_2$. The reaction was stirred at room temperature for 1 h, and purified by column chromatography [(C18, eluting with 0-100% (0.07% $CF_3CO_2H$ in acetonitrile) in (0.1% $CF_3CO_2H$ in water)]. The purified fractions were combined and concentrated. The residue was partitioned between EtOAc (100 mL) and sat. aq. $NaHCO_3$ (100 mL). The layers were separated, and the aqueous layer was extracted with EtOAc (3×50 mL). The combined organic extracts were washed with brine; dried with $Na_2SO_4$; filtered and concentrated to give compound 142 (288 mg, 90% yield) as a white solid. m/z=576.5 (M+1).

Compound 143: A mixture of compound 142 (284 mg, 0.493 mmol) and potassium carbonate (273 mg, 1.97 mmol) in MeOH (15 mL) was stirred at room temperature for overnight. The mixture was diluted with water (10 mL) and neutralized with 2 M aq. HCl (1.924 mL, 3.847 mmol). The mixture was partitioned between EtOAc (50 mL) and water (50 mL). The layers were separated, and the aqueous layer was extracted with EtOAc (2×40 mL). The combined organic extracts were washed with brine; dried with $Na_2SO_4$; filtered and concentrated to give compound 143 (272 mg, 96% yield) as a white solid, which was used in the next step without further purification. m/z=576.5 (M+1).

T54: Compound 143 (238 mg, 0.413) was dissolved in DMF (5 mL), and cooled to 0° C. 1,3-Dibromo-5,5-dimethylhydantoin (60 mg, 0.21 mmol) was added. The reaction was stirred at 0° C. for 35 min, and then pyridine (134 μL, 1.65 mmol) was added. The reaction was stirred at room temperature for 4 h; at 60° C. for 2 h; and then at room temperature for overnight. The mixture was partitioned between EtOAc (40 mL) and water (40 mL). The layers were separated, and the aqueous layer was extracted with EtOAc (3×30 mL). The combined organic extracts were washed with brine; dried with $Na_2SO_4$; filtered and concentrated. The residue was purified by column chromatography (silica gel, eluting with 0-100% acetone in $CH_2Cl_2$). The partially purified product was purified again by column chromatography [Agela Technologies AQ C18 spherical 20-35 μm 100 Å silica gel column, eluting with 10-100% (0.07% $CF_3CO_2H$ in acetonitrile) in (0.1% $CF_3CO_2H$ in water)]. The purified fractions were combined and concentrated. The residue was partitioned between EtOAc (40 mL) and sat. aq. $NaHCO_3$ (40 mL). The layers were separated, and the aqueous layer was extracted with EtOAc (2×30 mL). The combined organic extracts were washed with brine; dried with $Na_2SO_4$; filtered and concentrated to give compound T54 (140 mg, 59% yield) as a solid. m/z=574.3 (M+1); $^1H$ NMR (400 MHz, $CDCl_3$) δ 8.02 (s, 1H), 5.95 (s, 1H), 3.90 (bs, 4H), 2.93 (s, 3H), 1.90-1.00 (m, 17H), 1.62 (s, 3H), 1.47 (s, 3H), 1.31 (s, 3H), 1.24 (s, 3H), 1.15 (s, 3H), 1.03 (s, 3H), 0.90 (s, 3H).

T55: To a 40 mL vial containing compound 144 (0.736 g, 1.50 mmol), di-tert-butyl azodicarboxylate (0.431 g, 1.87 mmol), 9-mesityl-10-methylacridinium perchlorate (0.0308 g, 0.0748 mmol) was added 1,2-dichloroethane (14.6 mL) and 1,8-diazabicyclo[5.4.0]-undec-7-ene (0.056 mL, 0.37 mmol) sequentially. The mixture was sparged with $N_2$ for 10 min; sealed; and was placed in the blue LED reactor for overnight at room temperature. The mixture was quenched with sat. aq. potassium phosphate (2 mL) and extracted with EtOAc (50 mL). The organic extract was washed with brine (5 mL); dried with $Na_2SO_4$; filtered and concentrated in vacuo. The residue was purified by column chromatography (silica gel, eluting with 0-40% EtOAc in hexanes) to give compound T55 (400 mg, 39% yield) as a solid. m/z=700.6 (M+Na).

T56: Trifluoroacetic Acid (0.5 mL, 6 mmol) was added to a solution of compound T55 (0.042 g, 0.062 mmol) in $CH_2Cl_2$ (0.5 mL) at room temperature. The mixture was stirred at room temperature for overnight, and then concentrated. The residue was diluted with EtOAc (20 mL) and washed with water (2×10 mL), sat. aq. $NaHCO_3$ (10 mL) and brine (10 mL). The organic extract was dried with $Na_2SO_4$, filtered and concentrated. The residue was purified by column chromatography (silica gel, eluting with 0-40% EtOAc in hexanes) to give compound T56 (15 mg, 42% yield) as a solid. m/z=574.4 (M+1); $^1H$ NMR (400 MHz, $CDCl_3$) δ 8.01 (s, 1H), 5.94 (s, 1H), 3.51 (d, J=4.7 Hz, 1H), 2.44 (m, 1H), 2.17-1.95 (m, 3H), 1.90-0.90 (m, 12H), 1.47 (s, 6H), 1.25 (s, 3H), 1.17 (s, 3H), 1.00 (s, 3H), 0.94 (s, 3H), 0.87 (s, 3H).

T57: Trifluoroacetic Acid (3 mL, 40 mmol) was added to a solution of compound T55 (0.500 g, 0.738 mmol) in $CH_2Cl_2$ (6 mL) at room temperature. The mixture was stirred at room temperature for 70 min; concentrated; and dried under high vacuum for 2 h. The residue was purified by reverse phase column chromatography [C18, eluting with 0-50% MeCN in (0.1% $CF_3CO_2H$ in water)] to give partially purified compound T57 (300 mg, 69% yield) as a white solid. m/z=478.4 (M of free base+1).

T58: 3-Chloropropionyl chloride (9.1 μL, 0.095 mmol) in acetonitrile (0.25 mL) was added to a mixture of compound T57 (51 mg, 0.086 mmol) and MeCN (0.38 mL) at room temperature. The mixture was stirred at room temperature for 1 h, and was treated with triethylamine (0.026 mL, 0.19 mmol). The mixture was stirred at room temperature over the weekend, and then heated at 50° C. for overnight. The mixture was cooled and concentrated. The residue was purified by column chromatography (silica gel, eluting with 0-100% EtOAc in hexanes) to give compound T58 (26 mg, 57% yield) as a white solid. m/z=532.5 (M+1); $^1H$ NMR (400 MHz, $CDCl_3$) δ 8.04 (s, 1H), 7.51 (bs, 1H), 5.96 (s, 1H), 3.48-3.27 (m, 3H), 2.65-2.32 (m, 3H), 2.10-0.90 (m, 15H), 1.49 (s, 3H), 1.45 (s, 3H), 1.25 (s, 3H), 1.17 (s, 3H), 0.99 (s, 3H), 0.95 (s, 3H), 0.88 (s, 3H).

T59 and T60: To a mixture of compound T57 (67 mg, 0.11 mmol) in ethanol (0.34 mL) was added compound 145 (18 μL, 0.12 mmol). The mixture was heated at 70° C. for 3.5 h, and then concentrated. The residue was purified by column chromatography (silica gel, eluting with 0-30% EtOAc in hexanes) to give compound T59 (49 mg, 74% yield) as a solid. From the column, partially purified compound T60 (6 mg) was obtained, which was further purified by preparative TLC (silica gel, eluting with 20% EtOAc in hexanes) to give compound T60 (4.4 mg, 7% yield). T59: m/z=604.4

(M+Na); $^{1}$H NMR (400 MHz, $CDCl_3$) δ 8.01 (s, 1H), 7.51 (bs, 1H), 6.75 (m, 1H), 5.94 (s, 1H), 3.84 (m, 1H), 3.27 (d, J=4.6 Hz, 1H), 2.32 (td, J=14.5, 13.2, 3.7 Hz, 1H), 2.20 (m, 1H), 1.95-1.00 (m, 13H), 1.56 (s, 3H), 1.42 (s, 3H), 1.23 (s, 3H), 1.13 (s, 3H), 1.07 (s, 6H), 0.94 (s, 3H). T60: m/z=582.5 (M+1); $^{1}$H NMR (400 MHz, $CDCl_3$) δ 8.01 (s, 1H), 7.63 (bs, 1H), 6.57 (bs, 1H), 5.94 (s, 1H), 3.38 (m, 1H), 2.97 (m, 1H), 2.38-2.14 (m, 2H), 1.95-1.00 (m, 13H), 1.42 (s, 3H), 1.25 (s, 3H), 1.14 (s, 3H), 1.10 (s, 3H), 1.06 (s, 3H), 0.97 (s, 3H), 0.94 (s, 3H).

Compound 146: To a solution of compound 139 (186 mg, 0.292 mmol) and N,N-diisopropylethylamine (204 μL, 1.17 mmol) in DMF (6.0 mL) was added HATU ((244 mg, 0.643 mmol) at 0° C. The mixture was stirred at 0° C. for 15 min, and then added to a solution of 2,2-dimethoxy-N-methylethanamine (78.8 μL, 0.613 mmol) in DMF (3 mL) at 0° C. The mixture was stirred at 0° C. for 30 min, and then at room temperature for 60 min. The mixture was partitioned between EtOAc (30 mL) and aq. $NaHCO_3$ (30 mL). The layers were separated. The aqueous layer was extracted EtOAc (3×30 mL). The combined organic extracts were washed with brine; dried with $Na_2SO_4$; filtered and concentrated. The residue was purified by column chromatography (silica gel, eluting with 0-16% EtOH in $CH_2Cl_2$) to give compound 146 (122 mg, 67% yield) as a yellow solid. m/z=624.5 (M+1).

Compound 147: To a stirring mixture of compound 146 (12.4 mg, 0.0199 mmol), THF (1.0 mL) and HCl (2.0 M aqueous solution, 1.0 mL, 2.0 mmol) was added sodium cyanoborohydride (2.50 mg, 0.0398 mmol) at room temperature. The reaction was stirred at room temperature for overnight, and then treated with additional amount of sodium cyanoborohydride (3.75 mg, 0.0596 mmol). The reaction was stirred at room temperature for another 5 h, and was then quenched with sat. aq. $NaHCO_3$ (5 mL). The mixture was partitioned between EtOAc (40 mL) and brine (40 mL). The layers were separated. The aqueous layer was extracted EtOAc (3×30 mL). The combined organic extracts were washed with brine; dried with $Na_2SO_4$; filtered and concentrated. The residue was purified by reverse phase column chromatography [C18, eluting with 10-90% (0.07% $CF_3CO_2H$ in MeCN) in (0.1% aqueous $CF_3CO_2H$)] to give compound 147 (7.5 mg, 56% yield) as a solid. m/z=562.4 (M of the free amine+1).

Compound 148: A mixture of compound 147 (78.0 mg, 0.115 mmol) and potassium carbonate (63.8 mg, 0.462 mmol) in methanol (3.0 mL) was stirred at room temperature for 16 h. The reaction mixture was neutralized with HCl (2.0 M aqueous, 0.45 mL, 0.90 mmol) and then partitioned between EtOAc (30 mL) and water (30 mL). The aqueous phase was separated and extracted with EtOAc (2×30 mL). The combined organic extracts were dried with $Na_2SO_4$, filtered, and concentrated in vacuo to give compound 148 (53 mg, 82% yield) as a white solid. m/z=562.5 (M+1).

T61: A mixture of compound 148 (170 mg, 0.303 mmol) in toluene (10 mL) was sparged with argon for 5 min. DDQ (75.6 mg, 0.333 mmol) was added. The mixture was stirred at room temperature for 90 min, and then heated at 50° C. for 90 min. The mixture was cooled to room temperature and then partitioned between EtOAc (30 mL) and sat. aq. $NaHCO_3$ (30 mL). The aqueous phase was separated and extracted with EtOAc (3×30 mL). The combined organic extracts were washed with brine; dried with $Na_2SO_4$; filtered; and concentrated. The residue was purified by reverse phase column chromatography [C18, eluting with 20-100% (0.07% $CF_3CO_2H$ in MeCN) in (0.1% aqueous $CF_3CO_2H$)] to give compound T61 (18 mg, 9% yield) as a solid. m/z=560.5 (M of the free amine+1); $^{1}$H NMR (400 MHz, $CDCl_3$) δ 8.02 (s, 1H), 5.96 (s, 1H), 3.40-0.90 (m, 23H), 2.97 (s, 3H), 1.47 (s, 3H), 1.41 (s, 3H), 1.25 (s, 3H), 1.16 (s, 3H), 0.99 (s, 3H), 0.96 (s, 3H), 0.89 (s, 3H).

T62: To a mixture of compound CC2 (50.0 mg, 0.105 mmol) and 2,2-difluoropropanoic acid (17 mg, 0.15 mmol) in $CH_2Cl_2$ (1 mL) was added triethylamine (37 μL, 0.27 mmol) and propylphosphonic anhydride (50 wt. % solution in EtOAc, 78 μL, 0.13 mmol) sequentially at room temperature. The mixture was stirred at room temperature for 1 h, and then treated with sat. aq. $NaHCO_3$ (1 mL). After stirring at room temperature for 5 min, the mixture was diluted with EtOAc (20 mL), and washed with sat. $NaHCO_3$ (2×10 mL), 1N aq. HCl (10 mL), and water (10 mL) sequentially. The organic extract was dried with $MgSO_4$, filtered and concentrated. The residue was purified by column chromatography (silica gel, eluting with 0-55% EtOAc in hexanes) to give partially purified product, which was purified again by column chromatography (silica gel, eluting with 0-30% acetone in hexanes) to give compound T62 (27 mg, 45% yield) as a white solid. m/z=569.3 (M+1); $^{1}$H NMR (400 MHz, $CDCl_3$) δ 8.02 (s, 1H), 6.43 (bs, 1H), 5.96 (s, 1H), 3.56 (dd, J=13.7, 7.4 Hz, 1H), 3.23-3.14 (m, 2H), 2.22 (m, 1H), 2.10-0.90 (m, 14H), 2.00 (m, 1H), 1.80 (t, J=19.3 Hz, 3H), 1.57 (s, 3H), 1.50 (s, 3H), 1.25 (s, 3H), 1.17 (s, 3H), 1.00 (s, 3H), 0.92 (s, 3H), 0.88 (s, 3H).

T63: To a mixture of compound CC2 (100 mg, 0.210 mmol) and 2,2-difluoroacetic acid (20 μg, 0.32 mmol) in $CH_2Cl_2$ (2 mL) was added triethylamine (73 μL, 0.52 mmol) and propylphosphonic anhydride (50 wt. % solution in EtOAc, 150 μL, 0.252 mmol) sequentially at room temperature. The mixture was stirred at room temperature for 1 h, and then treated with sat. aq. $NaHCO_3$ (1 mL). After stirring at room temperature for 5 min, the mixture was diluted with EtOAc (20 mL), and washed with sat. $NaHCO_3$ (2×10 mL), 1N aq. HCl (10 mL), and water (10 mL) sequentially. The organic extract was dried with $MgSO_4$, filtered and concentrated. The residue was purified by column chromatography (silica gel, eluting with 0-30% acetone in hexanes) to give compound T63 (71 mg, 61% yield) as a white solid. m/z=555.2 (M+1); $^{1}$H NMR (400 MHz, $CDCl_3$) δ 8.03 (s, 1H), 6.37 (bs, 1H), 5.97 (s, 1H), 5.91 (t, J=54.4 Hz, 1H), 3.65 (dd, J=13.7, 7.7 Hz, 1H), 3.11-3.20 (m, 2H), 2.23 (m, 1H), 1.99 (m, 1H), 1.88 (td, J=13.8, 3.9 Hz, 1H), 1.82-0.95 (m, 13H), 1.55 (s, 3H), 1.50 (s, 3H), 1.25 (s, 3H), 1.17 (s, 3H), 1.00 (s, 3H), 0.92 (s, 3H), 0.88 (s, 3H).

T64: Dess-Martin periodinane (44.6 mg, 0.105 mmol) was added in one portion to a solution of compound T28 (56.0 mg, 0.105 mmol) in $CH_2Cl_2$ (2 mL) at 0° C. under $N_2$. The mixture was stirred at room temperature for 90 min, and then partitioned between $CH_2Cl_2$ (30 mL) and brine (30 mL). The aqueous phase was separated and extracted with $CH_2Cl_2$ (3×30 mL). The combined organic extracts were dried with $Na_2SO_4$, filtered and concentrated. The residue was first triturated with EtOAc. The precipitated solid was collected to give partially purified compound T64, which was purified by column chromatography (Agela Technologies AQ C18 spherical 20-35 μm 100 Å silica gel column, eluting with 0-80% acetonitrile in water) to give compound T64 (8 mg, 14% yield). The mother liquor was concentrated. The residue was purified by column chromatography (Agela Technologies AQ C18 spherical 20-35 μm 100 Å silica gel column, eluting with 0-80% acetonitrile in water) to give the 2$^{nd}$ crop of compound T64 (12 mg, 21% yield). m/z=549.3 (M+1); $^{1}$H NMR (400 MHz, $CDCl_3$) δ 8.09 (s, 1H), 5.94 (s, 1H), 4.43 (p, J=6.0 Hz, 1H), 3.96-3.88 (m, 1H), 3.70-3.648 (m, 1H), 3.30-3.00 (m, 3H), 2.46-2.38 (m, 1H), 2.14-2.01

(m, 2H), 2.00-1.00 (m, 14H), 1.60 (s, 3H), 1.53 (s, 3H), 1.26 (s, 3H), 1.14 (s, 3H), 0.95 (s, 3H), 0.94 (s, 3H), 0.85 (s, 3H).

T68: Compound CC4 (100 mg, 0.216 mmol) was dissolved in $CH_2Cl_2$ (1.1 mL). The solution was cooled to 0° C. Triethylamine (60 μL, 0.43 mmol) and cyclopropanecarbonyl chloride (22 μL, 0.24 mmol) were added sequentially. The mixture was stirred at 0° C. for 30 min; diluted with EtOAc (30 mL); washed with 1N aq. HCl (10 mL); sat. aq. $NaHCO_3$ (10 mL) and water (10 mL) sequentially. The organic extract was dried with $MgSO_4$, filtered and concentrated. The residue was purified by column chromatography (silica gel, eluting with 0-60% acetone in hexanes) to give compound T68 (86 mg, 75% yield) as a white solid. m/z=531.3 (M+1); $^1$H NMR (400 MHz, $CDCl_3$) δ 8.03 (s, 1H), 5.98 (s, 1H), 5.24 (bs, 1H), 3.13 (d, J=4.7 Hz, 1H), 2.63 (dt, J=13.1, 4.9 Hz, 1H), 2.24 (m, 1H), 2.01 (m, 1H), 1.94-1.68 (m, 7H), 1.60-1.05 (m, 7H), 1.48 (s, 3H), 1.45 (s, 3H), 1.25 (s, 3H), 1.17 (s, 3H), 1.03 (s, 3H), 1.01 (s, 3H), 0.93-0.87 (m, 2H), 0.88 (s, 3H), 0.67 (m, 2H).

Compound 150: Compound 149 (200 mg, 0.43 mmol) and tert-butyl 3-aminopropanoate hydrochloride (157 mg, 0.86 mmol) were combined and dissolved in THF (4 mL). The reaction was stirred at room temperature for 1 h. $Et_3N$ (0.12 mL, 0.86 mmol) was added. The mixture was stirred at room temperature for overnight. $NaBH(OAc)_3$ (27 mg, 0.13 mmol) was added and the reaction was stirred for another 1 h. $NaBH_4$ (33 mg, 0.86 mmol) and EtOH (4 mL) were added. The mixture was stirred at room temperature for 2 h. The reaction was cooled down in an ice bath, and was quenched with sat. aq. $NaHCO_3$ (20 mL). The mixture was extracted with EtOAc (3×20 mL). The combined organic extracts were washed with brine (25 mL), dried with $Na_2SO_4$, filtered, and concentrated. The residue was purified by column chromatography (silica gel, eluting with 0-10% MeOH in $CH_2Cl_2$) to give compound 150 (211 mg, 82% yield) as a white solid. m/z=593 (M+1).

Compound 151: Compound 150 (211 mg, 0.36 mmol) in 1,4-dioxane (5 mL) was treated with HCl (4.0 M in 1,4-dioxane, 2 mL, 8 mmol) at room temperature under $N_2$. The mixture was stirred at room temperature for 4 h. Additional amount of HCl (4.0 M in 1,4-dioxane, 5 mL, 20 mmol) was added. The reaction was stirred overnight, and then concentrated. The residue was dissolved in $CH_2Cl_2$ (5 mL); cooled to 0° C. and treated with trifluoroacetic acid (2.5 mL). The reaction was stirred at room temperature for 3 h, and then concentrated. The residue was azeotroped with toluene (3×20 mL), and dried under vacuum to give compound 151 (191 mg, quantitative yield) as a white solid. m/z=537 (M+1 of free amine).

Compound 152: Compound 151 (191 mg, 0.36 mmol) was dissolved in $CH_2Cl_2$ (8 mL), and cooled to 0° C. $Et_3N$ (149 μL, 1.07 mmol) and $POCl_3$ (50 μL, 0.53 mmol) were added sequentially. The mixture was stirred at 0° C. for 15 min. Sat. aq. $NaHCO_3$ (10 mL) was added. The mixture was stirred at ambient temperature for 5 min, and then extracted with $CH_2Cl_2$ (2×20 mL). The combined organic extracts were washed with brine (20 mL), dried with $Na_2SO_4$, filtered and concentrated. The residue was purified by column chromatography (silica gel, eluting with 0-100% EtOAc in hexanes) to give compound 152 (81 mg, 44% yield) as a white solid. m/z=519 (M+1).

Compound 153: Compound 152 (80 mg, 0.15 mmol) was mixed with MeOH (2 mL) at room temperature. Sodium methoxide (25 wt. % solution in MeOH, 71 μL, 0.31 mmol) was added at room temperature. The mixture was stirred at 55° C. for 2 h. After cooled to 0° C., 10% aq. $NaH_2PO_4$ (20 mL) was added. The mixture was extracted with EtOAc (2×20 mL). The combined organic extracts were washed with brine (20 mL), dried with $Na_2SO_4$, filtered and concentrated. The crude product 153 (78 mg, 98% yield) was carried to the next step without further purification. m/z=519 (M+1).

T65: Compound 153 (78 mg, 0.15 mmol) was dissolved in DMF (3 mL) and cooled to 0° C. under $N_2$. 1,3-Dibromo-5,5-dimethylhydantoin (21 mg, 0.075 mmol) was added. The mixture was stirred at 0° C. for 1 h. Pyridine (49 μL, 0.60 mmol) was added. The mixture was heated at 60° C. for 4 h. After cooled to room temperature, the mixture was diluted with EtOAc (20 mL) and washed with 1N aq. HCl (10 mL), water (2×10 mL) and brine (20 mL). The organic extract was dried with $Na_2SO_4$, filtered, and concentrated. The residue was purified by column chromatography (silica gel, eluting with 0-50% acetone in hexanes) to give compound T65 (48 mg, 62% yield) as a white solid. m/z=517 (M+1); $^1$H NMR (400 MHz, $CDCl_3$) δ 8.01 (s, 1H), 6.01 (s, 1H), 3.43 (d, J=14.3 Hz, 1H), 3.37 (q, J=4.2 Hz, 2H), 3.11 (d, J=4.7 Hz, 1H), 3.00-2.95 (m, 2H), 2.93 (d, J=5.0 Hz, 1H), 2.46 (dq, J=13.4, 6.7 Hz, 1H), 2.30-2.22 (m, 1H), 2.03 (td, J=13.9, 4.7 Hz, 1H), 1.54 (s, 3H), 1.45 (s, 3H), 1.24 (d, J=6.7 Hz, 3H), 1.00 (s, 3H), 1.91-1.00 (m, 14H), 0.91 (s, 3H), 0.86 (s, 3H).

Compound 154: To a suspension of methyl 4-aminobutanoate hydrochloride (133 mg, 0.86 mmol) in THF (2 mL) was added $Et_3N$ (0.12 mL, 0.86 mmol). After the mixture was stirred at room temperature for 10 min, a solution of compound 149 (200 mg, 0.43 mmol) in THF (2 mL) was added at room temperature. The mixture was stirred at room temperature for 1.5 h; treated with sodium triacetoxyborohydride (366 mg, 1.73 mmol); and stirred at room temperature for another 4.5 h. MeOH (4 mL) and sodium borohydride (38 mg, 0.99 mmol) were added sequentially, and the mixture was stirred at room temperature for 30 min. Sat. aq. $NaHCO_3$ (20 mL) was added. The mixture was extracted with EtOAc (3×30 mL). The combined organic extracts were washed with brine (30 mL), dried with $Na_2SO_4$, filtered and concentrated to give compound 154 (227 mg, 93% yield) as a white solid, which was used in the next step without further purification. m/z=565 (M+1).

Compound 155: Compound 154 (227 mg, 0.4 mmol) in toluene (6 mL) was refluxed with Dean-stark apparatus to remove water for 6.5 h. Upon completion, toluene was removed under rotovap and the mixture was purified by column chromatography (silica gel, eluting with 0-100% EtOAc in hexanes) to give compound 155 (189 mg, 88% yield) as a white solid. m/z=533 (M+1).

Compound 156: A solution of compound 155 (189 mg, 0.35 mmol) in MeOH (3 mL) and THF (1 mL) was treated with sodium methoxide (25 wt. % solution in MeOH, 162 μL, 0.71 mmol) at room temperature. The mixture was heated at 55° C. for 2 h, and then cooled to room temperature. The mixture was treated with 10% aq. $NaH_2PO_4$ (20 mL) and extracted with EtOAc (2×20 mL). The combined organic extracts were washed with brine (20 mL), dried with $Na_2SO_4$, filtered and concentrated to give compound 156 (181 mg, 96% yield) as a white solid, which was used in the next step without further purification. m/z=533 (M+1).

T66: Compound 156 (181 mg, 0.33 mmol) in DMF (2 mL) was cooled to 0° C. A solution of 1,3-dibromo-5,5-dimethylhydantoin (47 mg, 0.165 mmol) in DMF (1 mL) was added. The mixture was stirred at 0° C. for 1 h. Pyridine (0.1 mL, 1.32 mmol) was added. The mixture was heated at 60° C. for 3 h. The mixture was cooled to room temperature; diluted with EtOAc (20 mL); and washed with 1N aq. HCl (10 mL), water (2×10 mL) and brine (20 mL) sequentially. The organic extract was dried with $Na_2SO_4$, filtered and concentrated. The residue was purified by column chromatography (silica gel, eluting with 0-50% acetone in hexanes) to give compound T66 (125 mg, 71% yield) as a white foam. m/z=531 (M+1); $^1$H NMR (400 MHz, $CDCl_3$) δ 8.01 (s, 1H), 6.00 (s, 1H), 3.61-3.39 (m, 3H), 3.35 (d, J=4.6 Hz, 1H), 3.02 (d, J=13.9 Hz, 1H), 2.45 (dt, J=13.2, 6.6 Hz, 1H), 2.35 (t, J=8.0 Hz, 2H), 2.29-2.15 (m, 2H), 2.05-2.01 (m, 2H), 1.57 (s, 3H), 1.44 (s, 3H), 1.23 (d, J=6.8 Hz, 3H), 1.91-0.97 (m, 14H), 0.99 (s, 3H), 0.91 (s, 3H), 0.85 (s, 3H).

T67: To the mixture of compound 137 (77 mg, 0.13 mmol) in $CH_2Cl_2$ (2 mL) was added 2-fluoroacetic acid (15 mg, 0.19 mmol), $Et_3N$ (56 μL, 0.40 mmol), and propylphosphonic anhydride (≥50 wt. % in EtOAc, 0.12 mL, ≥0.20 mmol) sequentially at room temperature. The mixture was stirred at room temperature for 1 h. Sat. aq. $NaHCO_3$ (3 mL) was added. The mixture was stirred at room temperature for 5 min; diluted with EtOAc (20 mL); and washed sequentially with sat. $NaHCO_3$ (2×10 mL), 1N aq. HCl (10 mL), water (10 mL) and brine (5 mL). The organic extract was dried with $MgSO_4$, filtered and concentrated. The residue was purified by column chromatography (silica gel, eluting with 0-50% acetone in hexanes) to give partially purified product, which was purified again by column chromatography (silica gel, eluting with 0-100% EtOAc in hexanes) to give compound T67 (32 mg, 45% yield) as a white solid. m/z=537 (M+1); $^1$H NMR (400 MHz, $CDCl_3$) δ 8.04 (s, 1H), 6.42 (bs, 1H), 5.98 (s, 1H), 4.83 (dd, J=47.4, 2.6 Hz, 2H), 3.56 (dd, J=13.7, 7.2 Hz, 1H), 3.26 (dd, J=13.6, 6.0 Hz, 1H), 3.22 (d, J=4.8 Hz, 1H), 2.25 (m, 1H), 2.03 (td, J=13.4, 4.2 Hz, 1H), 1.89 (td, J=13.7, 4.1 Hz, 1H), 1.58 (s, 3H), 1.51 (s, 3H), 1.26 (s, 3H), 1.18 (s, 3H), 1.01 (s, 3H), 0.97-1.83 (m, 13H), 0.93 (s, 3H), 0.89 (s, 3H).

Example 2: Prophetic Examples

Future work will include the synthesis of compounds having still other modifications at the C4 and C17 positions. Non-limiting examples of such compounds to be synthesized include P3:

P3

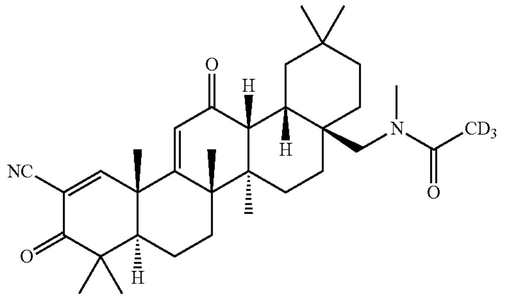

Proposed Synthesis of Prophetic Examples

Scheme 55

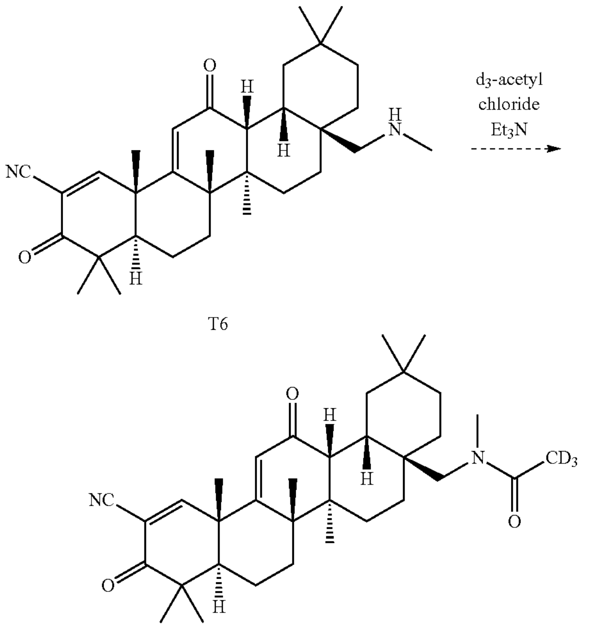

T6

P3

Example 3: Nitric Oxide Suppression Data

Tissue Culture: RAW 264.7, a mouse macrophage cell line, was obtained from American Type Culture Collection (Manassas Va.) and maintained in the log phase of growth in Roswell Park Memorial Institute Medium 1640 (RPMI 1640) supplemented with 10% heat inactivated fetal bovine serum and 1% penicillin-streptomycin. Cells were cultured and maintained in a humidified incubator at 37° C. under 5% $CO_2$. Cells were sub-cultured every 2-4 days. All cell culture supplies were obtained from Life Technologies (Grand Island, NY) and VWR (Radnor, PA).

Nitric Oxide Suppression Assay. RAW 264.7 cells were plated 1 day in advance of experimental treatments at a concentration of 30,000 cells per well onto Falcon-96 well clear bottom plates (Corning, NY) in a total volume of 200 μL per well using RPMI 1640 supplemented with 0.5% fetal bovine serum and 1% penicillin-streptomycin. The next day, cells were pretreated with compounds serially diluted from 1000× stocks. All compounds were dissolved in dimethyl sulfoxide (DMSO) usually at 10 mM stock solutions. Compounds were subsequently diluted in DMSO and RPMI 1640. Each well received a final concentration of 0.1% DMSO. Cells were pretreated for 2 hours and incubation at 37° C., followed by treatment with 20 ng/mL of interferon gamma (R&D Systems, Minneapolis, MN) per well for 24 hours. The next day, a nitrite standard was serially diluted from 100 μM to 1.6 μM in RPMI 1640. Afterwards, 50 μL of cell culture supernatant was transferred from each well into a new Falcon-96 well clear bottom plate. Nitrite was measured as surrogate for nitric oxide using Promega's Griess Detection Kit #G2930 (Madison, WI) which involves the addition of 50 μL of the provided sulfanilamide solution to each well of the transferred cell culture supernatant and standards, followed by a 10-minute incubation at room temperature in the dark. Next, 50 μL of the provided N-1-naphtylethylenediamine dihydrochloride (NED) solution was added to the sulfanilamide reaction and incubated for 10 minutes at room temperature in the dark. Afterwards, air bubbles were removed using ethanol vapor and absorbance was measured using a Spectramax M2e plate reader with a wavelength set to 525 nm. Viability was assessed using WST-1 cell proliferation reagent from Roche (Basel, Switzerland). After media was removed for the Nitric Oxide suppression assay, 15 μL of WST-1 reagent was added to each well of cells. Plates were briefly mixed on an orbital shaker and the cells were incubated at 37° C. for 30 to 60 minutes. Absorbance was measured using a Spectramax M2e plate reader with wavelengths set to 440 nm and 700 nm.

For the ability of compounds to suppress the increase in nitric oxide release caused by interferon gamma, the absolute amount of nitrite that was produced in each well was extrapolated from the nitrite standards using a linear regression fit. All values were then background corrected and normalized to the DMSO-interferon gamma treated wells and plotted as percent nitric oxide. $IC_{50}$ values were calculated using Excel and GraphPad Prism (San Diego, CA). The data is shown in Table 10.

TABLE 10

Nitric Oxide Inhibition

| Compound ID | NO $IC_{50}$ (nM) | NO $IC_{50}$ Rel. to RTA 402 (fold) |
|---|---|---|
| RTA 402 | 2.58 ± 1.19[a] | 1.00 ± 0.00 |
| CC1 | 5.04 ± 2.62[e] | 2.06 ± 0.56[e] |
| CC2 | 3.15 ± 1.48[e] | 1.55 ± 0.30[e] |
| CC4 | 3.75 ± 0.96[b] | 2.41 ± 0.49[b] |
| T3 | 0.44 ± 0.18[e] | 0.17 ± 0.04[e] |
| T4 | 0.51 ± 0.21[h] | 0.26 ± 0.08[h] |
| T5 | 14.20 ± 6.51[d] | 6.04 ± 2.02[d] |
| T6 | 3.35 ± 1.62[e] | 1.60 ± 0.23[e] |
| T7 | 0.84 ± 0.37[e] | 0.49 ± 0.14[e] |
| T8 | 0.46 ± 0.22[d] | 0.21 ± 0.05[d] |
| T9 | 0.70 ± 0.18[e] | 0.38 ± 0.15[e] |
| T10 | 1.12 ± 0.44[g] | 0.45 ± 0.08[g] |
| T11 | 1.08 ± 0.44[f] | 0.58 ± 0.18[f] |
| T12 | 7.47 ± 0.85[e] | 4.07 ± 1.08[e] |
| T13 | 1.74 ± 0.55[e] | 0.65 ± 0.21[e] |
| T14 | 0.89 ± 0.08[e] | 0.51 ± 0.09[e] |
| T15 | 1.18 ± 0.50[d] | 0.64 ± 0.26[d] |
| T16 | 0.37 ± 0.04[d] | 0.21 ± 0.05[d] |
| T17•HCl | 3.94 ± 2.75[d] | 1.42 ± 0.20[d] |
| T18 | 0.92 ± 0.23[e] | 0.76 ± 0.10[e] |
| T19 | 1.11 ± 0.14[e] | 0.93 ± 0.22[e] |
| T20 | 3.28 ± 0.32[e] | 1.93 ± 0.41[e] |
| T21 | 1.18 ± 0.21[e] | 0.57 ± 0.07[e] |
| T22 | 9.18 ± 1.72[d] | 5.29 ± 1.29[d] |
| T23 | 4.16 ± 1.19[e] | 2.01 ± 0.53[e] |
| T24 | 3.60 ± 0.08[e] | 2.17 ± 0.72[e] |
| T25 | 2.50 ± 0.92[e] | 1.21 ± 0.45[e] |
| T26 | 5.61 ± 1.84[e] | 2.73 ± 1.01[e] |
| T27 | 17.81 ± 1.79[e] | 8.68 ± 2.12[e] |
| T28 | 2.83 ± 0.92[e] | 1.09 ± 0.16[e] |
| T29 | 6.09 ± 1.46[d] | 1.49 ± 0.30[d] |
| T30 | 15.01 ± 2.92[d] | 3.68 ± 0.33[d] |
| T31 | 12.64 ± 1.65[d] | 3.13 ± 0.36[d] |
| T32 | 4.89 ± 1.42[e] | 2.58 ± 0.60[e] |
| T33 | 5.62 ± 1.81[d] | 1.35 ± 0.26[d] |
| T34 | 2.23 ± 0.57[e] | 1.23 ± 0.23[e] |
| T35 | 1.30 ± 0.10[e] | 0.64 ± 0.04[e] |
| T36 | 1.96 ± 0.90[e] | 0.77 ± 0.16[e] |
| T37 | 3.22 ± 1.52[e] | 1.37 ± 0.26[e] |
| T38 | 4.32 ± 3.51[e] | 1.69 ± 0.84[e] |
| T39 | 84.49 ± 18.93[e] | 42.82 ± 14.24[e] |
| T40 | 5.56 ± 0.72[d] | 1.37 ± 0.18[d] |

TABLE 10-continued

Nitric Oxide Inhibition

| Compound ID | NO $IC_{50}$ (nM) | NO $IC_{50}$ Rel. to RTA 402 (fold) |
|---|---|---|
| T41 | 4.96 ± 1.58[d] | 1.19 ± 0.22[d] |
| T42 | 12.40 ± 3.92[d] | 2.97 ± 0.47[d] |
| T43 | 2.68 ± 0.43[d] | 0.66 ± 0.09[d] |
| T44 | 4.39 ± 0.73[d] | 1.07 ± 0.11[d] |
| T45 | 16.39 ± 2.94[d] | 4.02 ± 0.61[d] |
| T46 | 10.73 ± 1.35[d] | 2.62 ± 0.10[d] |
| T47 | 17.28 ± 8.55[d] | 7.54 ± 2.47[d] |
| T48 | 2.50 ± 0.60[e] | 1.19 ± 0.18[e] |
| T49 | 26.88 ± 10.49[e] | 13.72 ± 3.47[e] |
| T50 | 4.82 ± 1.30[d] | 1.17 ± 0.18[d] |
| T51 | 8.55 ± 3.65[d] | 2.04 ± 0.73[d] |
| T52 | 0.52 ± 0.24[e] | 0.28 ± 0.13[e] |
| T53 | 0.38 ± 0.12[e] | 0.21 ± 0.05[e] |
| T54 | 64.64 ± 19.69[e] | 16.18 ± 3.50[e] |
| T55 | 68.93 ± 10.00[e] | 17.42 ± 0.43[e] |
| T56 | 7.04 ± 1.91[d] | 1.70 ± 0.32[d] |
| T58 | 12.23 ± 3.32[d] | 2.97 ± 0.65[d] |
| T59 | 49.46 ± 13.83[d] | 12.08 ± 2.93[d] |
| T60 | 45.10 ± 10.60[e] | 11.32 ± 1.49[e] |
| T61 | 13.20 ± 3.78[d] | 3.18 ± 0.67[d] |
| T62 | 2.12 ± 0.85[d] | 0.51 ± 0.18[d] |
| T63 | 1.48 ± 0.54[d] | 0.36 ± 0.11[d] |
| T64 | 3.82 ± 1.76[e] | 1.64 ± 0.16[e] |
| T65 | 0.42 ± 0.13[e] | 0.36 ± 0.12[e] |
| T66 | 0.45 ± 0.09[e] | 0.39 ± 0.09[e] |
| T67 | 0.51 ± 0.31[d] | 0.38 ± 0.15[d] |
| T68 | 11.43 ± 5.17 | 6.51 ± 1.38[i] |

[a]Average of 52 trials;
[b]average of 6 trials;
[c]average of 13 trials;
[d]average of 4 trials;
[e]average of 3 trials;
[f]average of 5 trials;
[g]average of 7 trials;
[h]average of 8 trials;
[i]average of 2 trials.

Example 4: CYP3A4 Inhibition Data

Methods. Several compounds were evaluated for CYP3A4 (midazolam) inhibition in human liver microsomes at 1 μM. CYP3A4 inhibition was tested using an in vitro assay as generally described in Dierks et al. (Drug Metabolism Deposition, 29:23-29, 2001, which is incorporated by reference herein). Each sample, containing 0.1 mg/mL human liver microsomes, M midazolam as substrate, and 1 μM of test compound, was incubated at 37° C. for 10 min. Following incubation, the metabolite 1-hydroxymidazolam was measured using HPLC-MS/MS. Peak areas corresponding to the metabolite of the substrate were recorded. The percent of control activity was then calculated by comparing the peak area obtained in the presence of the test compound to that obtained in the absence of the test compound. Subsequently, the percent inhibition was calculated by subtracting the percent control activity from 100 for each compound. The results of the CYP3A4 assays are show below in Table 11.

TABLE 11

CYP3A4 (Midazolam) Inhibition.

| Compound ID | CYP3A4 (Midazolam) % Inhibition @ 1 μM |
|---|---|
| RTA 402 | 48.4 |
| RTA 408 | 56.6 |

TABLE 11-continued

| CYP3A4 (Midazolam) Inhibition. | |
|---|---|
| Compound ID | CYP3A4 (Midazolam) % Inhibition @ 1 μM |
| T4 | 30.7 |
| T10 | 33.2 |
| T11 | 12.5 |
| T17 | 31.8 |
| T18 | 46.5 |
| T19 | 33.8 |
| T20 | 13.2 |
| T21 | 18.9 |
| T48 | 29.8 |
| T33 | 49.0 |
| T35 | 41.7 |
| T36 | 52.8 |
| T37 | 86.5 |
| T41 | 17.1 |
| T43 | 17.0 |
| T44 | 29.1 |

Example 5: Effect on Luciferase Reporter Activation

AREc32 reporter cell line (derived from human breast carcinoma MCF7 cells) was obtained was from CXR Bioscience Limited (Dundee, UK) and cultured in DMEM (low glucose) supplemented with 10% FBS, 1% penicillin/streptomycin, and 0.8 mg/ml Geneticin (G418). This cell line is stably transfected with a luciferase reporter gene under the transcriptional control of eight copies of the rat GSTA2 ARE sequence.

The effect of several compounds disclosed herein on luciferase reporter activation was assessed in the AREc32 reporter cell line (see Table 9 and Table 10). This cell line is derived from human breast carcinoma MCF-7 cells and is stably transfected with a luciferase reporter gene under the transcriptional control of eight copies of the antioxidant response element from the rat Gsta2 gene, an Nrf2 target gene (Frilling et al., 1990). AREc32 cells were plated in black 96-well plates in 200 μL media at 20,000 cells per well. Twenty-four hours after plating, cells were treated with vehicle (DMSO) or test compounds at concentrations ranging from 0.03 to 1000 nM for nineteen hours. Media was removed and 100 μL of 1:1 mixture of the One-Glo Luciferase assay reagent and culture medium was added to each well. After incubation for 5 min at room temperature, the luminescence signal was measured on a PHERAstar plate reader. The $EC_{2X}$ value was determined using Excel and GraphPad Prism software. The fold increase in luminescence signal for cells treated with each concentration of compound relative to cells treated with vehicle was determined and a dose-response curve was generated. The dose-response curve was fit using nonlinear regression analysis and used to extrapolate the $EC_{2X}$ value. The $EC_{2X}$ value is defined as the concentration of test compound required to increase the luminescence signal 2-fold above levels in vehicle-treated samples.

TABLE 12

| AREc32 $EC_{2X}$ Data. | | |
|---|---|---|
| ID # | AREc32 $EC_{2X}$ (nM) (Mean ± SD) | AREc32 $EC_{2X}$ Relative to RTA 402 (fold) (Mean ± SD) |
| RTA 402 | 11.8 ± 2.90[h] | 1.00 |
| CC1 | 21.1 ± 4.75[a] | 2.1 ± 0.00[a] |
| CC2 | 16.1 ± 0.81[g] | 1.6 ± 0.17[g] |
| T3 | 2.4 ± 0.44[a] | 0.2 ± 0.08[a] |
| T4 | 3.2 ± 0.32[b] | 0.3 ± 0.08[b] |
| T5 | 42.5 ± 9.47[a] | 3.9 ± 0.36[a] |
| T6 | 16.9 ± 0.03[a] | 1.2 ± 0.35[a] |
| T7 | 6.8 ± 0.03[a] | 0.5 ± 0.14[a] |
| T8 | 2.8 ± 0.04[a] | 0.2 ± 0.06[a] |
| T9 | 7.2 ± 0.77[a] | 0.5 ± 0.20[a] |
| T10 | 5.2 ± 2.49[c] | 0.5 ± 0.13[c] |
| T11 | 6.7 ± 1.7[d] | 0.5 ± 0.08[d] |
| T12 | 21.8[e] | 1.7[e] |
| T13 | 5.12[e] | 0.5[e] |
| T14 | 4.37[e] | 0.4[e] |
| T15 | 6.07[e] | 0.5[e] |
| T16 | 2.0 ± 0.18[f] | 0.2 ± 0.05[f] |
| T17 | 16.2 ± 0.85[g] | 1.6 ± 0.22[g] |
| T18 | 5.7 ± 0.44[g] | 0.6 ± 0.05[g] |
| T19 | 8.4 ± 1.26[g] | 0 9 ± 0.16[g] |
| T20 | 15.3 ± 0.84[g] | 1 6 ± 0.17[g] |
| T21 | 10.5 ± 1.65[g] | 1.1 ± 0.20[g] |
| T22 | 44.5[e] | 3.7[e] |
| T23 | 18.5[e] | 1.9[e] |
| T24 | 37.9[e] | 3.8[e] |
| T25 | 22.0[e] | 1.5[e] |
| T26 | 23.6[e] | 1.6[e] |
| T27 | 26.6[e] | 1.8[e] |
| T28 | 13.9 ± 1.57[a] | 0.9 ± 0.12[a] |
| T29 | 13.3[e] | 1.2[e] |
| T31 | 45.5[e] | 4.3[e] |
| T32 | 32.3 ± 1.39[f] | 2.8 ± 0.62[f] |
| T33 | 13.6 ± 1.31[f] | 1.2 ± 0.18[f] |
| T34 | 23.6[e] | 2.2[e] |
| T35 | 7.1 ± 0.73[f] | 0.6 ± 0.18[f] |
| T36 | 5.6 ± 0.59[f] | 0.5 ± 0.13[f] |
| T37 | 24.3 ± 2.70[f] | 2.1 ± 0.50[f] |
| T38 | 36.1[e] | 2.1[e] |
| T39 | 94.3 ± 4.26[a] | 9.8 ± 1.1[a] |
| T40 | 19.6[e] | 1.8[e] |
| T41 | 9.4 ± 1.35[f] | 0.8 ± 0.16[f] |
| T42 | 14.8 ± 2.77[f] | 1.3 ± 0.34[f] |
| T43 | 8.5 ± 0.55[f] | 0.7 ± 0.15[f] |
| T44 | 10.6 ± 0.83[f] | 0.9 ± 0.15[f] |
| T46 | 31.6[e] | 3.0[e] |
| T47 | 122[e] | 8.6[e] |
| T48 | 12.9 ± 1.43[g] | 1.3 ± 0.21[g] |
| T49 | 38.9[e] | 4.5[e] |
| T51 | 11.7[e] | 1.1[e] |
| T52 | 3.0[e] | 0.3[e] |
| T53 | 2.4[e] | 0.2[e] |
| T56 | 15.5[e] | 1.5[e] |
| T58 | 56.5[e] | 5.3[e] |
| T62 | 3.5[e] | 0.3[e] |
| T63 | 4.0[e] | 0.4[e] |
| T65 | 4.7[e] | 0.4[e] |
| T66 | 4.6[e] | 0.4[e] |
| T67 | 3.3[e] | 0.3[e] |

[a]Average of 2 trials;
[b]average of 7 trials;
[c]average of 6 trials;
[d]average of 5 trials;
[e]result of 1 trial;
[f]average of 4 trials;
[g]average of 3 trials;
[h]average of 22 trials

TABLE 13

AREc32 $EC_{2X}$ Relative to Comparison Compounds.

| ID # | Comparison Compound (CC) | AREc32 Relative to CC in Same Experiment[a] (Mean ± SD) |
|---|---|---|
| T17 | CC2 | 1.009 ± 0.052 |
| T18 | CC2 | 0.356 ± 0.015 |
| T19 | CC2 | 0.522 ± 0.052 |
| T20 | CC2 | 0.954 ± 0.101 |
| T21 | CC2 | 0.649 ± 0.070 |
| T48 | CC2 | 0.802 ± 0.050 |
| T33 | CC4 | 0.484 ± 0.060 |
| T35 | CC4 | 0.262 ± 0.020 |
| T36 | CC4 | 0.191 ± 0.009 |
| T37 | CC4 | 0.878 ± 0.094 |
| T41 | CC4 | 0.320 ± 0.037 |
| T42 | CC4 | 0.490 ± 0.057 |
| T43 | CC4 | 0.299 ± 0.015 |
| T44 | CC4 | 0.387 ± 0.037 |

[a]Average of ratios from three replicate experiments with direct comparisons.

All the compounds, formulations, and methods disclosed and claimed herein can be made and executed without undue experimentation in light of the present disclosure. While the compounds, formulations, and methods of this invention have been described in terms of preferred embodiments, it will be apparent to those of skill in the art that variations may be applied to the compounds, formulations, and methods, as well as in the steps or in the sequence of steps of the method described herein without departing from the concept, spirit, and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references to the extent that they provide exemplary procedural or other details supplementary to those set forth herein, are specifically incorporated herein by reference.

U.S. Pat. No. 7,915,402
U.S. Pat. No. 7,943,778
U.S. Pat. No. 8,071,632
U.S. Pat. No. 8,124,799
U.S. Pat. No. 8,129,429
U.S. Pat. No. 8,338,618
U.S. Pat. No. 8,993,640
U.S. Pat. No. 9,512,094
U.S. Pat. No. 9,701,709
U.S. Pat. No. 9,889,143
WO 2012/125488
WO 2014/040056
Abraham and Kappas, *Free Radical Biol. Med.,* 39:1-25, 2005.
Ahmad et al., *Cancer Res.,* 68:2920-2926, 2008.
Ahmad et al., *J. Biol. Chem.,* 281:35764-9, 2006.
Anderson, *Practical Process Research & Development—A Guide for Organic Chemists,* 2nd ed., Academic Press, New York, 2012.
Araujo et al., *J. Immunol.,* 171(3):1572-1580, 2003.
Bach, *Hum. Immunol.,* 67(6):430-432, 2006.
Chauhan and Chauhan, *Pathophysiology,* 13(3):171-181 2006.
Dickerson et al., *Prog Neuropsychopharmacol Biol. Psychiatry,* Mar. 6, 2007.
Dinkova-Kostova et al., *Proc. Natl. Acad. Sci. USA,* 102(12):4584-4589, 2005.
Dudhgaonkar et al., *Eur. J. Pain,* 10(7):573-9, 2006.
Favaloro, et al., *J. Med. Chem.,* 45:4801-4805, 2002.
Forstermann, *Biol. Chem.,* 387:1521, 2006.
*Handbook of Pharmaceutical Salts: Properties, and Use,* Stahl and Wermuth Eds., Verlag Helvetica Chimica Acta, 2002.
Hanson et al., *BMC Medical Genetics,* 6(7), 2005.
Honda et al. *Bioorg. Med. Chem. Lett.,* 12:1027-1030, 2002.
Honda et al., *Bioorg. Med. Chem. Lett.,* 16(24):6306-6309, 2006.
Honda et al., *Bioorg. Med. Chem. Lett.,* 7:1623-1628, 1997.
Honda et al., *Bioorg. Med. Chem. Lett.,* 8(19):2711-2714, 1998.
Honda et al., *Bioorg. Med. Chem. Lett.,* 9(24):3429-3434, 1999.
Honda et al., *J. Med. Chem.,* 43:4233-4246, 2000a.
Honda et al., *Org. Biomol. Chem.,* 1:4384-4391, 2003.
Honda, et al., *J. Med Chem.,* 43:1866-1877, 2000b.
Honda, et al., *J Med Chem.,* 54(6):1762-1778, 2011.
Hong, et al., 2012.
Ishikawa et al., *Circulation,* 104(15):1831-1836, 2001.
Kawakami et al., *Brain Dev.,* 28(4):243-246, 2006.
Kendall-Tackett, Trauma Violence Abuse, 8(2):117-126, 2007.
Kruger et al., *J Pharmacol. Exp. Ther.,* 319(3):1144-1152, 2006.
Lee et al., Glia., 55(7):712-22, 2007.
Lencz et al., *Mol. Psychiatry,* 12(6):572-80, 2007.
Liby et al., *Cancer Res.,* 65(11):4789-4798, 2005.
Liby et al., *Mol. Cancer Ther.,* 6(7):2113-9, 2007b.
Liby et al., *Nat. Rev. Cancer,* 7(5):357-356, 2007a.
Liu et al., *FASEB J,* 20(2):207-216, 2006.
Lu et al., *J. Clin. Invest.,* 121(10):4015-29, 2011.
McIver et al., *Pain,* 120 (1-2):161-9, 2005.
Morris et al., *J. Mol. Med.,* 80(2):96-104, 2002.
Morse and Choi, *Am. J. Respir. Crit. Care Med.,* 172(6): 660-670, 2005.
Morse and Choi, *Am. J. Respir. Crit. Care Med.,* 27(1): 8-16, 2002.
Pall, *Med. Hypoth.,* 69:821-825, 2007.
Pergola et al., 2011.
Place et al., *Clin. Cancer Res.,* 9(7):2798-806, 2003.
Rajakariar et al., *Proc. Natl. Acad. Sci. USA,* 104(52): 20979-84, 2007.
Reagan-Shaw et al., *FASEB J.,* 22(3):659-661, 2008
Reisman et al., *Arch. Dermatol. Res.,* 306(5):447-454, 2014.
Ross et al., *Am. J Clin. Pathol.,* 120 (Suppl):S53-71, 2003.
Ross et al., *Expert Rev. Mol. Diagn.,* 3(5):573-585, 2003.
Ruster et al., *Scand J. Rheumatol.,* 34(6):460-3, 2005.
Sacerdoti et al., *Curr Neurovasc Res.* 2(2):103-111, 2005.
Salvemini et al., *J. Clin. Invest.,* 93(5):1940-1947, 1994.
Sarchielli et al., *Cephalalgia,* 26(9):1071-1079, 2006.
Satoh et al., *Proc. Natl. Acad. Sci. USA,* 103(3):768-773, 2006.
Schulz et al., *Antioxid. Redox. Sig.,* 10:115, 2008.
Sharma et al., *Synth. Comm.,* 34(10):1855-1862, 2004.
Smith, *March's Advanced Organic Chemistry: Reactions, Mechanisms, and Structure,* 7th Ed., Wiley, 2013.
Suh et al., *Cancer Res.,* 58:717-723, 1998.

Suh et al., *Cancer Res.,* 59(2):336-341, 1999.
Szabo et al., *Nature Rev. Drug Disc.,* 6:662-680, 2007.
Takahashi et al., *Cancer Res.,* 57:1233-1237, 1997.
Tamir and Tannebaum, *Biochim. Biophys. Acta,* 1288: F31-F36, 1996.
van Berkel et al., *Angew. Chem. Int. Ed.,* 51(22):5343-5346, 2012.
Xie T et al., *J Biol Chem.* 270(12):6894-6900, 1995.
Zhou et al., *Am. J. Pathol.,* 166(1):27-37, 2005.

What is claimed is:

1. A compound of the formula:

(I)

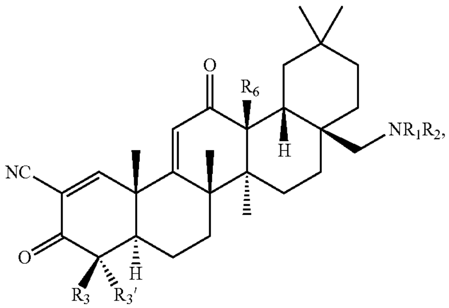

wherein:

$R_1$ is hydrogen; or
alkyl$_{(C\leq8)}$ or substituted alkyl$_{(C\leq8)}$
or
$R_1$ and $R_2$ are taken together as defined below;
$R_2$ is alkyl$_{(C\leq8)}$ or substituted alkyl$_{(C\leq8)}$; or
—C(O) $R_5$, wherein:
$R_5$ is hydrogen; or
alkyl$_{(C\leq8)}$, alkenyl$_{(C\leq8)}$, alkynyl$_{(C\leq8)}$, alkylamino$_{(C\leq8)}$, dialkylamino$_{(C\leq8)}$, cycloalkyl$_{(C\leq8)}$, cycloalkoxy$_{(C\leq8)}$, cycloalkylamino$_{(C\leq8)}$, heterocycloalkyl$_{(C\leq8)}$, or a substituted version of any one of these groups; or
$R_2$ and $R_1$ are taken together as defined below;
$R_1$ and $R_2$, when taken together with the nitrogen atom of the —$NR_1R_2$ group, is N-heteroaryl$_{(C\leq8)}$, substituted N-heteroaryl$_{(C\leq8)}$, N-heterocycloalkyl$_{(C\leq8)}$, substituted N-heterocycloalkyl$_{(C\leq8)}$, or 3-oxo-1-(t-butoxycarbonyl) pyrazolidin-2-yl;
$R_3$ and $R_3$' are each independently hydrogen, alkyl$_{(C\leq8)}$, or substituted alkyl$_{(C\leq8)}$; and
$R_6$ is hydrogen or hydroxy;

or a pharmaceutically acceptable salt thereof.

2. The compound of claim 1, wherein the compound is further defined as:

(I-A)

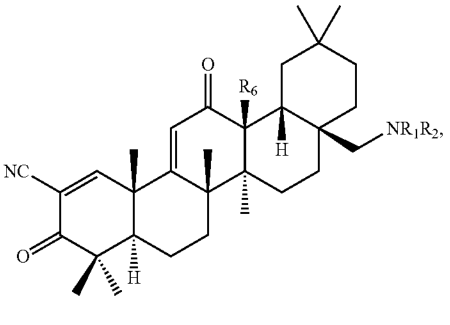

wherein:

$R_1$ is hydrogen; or
alkyl$_{(C\leq8)}$ or substituted alkyl$_{(C\leq8)}$
or
$R_1$ and $R_2$ are taken together as defined below;
$R_2$ is alkyl$_{(C\leq8)}$ or substituted alkyl$_{(C\leq8)}$; or
—C(O) $R_5$, wherein:
$R_5$ is hydrogen; or
alkyl$_{(C\leq8)}$, alkenyl$_{(C\leq8)}$, alkynyl$_{(C\leq8)}$, alkylamino$_{(C\leq8)}$, dialkylamino$_{(C\leq8)}$, cycloalkyl$_{(C\leq8)}$, cycloalkoxy$_{(C\leq8)}$, cycloalkylamino$_{(C\leq8)}$, heterocycloalkyl$_{(C\leq8)}$, or a substituted version of any one of these groups; or
$R_2$ and $R_1$ are taken together as defined below;
$R_1$ and $R_2$, when taken together with the nitrogen atom of the —$NR_1R_2$ group, is N-heteroaryl$_{(C\leq8)}$, substituted N-heteroaryl$_{(C\leq8)}$, N-heterocycloalkyl$_{(C\leq8)}$, substituted N-heterocycloalkyl$_{(C\leq8)}$, or 3-oxo-1-(t-butoxycarbonyl) pyrazolidin-2-yl; and
$R_6$ is hydrogen or hydroxy;

or a pharmaceutically acceptable salt thereof.

3. The compound of claim 2, wherein the compound is further defined as:

(I-B)

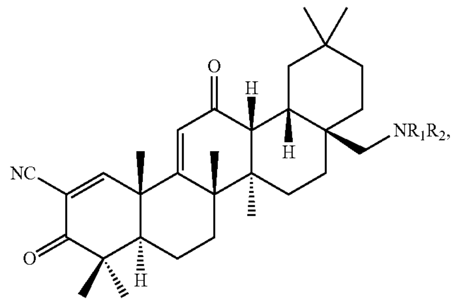

wherein:

$R_1$ is hydrogen; or
alkyl$_{(C\leq8)}$ or substituted alkyl$_{(C\leq8)}$
or
$R_1$ and $R_2$ are taken together as defined below;
$R_2$ is alkyl$_{(C\leq8)}$ or substituted alkyl$_{(C\leq8)}$; or
—C(O) $R_5$, wherein:
$R_5$ is hydrogen; or
alkyl$_{(C\leq8)}$, alkenyl$_{(C\leq8)}$, alkynyl$_{(C\leq8)}$, alkylamino$_{(C\leq8)}$, dialkylamino$_{(C\leq8)}$, cycloalkyl$_{(C\leq8)}$, cycloalkoxy$_{(C\leq8)}$, cycloalkylamino$_{(C\leq8)}$, heterocycloalkyl$_{(C\leq8)}$, or a substituted version of any one of these groups; or
$R_2$ and $R_1$ are taken together as defined below; and
$R_1$ and $R_2$, when taken together with the nitrogen atom of the —$NR_1R_2$ group, is N-heteroaryl$_{(C\leq8)}$, substituted N-heteroaryl$_{(C\leq8)}$, N-heterocycloalkyl$_{(C\leq8)}$, substituted N-heterocycloalkyl$_{(C\leq8)}$, or 3-oxo-1-(t-butoxycarbonyl) pyrazolidin-2-yl;

or a pharmaceutically acceptable salt thereof.

4. The compound of claim 1, wherein $R_3$ is hydrogen.

5. The compound of claim 1, wherein $R_3$ is methyl.

6. The compound of claim 1, wherein $R_3$' is methyl.

7. The compound of claim 1, wherein $R_6$ is hydrogen.

8. The compound of claim 1, wherein $R_1$ is hydrogen, alkyl$_{(C\leq8)}$, or substituted alkyl$_{(C\leq8)}$.

9. The compound of claim 8, wherein $R_1$ is hydrogen.

10. The compound of claim 8, wherein $R_1$ is alkyl$_{(C\leq8)}$ or substituted alkyl$_{(C\leq8)}$.

11. The compound of claim 10, wherein $R_1$ is alkyl$_{(C\leq8)}$.

12. The compound of claim 11, wherein $R_1$ is methyl.

13. The compound of claim 1, wherein:

$R_2$ is substituted alkyl$_{(C\leq8)}$ or —C(O) $R_5$, wherein:

$R_5$ is hydrogen; or alkyl$_{(C\leq8)}$, alkenyl$_{(C\leq8)}$, alkynyl$_{(C\leq8)}$, alkylamino$_{(C\leq8)}$, dialkylamino$_{(C\leq8)}$, cycloalkyl$_{(C\leq8)}$, cycloalkoxy$_{(C\leq8)}$, cycloalkylamino$_{(C\leq8)}$, heterocyclo-alkyl$_{(C\leq8)}$, or a substituted version of any one of these groups.

14. The compound of claim 1, wherein:

$R_2$ is alkyl$_{(C\leq8)}$, substituted alkyl$_{(C\leq8)}$, or —C(O) $R_5$, wherein:

$R_5$ is hydrogen; or alkenyl$_{(C\leq8)}$, alkynyl$_{(C\leq8)}$, alkylamino$_{(C\leq8)}$, dialkylamino$_{(C\leq8)}$, cycloalkyl$_{(C\leq8)}$, cycloalkoxy$_{(C\leq8)}$, cycloalkylamino$_{(C\leq8)}$, heterocycloalkyl$_{(C\leq8)}$, or a substituted version of any one of these groups.

15. The compound of claim 1, wherein:

$R_2$ is alkyl$_{(C\leq8)}$, substituted alkyl$_{(C\leq8)}$, or —C(O) $R_5$, wherein:

$R_5$ is hydrogen; or alkyl$_{(C\leq8)}$, alkenyl$_{(C\leq8)}$, alkynyl$_{(C\leq8)}$, dialkylamino$_{(C\leq8)}$, cycloalkyl$_{(C\leq8)}$, cycloalkoxy$_{(C\leq8)}$, cycloalkylamino$_{(C=8)}$, heterocycloalkyl$_{(C\leq8)}$, or a substituted version of any one of these groups.

16. The compound of claim 1, wherein:

$R_2$ is substituted alkyl$_{(C\leq8)}$, or —C(O) $R_5$, wherein:

$R_5$ is hydrogen; or alkenyl$_{(C\leq8)}$, alkynyl$_{(C\leq8)}$, dialkylamino$_{(C\leq8)}$, cycloalkyl$_{(C\leq8)}$, cycloalkoxy$_{(C\leq8)}$, cycloalkylamino$_{(C\leq8)}$, heterocycloalkyl$_{(C\leq8)}$, or a substituted version of any one of these groups.

17. The compound of claim 1, wherein $R_2$ is alkyl$_{(C\leq8)}$ or substituted alkyl$_{(C\leq8)}$.

18. The compound of claim 17, wherein $R_2$ is alkyl$_{(C\leq8)}$.

19. The compound of claim 18, wherein $R_2$ is methyl.

20. The compound of claim 17, wherein $R_2$ is substituted alkyl$_{(C\leq8)}$.

21. The compound of claim 20, wherein $R_2$ is 1-hydroxy-eth-2-yl.

22. The compound of claim 1, wherein $R_5$ is alkyl$_{(C\leq8)}$ or substituted alkyl$_{(C\leq8)}$.

23. The compound of claim 22, wherein $R_5$ is alkyl$_{(C\leq8)}$.

24. The compound of claim 23, wherein $R_5$ is methyl or ethyl.

25. The compound of claim 24, wherein $R_5$ is methyl, further wherein the methyl is substantially trideuteriomethyl.

26. The compound of claim 25, wherein the isotopic enrichment of deuterium at each of the three positions is greater than 90%.

27. The compound of claim 22, wherein $R_5$ is substituted alkyl$_{(C\leq8)}$.

28. The compound of claim 27, wherein $R_5$ is 1,1-difluoroeth-1-yl, difluoromethyl, or fluoromethyl.

29. The compound of claim 1, wherein Rs is cycloalkyl$_{(C\leq8)}$ or substituted cycloalkyl$_{(C\leq8)}$.

30. The compound of claim 29, wherein $R_5$ is cycloalkyl$_{(C\leq8)}$.

31. The compound of claim 30, wherein $R_5$ is cyclopropyl.

32. The compound of claim 1, wherein $R_5$ is alkylamino$_{(C\leq8)}$.

33. The compound of claim 32, wherein $R_5$ is methylamino.

34. The compound of claim 1, wherein $R_1$ and $R_2$ are taken together with the nitrogen atom of the —$NR_1R_2$ group and is N-heteroaryl$_{(C\leq8)}$, substituted N-heteroaryl$_{(C\leq8)}$, N-heterocycloalkyl$_{(C\leq8)}$, or substituted N-heterocycloalkyl$_{(C\leq8)}$.

35. The compound of claim 34, wherein $R_1$ and $R_2$ are taken together with the nitrogen atom of the —$NR_1R_2$ group and is N-heteroaryl$_{(C\leq8)}$ or substituted N-heteroaryl$_{(C\leq8)}$.

36. The compound of claim 35, wherein $R_1$ and $R_2$ are taken together with the nitrogen atom of the —$NR_1R_2$ group and is N-heteroaryl$_{(C\leq8)}$.

37. The compound of claim 36, wherein $R_1$ and $R_2$ are taken together with the nitrogen atom of the —$NR_1R_2$ group and is 3,5-dimethylpyrazol-1-yl, triazol-1-yl, 4-methyltriazol-1-yl, 1,2,4-triazol-1-yl, 1H-1,2,4-triazol-1-yl, 4H-1,2,4-triazol-4-yl, pyrazol-1-yl, tetrazol-1-yl, or imidazol-1-yl.

38. The compound of claim 35, wherein $R_1$ and $R_2$ are taken together with the nitrogen atom of the —$NR_1R_2$ group and is substituted N-heteroaryl$_{(C\leq8)}$.

39. The compound of claim 38, wherein $R_1$ and $R_2$ are taken together with the nitrogen atom of the —$NR_1R_2$ group and is 4-methylcarbamoyl-triazol-1-yl, 4-(hydroxymethyl) triazol-1-yl, 4-(fluoromethyl) triazol-1-yl, 4-(difluoromethyl) triazol-1-yl, 5-(trifluoromethyl)-1H-pyrazol-1-yl, or 3-(trifluoromethyl)-1H-pyrazol-1-yl.

40. The compound of claim 34, wherein $R_1$ and $R_2$ are taken together with the nitrogen atom of the —$NR_1R_2$ group and is N-heterocycloalkyl$_{(C\leq8)}$ or substituted N-heterocycloalkyl$_{(C\leq8)}$.

41. The compound of claim 40, wherein $R_1$ and $R_2$ are taken together with the nitrogen atom of the —$NR_1R_2$ group and is N-heterocycloalkyl$_{(C\leq8)}$.

42. The compound of claim 41, wherein $R_1$ and $R_2$ are taken together with the nitrogen atom of the —$NR_1R_2$ group and is oxazolidin-3-yl, azetidin-1-yl, or

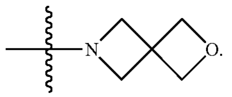 [SMILES: *N1CC2(COC2)C1]

43. The compound of claim 40, wherein $R_1$ and $R_2$ are taken together with the nitrogen atom of the —$NR_1R_2$ group and is substituted N-heterocycloalkyl$_{(C\leq8)}$.

44. The compound of claim 43, wherein $R_1$ and $R_2$ are taken together with the nitrogen atom of the —$NR_1R_2$ group, wherein the —$NR_1R_2$ group is imidazolidin-2-one-1-yl, 3-methylimidazolidin-2-one-1-yl, oxazolidin-2-one-3-yl, azetidin-2-one-1-yl, pyrrolidin-2-one-1-yl, 3-oxoazetidin-1-yl, 3-oxopyrazolidin-1-yl, 5-oxopyrazolidin-1-yl, 3-hydroxyazetidin-1-yl, 3-fluoroazetidin-1-yl, 2-oxooxazolidin-3-yl, 2-oxooxazol-3(2H)-yl, 2-oxo-2,3-dihydro-1H-imidazol-1-yl, 3-methyl-2-oxo-2,3-dihydro-1H-imidazol-1-yl, 3,3-difluoroazetidin-1-yl, 4-methyl-2,5-dioxopiperazin-1-yl, or 4-methyl-3-oxopiperazin-1-yl.

45. The compound of claim 43, wherein $R_1$ and $R_2$ are taken together with the nitrogen atom of the —$NR_1R_2$ group and is substituted N-heterocycloalkyl$_{(C\leq8)}$, further wherein the —$NR_1R_2$ group is of the formula:

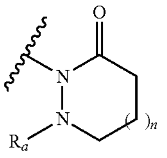

or

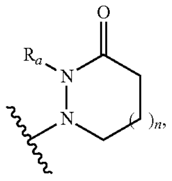

wherein:

n is 0, 1, 2, or 3;

$R_a$ is hydrogen, alkyl$_{(C\leq5)}$, or substituted alkyl$_{(C\leq5)}$.

46. The compound of claim 43, wherein $R_1$ and $R_2$ are taken together with the nitrogen atom of the —$NR_1R_2$ group and is substituted N-heterocycloalkyl$_{(C\leq8)}$, further wherein the —$NR_1R_2$ group is of the formula:

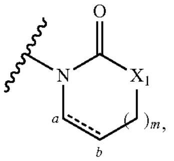

wherein:

the bond between atoms a and b is a single bond or a double bond;

m is 0, 1, 2, or 3; and $X_1$ is —$CH_2$—, —O— or —N($R_b$)—, wherein:

$R_b$ is hydrogen, alkyl$_{(C\leq8)}$, or substituted alkyl$_{(C\leq8)}$.

47. The compound of claim 43, wherein $R_1$ and $R_2$ are taken together with the nitrogen atom of the —$NR_1R_2$ group and is substituted N-heterocycloalkyl$_{(C\leq8)}$, further wherein the —$NR_1R_2$ group is of the formula:

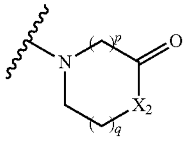

or

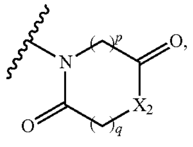

wherein:

p is 0 or 1;

q is 0 or 1; and $X_2$ is —$CH_2$—, —O—, or —N($R_e$)—, wherein:

$R_e$ is hydrogen, alkyl$_{(C\leq8)}$, or substituted alkyl$_{(C\leq8)}$.

48. The compound of claim 46, wherein the bond between atoms a and b is a single bond.

49. The compound of claim 46, wherein the bond between atoms a and b is a double bond.

50. The compound of claim 46, wherein m is 0 or 1.

51. The of claim 50, wherein m is 0.

52. The compound of claim 46, wherein $X_1$ is —O—.

53. The compound of claim 46, wherein $X_1$ is —N($R_b$)—.

54. The compound of claim 53, wherein $R_b$ is hydrogen.

55. The compound of claim 53, wherein $R_b$ is alkyl$_{(C\leq8)}$ or substituted alkyl$_{(C\leq8)}$.

56. The compound of claim 55, wherein $R_b$ is alkyl$_{(C\leq8)}$.

57. The compound of claim 56, wherein $R_b$ is methyl.

58. The compound of claim 1, wherein $R_1$ and $R_2$ are taken together with the nitrogen atom of the —$NR_1R_2$ group, wherein the —$NR_1R_2$ group is 3-oxo-1-(tert-butoxycarbonyl) pyrazolidin-2-yl.

59. The compound of claim 1, wherein the compound is further defined as:

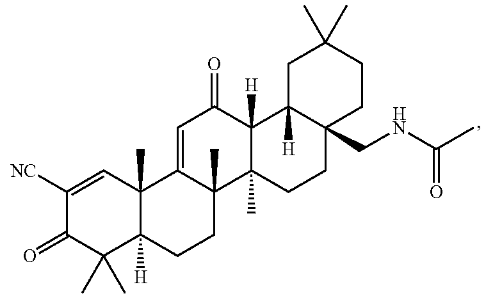

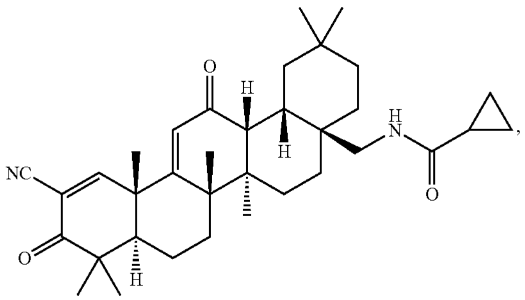

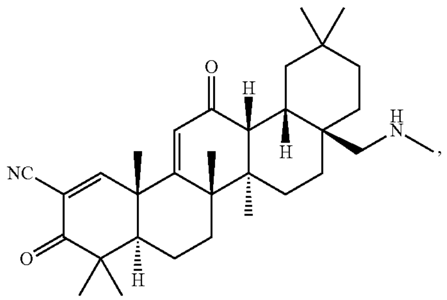

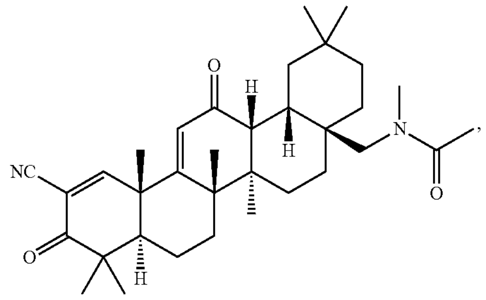

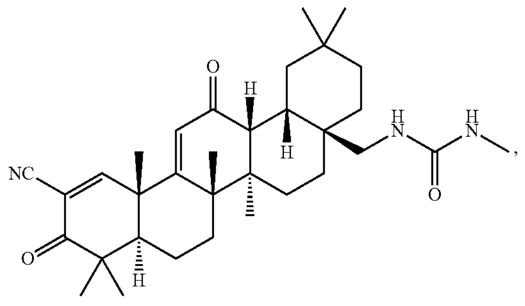

-continued
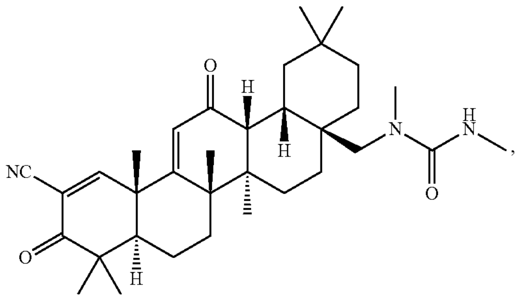
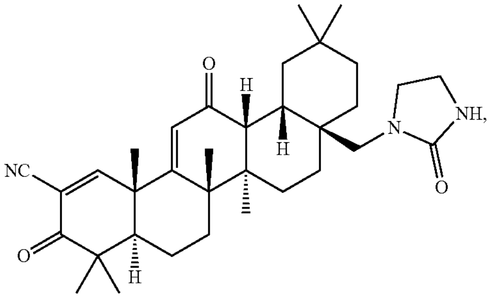
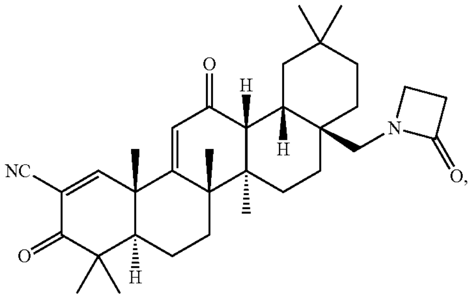
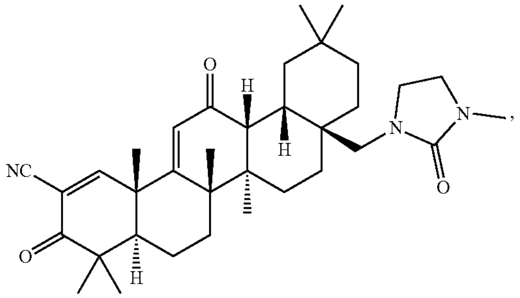
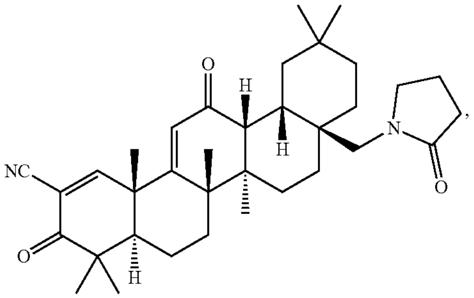
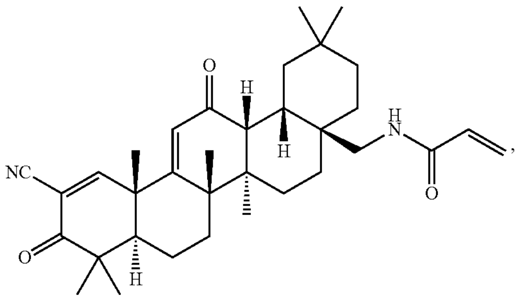
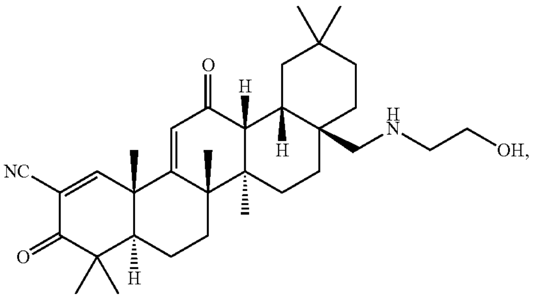
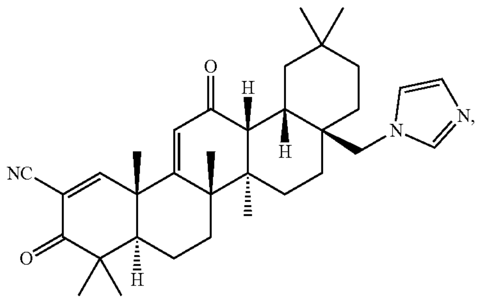
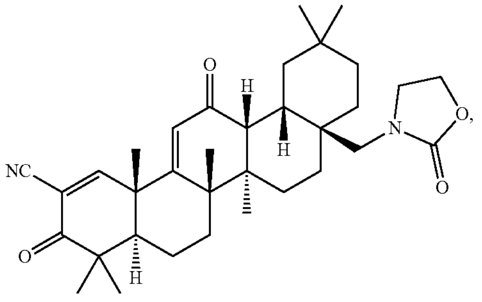
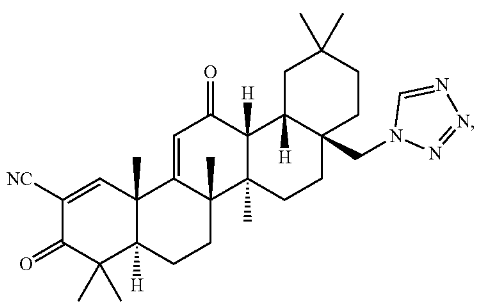

-continued
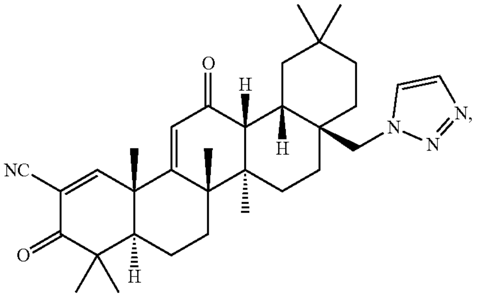
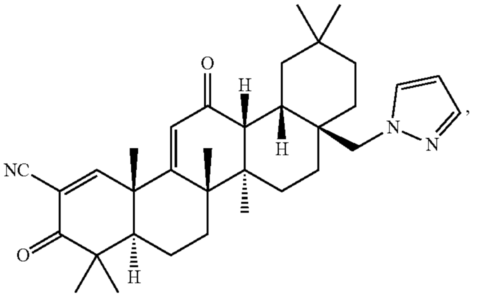
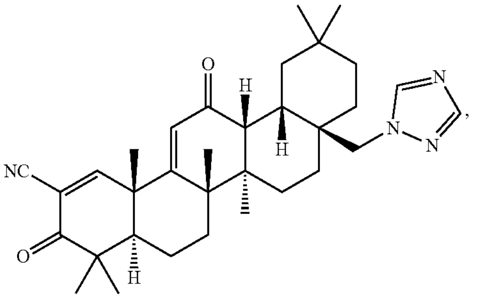
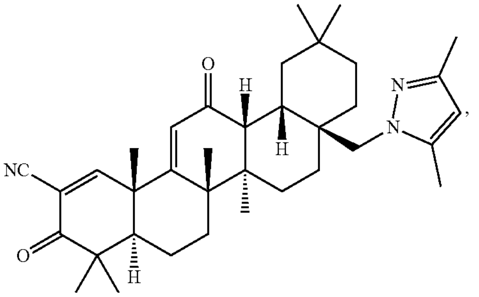
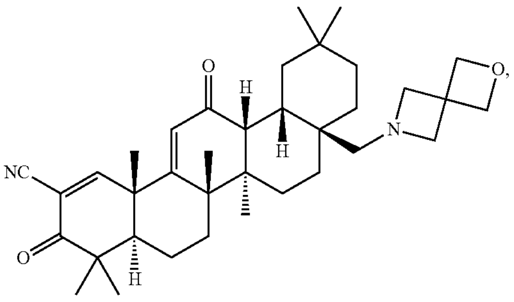
-continued
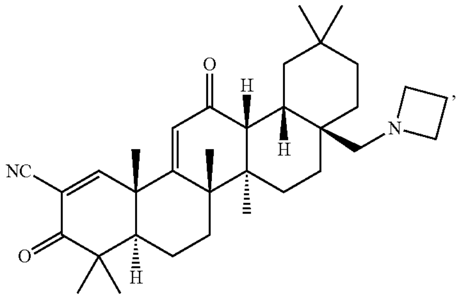
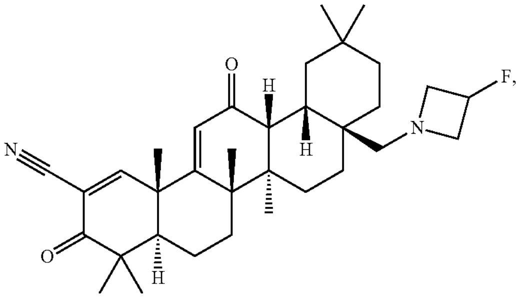
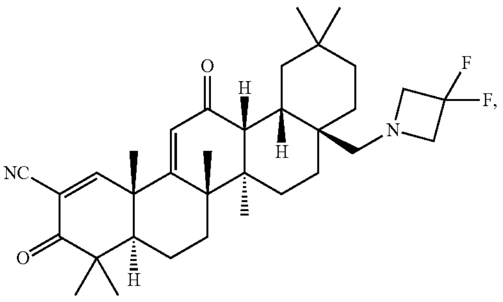
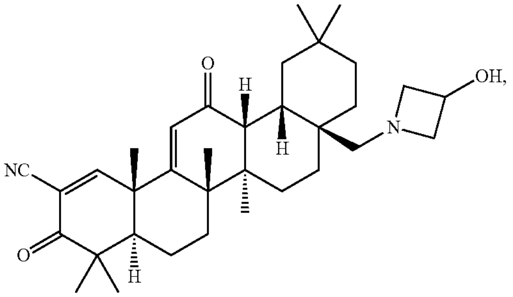
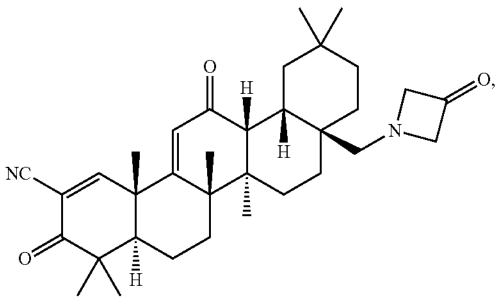

-continued
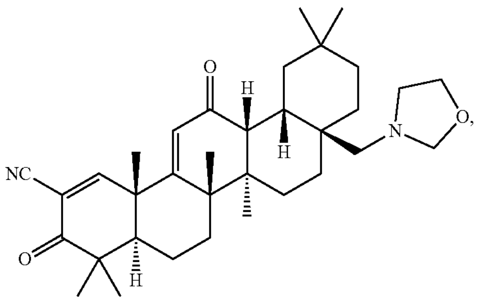
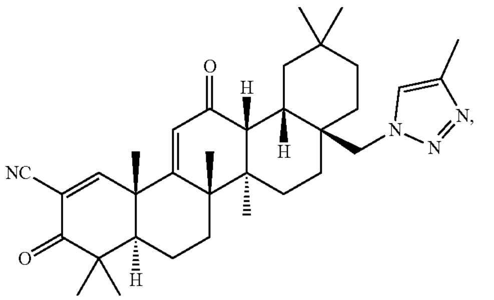
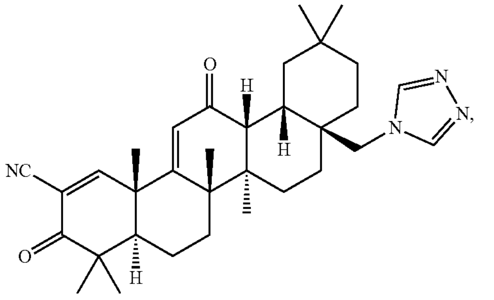
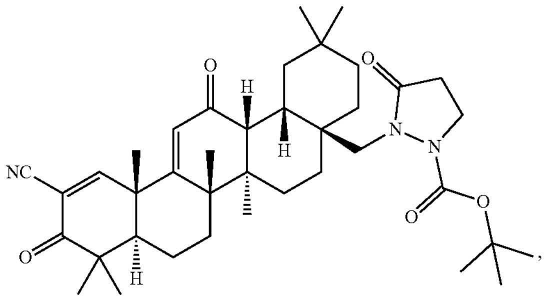
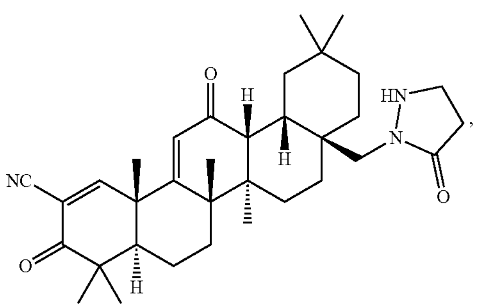
-continued
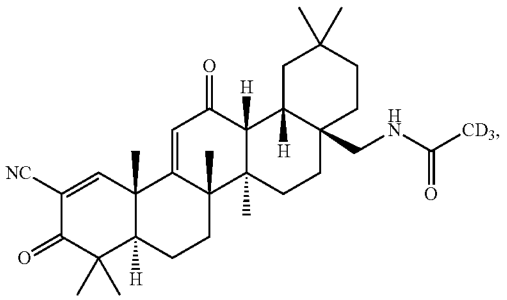
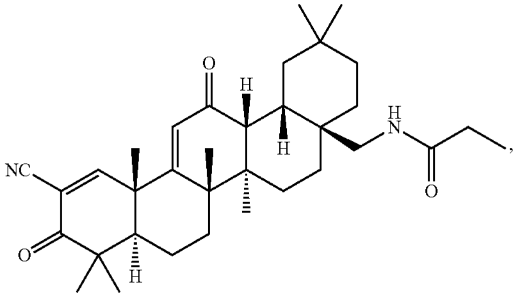
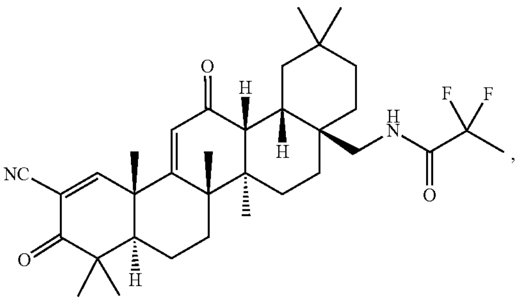
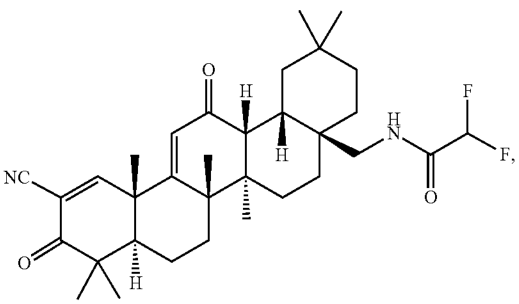
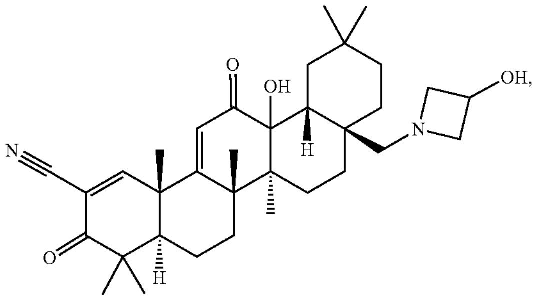

-continued

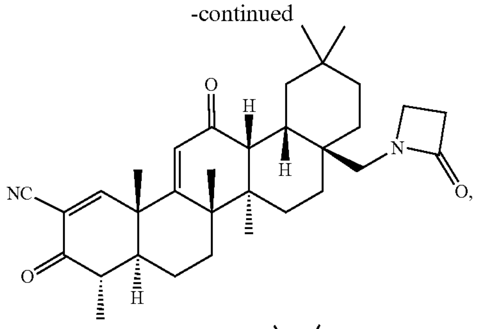

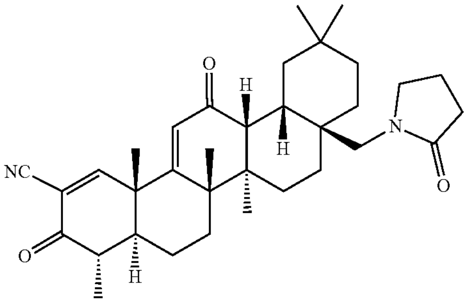

, or

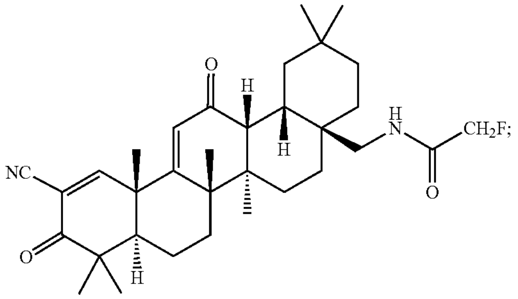

or a pharmaceutically acceptable salt of any of these formulas.

60. The compound of claim 1, wherein the compound is further defined as:

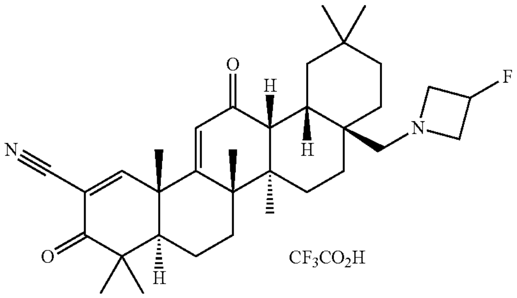

or

-continued

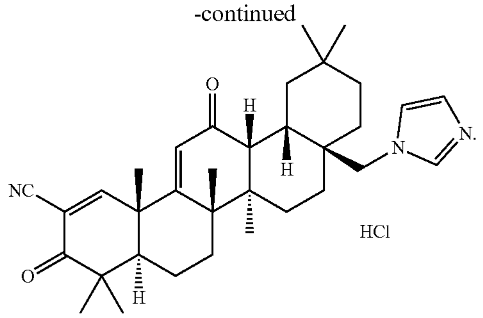

61. The compound of claim 1, wherein the compound is further defined as:

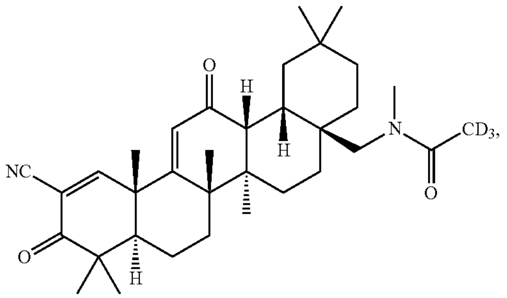

or a pharmaceutically acceptable salt thereof.

62. A pharmaceutical composition comprising:

(A) a compound of claim 1; and (B) an excipient.

63. The compound of claim 1, wherein the compound is further defined as:

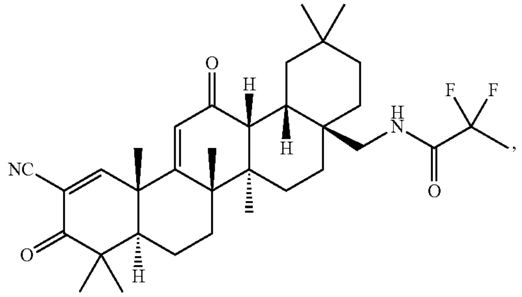

or a pharmaceutically acceptable salt thereof.

* * * * *